United States Patent
Kabasawa et al.

(10) Patent No.: US 11,158,813 B2
(45) Date of Patent: Oct. 26, 2021

(54) ORGANIC ELECTROLUMINESCENT DEVICE

(71) Applicant: Hodogaya Chemical Co., Ltd., Tokyo (JP)

(72) Inventors: Naoaki Kabasawa, Tokyo (JP); Shuichi Hayashi, Tokyo (JP); Kazuyuki Suruga, Tokyo (JP); Shunji Mochizuki, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 212 days.

(21) Appl. No.: 16/492,382

(22) PCT Filed: Mar. 15, 2018

(86) PCT No.: PCT/JP2018/010184
§ 371 (c)(1),
(2) Date: Sep. 9, 2019

(87) PCT Pub. No.: WO2018/168991
PCT Pub. Date: Sep. 20, 2018

(65) Prior Publication Data
US 2021/0143326 A1    May 13, 2021

(30) Foreign Application Priority Data
Mar. 15, 2017    (JP) ............................... JP2017-49607

(51) Int. Cl.
*H01L 51/50*    (2006.01)
*H01L 51/00*    (2006.01)
(Continued)

(52) U.S. Cl.
CPC ........ *H01L 51/006* (2013.01); *H01L 51/0058* (2013.01); *H01L 51/0069* (2013.01);
(Continued)

(58) Field of Classification Search
CPC .............. H01L 51/006; H01L 51/0069; H01L 51/0058; H01L 51/0073; H01L 51/0074; H01L 51/0072
See application file for complete search history.

(56) References Cited

U.S. PATENT DOCUMENTS 10,326,079 B2    6/2019    Hayashi et al.
2002/0025419 A1*    2/2002    Lee .................. H01L 51/504
                                            428/212

(Continued)

FOREIGN PATENT DOCUMENTS

WO    2016/175211 A1    11/2016

OTHER PUBLICATIONS

International Search Report dated Jun. 19, 2018, issued for PCT/JP2018/010184.

*Primary Examiner* — Dung A. Le
(74) *Attorney, Agent, or Firm* — Locke Lord LLP

(57) ABSTRACT

To provide an organic EL device having (1) high luminous efficiency and high power efficiency, (2) low turn on voltage, (3) low actual driving voltage, and (4) a long lifetime, by combining various materials for an organic EL device, which are excellent in hole injection/transport performances, electron injection/transport performances, electron blocking ability, stability in a thin-film state, and durability, so as to allow the respective materials to effectively reveal their characteristics. In the organic EL device having at least an anode, a hole transport layer, a light emitting layer, an electron transport layer and a cathode in this order, the hole transport layer includes an arylamine compound of the following general formula (1), and the electron transport layer includes a compound of the following general formula (2) having a benzazole ring structure.

(Continued)

← 9 CATHODE
← 8 ELECTRON INJECTION LAYER
← 7 ELECTRON TRANSPORT LAYER
← 6 LIGHT EMITTING LAYER
← 5 SECOND HOLE TRANSPORT LAYER
← 4 FIRST HOLE TRANSPORT LAYER
← 3 HOLE INJECTION LAYER
← 2 TRANSPARENT ANODE
← 1 GLASS SUBSTRATE

[Chemical Formula 1]

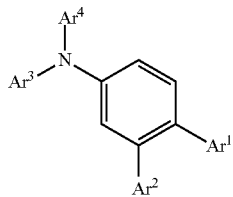

(1)

[Chemical Formula 2]

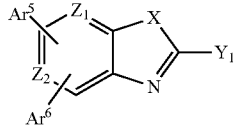

(2)

(51) Int. Cl.
C07D 307/91 (2006.01)
C07K 11/02 (2006.01)

(52) U.S. Cl.
CPC ...... H01L 51/0072 (2013.01); H01L 51/0073 (2013.01); H01L 51/0074 (2013.01); C07D 307/91 (2013.01); C07K 11/02 (2013.01); H01L 51/5064 (2013.01); H01L 51/5072 (2013.01); H01L 51/5092 (2013.01)

(56) References Cited

U.S. PATENT DOCUMENTS

2017/0170420 A1* 6/2017 Ito ................. H01L 51/0072
2018/0315928 A1   11/2018 Hayashi et al.
2020/0203618 A1*  6/2020 Weiwei ............... C09K 11/06

* cited by examiner

5 Claims, 1 Drawing Sheet

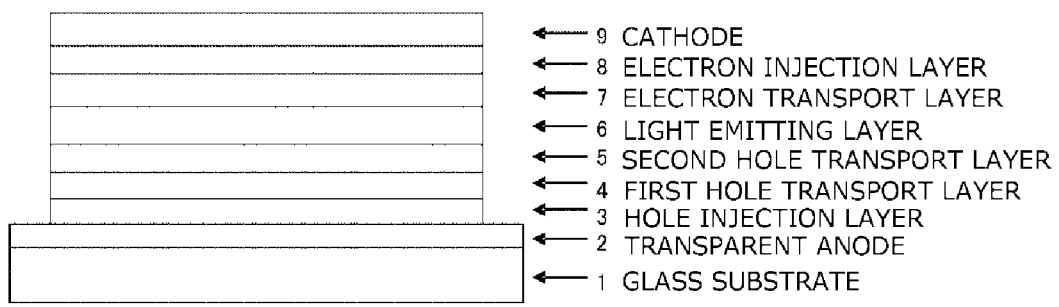

ORGANIC ELECTROLUMINESCENT DEVICE

TECHNICAL FIELD

The present invention relates to an organic electroluminescent device which is a preferred self-luminous device for various display devices.

Specifically, this invention relates to organic electroluminescent devices (hereinafter referred to as organic EL devices) using specific arylamine compounds and compounds having a specific benzazole ring structure.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to PTLs 1 and 2, for example).

To date, various improvements have been made for practical applications of the organic EL device. Various roles of the laminated structure are further subdivided to provide an EL device that includes an anode, a hole injection layer, a hole transport layer, a light emitting layer, an electron transport layer, an electron injection layer, and a cathode successively formed on a substrate, and high efficiency and durability have been achieved by the EL device (refer to NPL 1, for example).

Further, there have been attempts to use triplet excitons for further improvements of luminous efficiency, and the use of a phosphorescence-emitting compound has been examined (refer to NPL 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to NPL 3, for example).

The light emitting layer can be also fabricated by doping a charge-transporting compound generally called a host material, with a fluorescent compound, a phosphorescence-emitting compound, or a delayed fluorescent-emitting material. As described in the NPL, the selection of organic materials in an organic EL device greatly influences various device characteristics such as efficiency and durability (refer to NPL 2, for example).

In an organic EL device, charges injected from both electrodes recombine in a light emitting layer to cause emission. In order to obtain high luminous efficiency, efficient transfer of both charges of holes and electrons to the light emitting layer, balance of both charges injected to the light emitting layer, confinement of generated excitons, and the like are important. The probability that holes and electrons recombine in the light emitting layer can be improved by improving hole injectability from the hole transport layer to the light emitting layer and electron blocking performance of the hole transport layer preventing the leakage of electrons from the light emitting layer to the hole transport layer, and excitons can be generated efficiently. Furthermore, high luminous efficiency can be obtained by confining the excitons generated in the light emitting layer without leaking to the transport layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device. The materials in use are therefore required to have characteristics of high heat resistance and satisfactory amorphousness.

N,N'-diphenyl-N,N'-di(α-naphthyl)benzidine (NPD) and various aromatic amine derivatives are known as the hole transport materials used for the organic EL device (refer to PTLs 1 and 2, for example). Although NPD has desirable hole transportability, its glass transition point (Tg), which is an index of heat resistance, is as low as 96° C., which causes the degradation of device characteristics by crystallization under a high-temperature condition (refer to NPL 4, for example). The aromatic amine derivatives described in the PTLs include a compound known to have an excellent hole mobility of $10^{-3}$ cm$^2$/Vs or higher (refer to PTLs 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to PTL 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to PTLs 4 and 5, for example). However, while the devices using these compounds for the hole injection layer or the hole transport layer have been improved in heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Literature

PTL 1: JP-A-8-048656
PTL 2: Japanese Patent No. 3194657
PTL 3: Japanese Patent No. 4943840
PTL 4: JP-A-2006-151979
PTL 5: WO2008/062636
PTL 6: JP-A-7-126615

PTL 7: JP-A-8-048656
PTL 8: JP-A-2005-108804

Non Patent Literature

NPL 1: The Japan Society of Applied Physics, 9th Lecture Preprints, pp. 55 to 61 (2001)
NPL 2: The Japan Society of Applied Physics, 9th Lecture Preprints, pp. 23 to 31 (2001)
NPL 3: Appl. Phys. Let., 98, 083302 (2011)
NPL 4: Organic EL Symposium, the 3rd Regular presentation Preprints, pp. 13 to 14 (2006)

SUMMARY OF INVENTION

Technical Problem

An object of the present invention is to provide an organic EL device having (1) high luminous efficiency and high power efficiency, (2) low turn on voltage, (3) low actual driving voltage, and (4) a long lifetime, by combining various materials for an organic EL device, which are excellent in hole injection/transport performances, electron injection/transport performances, electron blocking ability, stability in a thin-film state, and durability, so as to allow the respective materials to effectively reveal their characteristics.

Physical properties of the organic EL device to be provided by the present invention include (1) high luminous efficiency and high power efficiency, (2) low turn on voltage, (3) low actual driving voltage, and (4) a long lifetime.

Solution to Problem

For achieving the object, the present inventors have focused the fact that an arylamine material is excellent in hole injection/transport performances, stability as a thin film, and durability. Furthermore, they have focused the fact that a compound having a benzazole derivative is excellent in electron injection/transport performances, stability as a thin film, and durability.

The present inventors found that holes can be efficiently injected and transported to the light emitting layer by selecting a hole transport layer as a two-layer structure and selecting an arylamine compound having a specific structure as the material of the hole transport layer (second hole transport layer) adjacent to the light emitting layer. Furthermore, they found that electrons can be efficiently injected and transported to the light emitting layer by selecting a benzazole derivative having a specific structure as the material of the electron transport layer.

And they combined various materials with the combination of such the arylamine compound and the benzazole derivative, and examined the combination of the material in which the carrier balance was refined, and they have intensively conducted characteristic evaluations of the devices. As a result, they have completed the present invention.

Specifically, according to the present invention, the following organic EL devices are provided.

1) An organic EL device comprising at least an anode, a hole transport layer, a light emitting layer, an electron transport layer and a cathode in this order, wherein the hole transport layer comprises an arylamine compound of the following general formula (1), and the electron transport layer comprises a compound of the following general formula (2) having a benzazole ring structure.

[Chemical Formula 1]

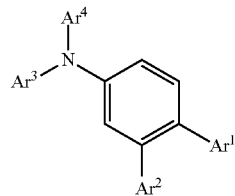

(1)

In the formula, $Ar^1$ to $Ar^4$ may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 2]

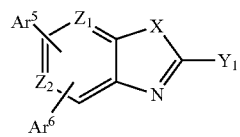

(2)

In the formula, $Ar^5$ to $Ar^6$ may be the same or different, and represent a hydrogen atom, a deuterium atom, a substituted or unsubstituted aromatic hydrocarbon group, a substituted or unsubstituted aromatic heterocyclic group, or a substituted or unsubstituted condensed polycyclic aromatic group, $Y_1$ represents a substituted or unsubstituted aromatic hydrocarbon group, a substituted or unsubstituted aromatic heterocyclic group, a substituted or unsubstituted condensed polycyclic aromatic group, or alkyl, X represents an oxygen atom or a sulfur atom, $Z_1$ and $Z_2$ may be the same or different, and represent a carbon atom or a nitrogen atom.

2) The organic EL device of 1), wherein the electron transport layer comprises a compound of the following general formula (3) having a benzazole ring structure.

[Chemical Formula 3]

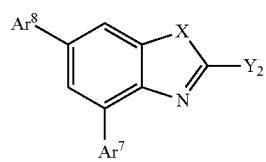

(3)

In the formula, $Ar^7$ to $Ar^8$ may be the same or different, and represent a hydrogen atom, a deuterium atom, a substituted or unsubstituted aromatic hydrocarbon group, a substituted or unsubstituted aromatic heterocyclic group, or a substituted or unsubstituted condensed polycyclic aromatic group, $Y_2$ represents a substituted or unsubstituted aromatic hydrocarbon group, a substituted or unsubstituted aromatic heterocyclic group, a substituted or unsubstituted condensed polycyclic aromatic group, or alkyl, X represents an oxygen atom or a sulfur atom.

3) The organic electroluminescent device of 1), wherein the hole transport layer has a two-layer structure of a first hole transport layer and a second hole transport layer, and the second hole transport layer comprises the arylamine compound.

4) The organic electroluminescent device of 1), wherein the first hole transport layer comprises a triphenylamine derivative different from the arylamine compound included in the second hole transport layer, and the triphenylamine derivative is a compound having a molecular structure containing two triphenylamine skeletons bonded to each other via a single bond or a divalent hydrocarbon group, and having 2 to 6 triphenylamine skeletons as a whole molecule.

5) The organic EL device of 4), wherein the triphenylamine derivative included in the first hole transport layer is represented by the following general formula (4).

[Chemical Formula 4]

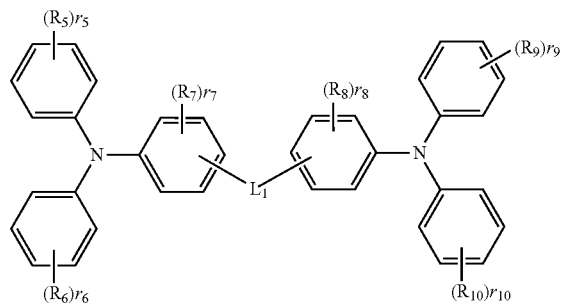

(4)

In the formula, $R_5$ to $R_{10}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy. $r_5$ to $r_{10}$ may be the same or different, $r_5$, $r_6$, $r_9$ and $r_{10}$ representing 0 to 5, and $r_7$ and $r_8$ representing 0 to 4, and when $r_5$, $r_6$, $r_9$ and $r_{10}$ are 2 to 5, or when $r_7$ and $r_8$ are 2 to 4, $R_5$ to $R_{10}$, a plurality of which bind to the same benzene ring, may be the same or different and may bind to each other via a single bond, substituted or unsubstituted methylene, an oxygen atom, or a sulfur atom to form a ring. $L_1$ represents a divalent group of the following structural formulas (C) to (G), or a single bond.

[Chemical Formula 5]

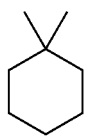

(C)

[Chemical Formula 6]

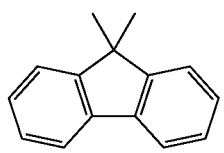

(D)

[Chemical Formula 7]

—CH$_2$—

(E)

[Chemical Formula 8]

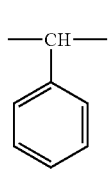

(F)

[Chemical Formula 9]

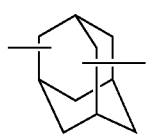

(G)

6) The organic EL device of 4), wherein the triphenylamine derivative included in the first hole transport layer is represented by the following general formula (5).

[Chemical Formula 10]

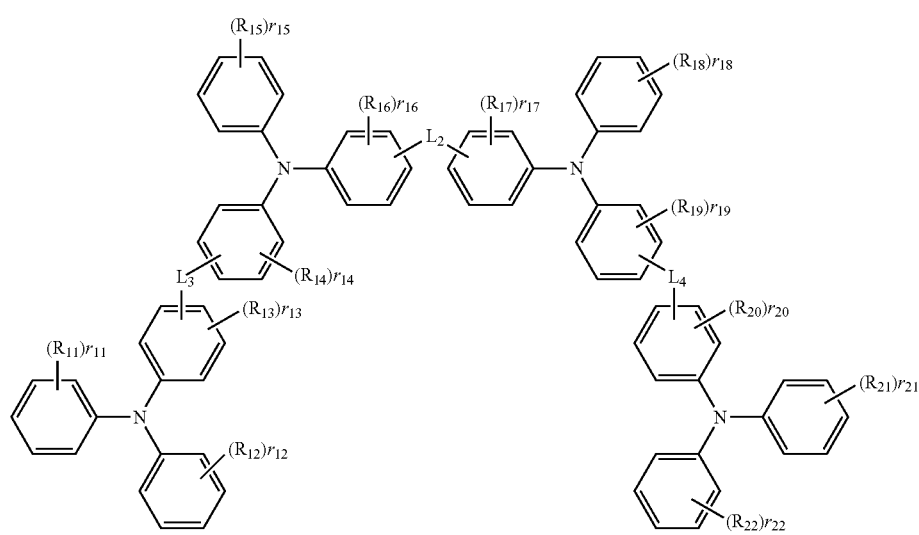

(5)

In the formula, $R_{11}$ to $R_{22}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and $r_{11}$ to $r_{22}$ may be the same or different, $r_{11}$, $r_{12}$, $r_{15}$, $r_{18}$, $r_{21}$ and $r_{22}$ representing 0 to 5, and $r_{13}$, $r_{14}$, $r_{16}$, $r_{17}$, $r_{19}$ and $r_{20}$ representing 0 to 4, and when $r_{11}$, $r_{12}$, $r_{15}$, $r_{18}$, $r_{21}$ and $r_{22}$ are 2 to 5, or when $r_{13}$, $r_{14}$, $r_{16}$, $r_{17}$, $r_{19}$ and $r_{20}$ are 2 to 4, $R_{11}$ to $R_{22}$, a plurality of which bind to the same benzene ring, may be the same or different and may bind to each other via a single bond, substituted or unsubstituted methylene, an oxygen atom, or a sulfur atom to form a ring, and $L_2$, $L_3$ and $L_4$ may be the same or different, and represent a divalent group of the following structural formulas (B) to (G), or a single bond.

[Chemical Formula 11]

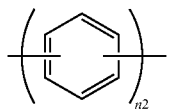

(B)

In the formula, n2 represents 1 to 3.

[Chemical Formula 12]

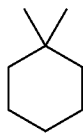

(C)

[Chemical Formula 13]

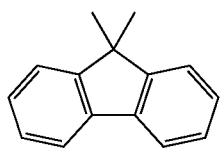

(D)

[Chemical Formula 14]

—CH$_2$—

(E)

[Chemical Formula 15]

—CH—

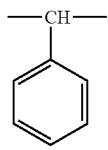

(F)

[Chemical Formula 16]

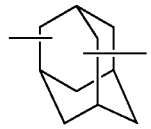

(G)

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar^1$ to $Ar^4$ in the general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Specific examples of the "substituent" in the "substituted aromatic hydrocarbon group", the "substituted aromatic heterocyclic group", or the "substituted condensed polycyclic aromatic group" represented by $Ar^1$ to $Ar^4$ in the general formula (1) include a deuterium atom, cyano, nitro; halogen atoms such as a fluorine atom, a chlorine atom, a bromine atom, and an iodine atom; linear or branched alkyls of 1 to 6 carbon atoms such as methyl; linear or branched alkyloxys of 1 to 6 carbon atoms such as methyloxy, ethyloxy, and propyloxy; alkenyls such as vinyl and allyl; aryloxys such as phenyloxy and tolyloxy; arylalkyloxys such as benzyloxy and phenethyloxy; an aromatic hydrocarbon group or a condensed polycyclic aromatic group such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group such as pyridyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar^5$ to $Ar^8$ in the general formula (2) and the general formula (3) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar^1$ to $Ar^4$ in the general formula (1), and possible embodiments may also be the same embodiments as the exemplified embodiments.

Examples of the "substituent" in the "substituted aromatic hydrocarbon group", the "substituted aromatic heterocyclic group", or the "substituted condensed polycyclic aromatic group" represented by $Ar^5$ to $Ar^8$ in the general formula (2) and the general formula (3) include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Y_1$ and $Y_2$ in the general formula (2) and the general formula (3) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, and carbolinyl.

Examples of the "substituent" in the "substituted or unsubstituted aromatic hydrocarbon group", the "substituted or unsubstituted aromatic heterocyclic group", or the "substituted or unsubstituted condensed polycyclic aromatic group" represented by $Y_1$ to $Y_2$ in the general formula (2) and the general formula (3) include the same groups exemplified as the groups for the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_5$ to $R_{10}$ in the general formula (4) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl, and these groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_5$ to $R_{10}$ in the general formula (4) include a deuterium atom; cyano; nitro; halogen atoms such as a fluorine atom, a chlorine atom, a bromine atom, and an iodine atom; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_5$ to $R_{10}$ in the general formula (4) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy, and these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_5$ to $R_{10}$ in the general formula (4), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_5$ to $R_{10}$ in the general formula (4) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar^1$ to $Ar^4$ in the general formula (1), and these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

Specific examples of the "aryloxy" in the "substituted or unsubstituted aryloxy" represented by $R_5$ to $R_{10}$ in the general formula (4) include phenyloxy, biphenylyloxy, terphenylyloxy, naphthyloxy, anthracenyloxy, phenanthrenyloxy, fluorenyloxy, indenyloxy, pyrenyloxy, and perylenyloxy, and these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

$R_5$ to $R_{10}$ in the general formula (4) may be the same or different, $r_5$, $r_6$, $r_9$, and $r_{10}$ representing 0 to 5, and $r_7$, and $r_9$ representing 0 to 4.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{11}$ to $R_{22}$ in the general formula (5) include the same groups exemplified as the groups for the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_5$ to $R_{10}$ in the general formula (4), and possible embodiments may also be the same embodiments as the exemplified embodiments.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_{11}$ to $R_{22}$ in the general formula (5) include the same groups exemplified as the groups for the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R_5$ to $R_{10}$ in the general formula (4), and possible embodiments may also be the same embodiments as the exemplified embodiments.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{11}$ to $R_{22}$ in the general formula (5) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar^1$ to $Ar^4$ in the general formula (1), when a plurality of these groups are bonded to the same aromatic ring (in the case where $r_{11}$, $r_{12}$, $r_{15}$, $r_{18}$, $r_{21}$, and $r_{22}$ are integers of 2 to 5, or $r_{13}$, $r_{14}$, $r_{16}$, $r_{17}$, $r_{19}$ and $r_{20}$ are integers of 2 to 4), these groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

Examples of the "aryloxy group" in the "substituted or unsubstituted aryloxy group" represented by $R_{11}$ to $R_{22}$ in the general formula (5) include the same groups exemplified as the groups for the "aryloxy group" in the "substituted or unsubstituted aryloxy group" represented by $R_5$ to $R_{10}$ in the general formula (4), and possible embodiments may also be the same embodiments as the exemplified embodiments.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar^1$ to $Ar^4$ in the general formula (1), and possible embodiments may also be the same embodiments as the exemplified embodiments.

$r_{11}$ to $r_{22}$ may be the same or different, $r_{11}$, $r_{12}$, $r_{15}$, $r_{18}$, $r_{21}$, and $r_{22}$ representing 0 to 5, and $r_{13}$, $r_{14}$, $r_{16}$, $r_{17}$, $r_{19}$, and $r_{20}$ representing 0 to 4. When $r_{11}$, $r_{12}$, $r_{13}$, $r_{14}$, $r_{15}$, $r_{16}$, $r_{17}$, $r_{18}$, $r_{19}$, $r_{20}$, $r_{21}$ or $r_{22}$ is 0, $R_{11}$, $R_{12}$, $R_{13}$, $R_{14}$, $R_{15}$, $R_{16}$, $R_{17}$, $R_{18}$, $R_{19}$, $R_{20}$, $R_{21}$ or $R_{22}$ on the benzene ring, is absent, that is, the benzene ring is not substituted with a group represented by $R_{11}$, $R_{12}$, $R_{13}$, $R_{14}$, $R_{15}$, $R_{16}$, $R_{17}$, $R_{18}$, $R_{19}$, $R_{20}$, $R_{21}$ or $R_{22}$.

The arylamine compounds of the general formula (1), an arylamine compounds having a structure in which two triarylamine structures are joined within a molecule via a single bond or a divalent group that does not contain a hetero atom represented by the general formula (4), and an arylamine compound having a structure in which four triarylamine structures are joined within a molecule via a single bond or a divalent group that does not contain a hetero atom represented by the general formula (5), for preferred use in the organic EL device of the present invention, can be used as a constitutive material of a hole injection layer, or a hole transport layer of an organic EL device.

The arylamine compounds of the general formula (1), the arylamine compounds having a structure in which two triarylamine structures are joined within a molecule via a single bond or a divalent group that does not contain a hetero atom represented by the general formula (4), and the arylamine compound having a structure in which four triarylamine structures are joined within a molecule via a single bond or a divalent group that does not contain a hetero atom represented by the general formula (5) have high hole mobility and are therefore preferred compounds as a material of a hole injection layer or a hole transport layer.

The compounds of the general formula (2) having a benzazole ring structure, for preferable use in the organic EL device of the present invention, can be used as a constitutive material of an electron transport layer of an organic EL device. The compounds of the general formula (2) excel in electron injection and transport abilities, and are therefore preferred compounds as a material of an electron transport layer.

In the organic EL device of the present invention, materials for an organic EL device having excellent hole and electron injection/transport performances, stability as a thin film, and durability are combined an arylamine compound having a specific structure with the compound having a benzazole ring structure having a specific structure while taking carrier balance into consideration. Therefore, compared with the conventional organic EL devices, hole transport efficiency to a light emitting layer from a hole transport layer is improved (further, by using an arylamine compound having a specific structure as the material of the first hole transport layer, in the embodiment in which the materials of the first hole transport layer and the second hole transport layer are combined so as to inject and transport hole more efficiently to the light emitting layer, the carrier balance is further refined) and electron transport efficiency to the light emitting layer from the electron transport layer is improved, and thereby luminous efficiency is improved, and also driving voltage is decreased, and durability of the organic EL device can be improved. Thus, an organic EL device having high efficiency, low driving voltage, and a long lifetime can be attained.

Advantageous Effects of Invention

The organic EL device of the present invention can achieve an organic EL device having high efficiency, low driving voltage and a long lifetime as a result of attaining efficient hole injection/transport to the light emitting layer from the hole transport layer and improving electron injection/transport efficiency to the light emitting layer from the electron transport layer by selecting specific arylamine compounds which can effectively exhibit hole injection/transport roles and selecting specific compounds having a benzazole ring structure which can effectively exhibit electron injection/transport roles.

The organic EL device of the present invention can improve luminous efficiency, driving voltage and durability of the conventional organic EL devices.

BRIEF DESCRIPTION OF DRAWINGS

FIG. 1 is a diagram illustrating the configuration of the organic EL devices of Examples 45 to 62 and Comparative Examples 1 to 4.

DESCRIPTION OF EMBODIMENTS

The following presents specific examples of preferred compounds among the arylamine compounds of the general formula (1) preferably used in the organic EL device of the present invention. The present invention, however, is not restricted to these compounds.

[Chemical Formula 17]

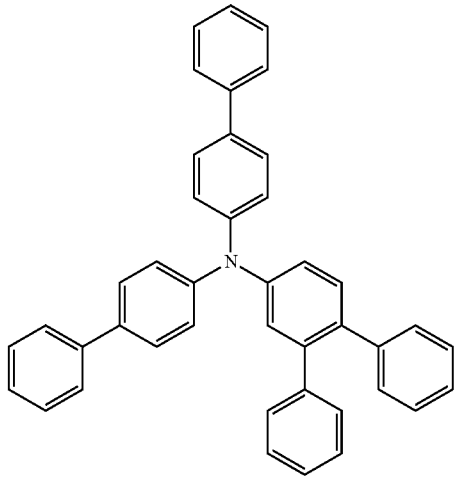

(1-1)

[Chemical Formula 18]

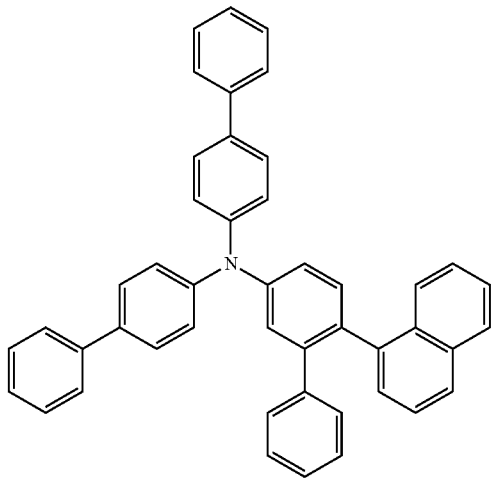

(1-2)

[Chemical Formula 19]

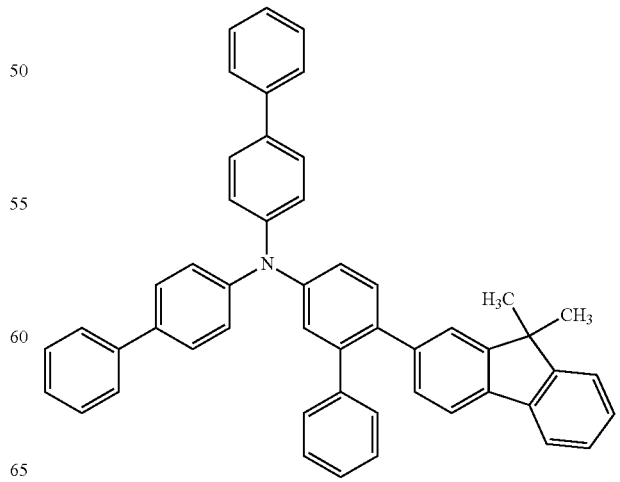

(1-3)

-continued
[Chemical Formula 20]
(1-4)
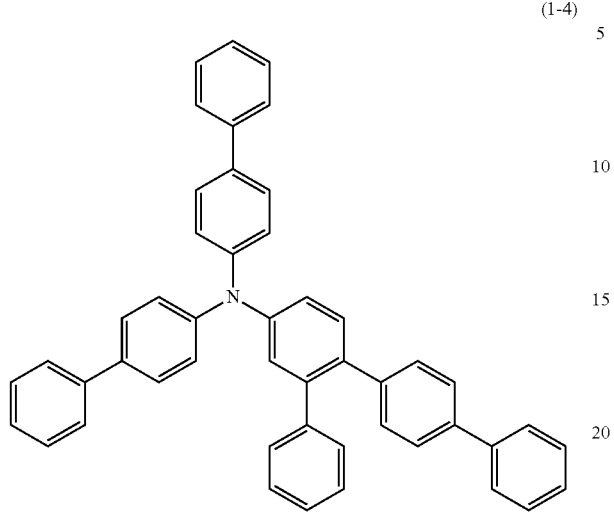
[Chemical Formula 21]
(1-5)
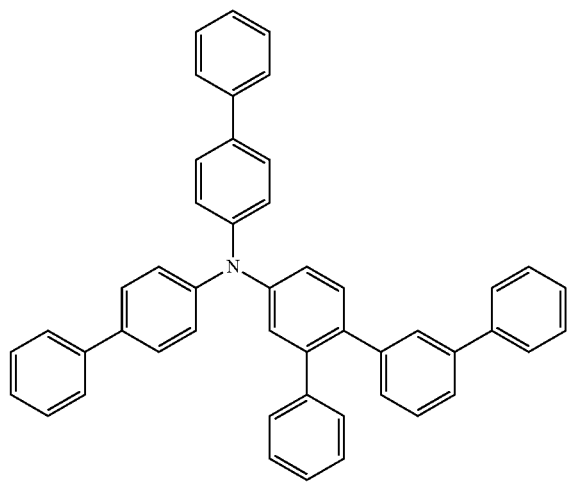
[Chemical Formula 22]
(1-6)
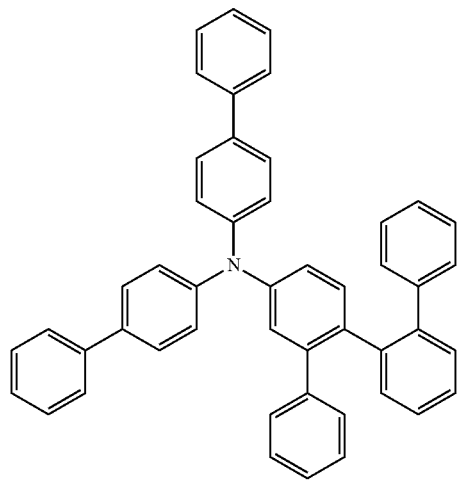
-continued
[Chemical Formula 23]
(1-7)
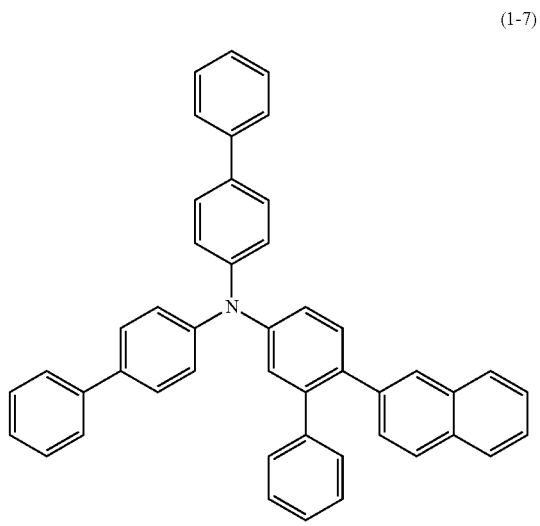
[Chemical Formula 24]
(1-8)
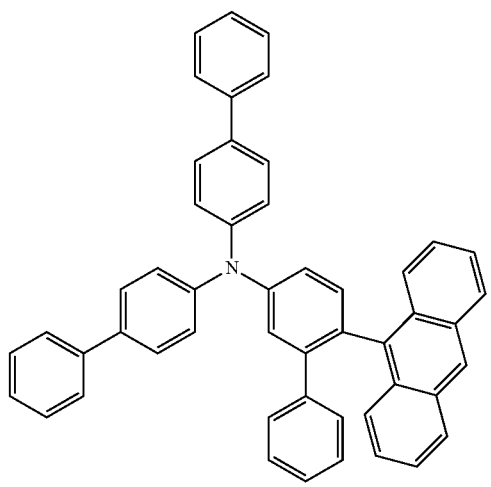
[Chemical Formula 25]
(1-9)
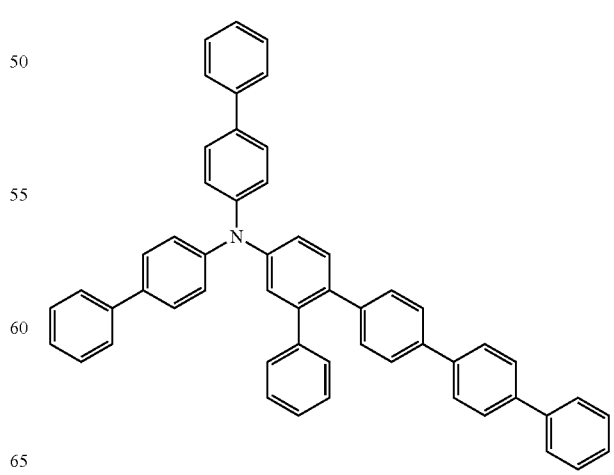

[Chemical Formula 26]
(1-10)
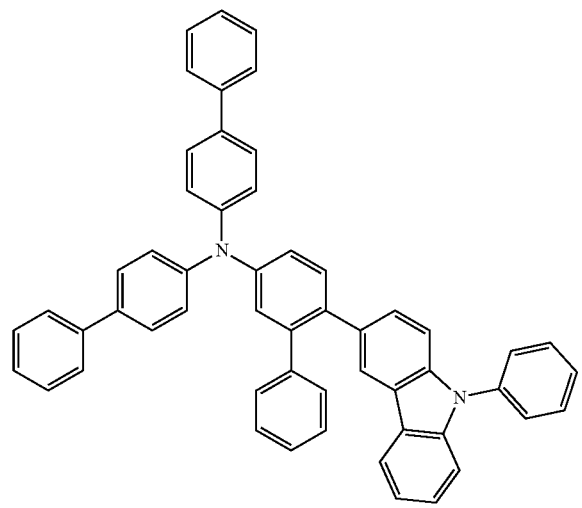
[Chemical Formula 27]
(1-11)
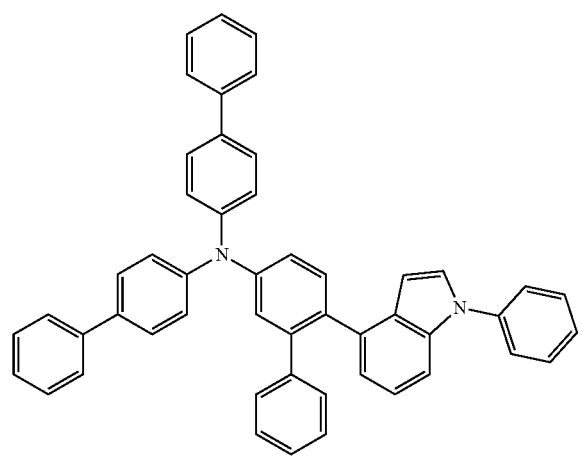
[Chemical Formula 28]
(1-12)
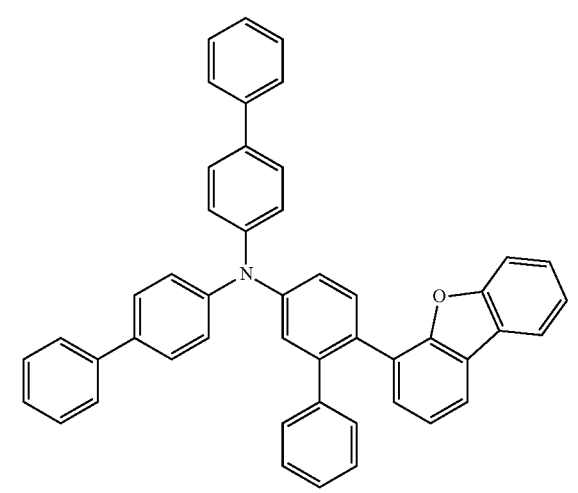
[Chemical Formula 29]
(1-13)
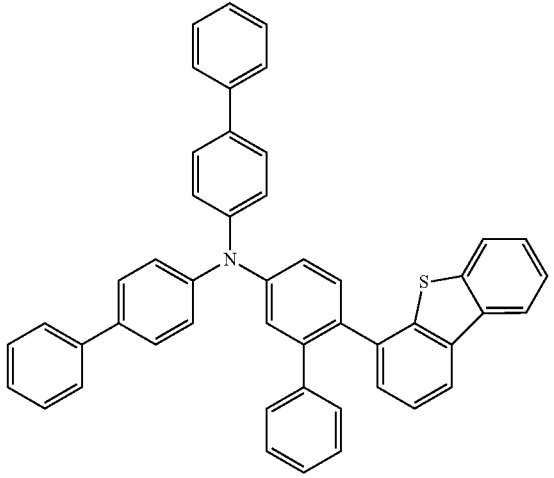
[Chemical Formula 30]
(1-14)
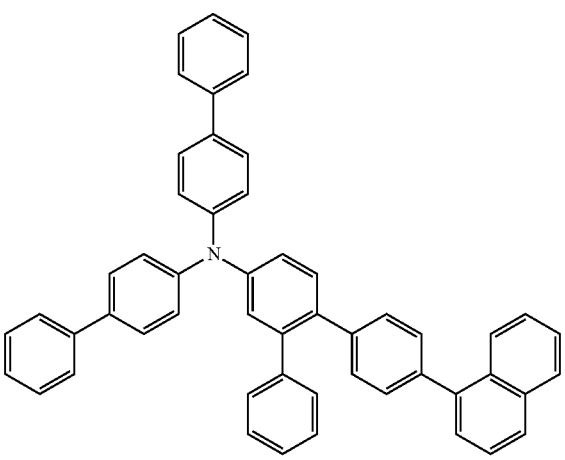
[Chemical Formula 31]
(1-15)
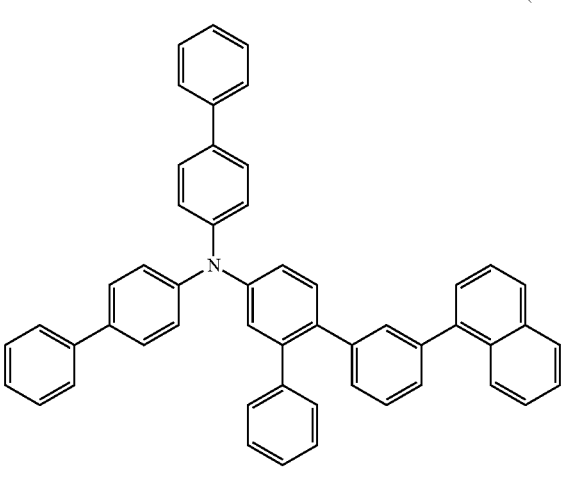

[Chemical Formula 32]
(1-16)
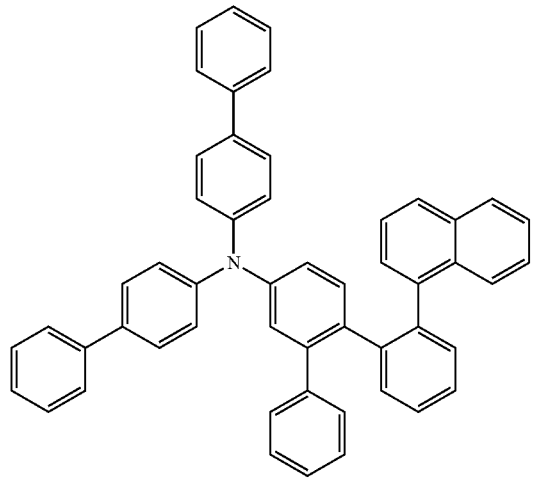
[Chemical Formula 33]
(1-17)
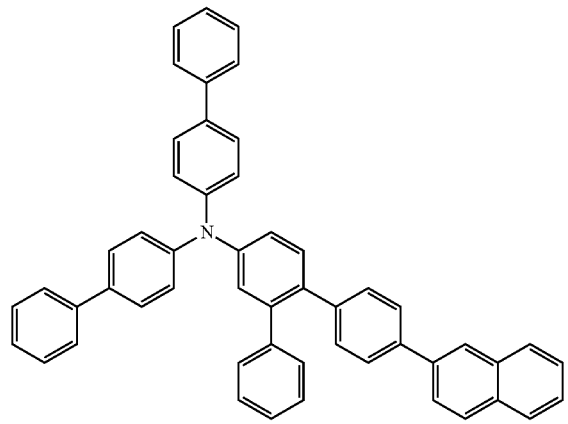
[Chemical Formula 34]
(1-18)
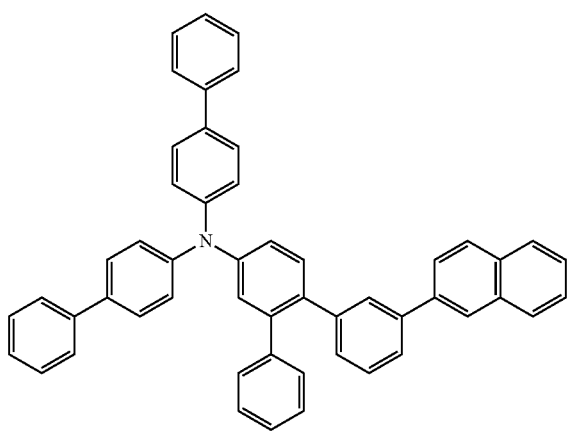
[Chemical Formula 35]
(1-19)
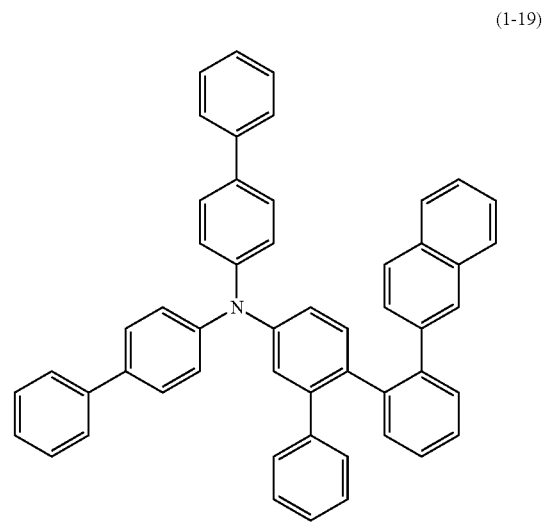
[Chemical Formula 36]
(1-20)
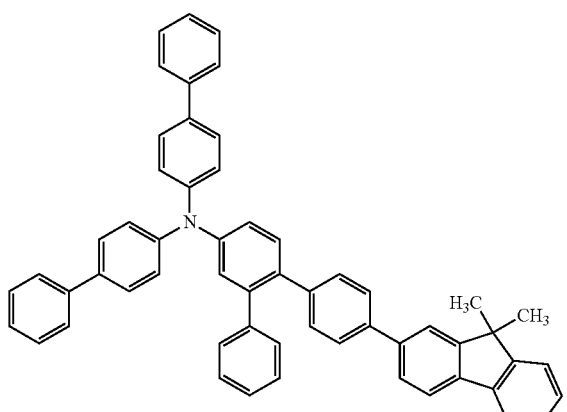
[Chemical Formula 37]
(1-21)
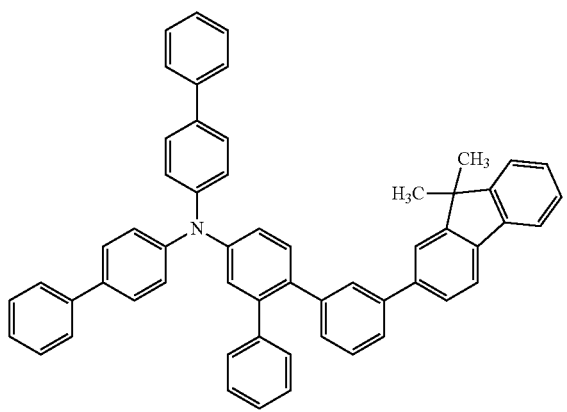

[Chemical Formula 38]
(1-22)
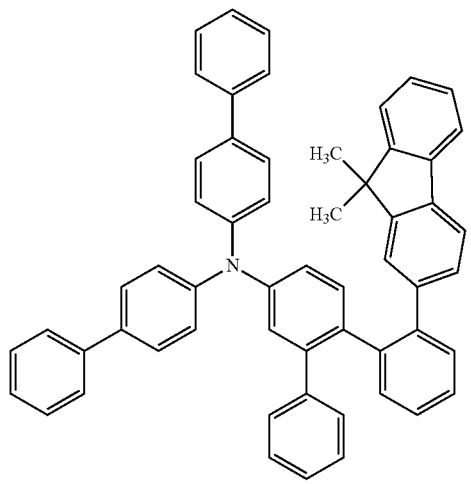
[Chemical Formula 39]
(1-23)
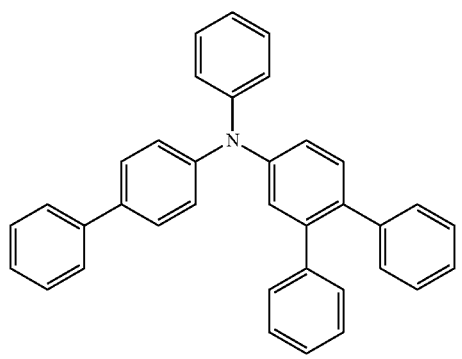
[Chemical Formula 40]
(1-24)
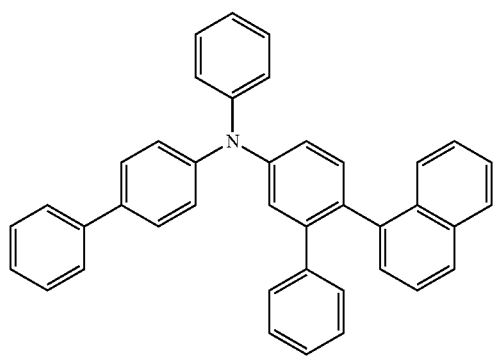
[Chemical Formula 41]
(1-25)
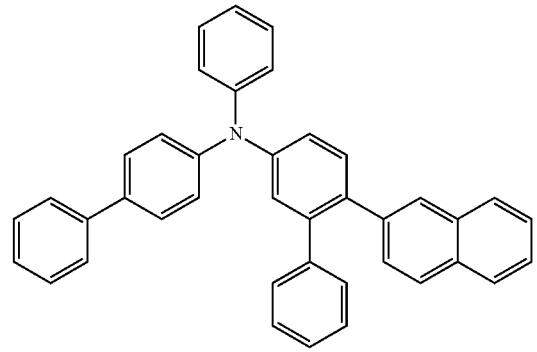
[Chemical Formula 42]
(1-26)
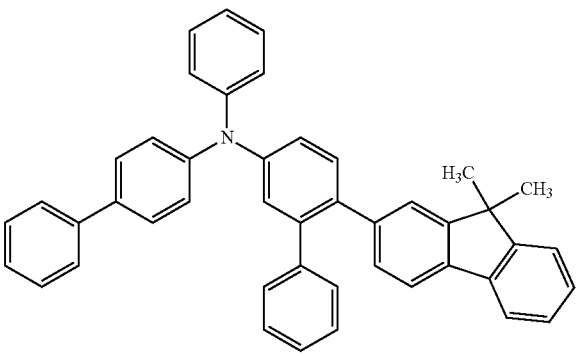
[Chemical Formula 43]
(1-27)
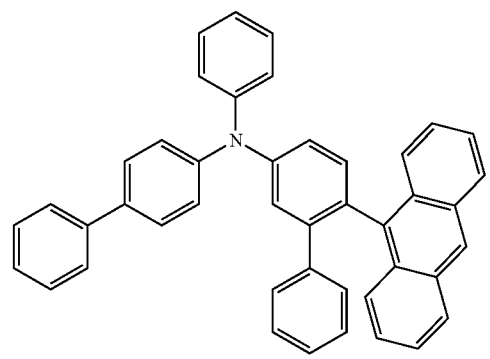

[Chemical Formula 44]
(1-28)
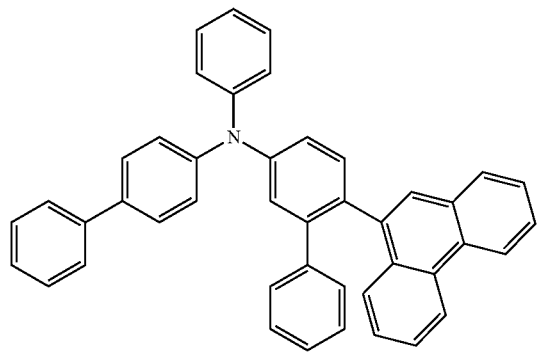
[Chemical Formula 45]
(1-29)
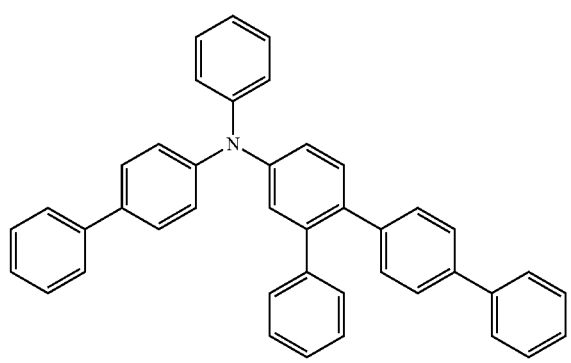
[Chemical Formula 46]
(1-30)
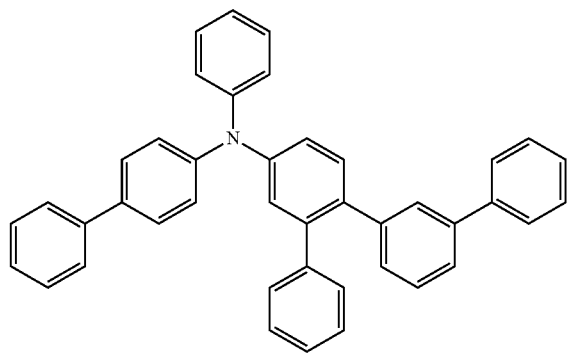
[Chemical Formula 47]
(1-31)
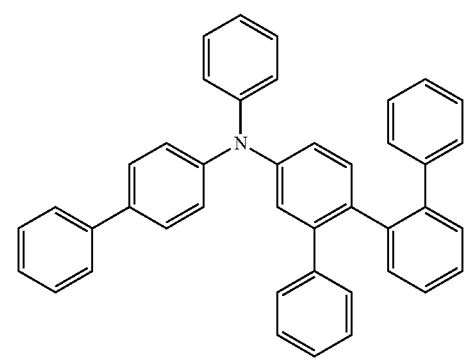
[Chemical Formula 48]
(1-32)
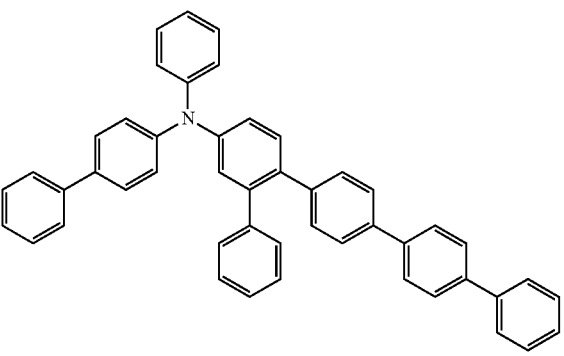
[Chemical Formula 49]
(1-33)
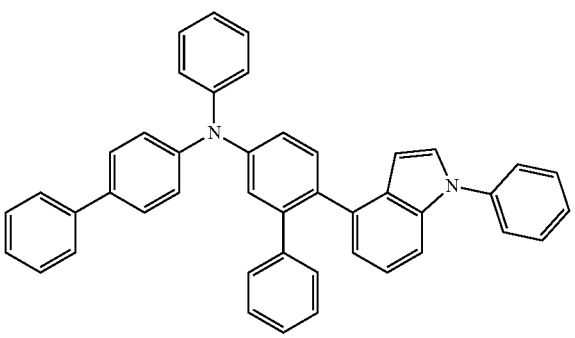
[Chemical Formula 50]
(1-34)
[Chemical Formula 51]
(1-35)
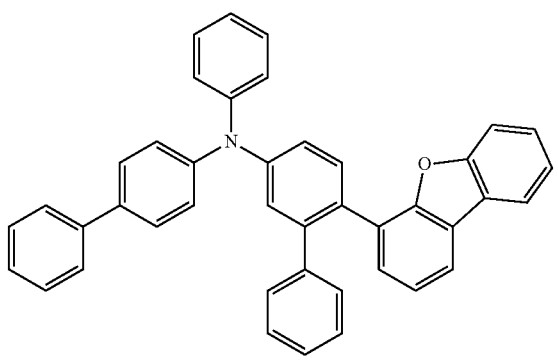

[Chemical Formula 52]
(1-36)
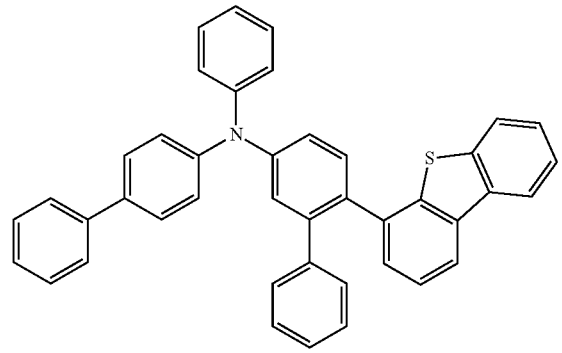
[Chemical Formula 53]
(1-37)
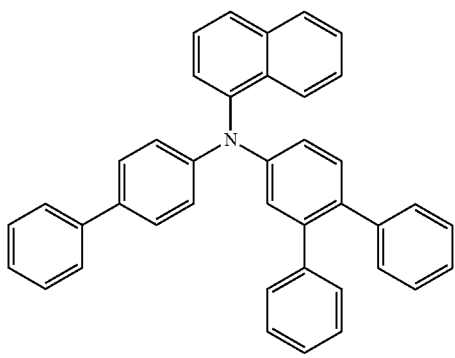
[Chemical Formula 54]
(1-38)
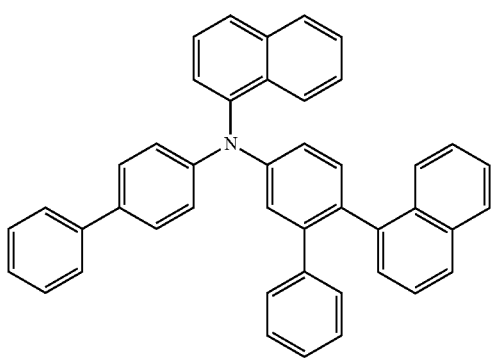
[Chemical Formula 55]
(1-39)
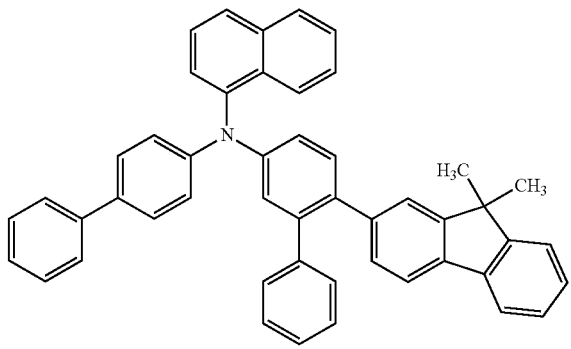
[Chemical Formula 56]
(1-40)
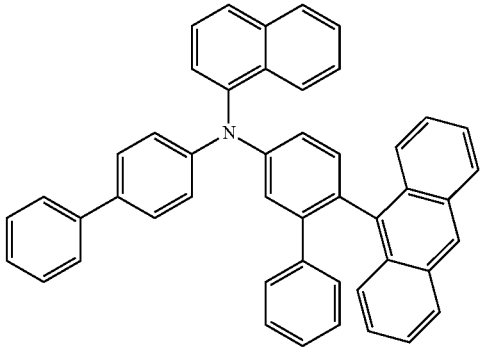
[Chemical Formula 57]
(1-41)
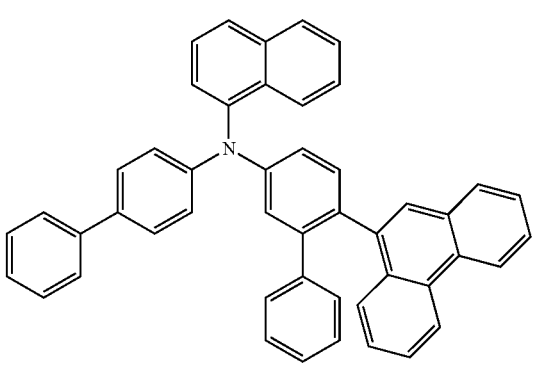
[Chemical Formula 58]
(1-42)
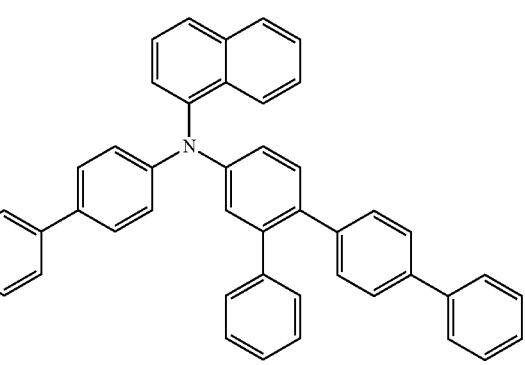
[Chemical Formula 59]
(1-43)
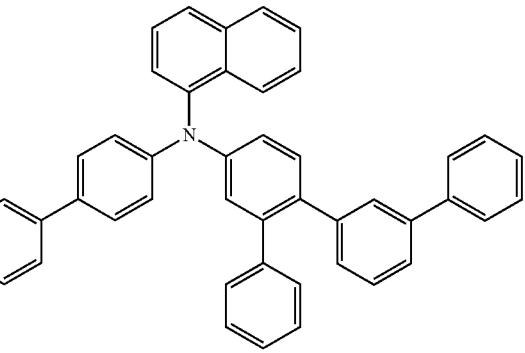

-continued
[Chemical Formula 60]
(1-44)
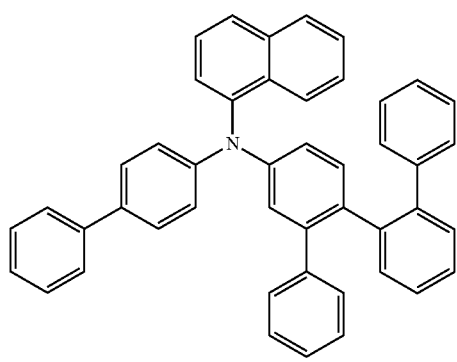
[Chemical Formula 61]
(1-45)
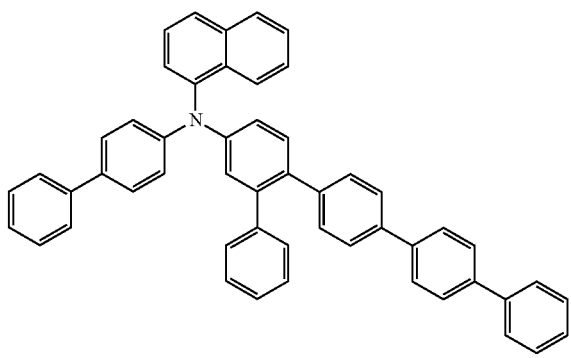
[Chemical Formula 62]
(1-46)
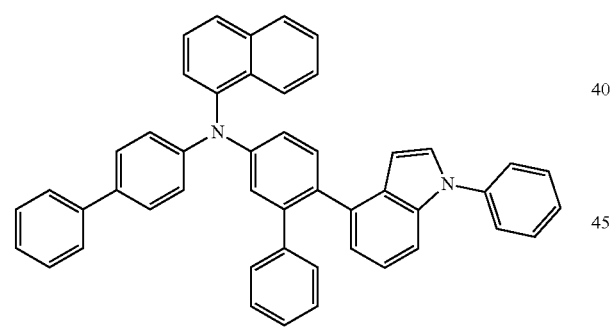
[Chemical Formula 63]
(1-47)
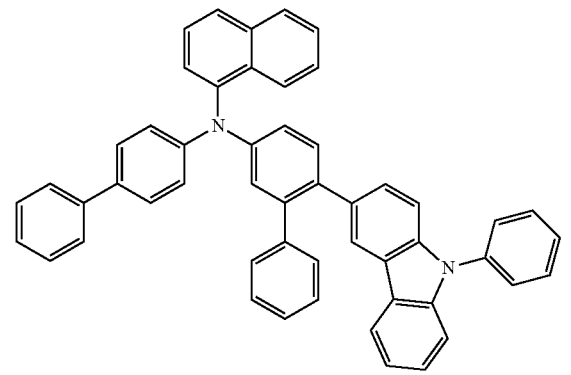
-continued
[Chemical Formula 64]
(1-48)
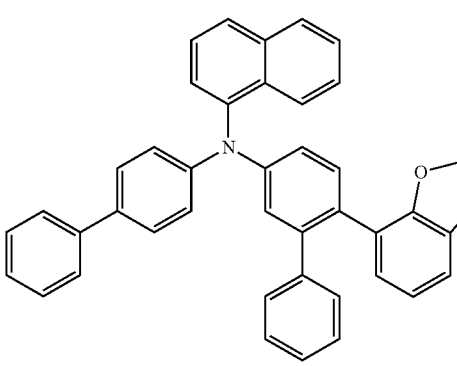
[Chemical Formula 65]
(1-49)
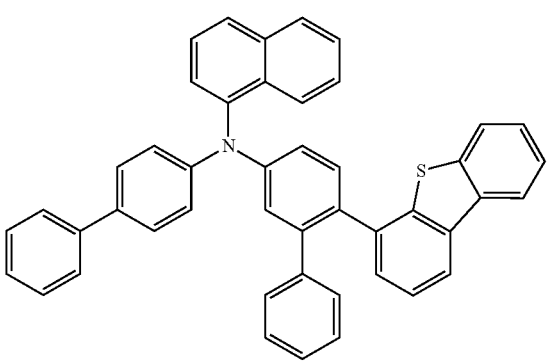
[Chemical Formula 66]
(1-50)
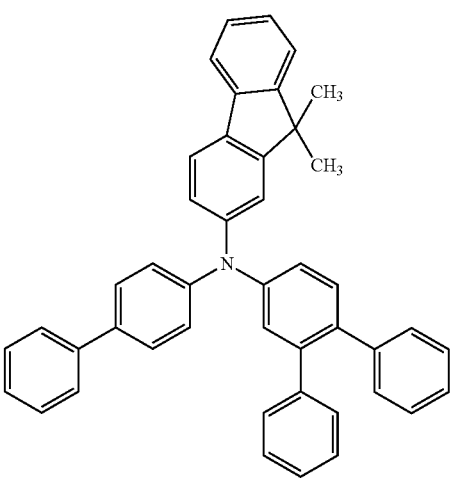

[Chemical Formula 67]
(1-51)
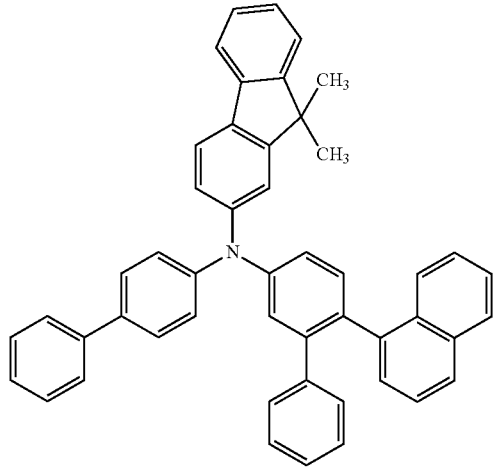
[Chemical Formula 68]
(1-52)
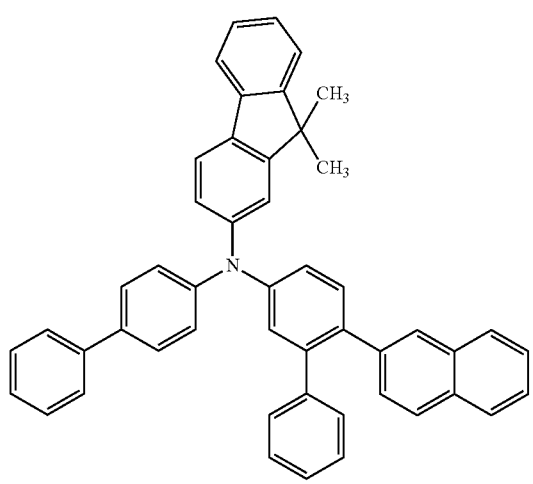
[Chemical Formula 69]
(1-53)
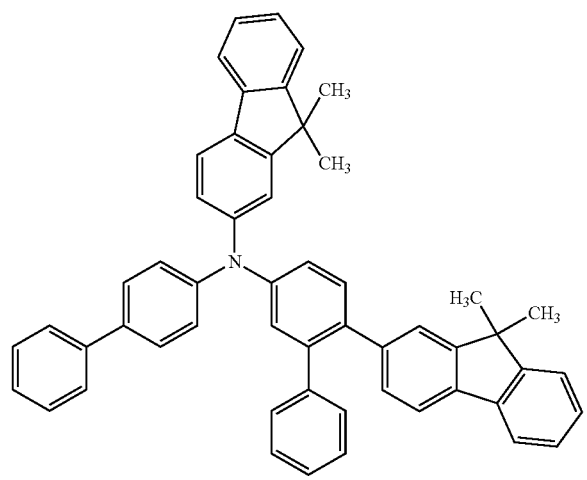
[Chemical Formula 70]
(1-54)
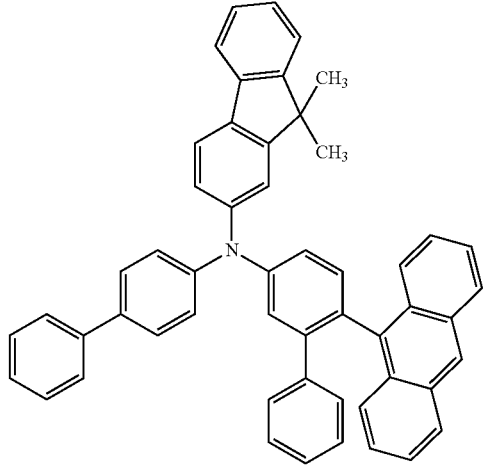
[Chemical Formula 71]
(1-55)
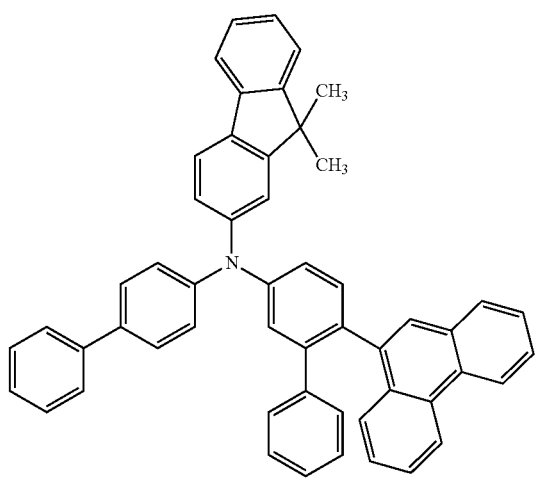
[Chemical Formula 72]
(1-56)
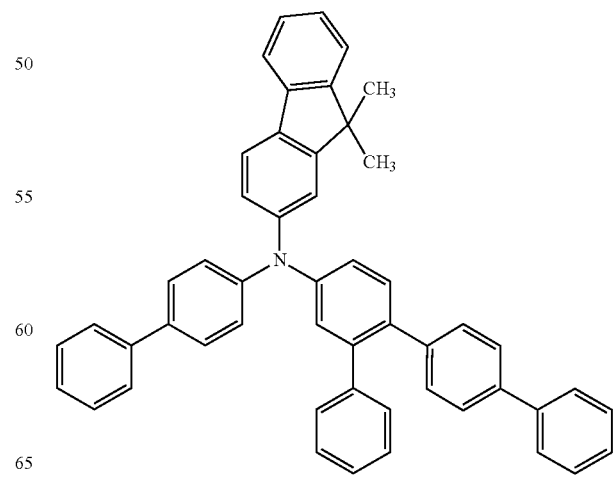

[Chemical Formula 73]
(1-57)
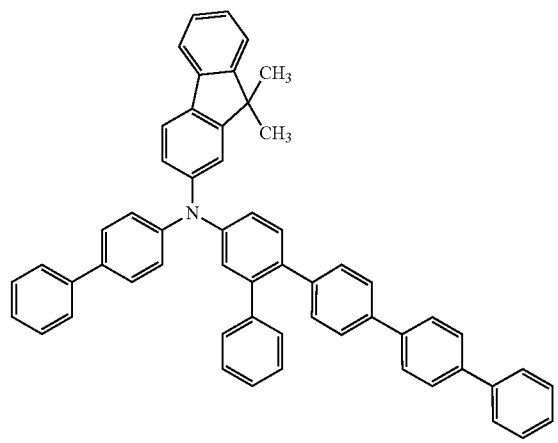
[Chemical Formula 74]
(1-58)
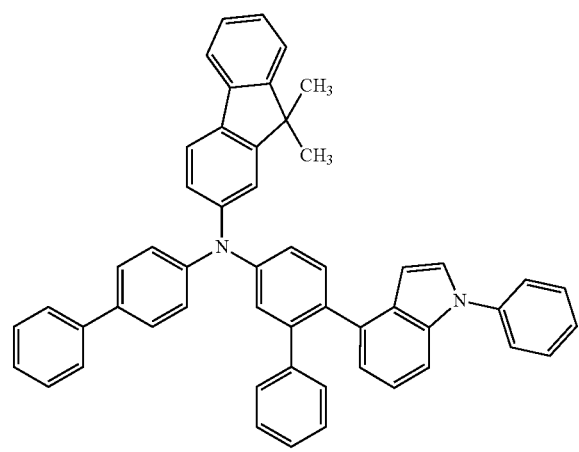
[Chemical Formula 75]
(1-59)
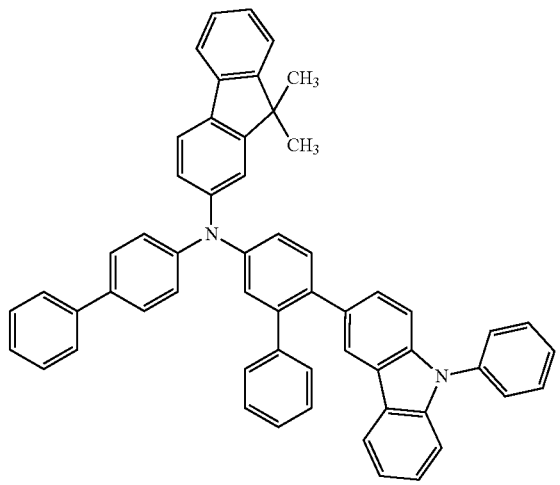
[Chemical Formula 76]
(1-60)
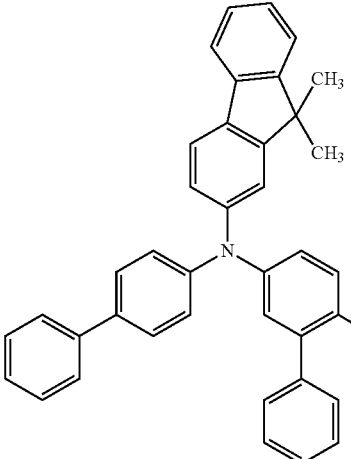
[Chemical Formula 77]
(1-61)
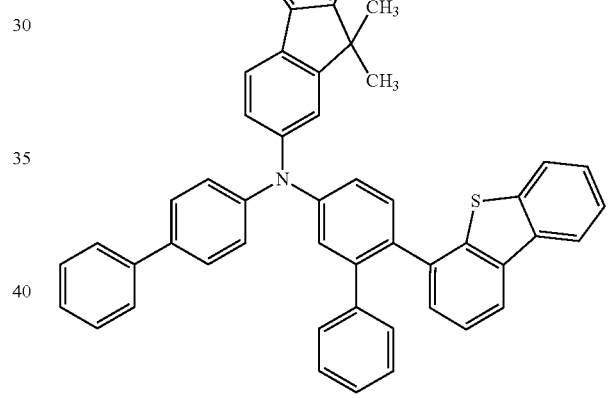
[Chemical Formula 78]
(1-62)
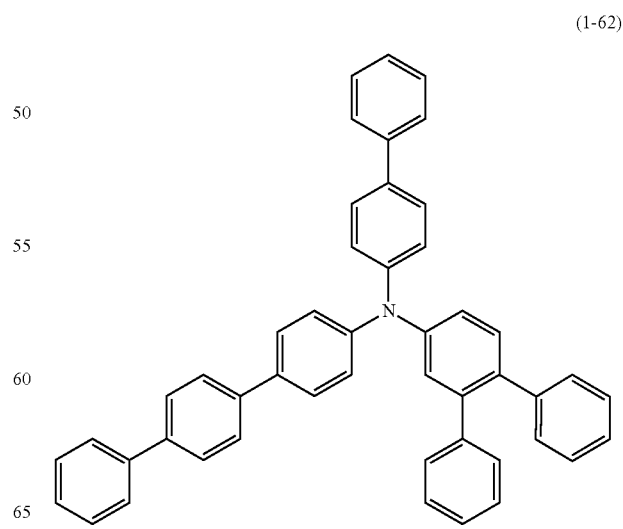

-continued
[Chemical Formula 79]
(1-63)
[Chemical Formula 80]
(1-64)
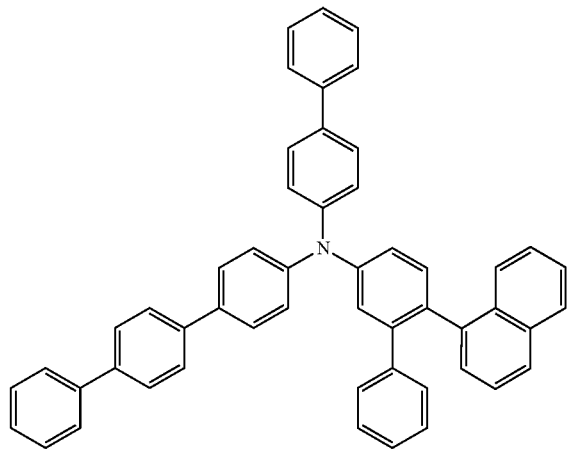
[Chemical Formula 81]
(1-65)
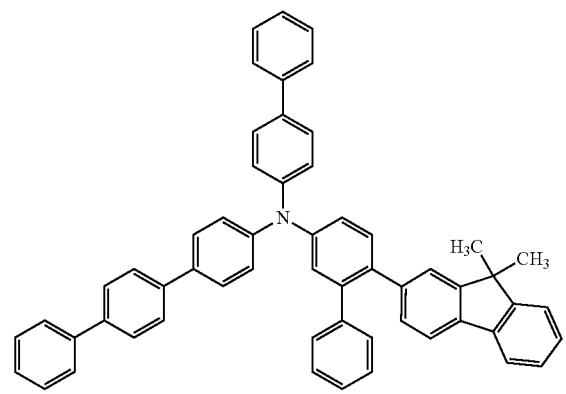
-continued
[Chemical Formula 82]
(1-66)
[Chemical Formula 83]
(1-67)
[Chemical Formula 84]
(1-68)
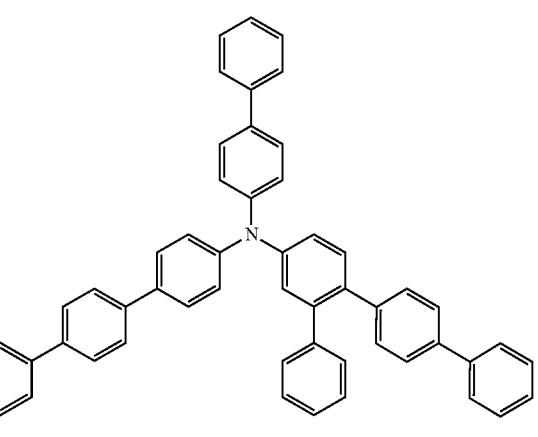

[Chemical Formula 85]
(1-69)
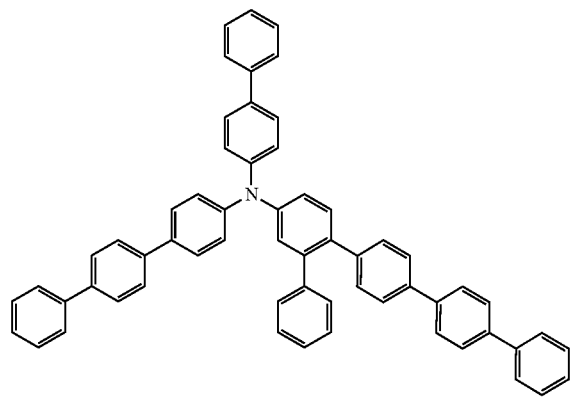
[Chemical Formula 86]
(1-70)
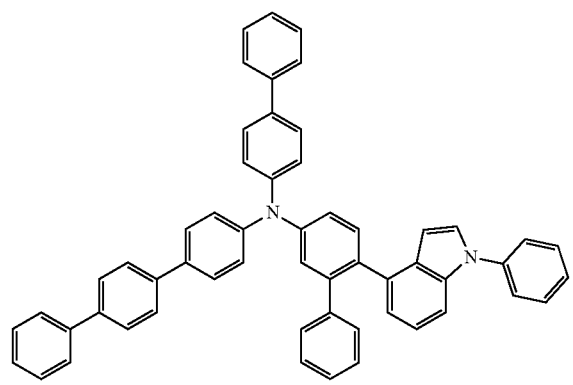
[Chemical Formula 87]
(1-71)
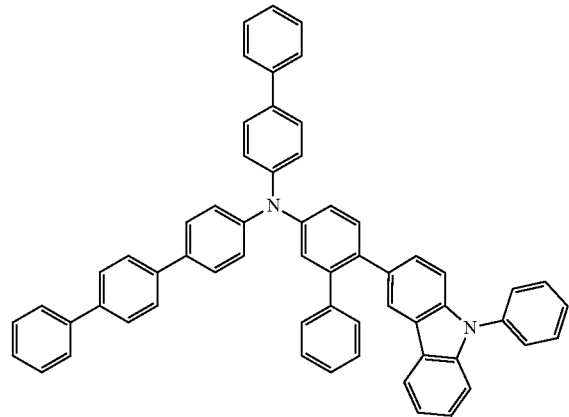
[Chemical Formula 88]
(1-72)
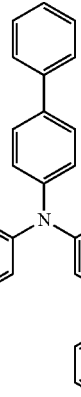
[Chemical Formula 89]
(1-73)
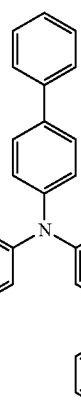
[Chemical Formula 90]
(1-74)
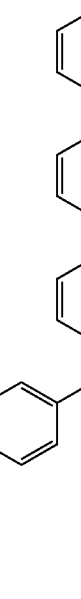

[Chemical Formula 91]
(1-75)
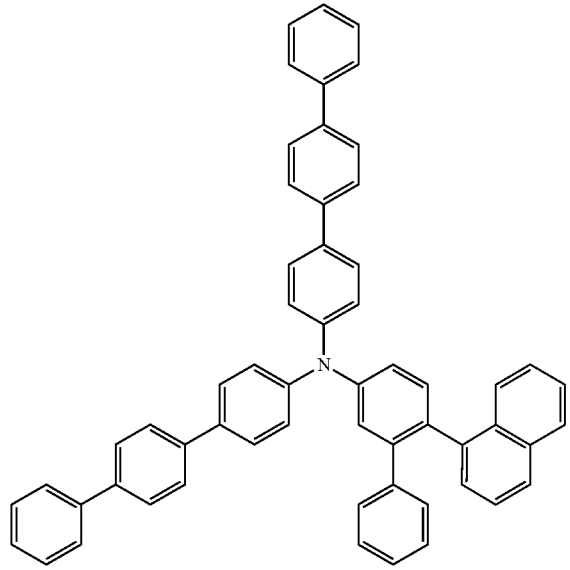
[Chemical Formula 92]
(1-76)
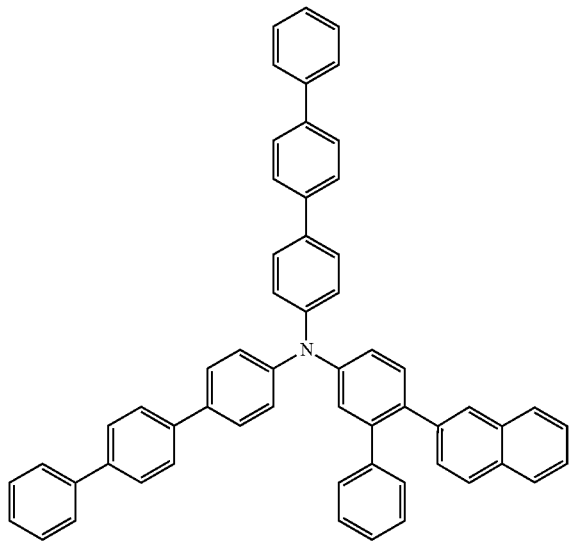
[Chemical Formula 93]
(1-77)
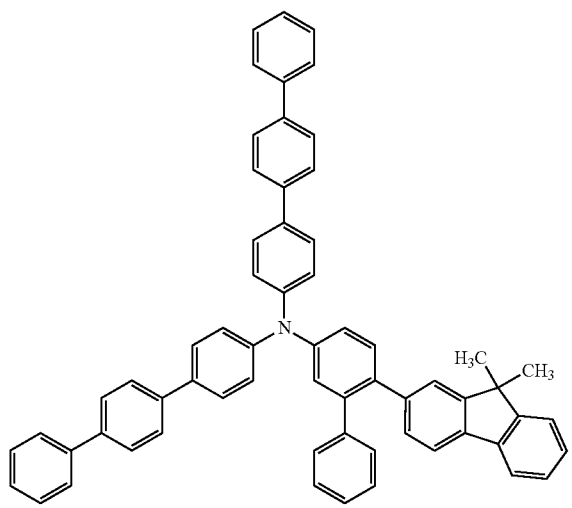
[Chemical Formula 94]
(1-78)
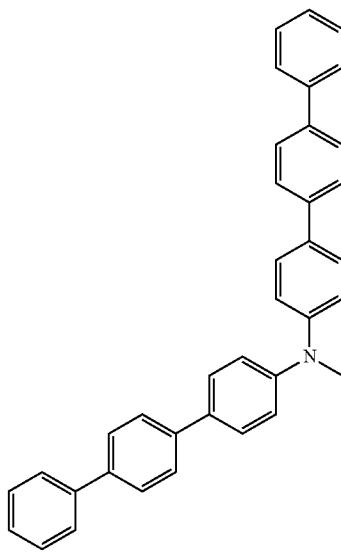

[Chemical Formula 95]
(1-79)
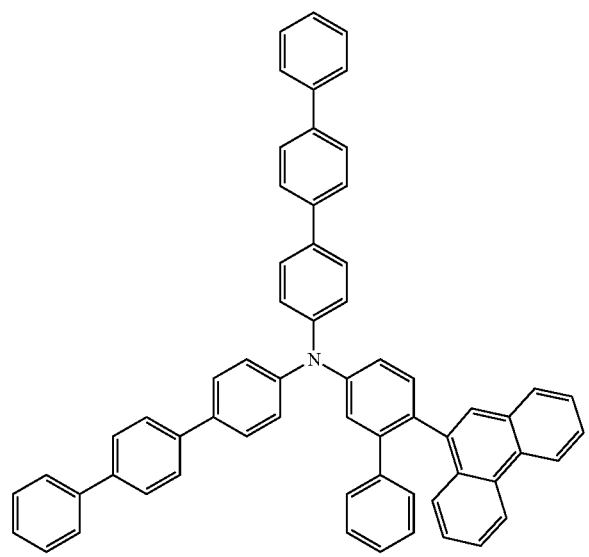
[Chemical Formula 96]
(1-80)
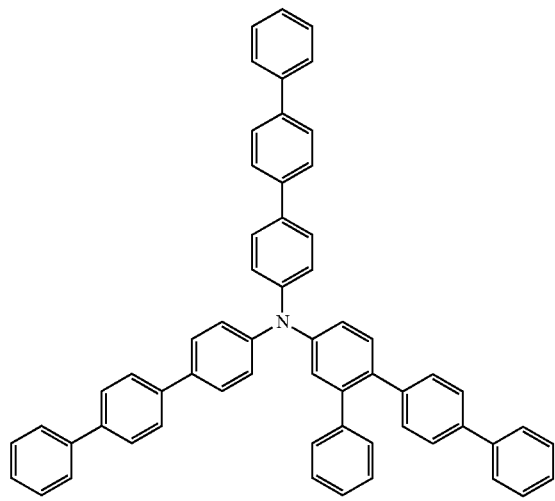
[Chemical Formula 97]
(1-81)
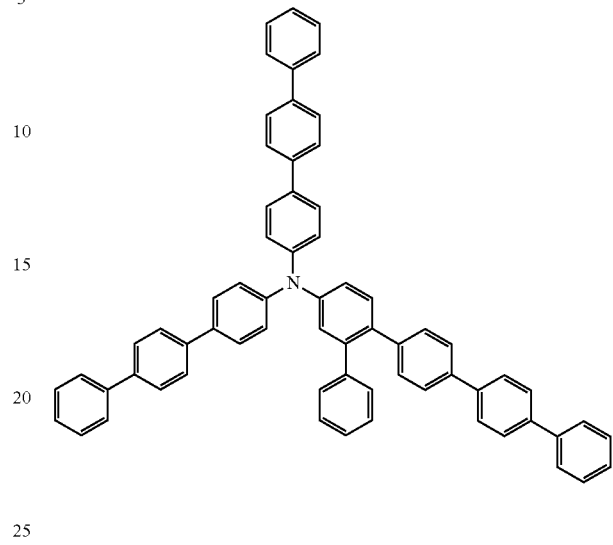
[Chemical Formula 98]
(1-82)
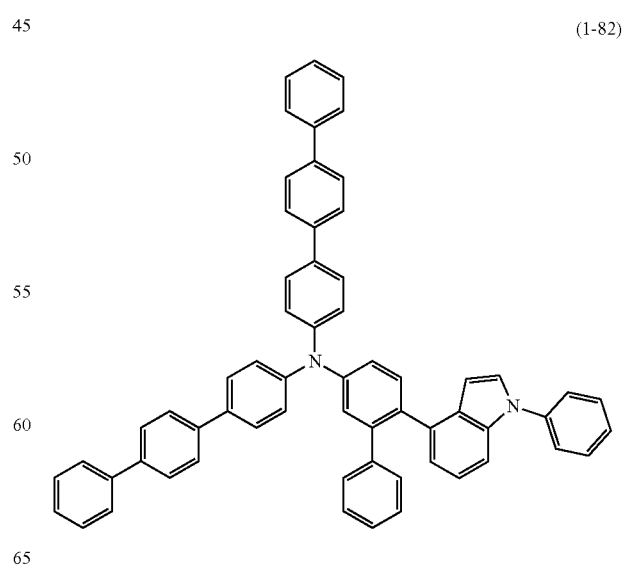

[Chemical Formula 99]
(1-83)
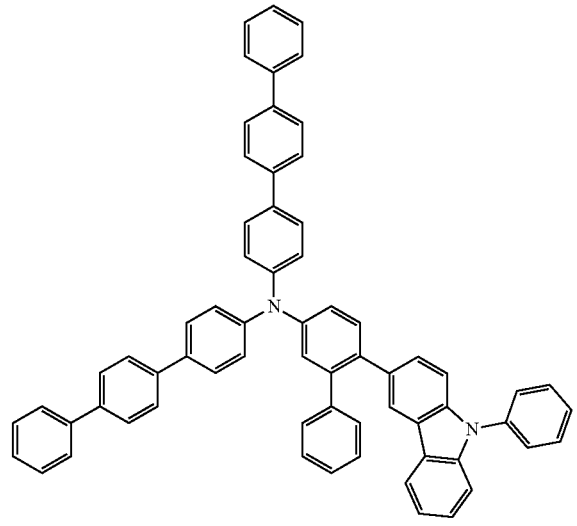
[Chemical Formula 100]
(1-84)
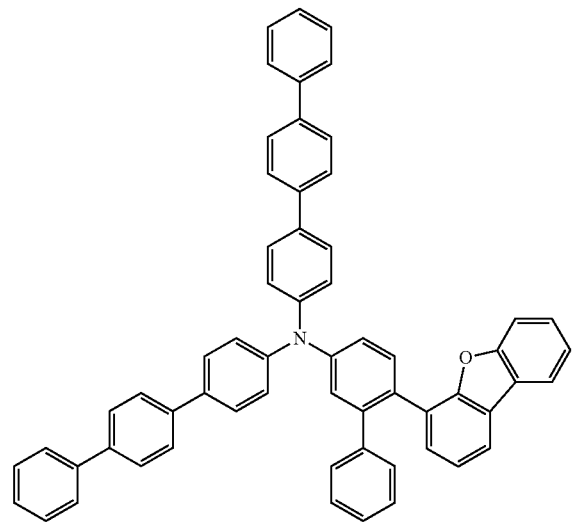
[Chemical Formula 101]
(1-85)
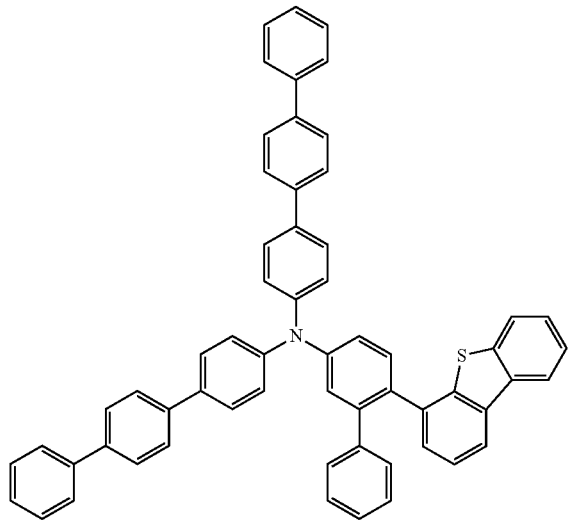
[Chemical Formula 102]
(1-86)
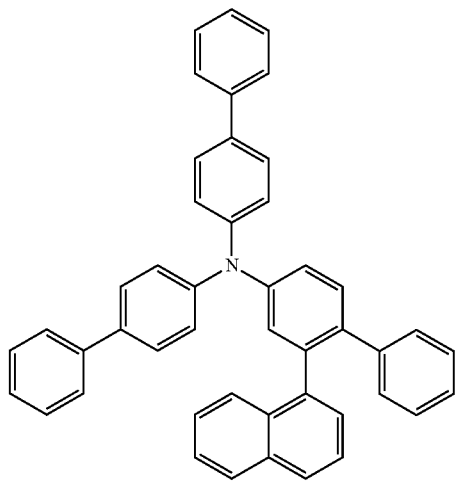

[Chemical Formula 103]
(1-87)
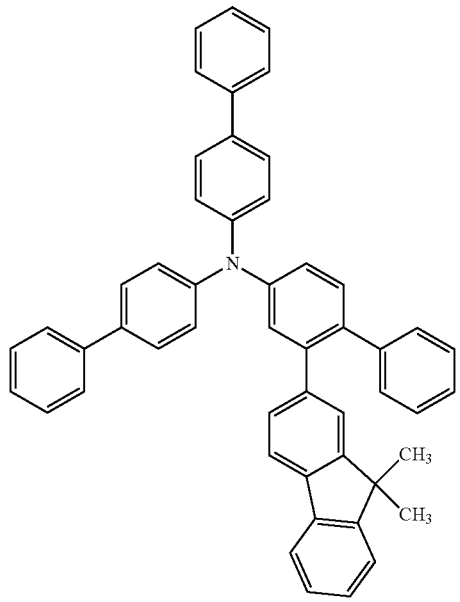
[Chemical Formula 104]
(1-88)
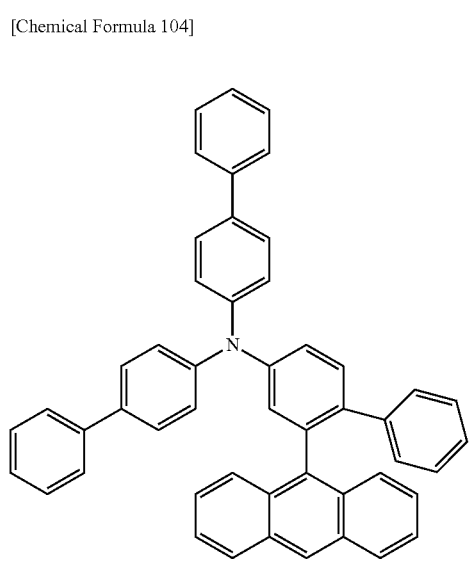
[Chemical Formula 105]
(1-89)
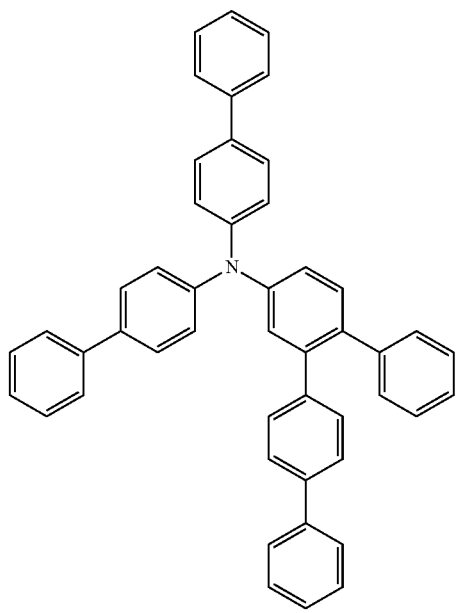
[Chemical Formula 106]
(1-90)

[Chemical Formula 107]
(1-91)
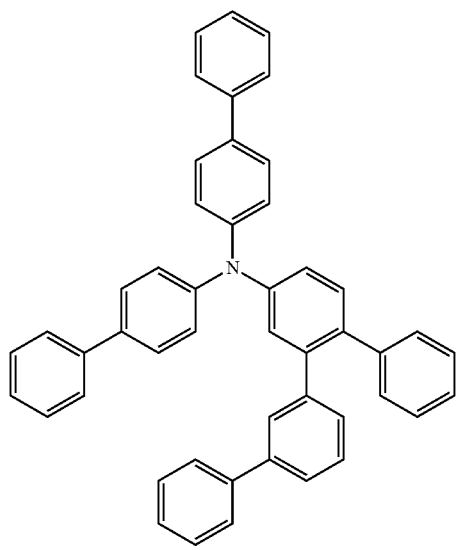
[Chemical Formula 108]
(1-92)
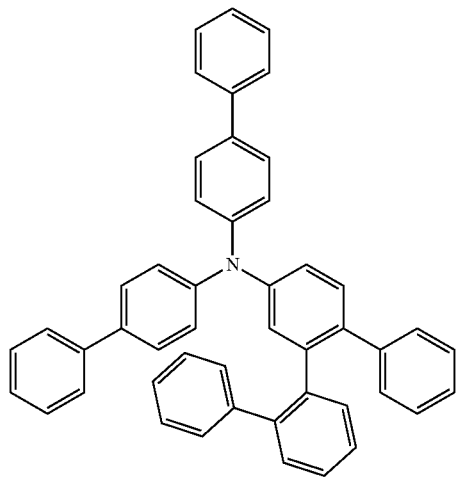
[Chemical Formula 109]
(1-93)
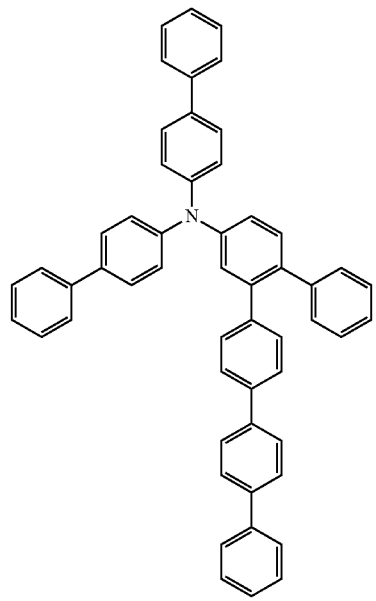
[Chemical Formula 110]
(1-94)
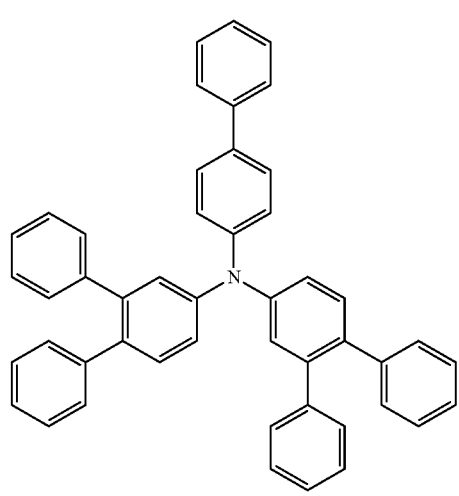
[Chemical Formula 111]
(1-95)
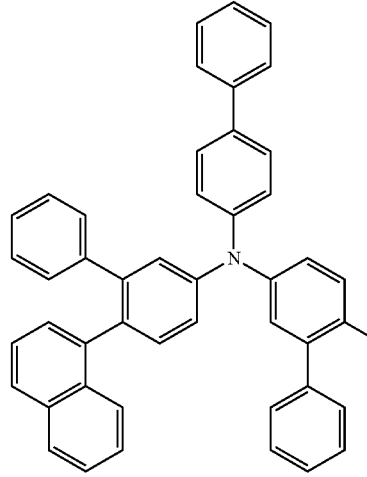

[Chemical Formula 112]
(1-96)
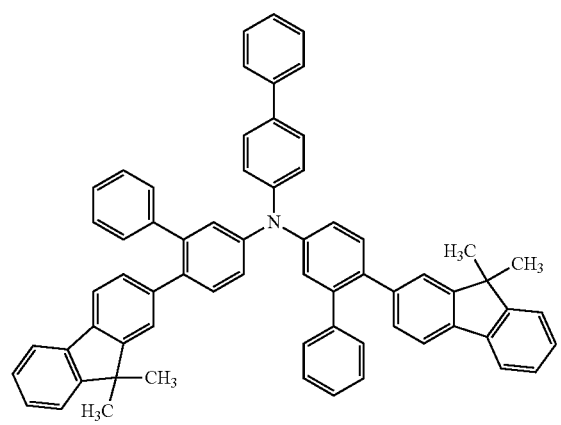
[Chemical Formula 113]
(1-97)
[Chemical Formula 114]
(1-98)
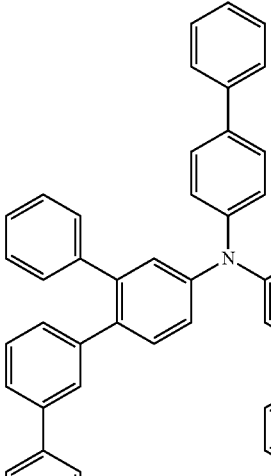
[Chemical Formula 115]
(1-99)
[Chemical Formula 116]
(1-100)
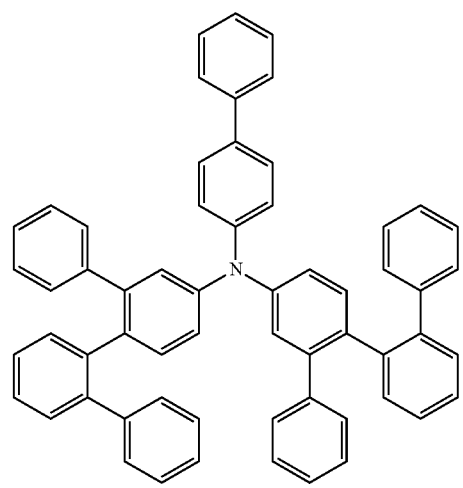
[Chemical Formula 117]
(1-101)
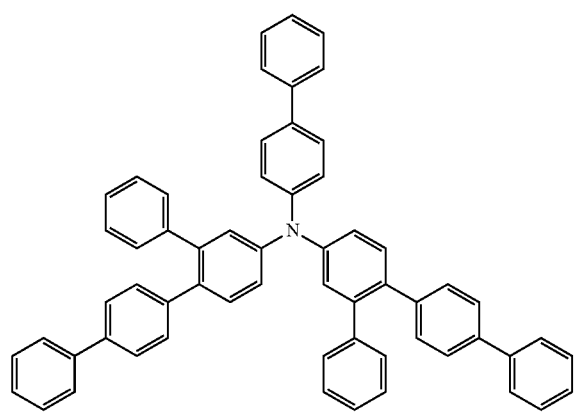
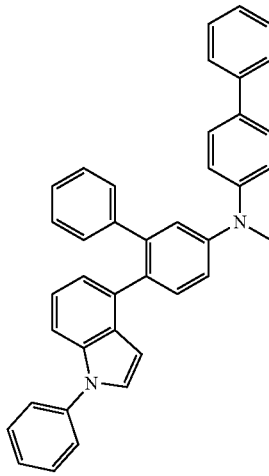

[Chemical Formula 118]
(1-102)
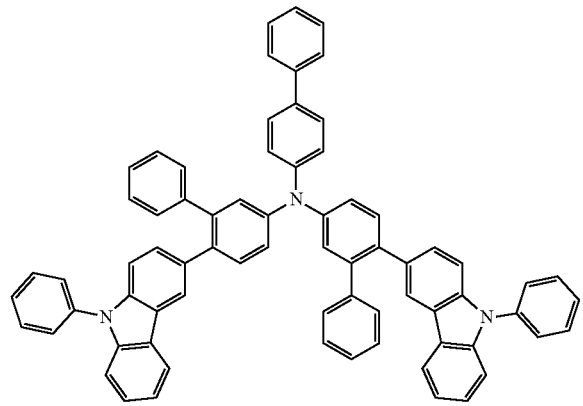
[Chemical Formula 119]
(1-103)
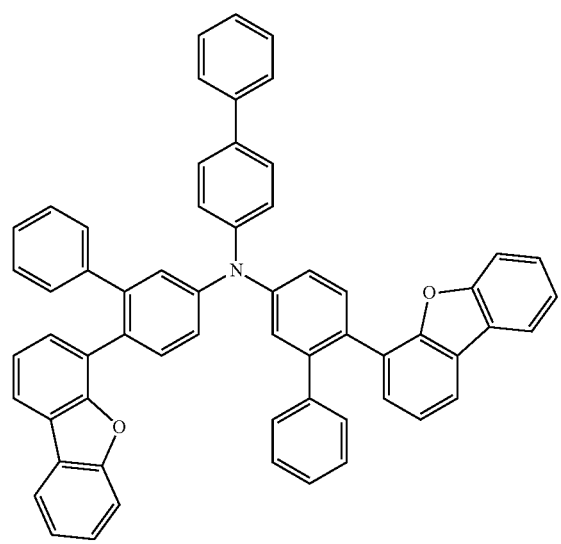
[Chemical Formula 120]
(1-104)
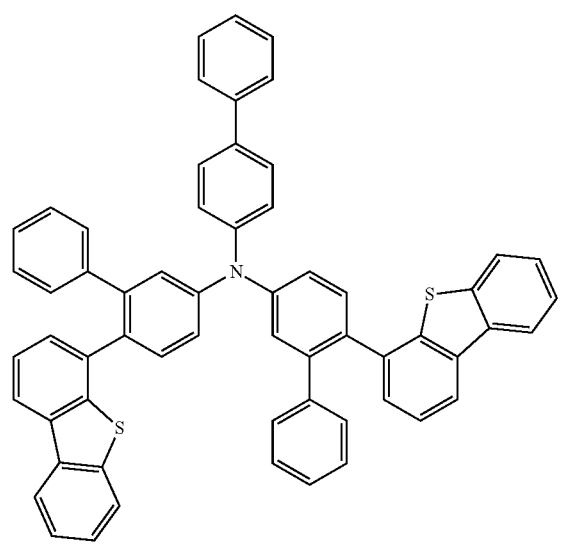
[Chemical Formula 121]
(1-105)
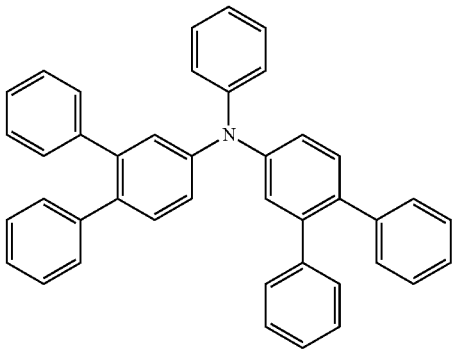
[Chemical Formula 122]
(1-106)
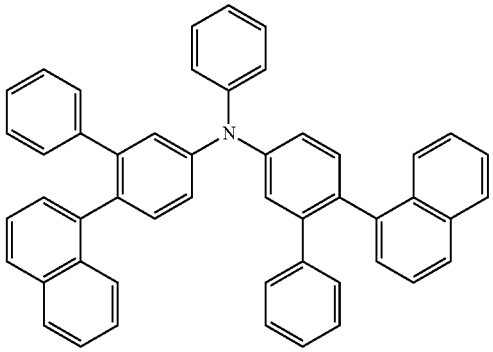
[Chemical Formula 123]
(1-107)
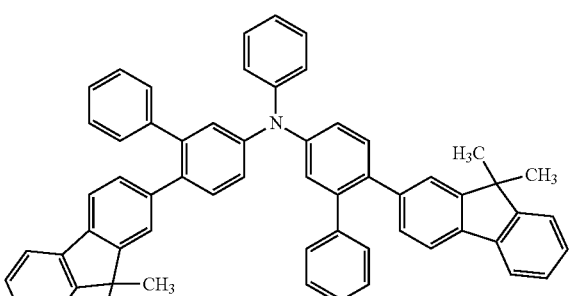
[Chemical Formula 124]
(1-108)
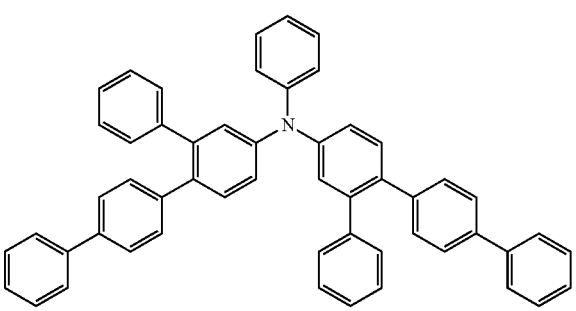

[Chemical Formula 125]
(1-109)
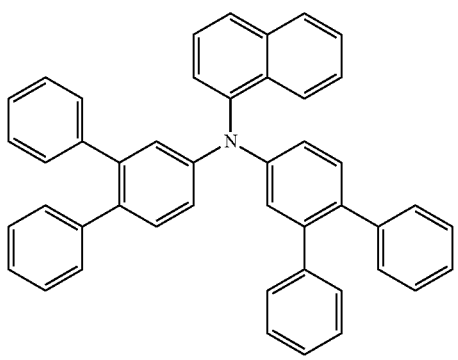
[Chemical Formula 126]
(1-110)
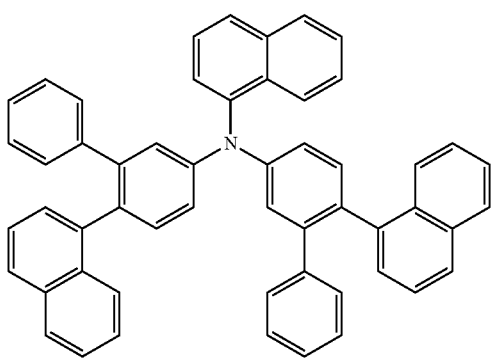
[Chemical Formula 127]
(1-111)
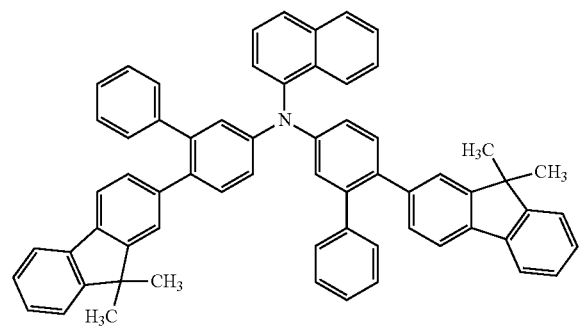
[Chemical Formula 128]
(1-112)
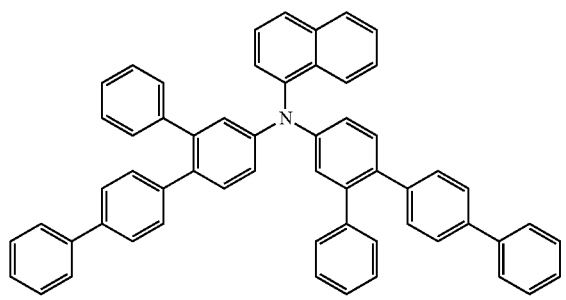
[Chemical Formula 129]
(1-113)
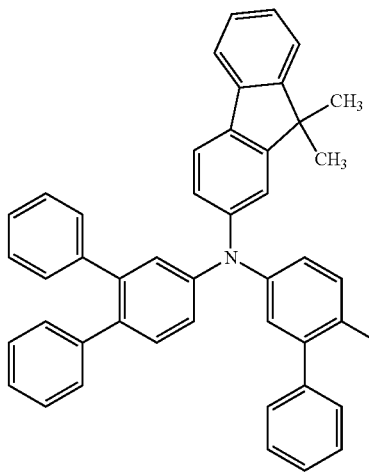
[Chemical Formula 130]
(1-114)
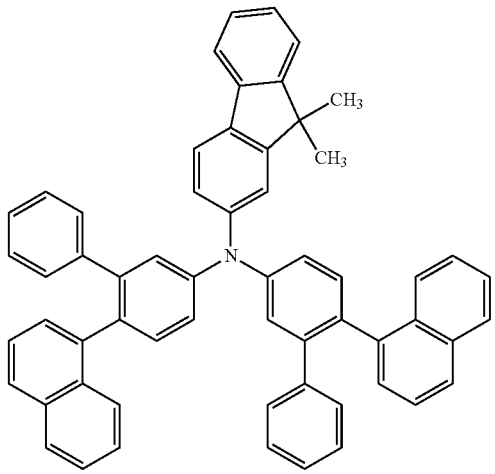
[Chemical Formula 131]
(1-115)
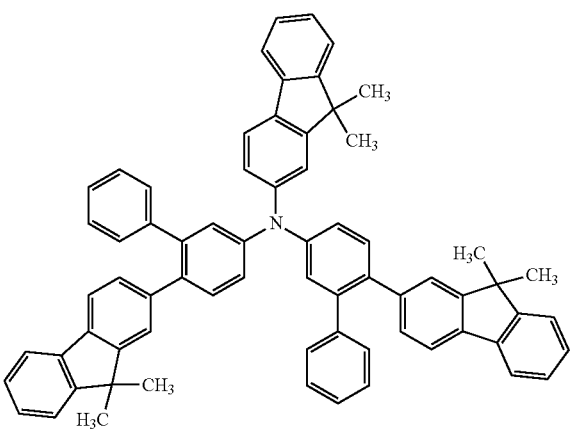

-continued
[Chemical Formula 132]
(1-116)
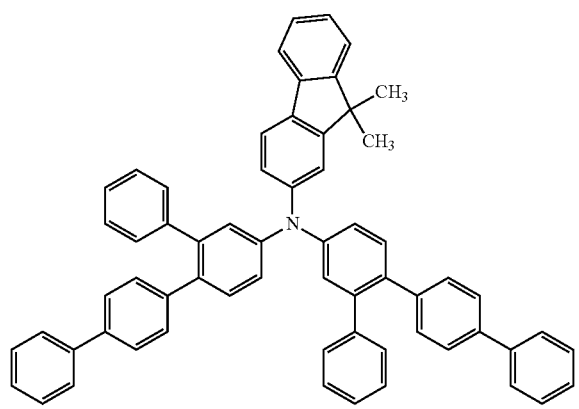
[Chemical Formula 133]
(1-117)
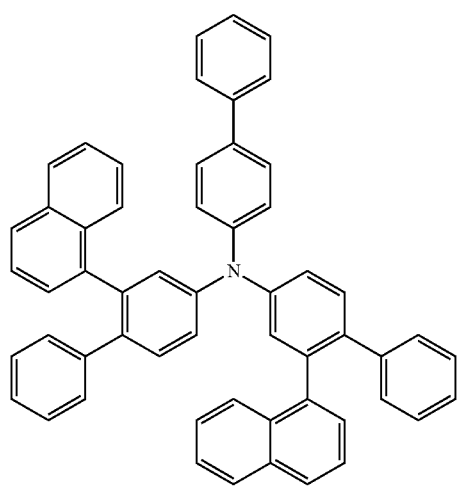
[Chemical Formula 134]
(1-118)
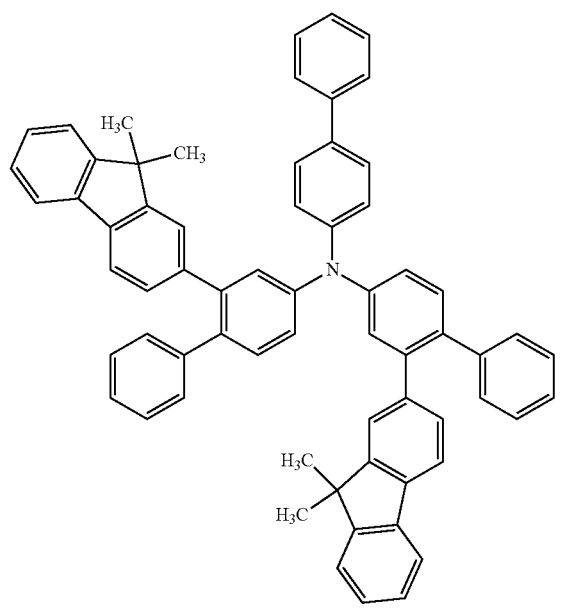
-continued
[Chemical Formula 135]
(1-119)
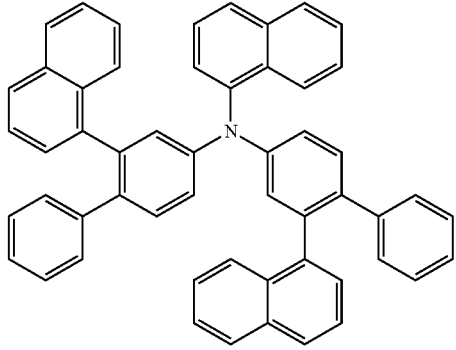
[Chemical Formula 136]
(1-120)
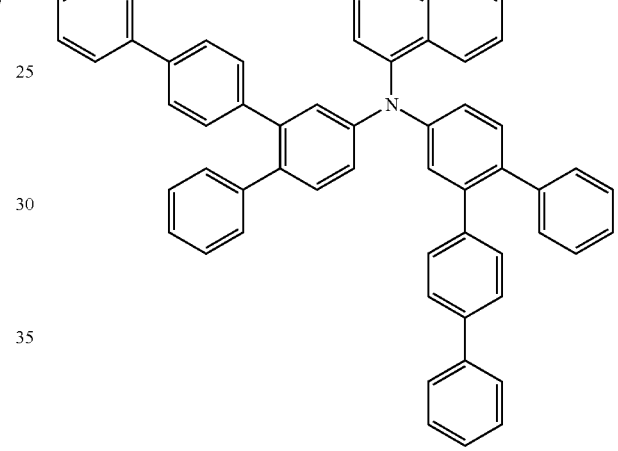
[Chemical Formula 137]
(1-121)
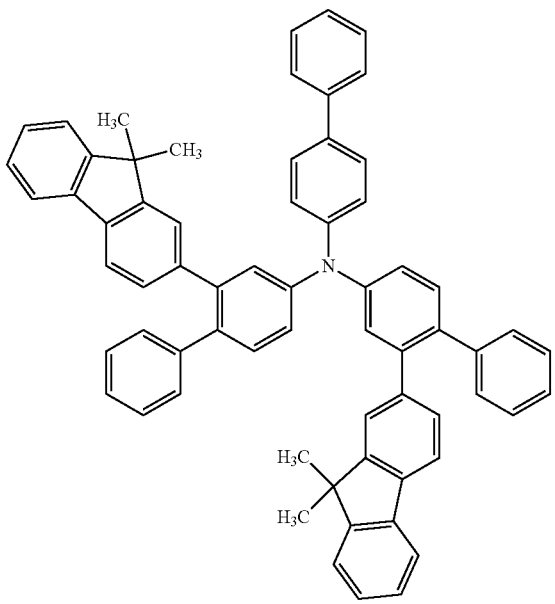

[Chemical Formula 138]
(1-122)
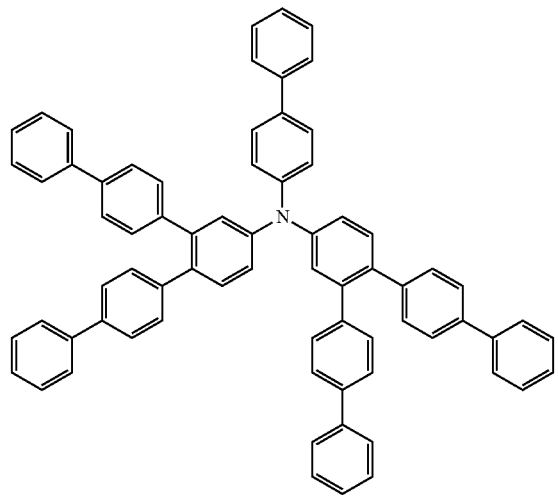
[Chemical Formula 139]
(1-123)
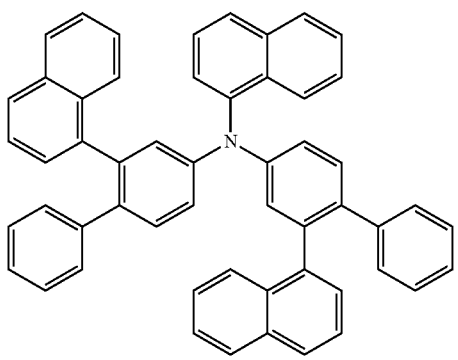
[Chemical Formula 140]
(1-124)
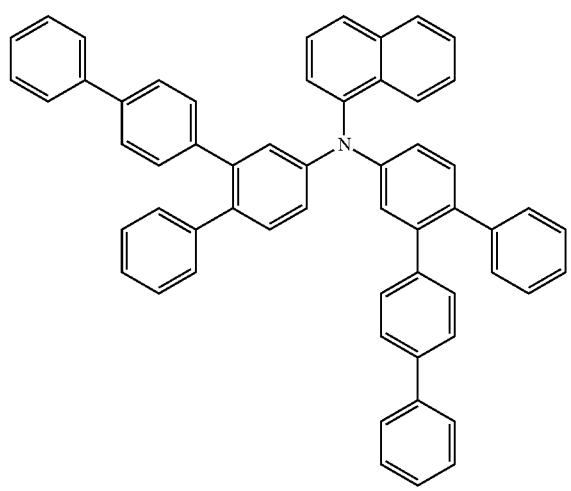
[Chemical Formula 141]
(1-125)
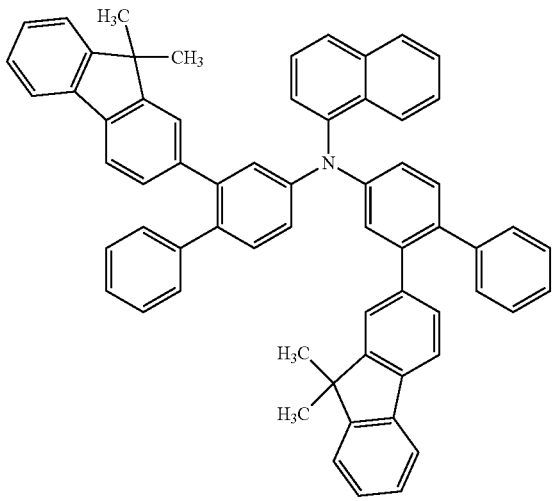
[Chemical Formula 142]
(1-126)
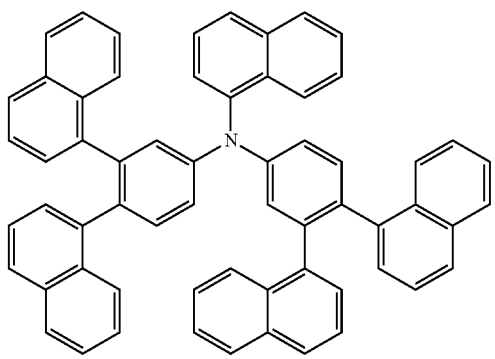
[Chemical Formula 143]
(1-127)
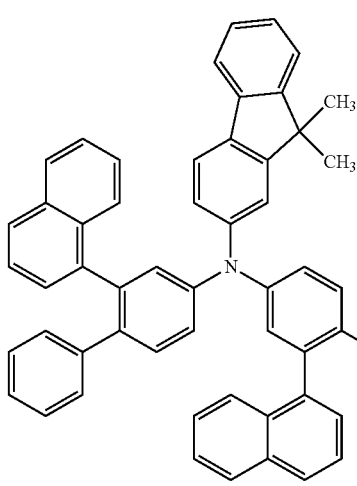

-continued
[Chemical Formula 144]
(1-128)
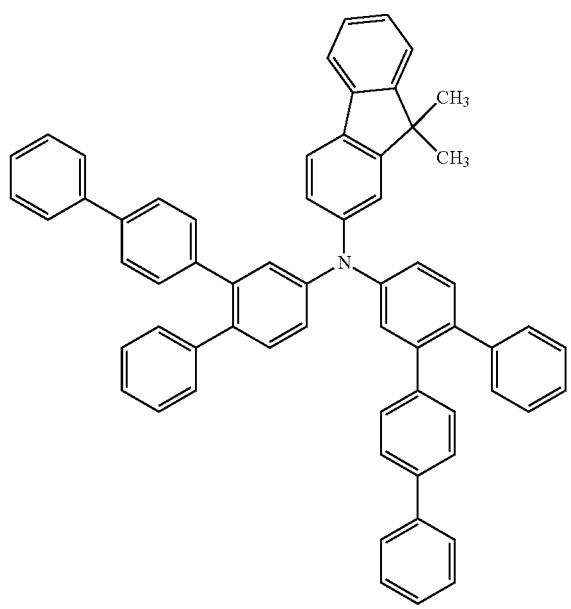
[Chemical Formula 145]
(1-129)
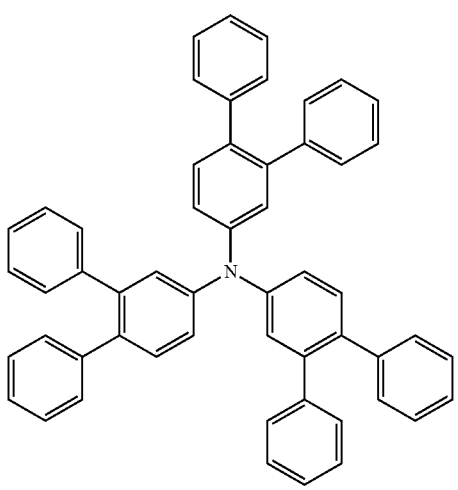
-continued
[Chemical Formula 146]
(1-130)
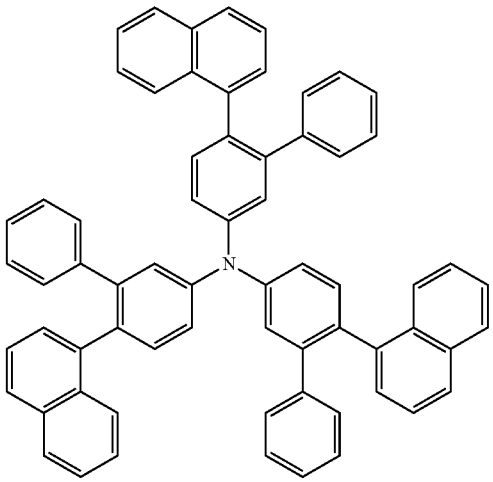
[Chemical Formula 147]
(1-131)
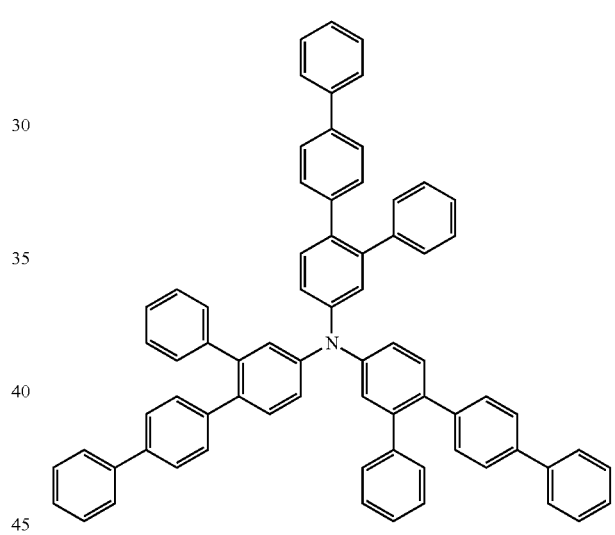
[Chemical Formula 148]
(1-132)
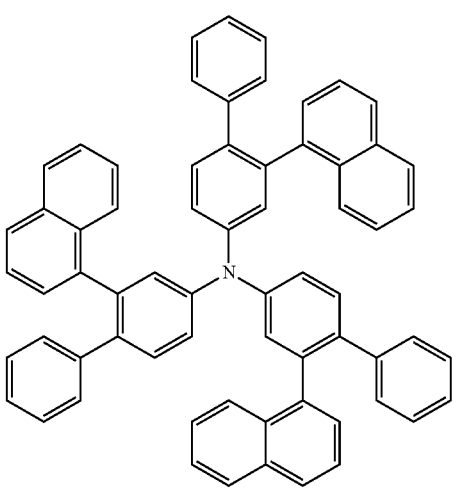

[Chemical Formula 149]
(1-133)
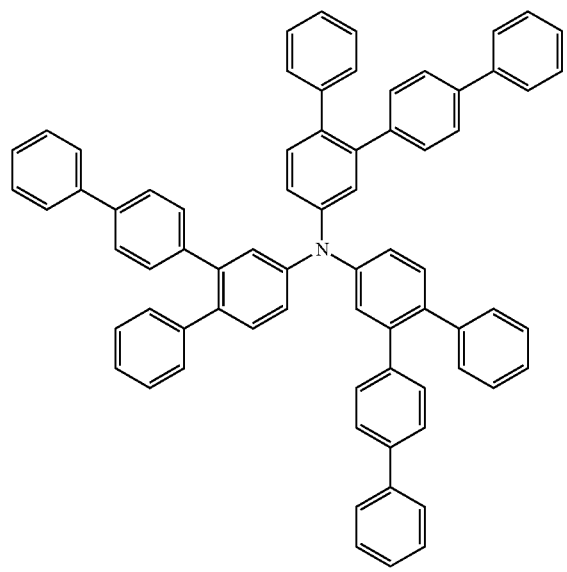
[Chemical Formula 150]
(1-134)
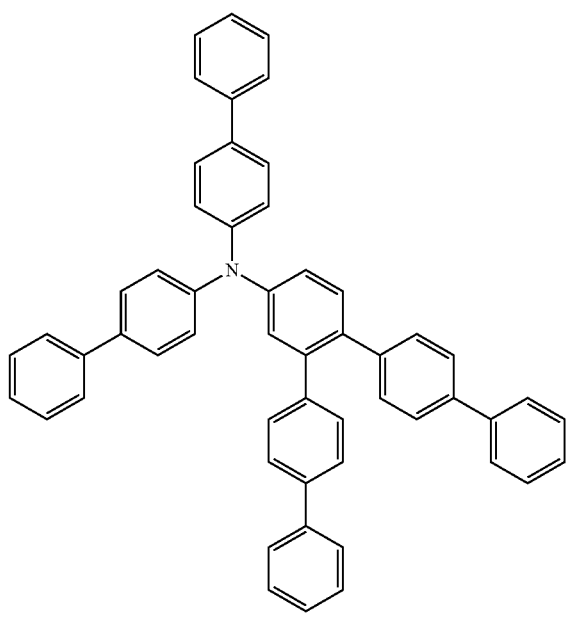
[Chemical Formula 151]
(1-135)
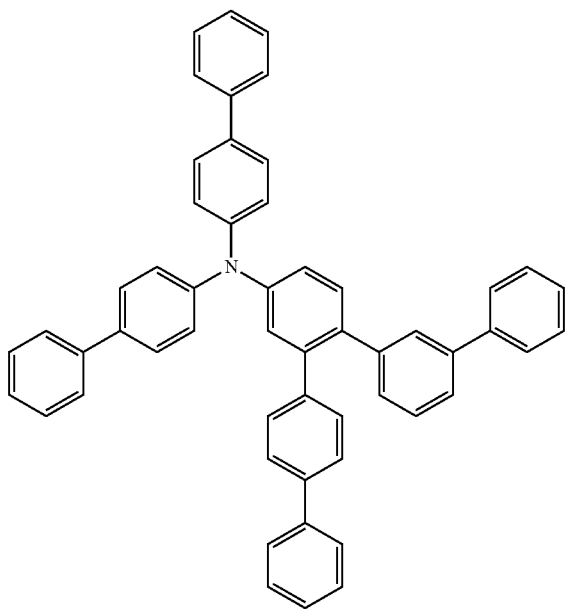
[Chemical Formula 152]
(1-136)
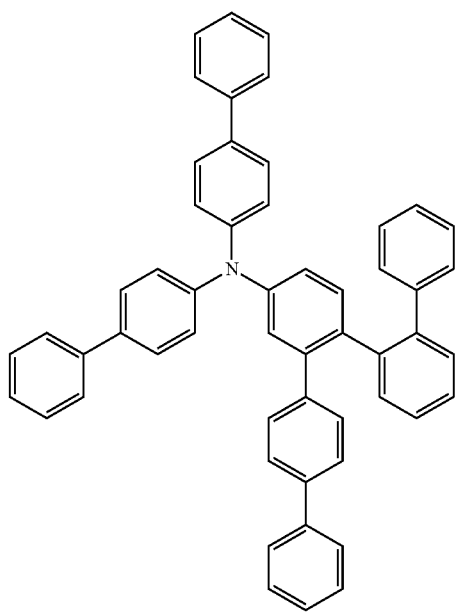

-continued
[Chemical Formula 153]
(1-137)
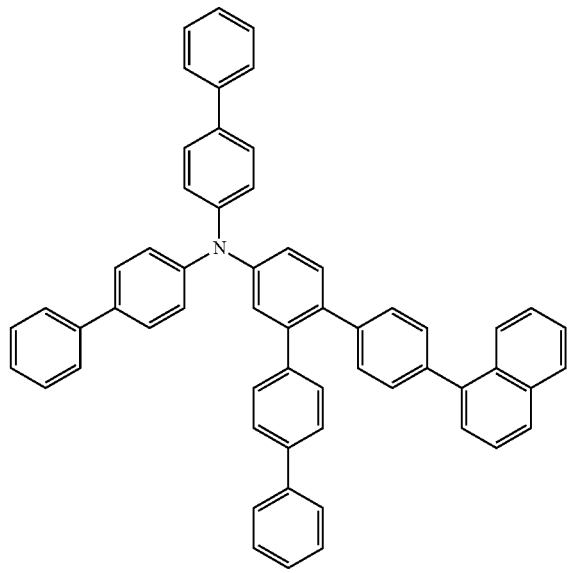
[Chemical Formula 154]
(1-138)
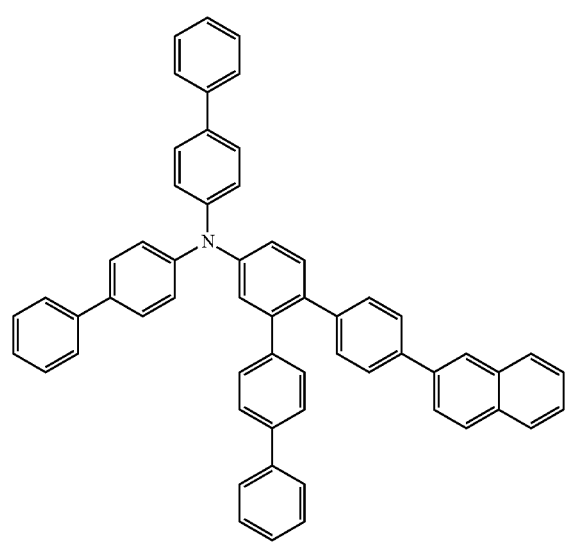
-continued
[Chemical Formula 155]
(1-139)
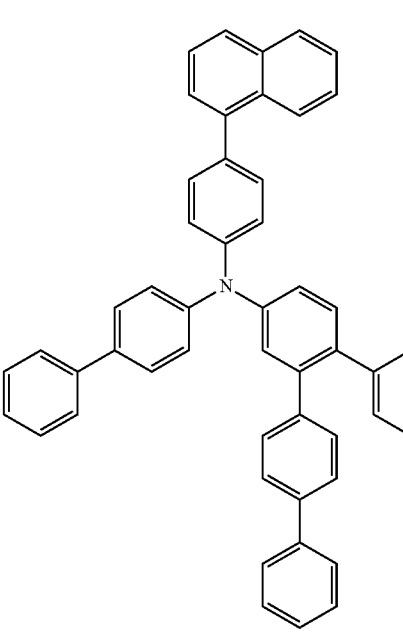
[Chemical Formula 156]
(1-140)
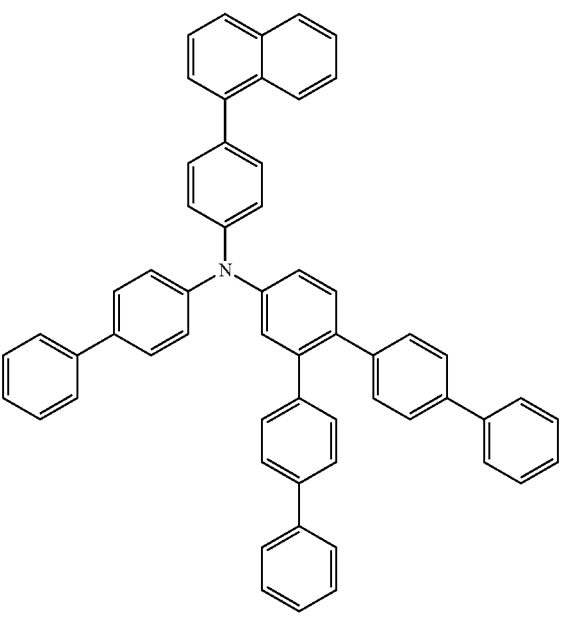

-continued
[Chemical Formula 157]
(1-141)
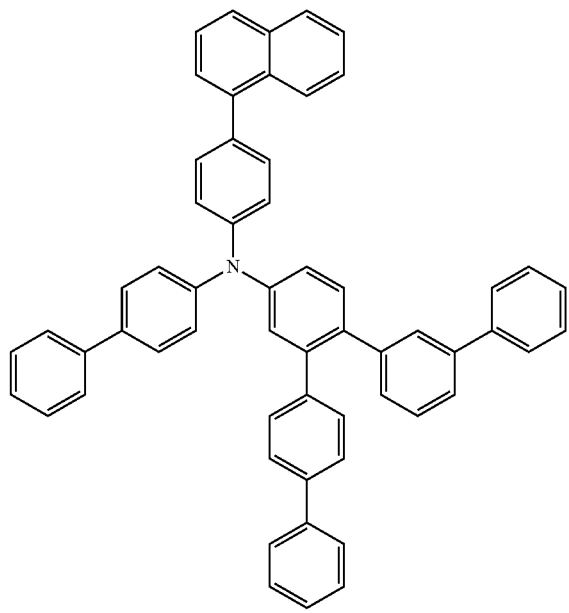
[Chemical Formula 158]
(1-142)
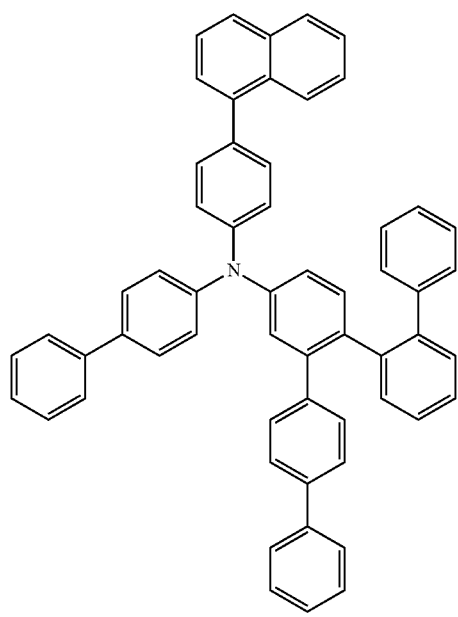
-continued
[Chemical Formula 159]
(1-143)
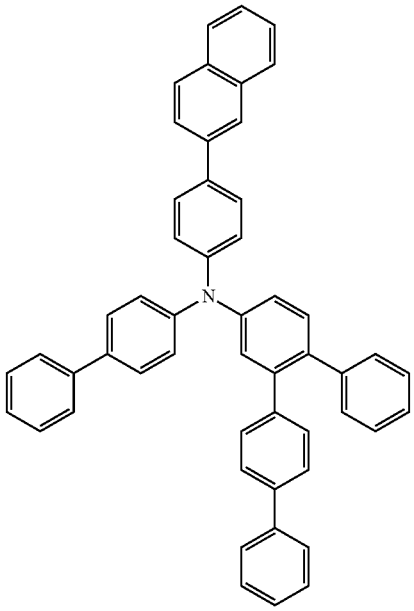
[Chemical Formula 160]
(1-144)
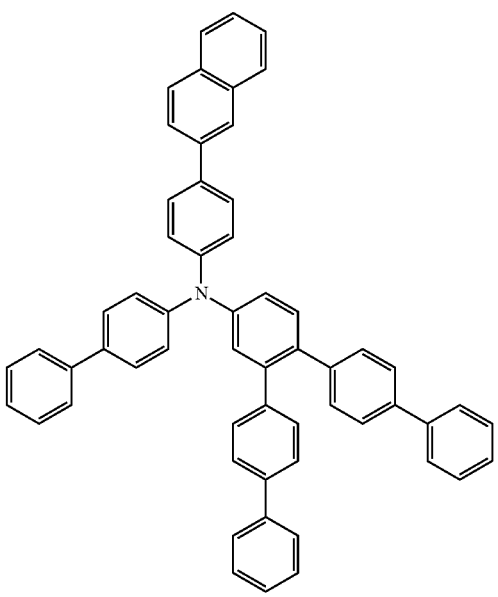

-continued
[Chemical Formula 161]
(1-145)
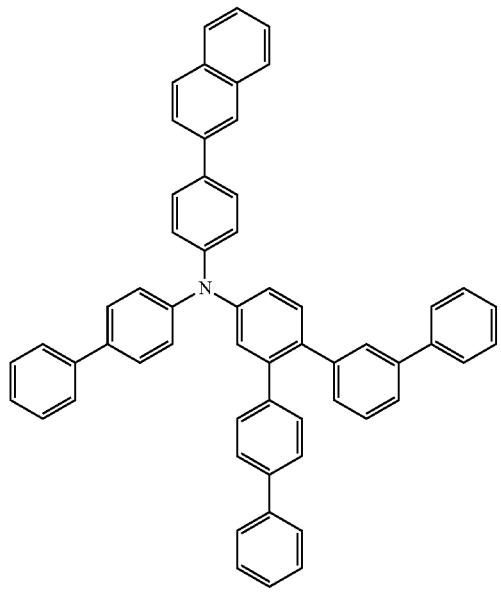
[Chemical Formula 162]
(1-146)
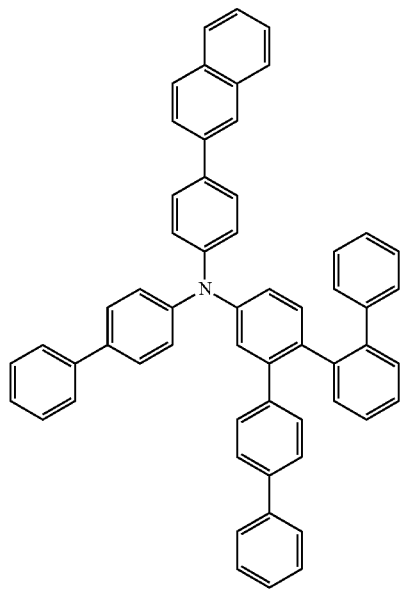
-continued
[Chemical Formula 163]
(1-147)
[Chemical Formula 164]
(1-148)
[Chemical Formula 165]
(1-149)

[Chemical Formula 166]
(1-150)
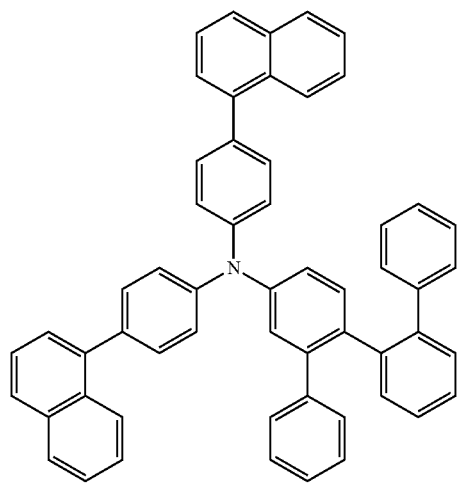
[Chemical Formula 167]
(1-151)
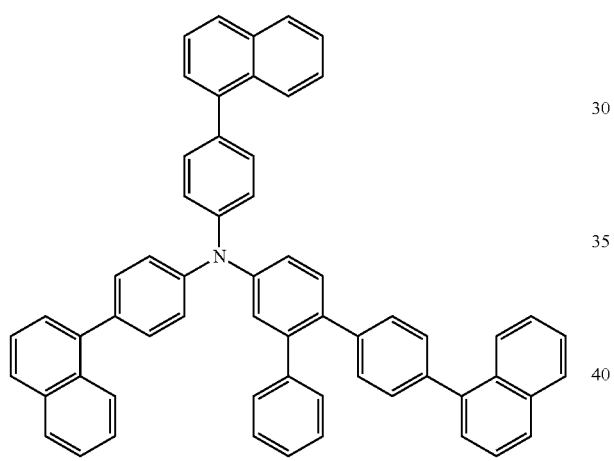
[Chemical Formula 168]
(1-152)
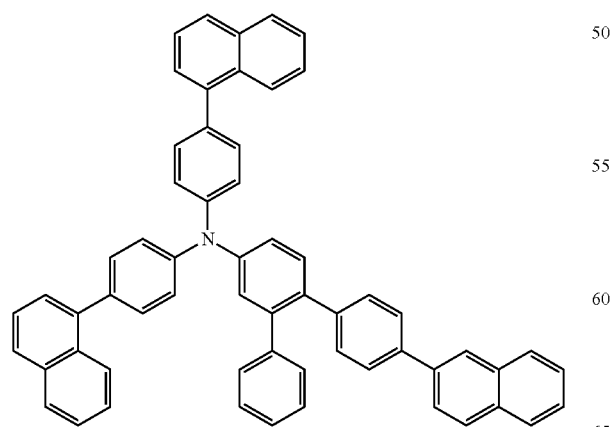
[Chemical Formula 169]
(1-153)
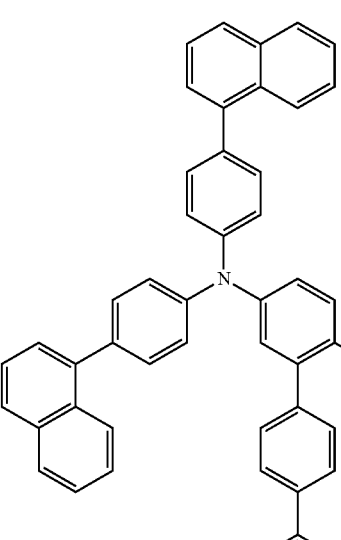
[Chemical Formula 170]
(1-154)
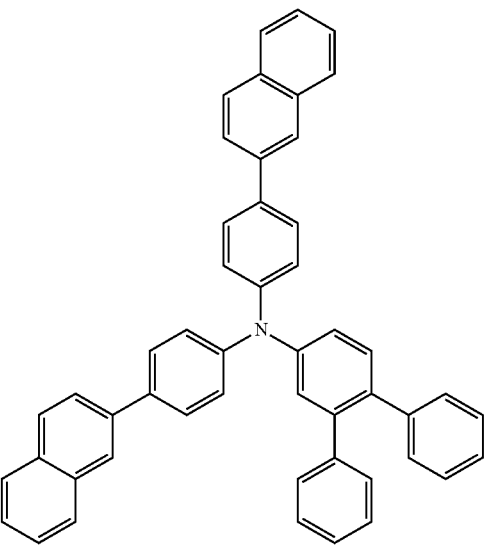

[Chemical Formula 171]
(1-155)
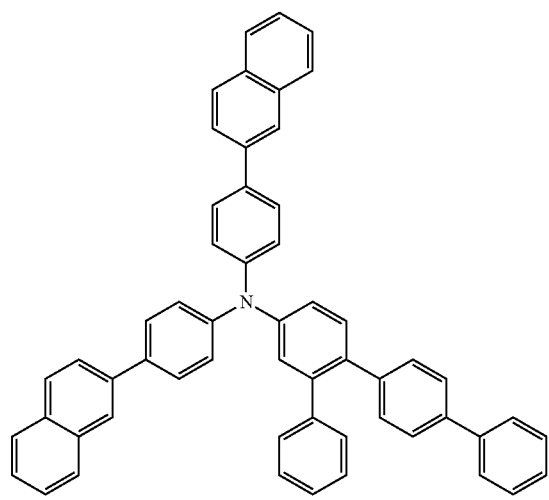
[Chemical Formula 172]
(1-156)
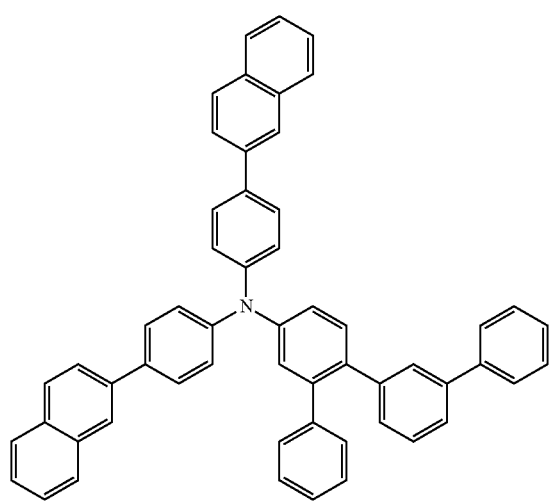
[Chemical Formula 173]
(1-157)
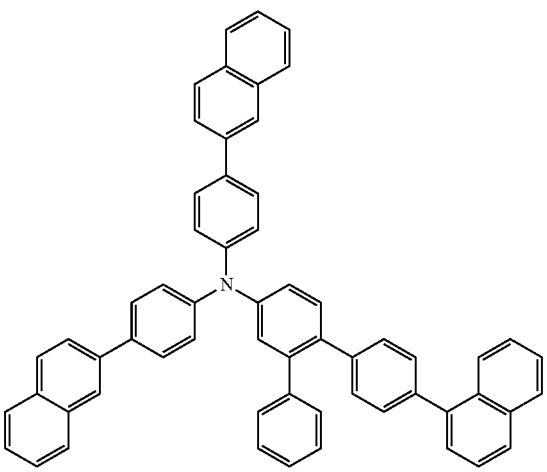
[Chemical Formula 174]
(1-158)
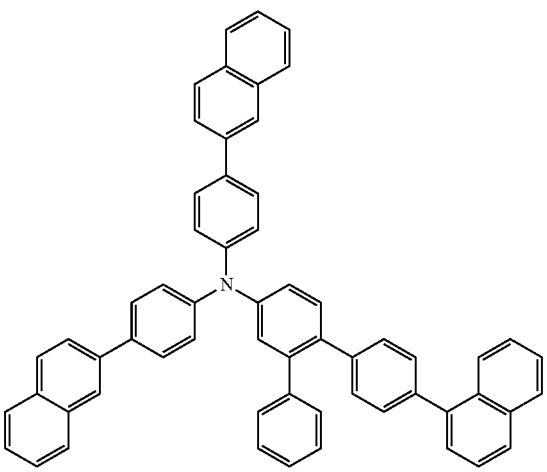
[Chemical Formula 175]
(1-159)
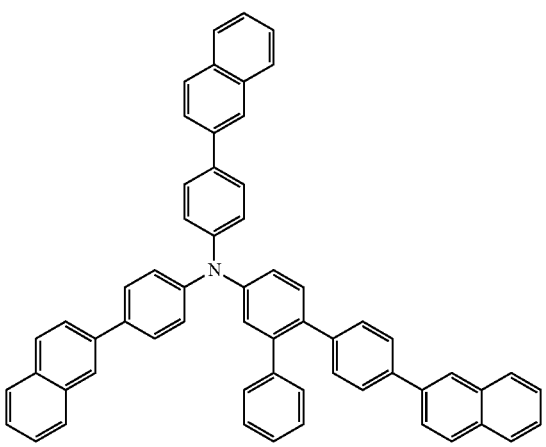

-continued
[Chemical Formula 176]
(1-160)
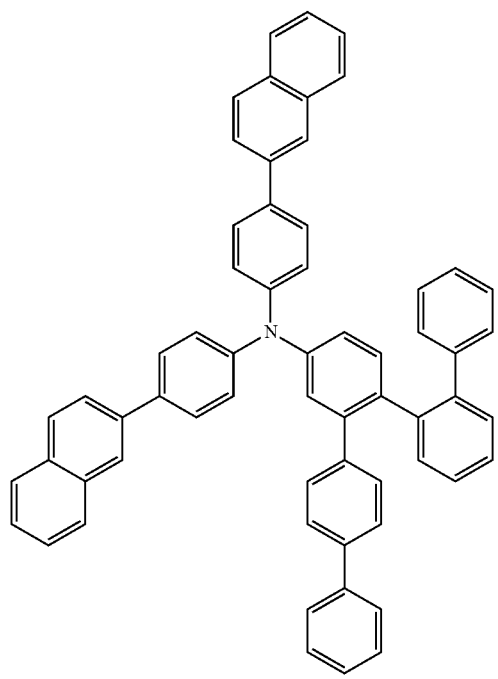
[Chemical Formula 177]
(1-161)
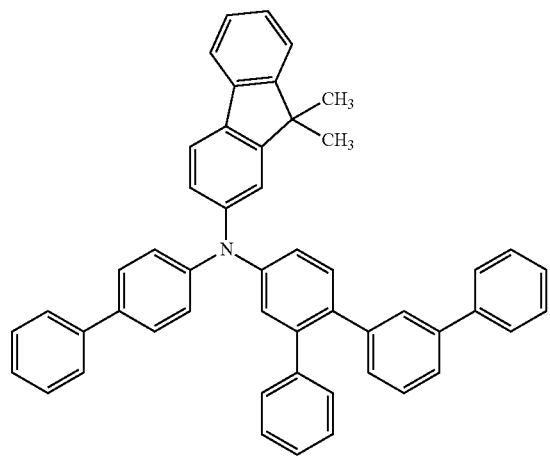
-continued
[Chemical Formula 178]
(1-162)
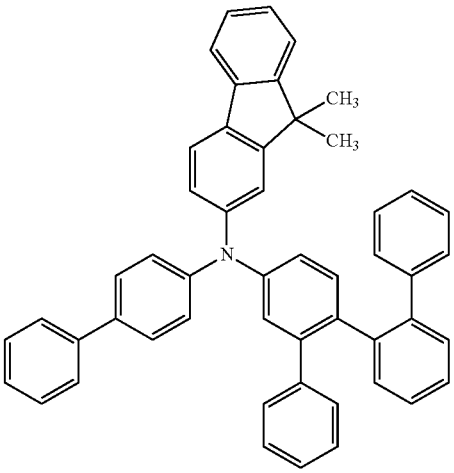
[Chemical Formula 179]
(1-163)
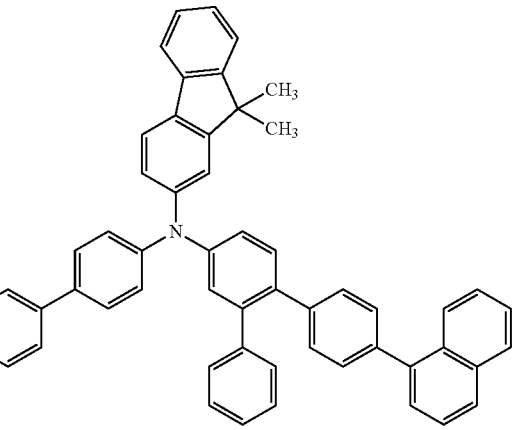
[Chemical Formula 180]
(1-164)
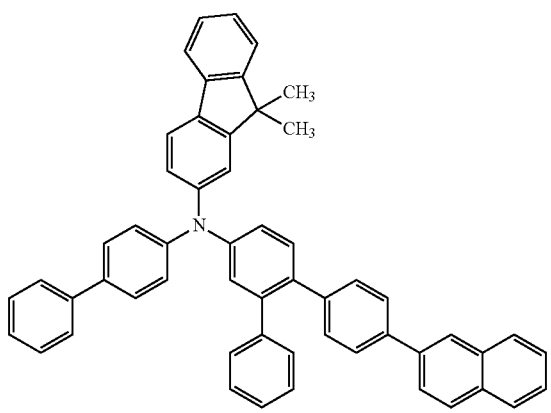

[Chemical Formula 181]
(1-165)
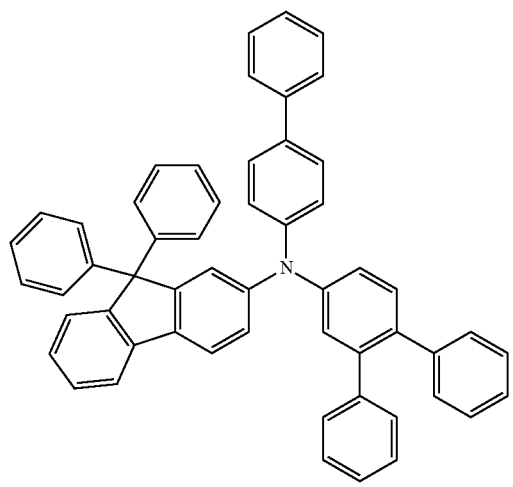
[Chemical Formula 182]
(1-166)
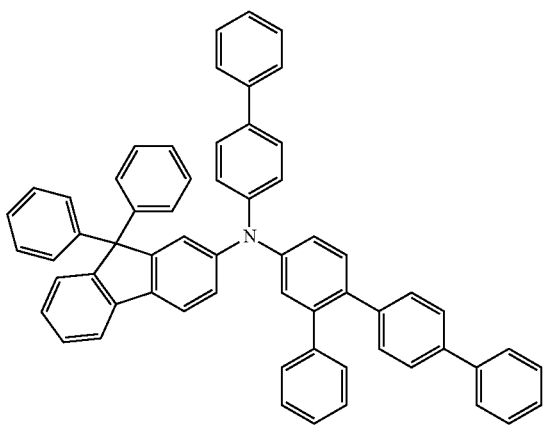
[Chemical Formula 183]
(1-167)
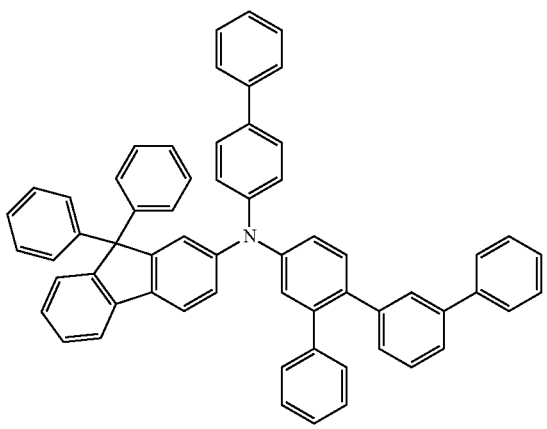
[Chemical Formula 184]
(1-168)
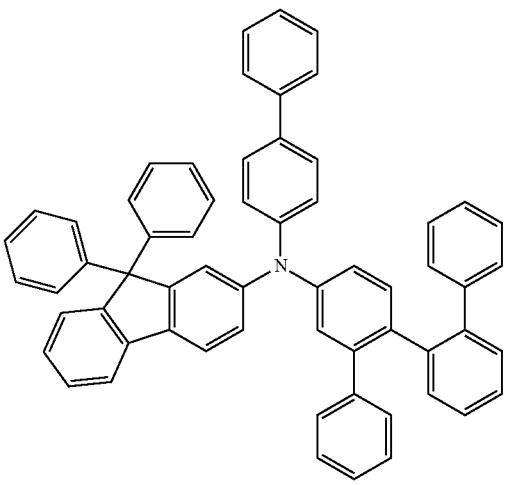
[Chemical Formula 185]
(1-169)
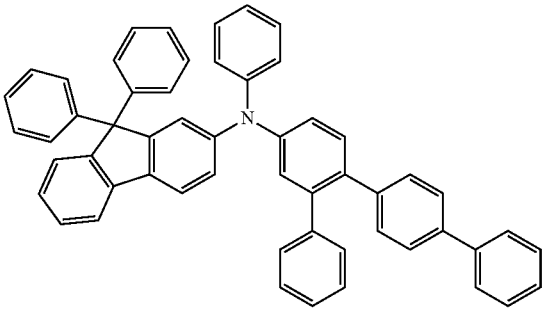
[Chemical Formula 186]
(1-170)
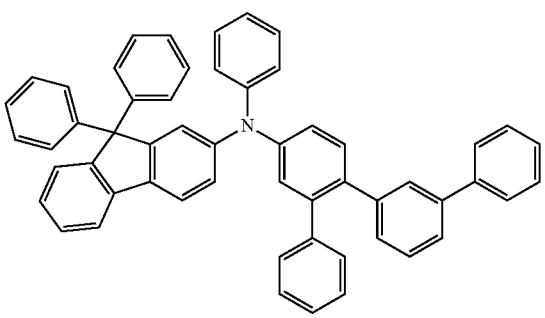

[Chemical Formula 187]
(1-171)
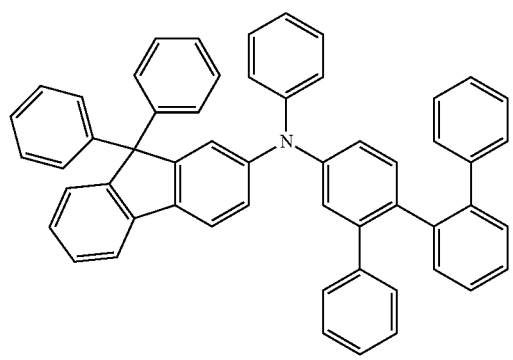
[Chemical Formula 188]
(1-172)
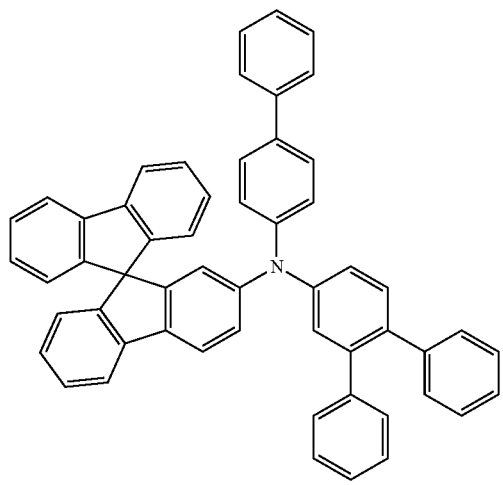
[Chemical Formula 189]
(1-173)
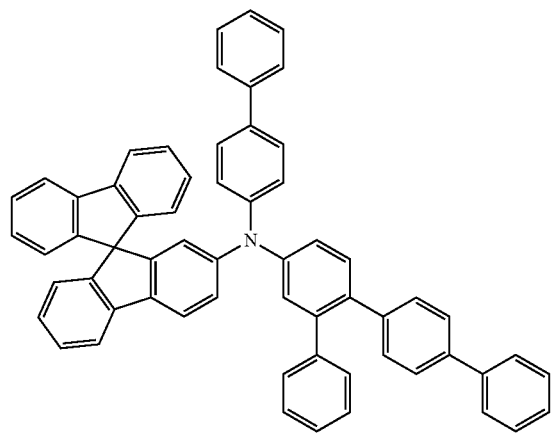
[Chemical Formula 190]
(1-174)
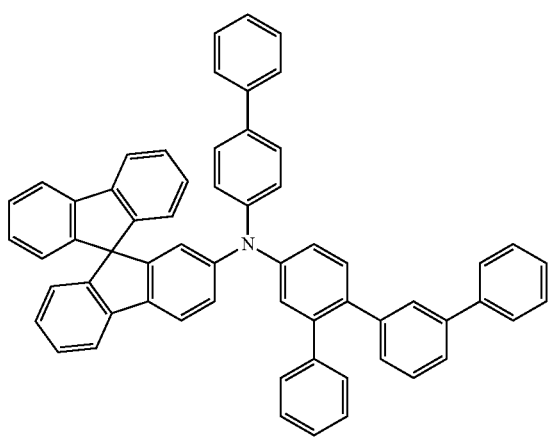
[Chemical Formula 191]
(1-175)
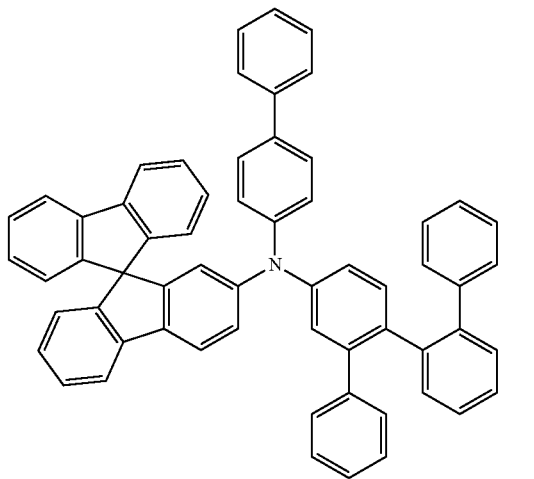
[Chemical Formula 192]
(1-176)
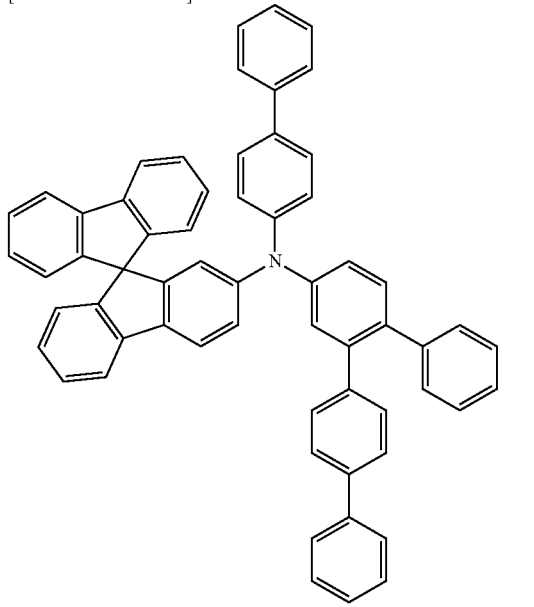

[Chemical Formula 193]
(1-177)
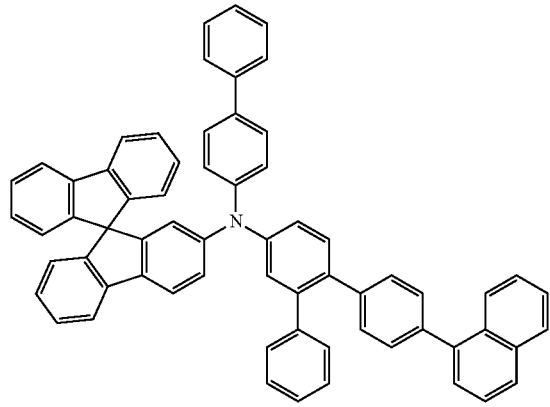
[Chemical Formula 194]
(1-178)
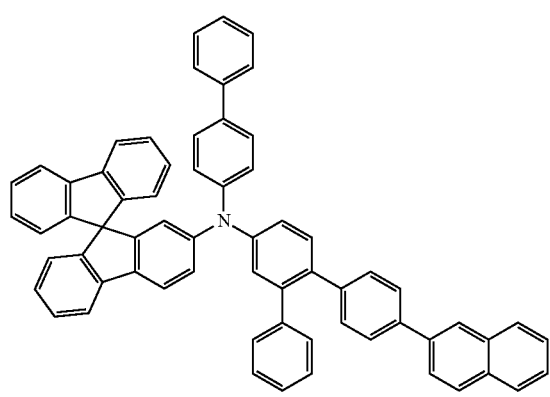
[Chemical Formula 195]
(1-179)
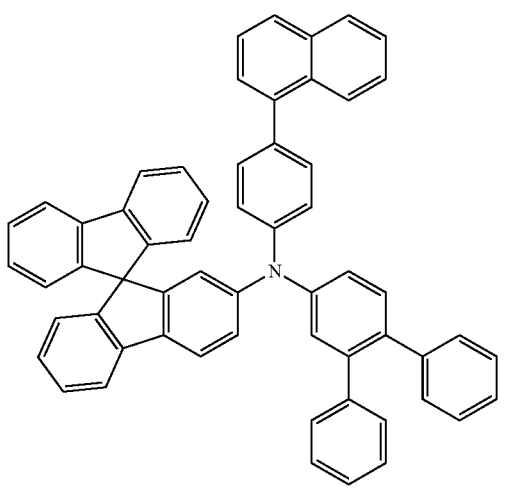
[Chemical Formula 196]
(1-180)
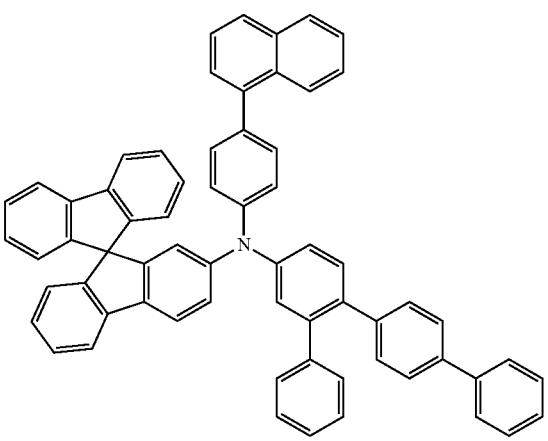
[Chemical Formula 197]
(1-181)
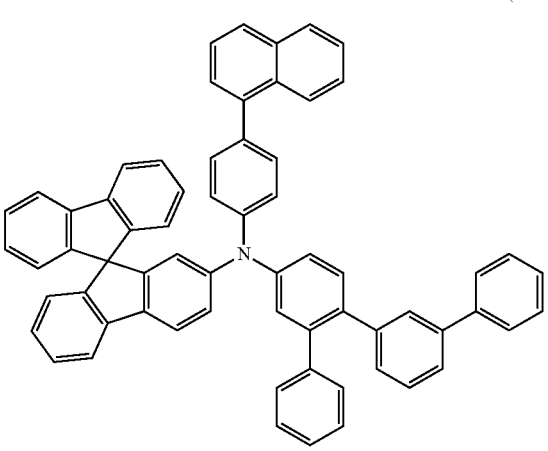
[Chemical Formula 198]
(1-182)
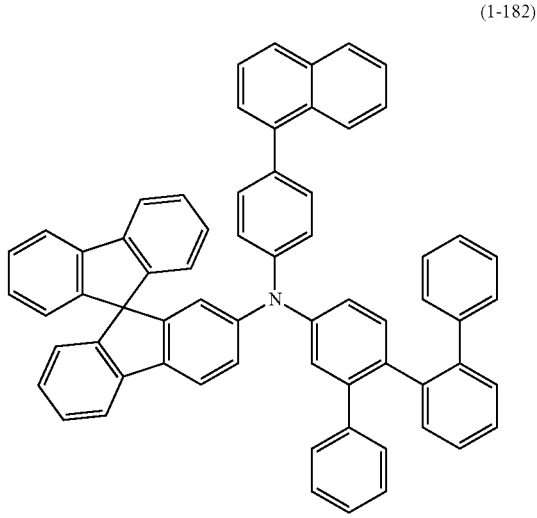

[Chemical Formula 199]
(1-183)
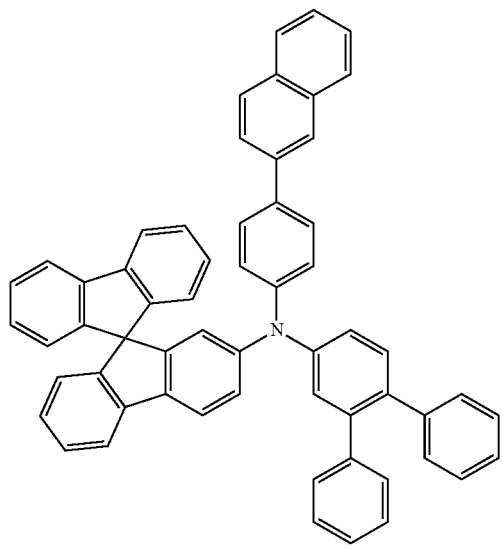
[Chemical Formula 200]
(1-184)
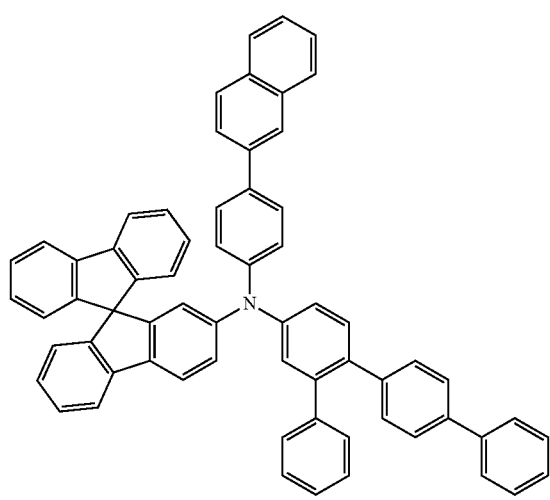
[Chemical Formula 201]
(1-185)
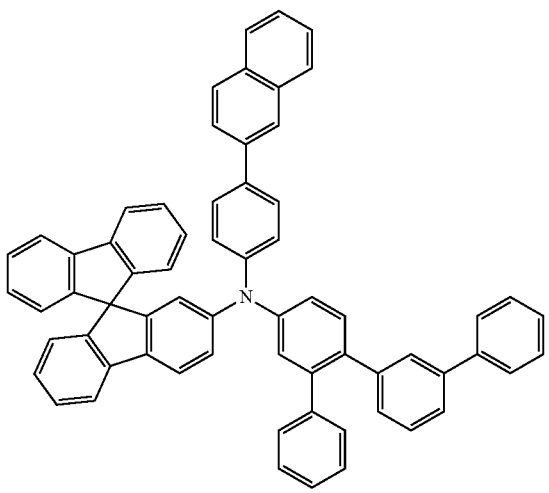
[Chemical Formula 202]
(1-186)
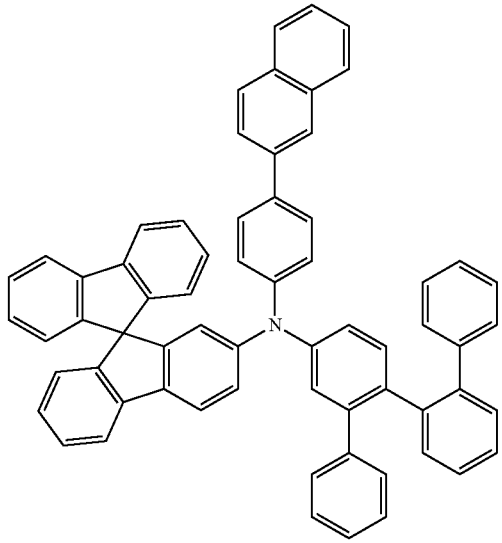
[Chemical Formula 203]
(1-187)
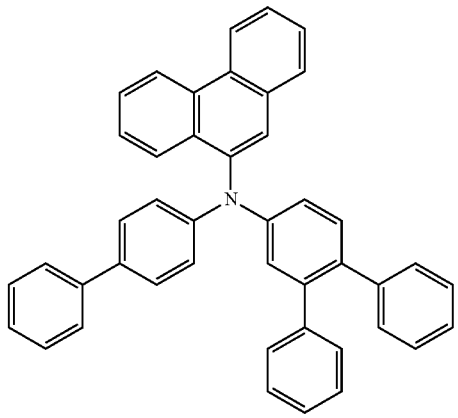

[Chemical Formula 204]
(1-188)
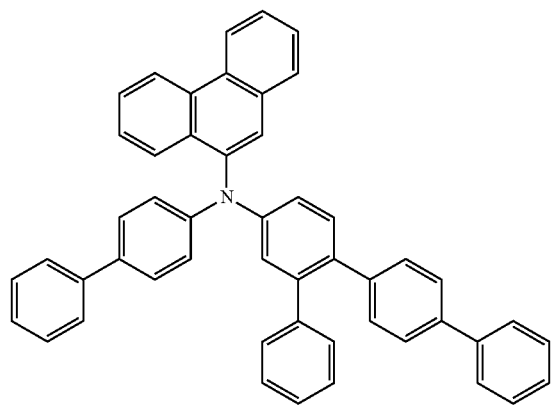
[Chemical Formula 205]
(1-189)
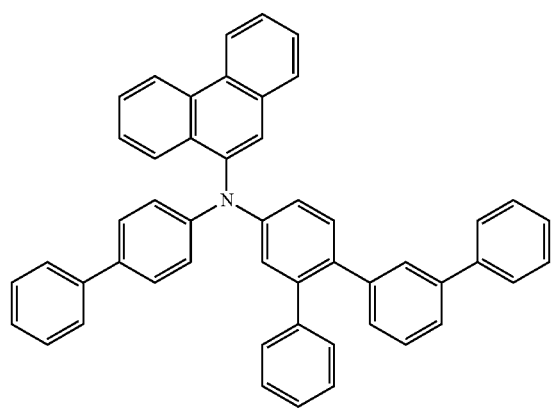
[Chemical Formula 206]
(1-190)
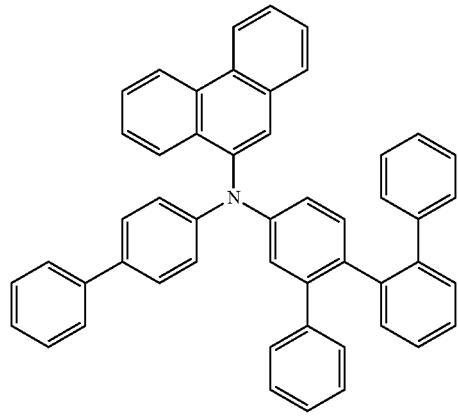
[Chemical Formula 207]
(1-191)
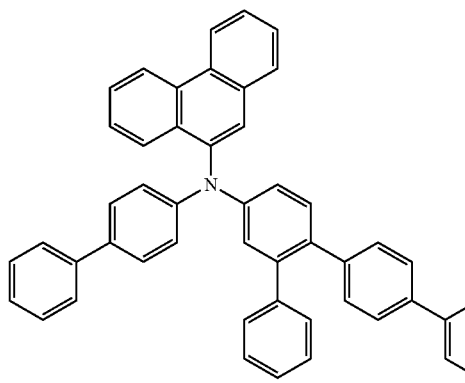
[Chemical Formula 208]
(1-192)
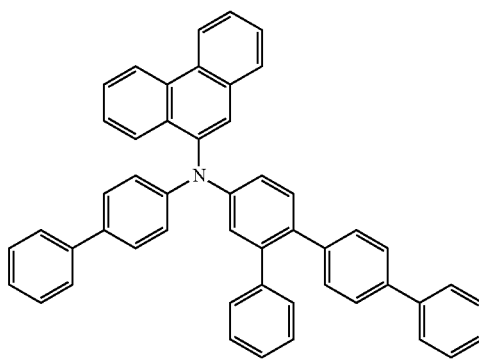
[Chemical Formula 209]
(1-193)
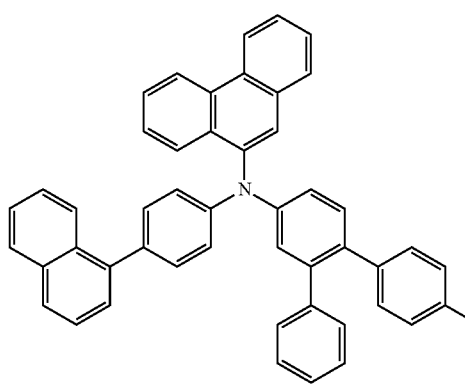

[Chemical Formula 210]
(1-194)
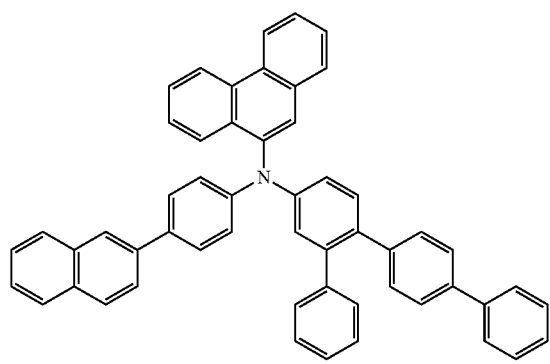
[Chemical Formula 211]
(1-195)
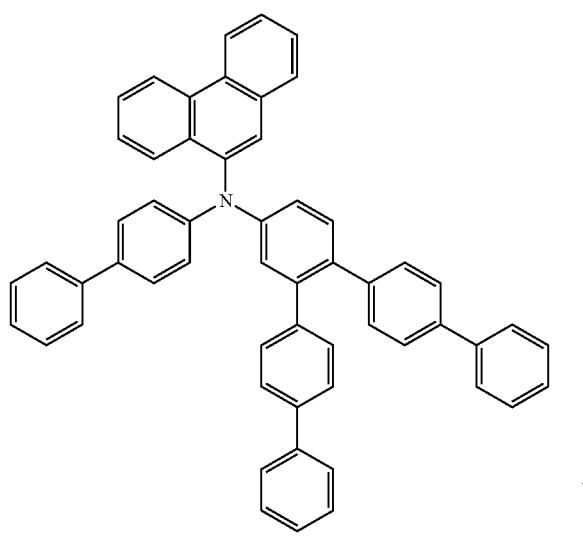
[Chemical Formula 212]
(1-196)
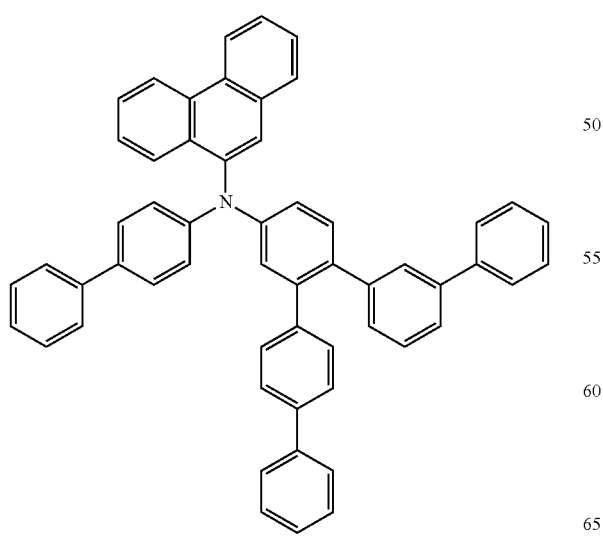
[Chemical Formula 213]
(1-197)
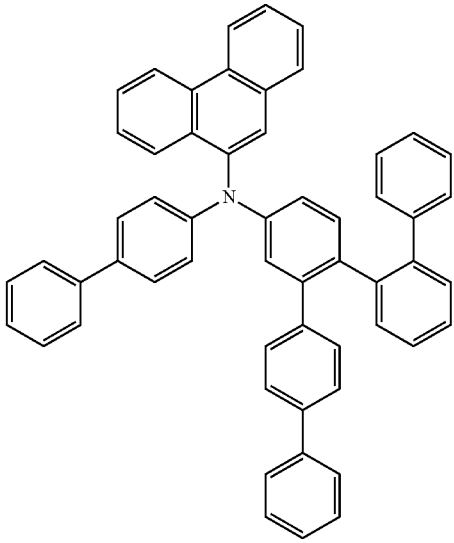
[Chemical Formula 214]
(1-198)
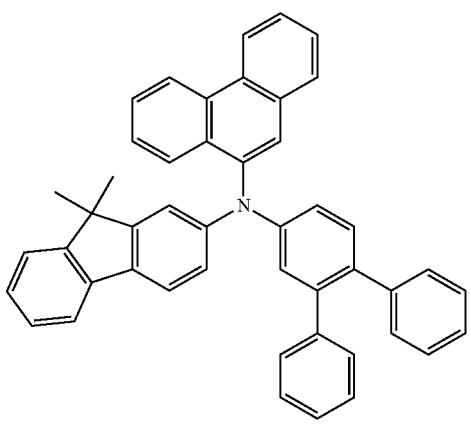

[Chemical Formula 215]

(1-199)

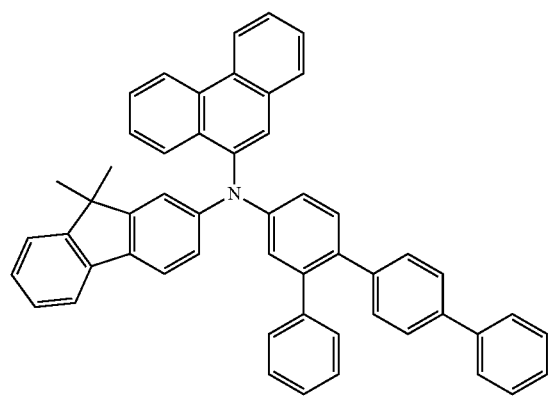

[Chemical Formula 216]

(1-200)

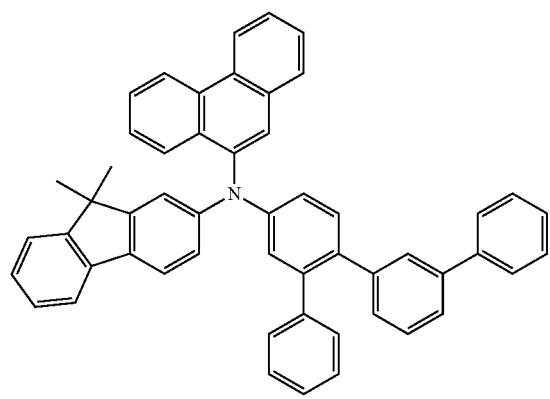

[Chemical Formula 217]

(1-201)

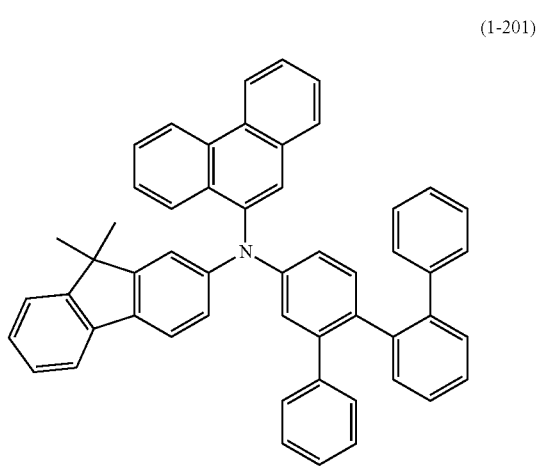

The following presents specific examples (X represents an oxygen atom) of preferred compounds among the compounds having a benzazole ring structure of the general formula (2) preferably used in the organic EL device of the present invention. The present invention, however, is not restricted to these compounds.

[Chemical Formula 218]

(2-1)

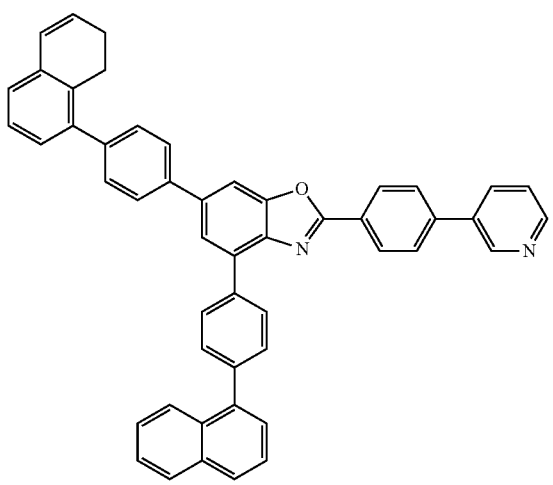

[Chemical Formula 219]

(2-2)

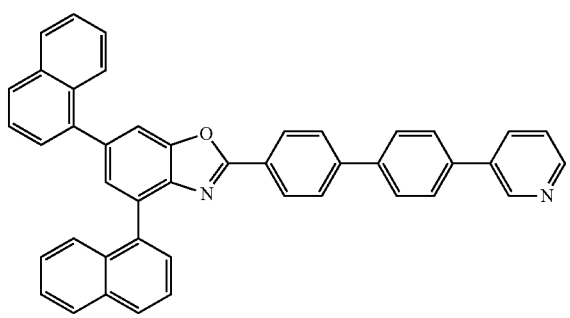

-continued
[Chemical Formula 220]
(2-3)
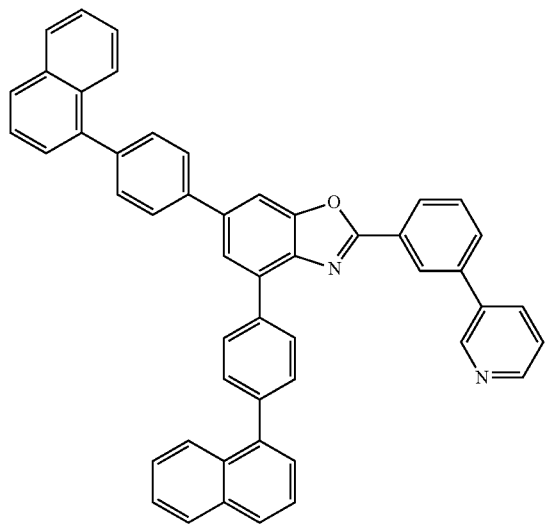
[Chemical Formula 221]
(2-4)
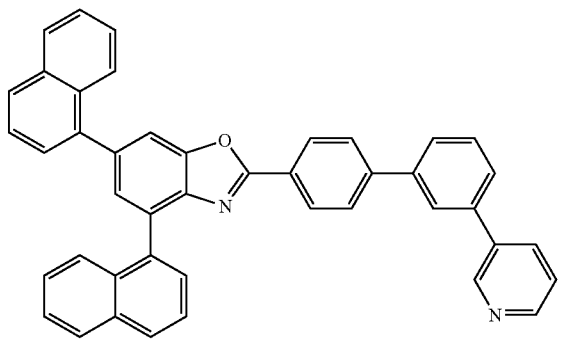
[Chemical Formula 222]
(2-5)
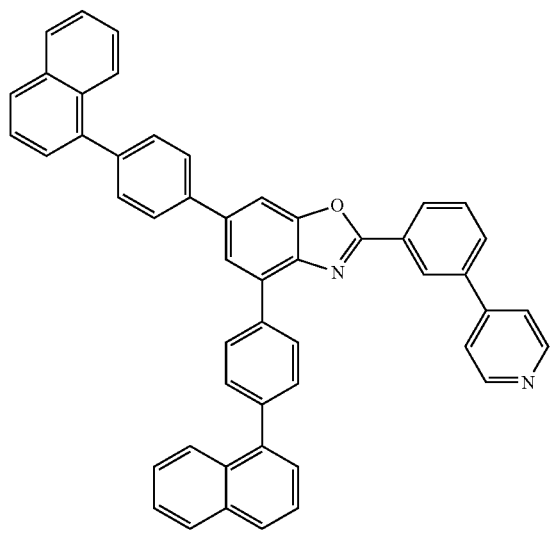
[Chemical Formula 223]
(2-6)
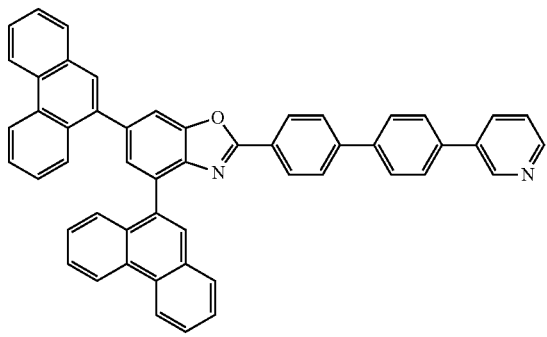
[Chemical Formula 224]
(2-7)
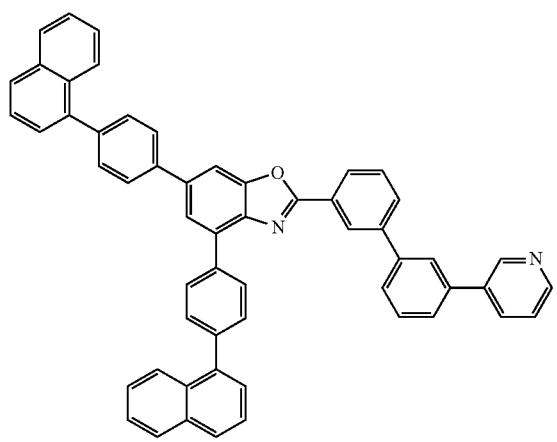
[Chemical Formula 225]
(2-8)
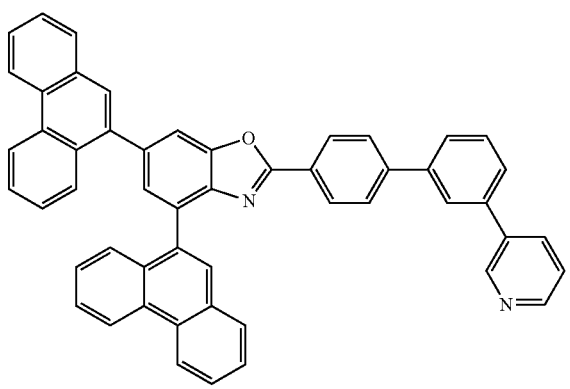

-continued
[Chemical Formula 226]
(2-9)
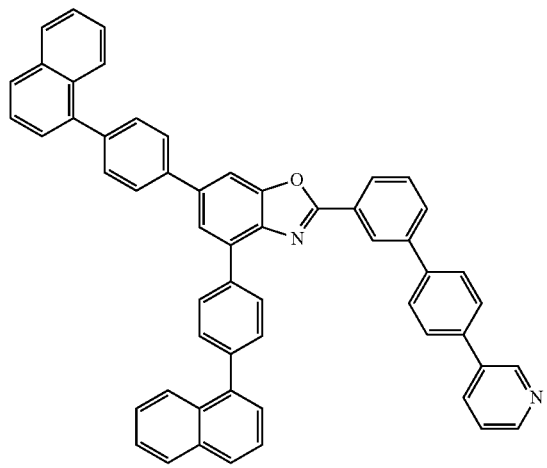
[Chemical Formula 227]
(2-10)
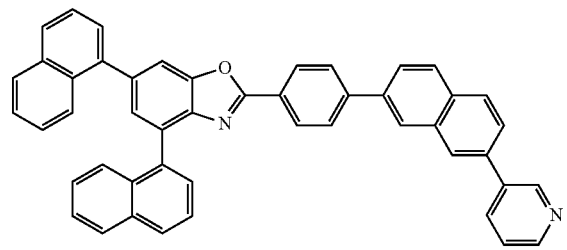
[Chemical Formula 228]
(2-11)
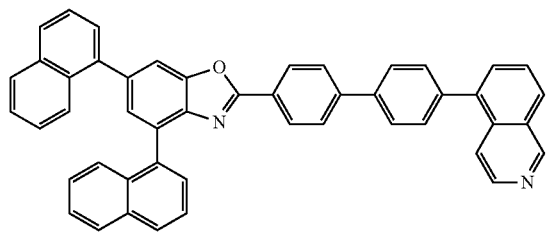
[Chemical Formula 229]
(2-12)
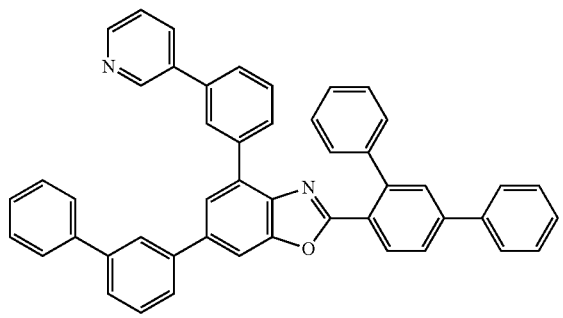
[Chemical Formula 230]
(2-13)
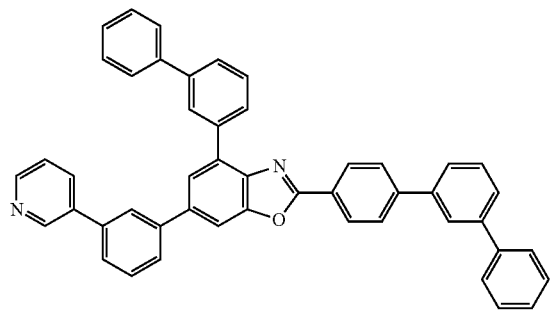
[Chemical Formula 231]
(2-14)
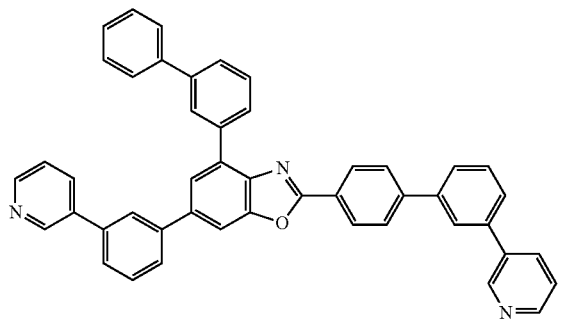

-continued
[Chemical Formula 232]
(2-15)
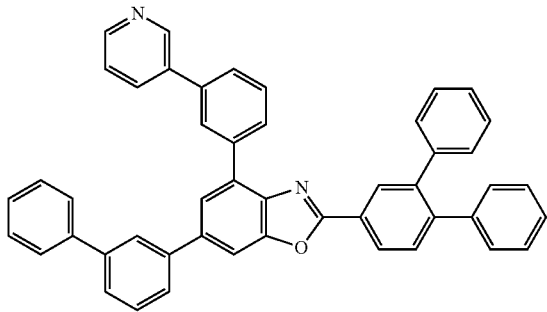
[Chemical Formula 233]
(2-16)
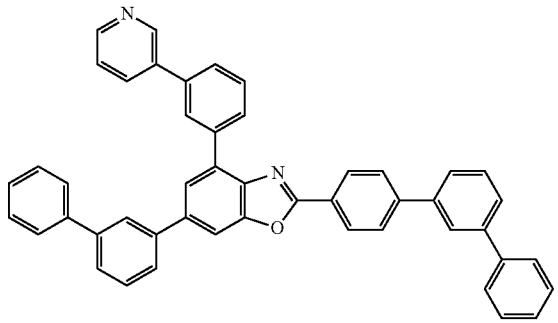
[Chemical Formula 234]
(2-17)
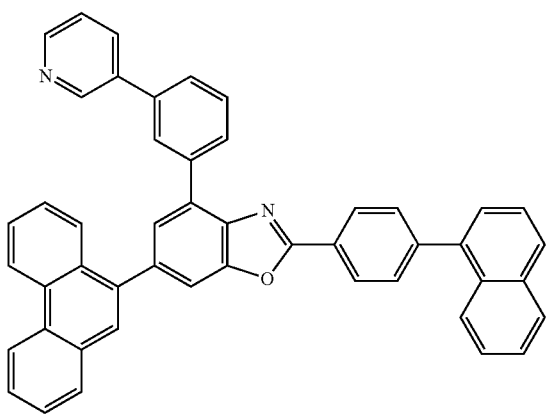
[Chemical Formula 235]
(2-18)
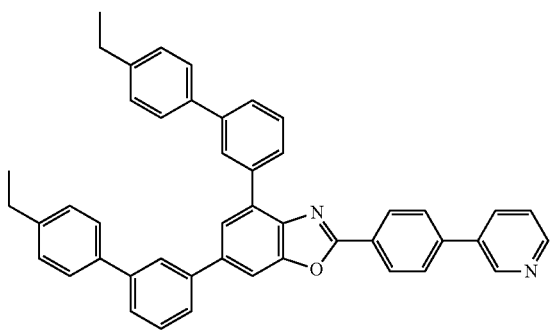
[Chemical Formula 236]
(2-19)
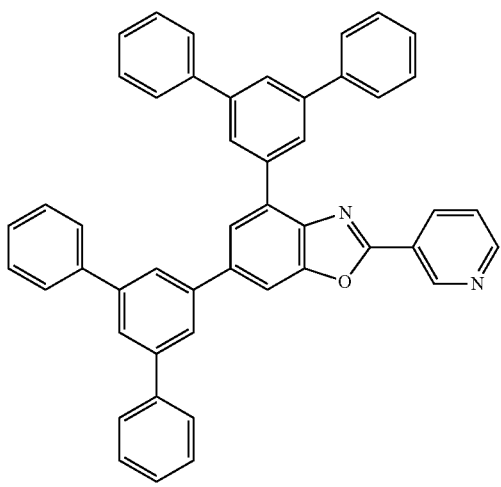
[Chemical Formula 237]
(2-20)
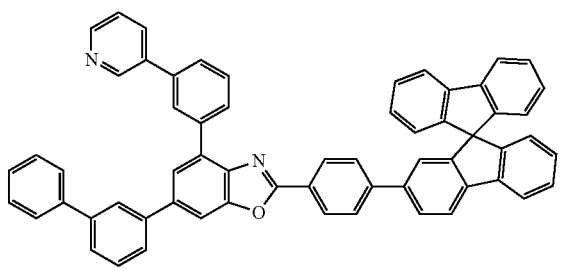

[Chemical Formula 238]
(2-21)
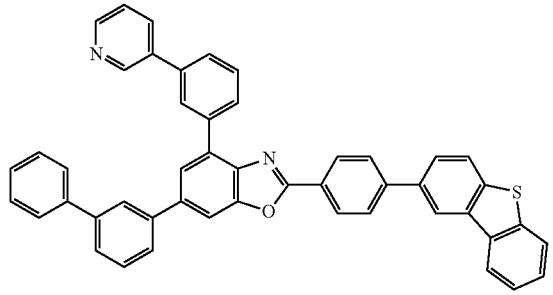
[Chemical Formula 239]
(2-22)
[Chemical Formula 240]
(2-23)
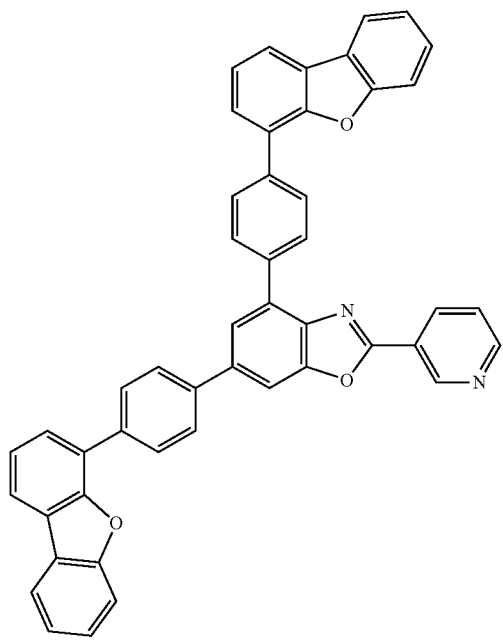
[Chemical Formula 241]
(2-24)
[Chemical Formula 242]
(2-25)
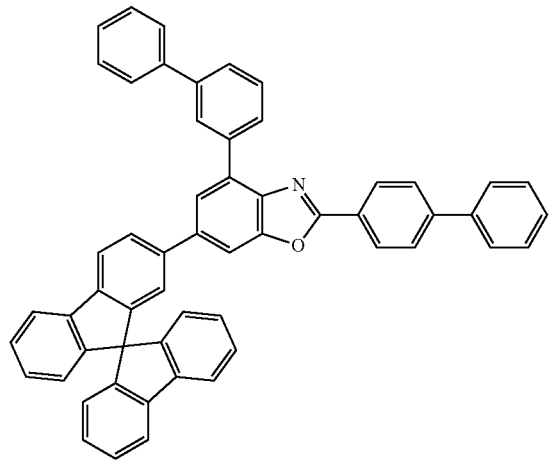
[Chemical Formula 243]
(2-26)
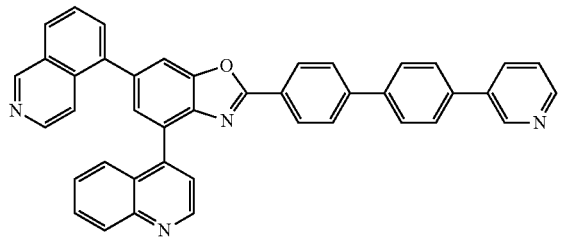

-continued
[Chemical Formula 244]
(2-27)
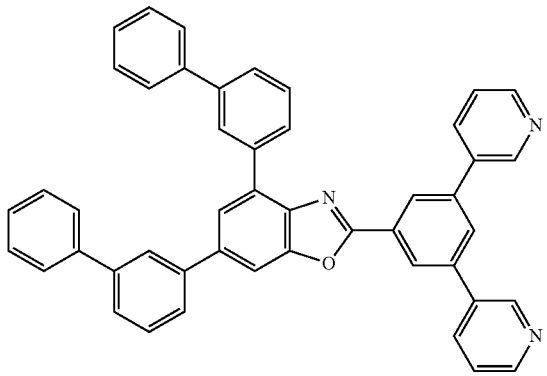
[Chemical Formula 245]
(2-28)
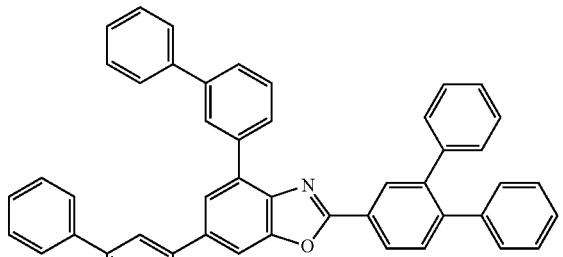
[Chemical Formula 246]
(2-29)
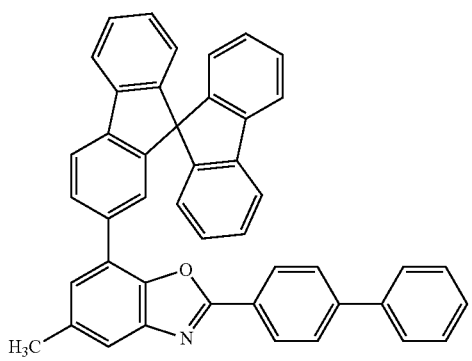
[Chemical Formula 247]
(2-30)
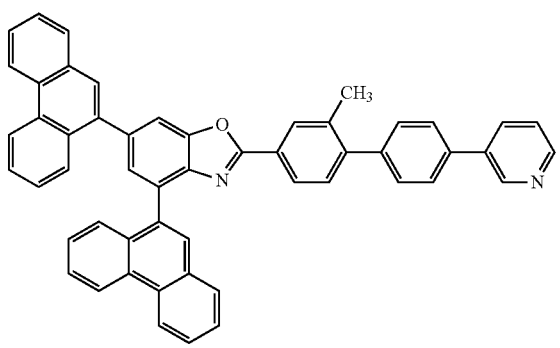
[Chemical Formula 248]
(2-31)
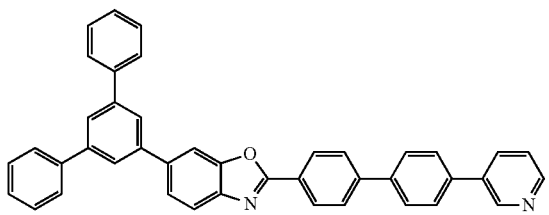
[Chemical Formula 249]
(2-32)
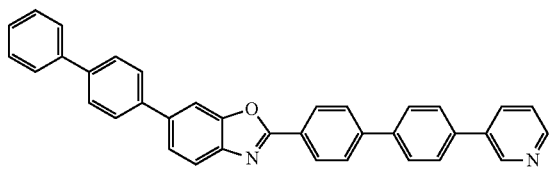
[Chemical Formula 250]
(2-33)
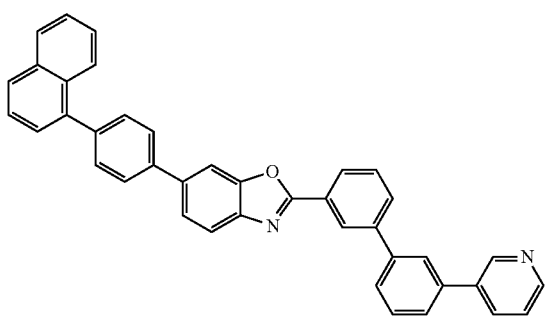
[Chemical Formula 251]
(2-34)
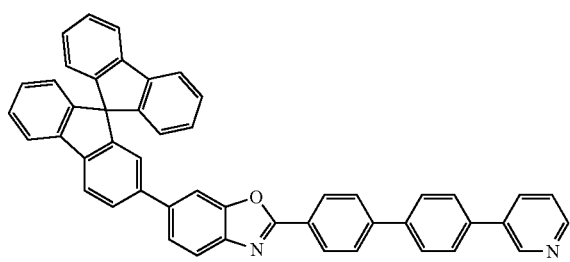

[Chemical Formula 252]
(2-35)
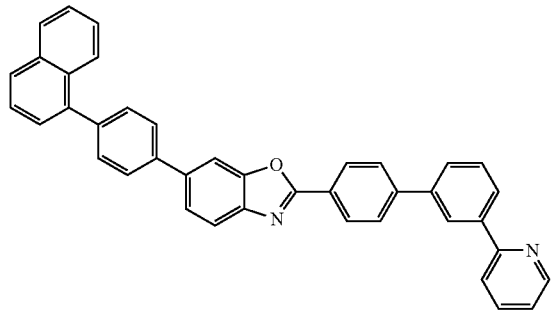
[Chemical Formula 253]
(2-36)
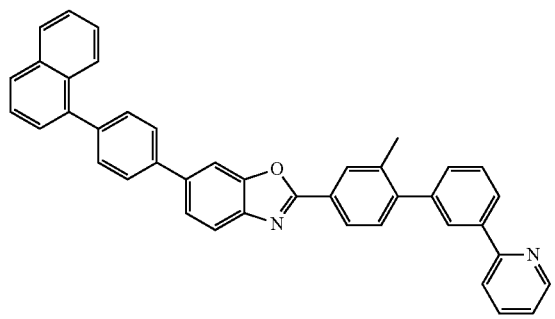
[Chemical Formula 254]
(2-37)
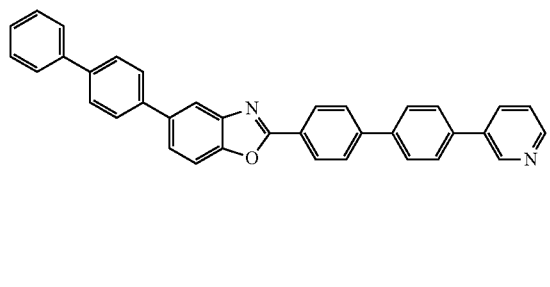
[Chemical Formula 255]
(2-38)
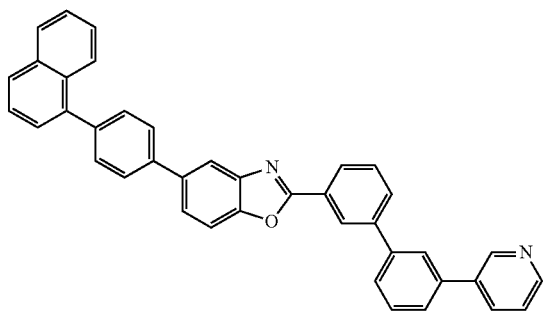
[Chemical Formula 256]
(2-39)
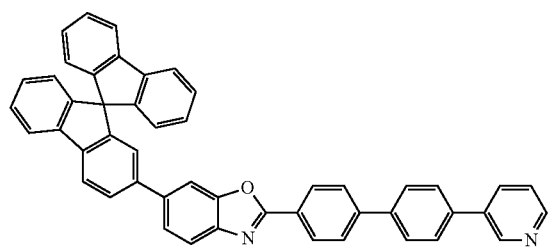
[Chemical Formula 257]
(2-40)
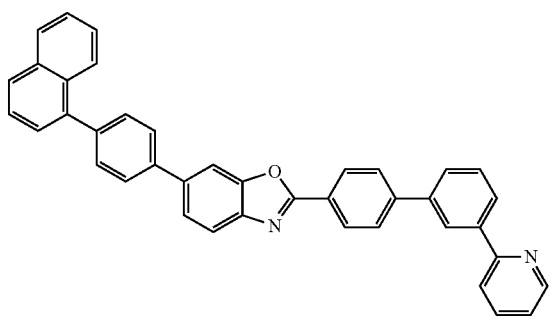
[Chemical Formula 258]
(2-41)
[Chemical Formula 259]
(2-42)

[Chemical Formula 260]
(2-43)
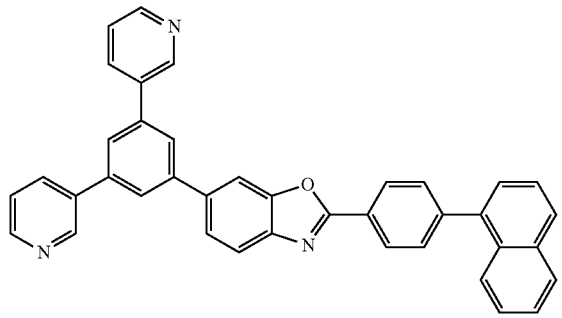
[Chemical Formula 261]
(2-44)
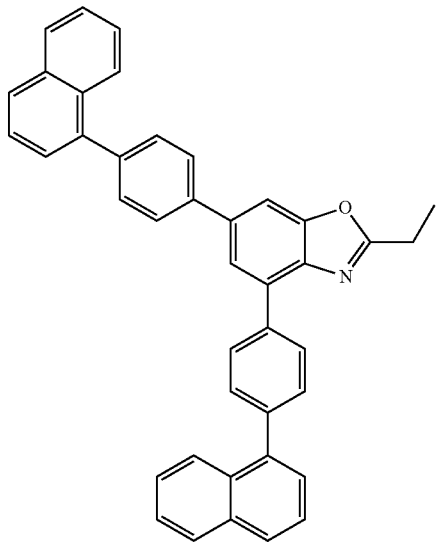
[Chemical Formula 262]
(2-45)
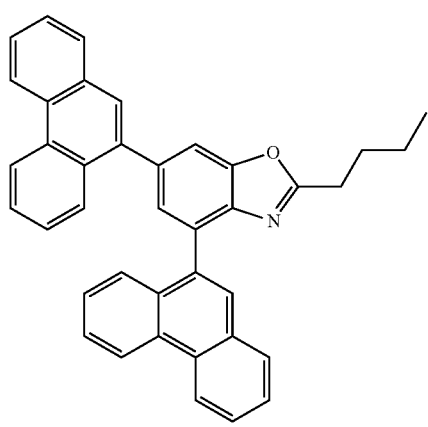
[Chemical Formula 263]
(2-46)
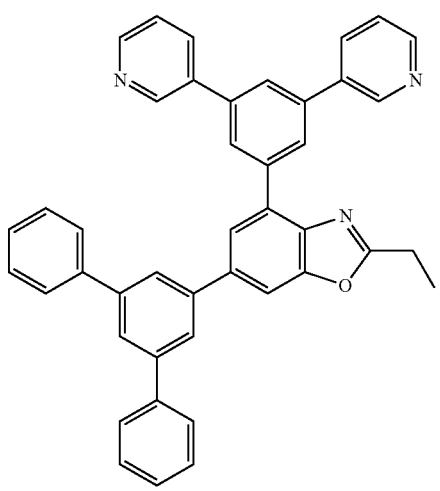

[Chemical Formula 264]
(2-47)
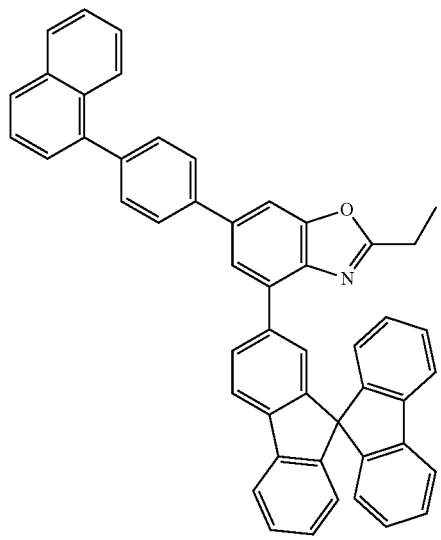
[Chemical Formula 265]
(2-48)
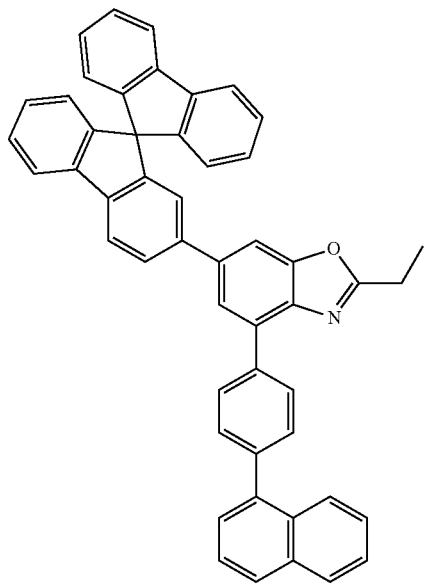
[Chemical Formula 266]
(2-49)
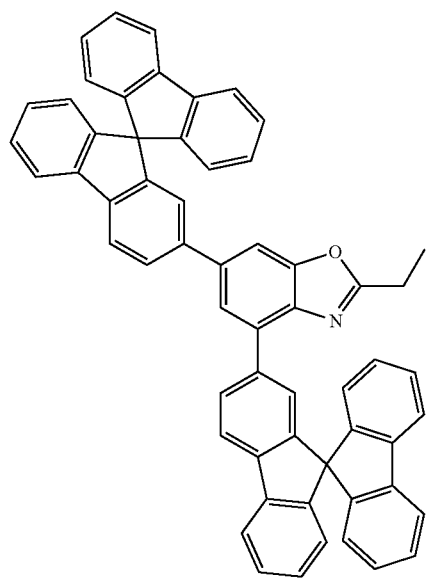
[Chemical Formula 267]
(2-50)
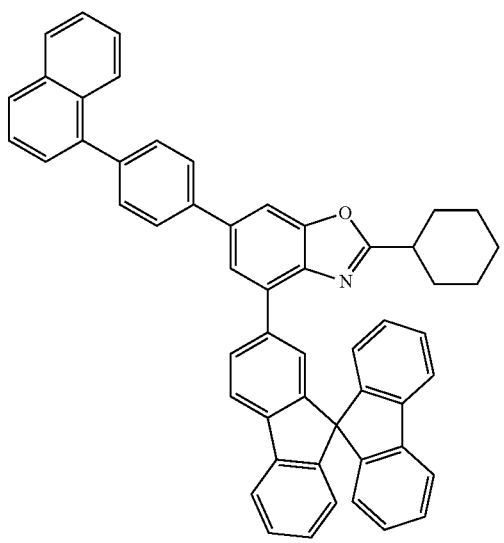

-continued
[Chemical Formula 268]
(2-51)
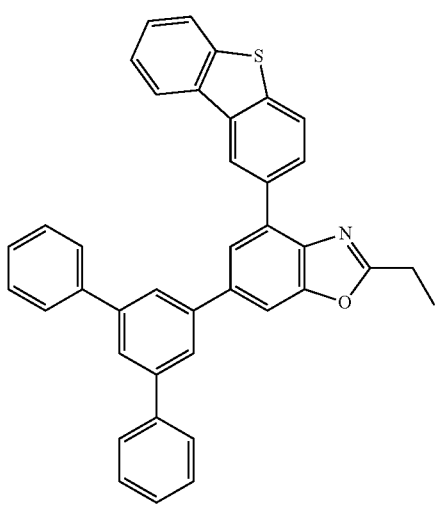
[Chemical Formula 269]
(2-52)
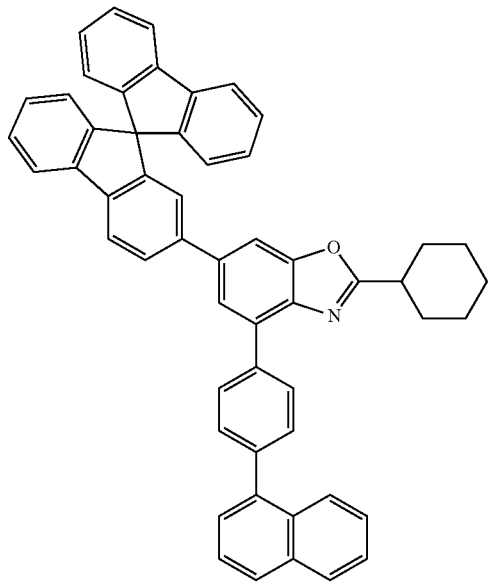
[Chemical Formula 270]
(2-53)
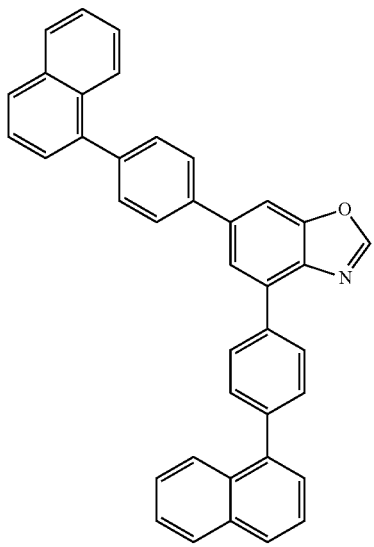
[Chemical Formula 271]
(2-54)
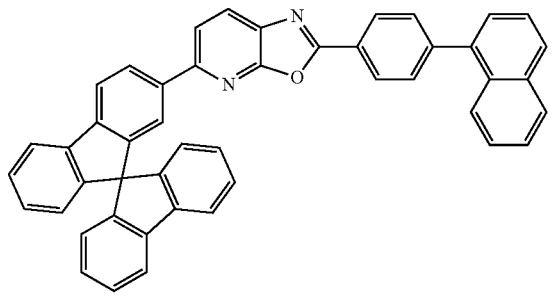
[Chemical Formula 272]
(2-55)
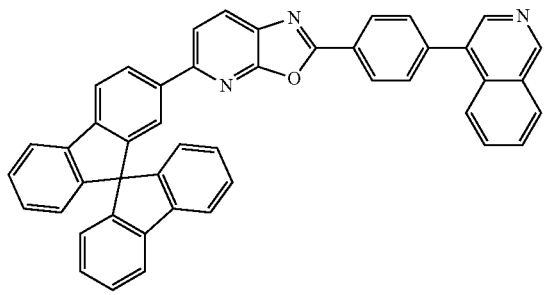
[Chemical Formula 273]
(2-56)
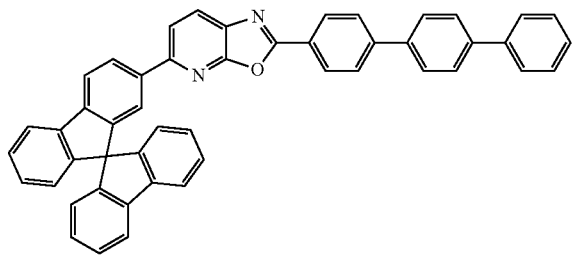

[Chemical Formula 274]
(2-57)
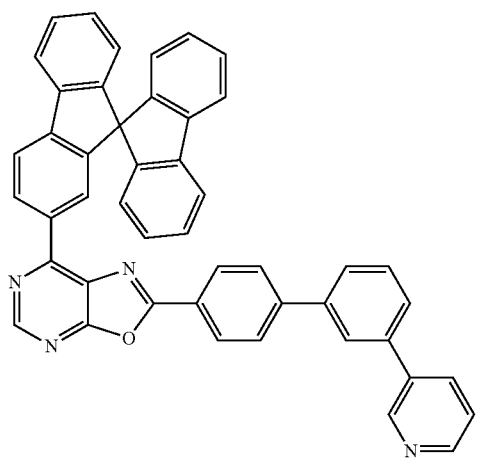
[Chemical Formula 275]
(2-58)
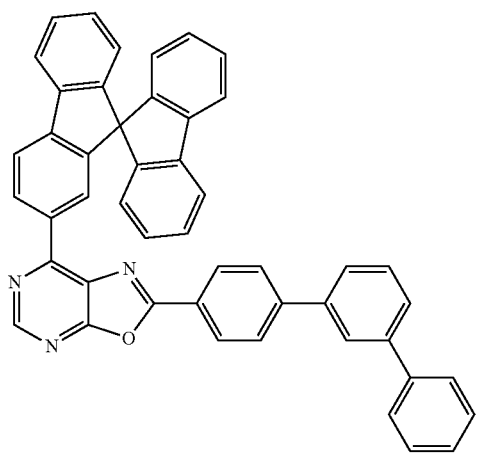
[Chemical Formula 276]
(2-59)
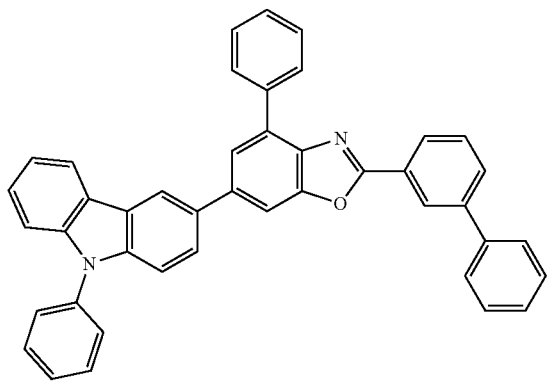
[Chemical Formula 277]
(2-60)
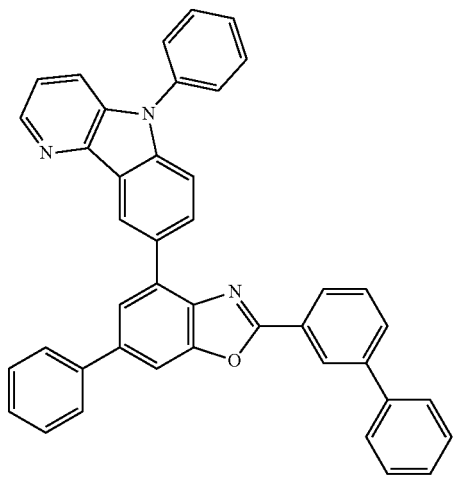
[Chemical Formula 278]
(2-61)
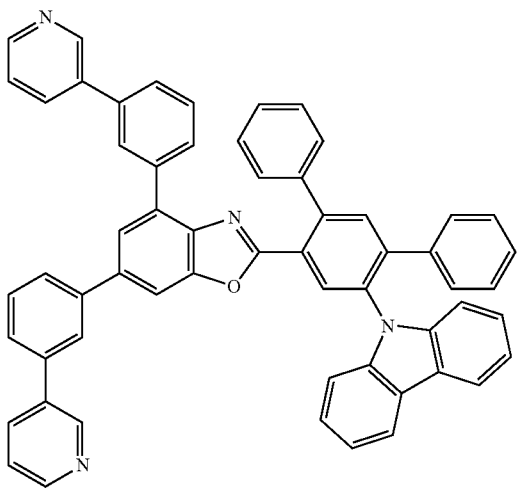
[Chemical Formula 279]
(2-62)
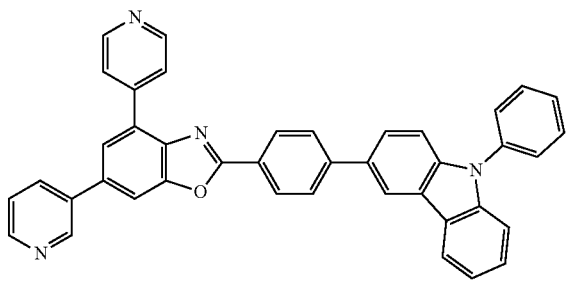

[Chemical Formula 280]
(2-63)
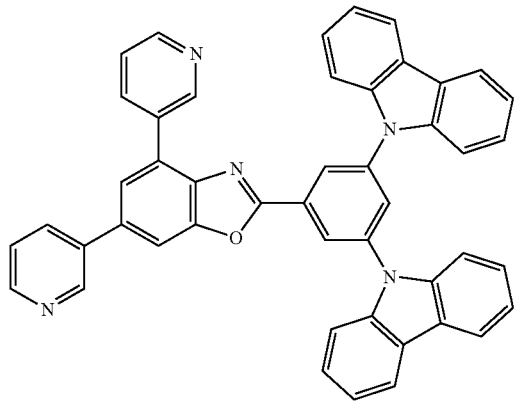
[Chemical Formula 281]
(2-64)
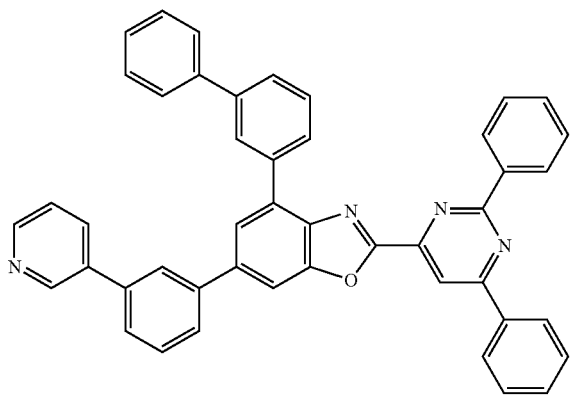
[Chemical Formula 282]
(2-65)
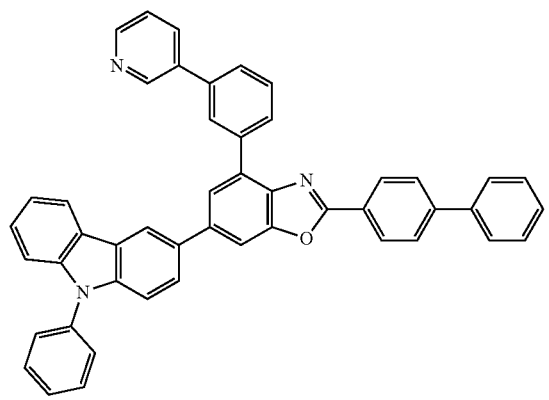
[Chemical Formula 283]
(2-66)
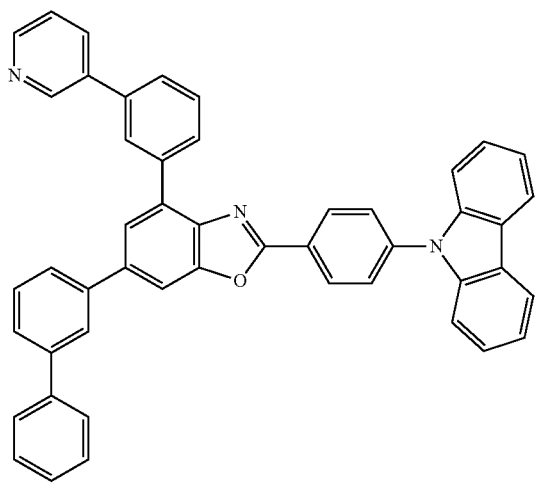
[Chemical Formula 284]
(2-67)
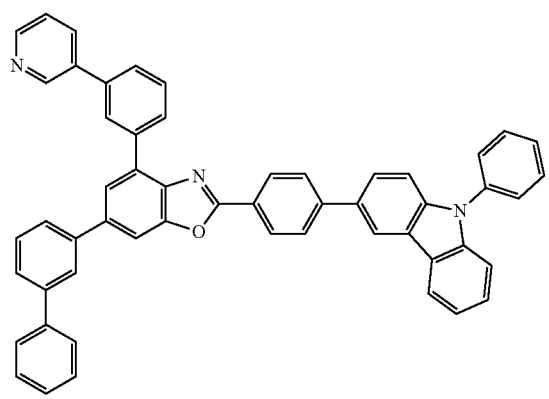
[Chemical Formula 285]
(2-68)
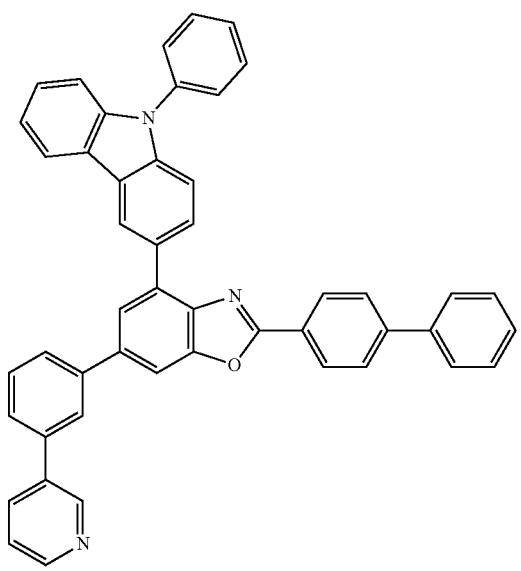

-continued
[Chemical Formula 286]
(2-69)
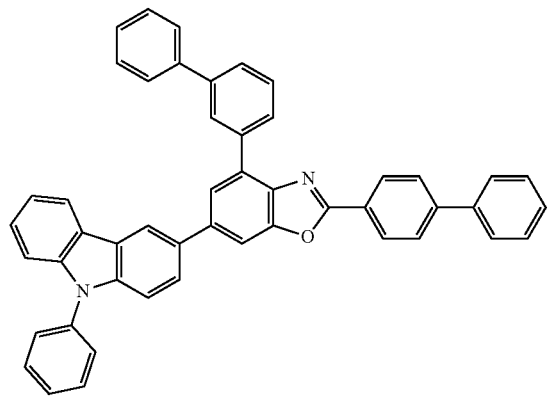
[Chemical Formula 287]
(2-70)
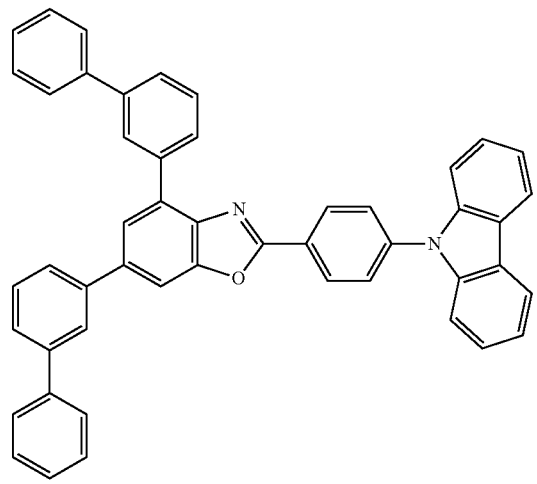
[Chemical Formula 288]
(2-71)
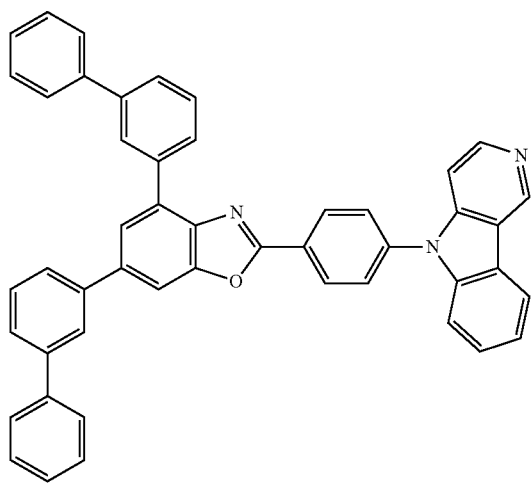
[Chemical Formula 289]
(2-72)
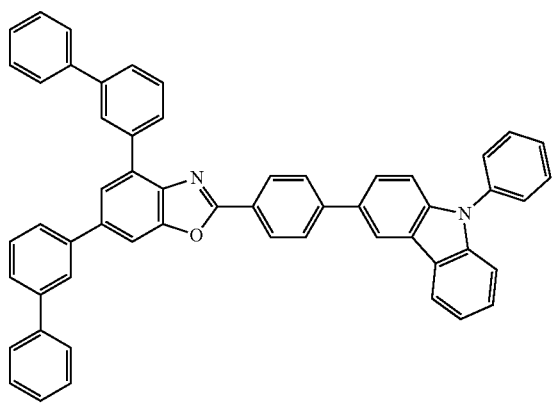

-continued
[Chemical Formula 290]
(2-73)
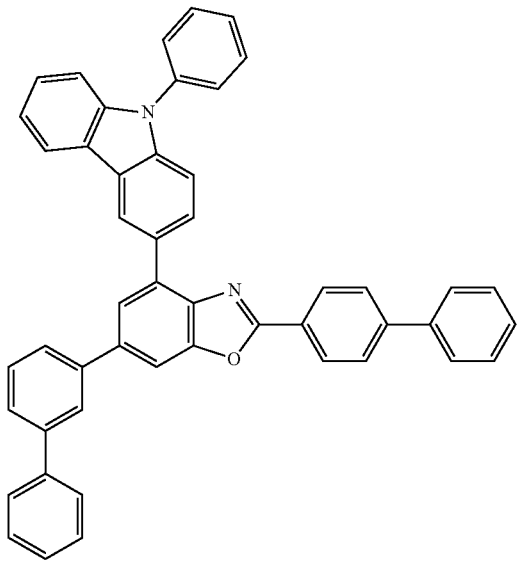
[Chemical Formula 291]
(2-74)
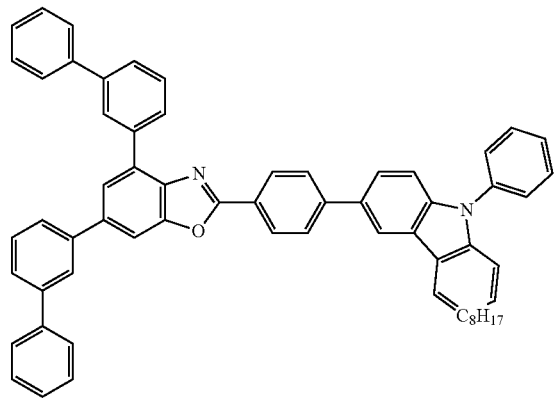
[Chemical Formula 292]
(2-75)
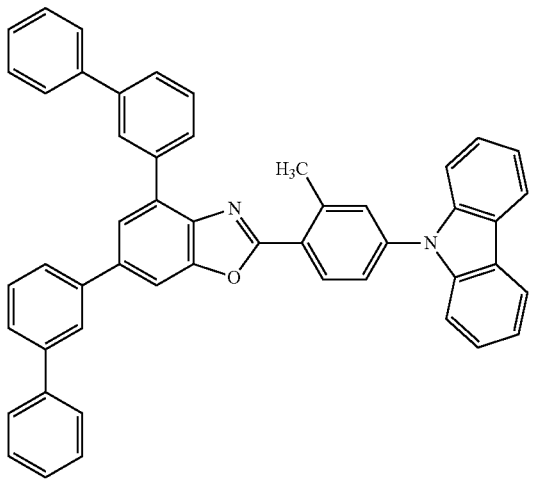
[Chemical Formula 293]
(2-76)
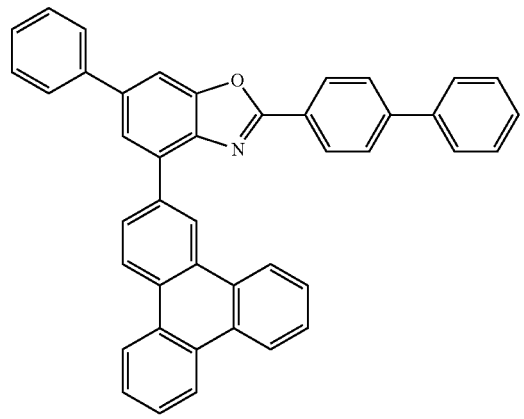
[Chemical Formula 294]
(2-77)
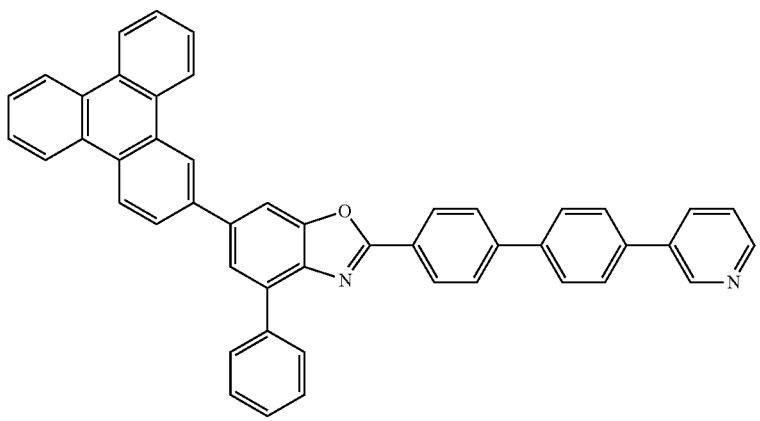

[Chemical Formula 295]
(2-78)
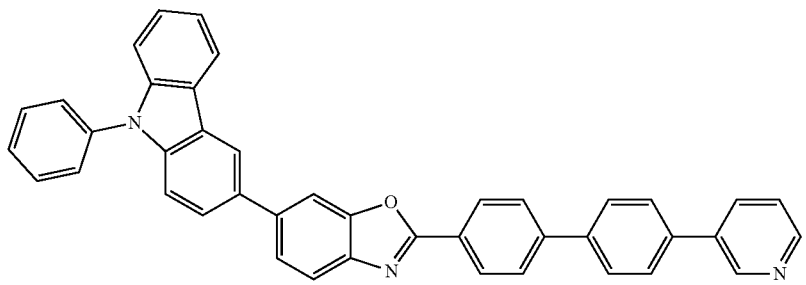
[Chemical Formula 296]
(2-79)
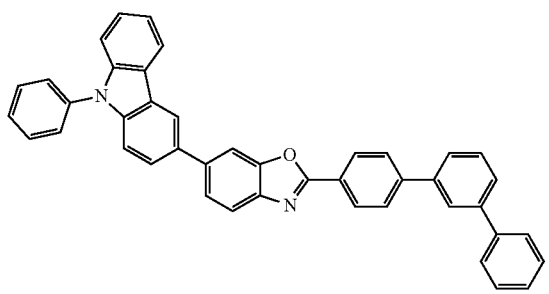
[Chemical Formula 297]
(2-80)
[Chemical Formula 298]
(2-81)
[Chemical Formula 299]
(2-82)
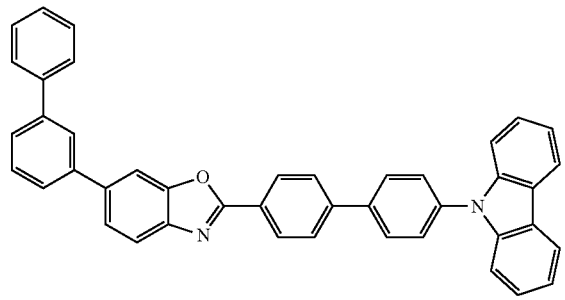
[Chemical Formula 300]
(2-83)
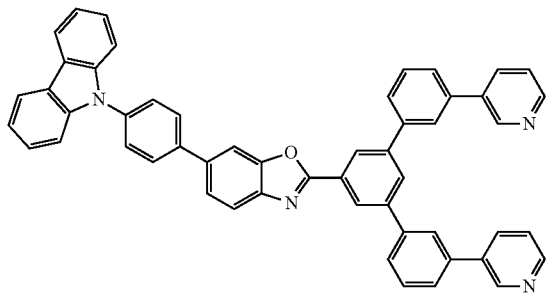
[Chemical Formula 301]
(2-84)
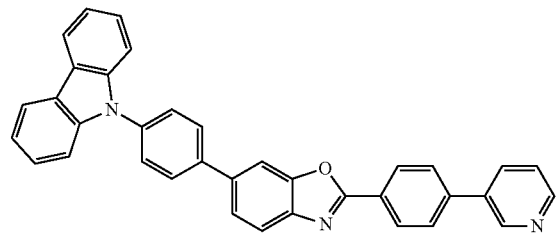

[Chemical Formula 302]
(2-85)
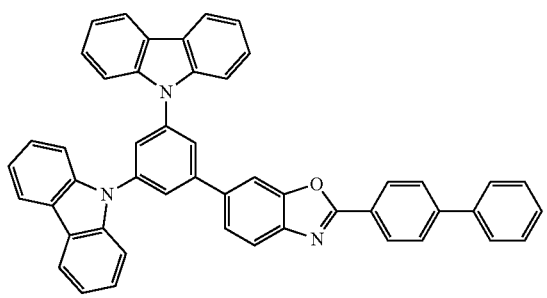
[Chemical Formula 303]
(2-86)
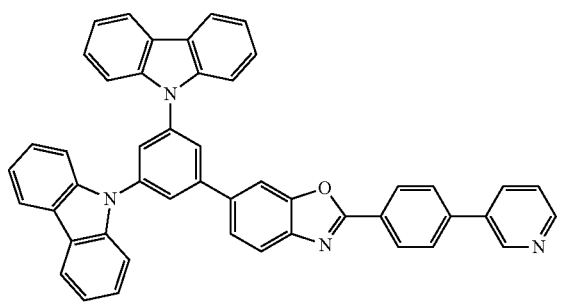
[Chemical Formula 304]
(2-87)
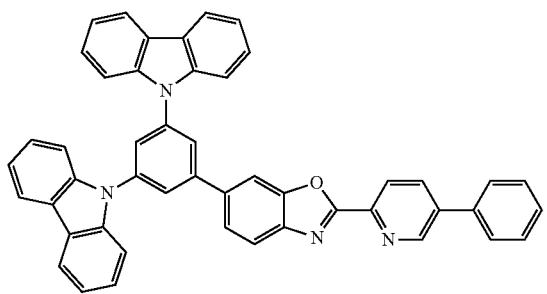
[Chemical Formula 305]
(2-88)
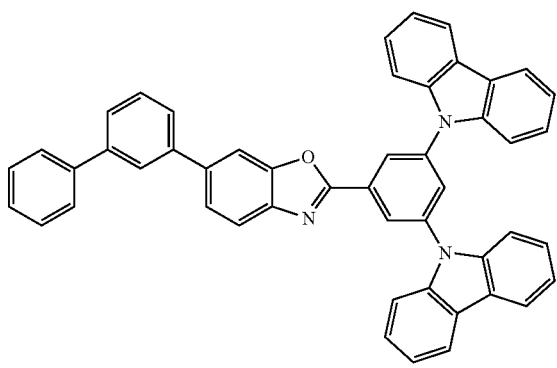
[Chemical Formula 306]
(2-89)
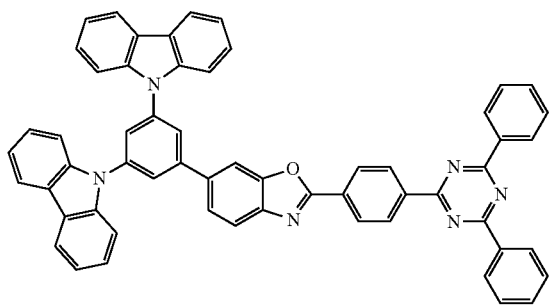
[Chemical Formula 307]
(2-90)
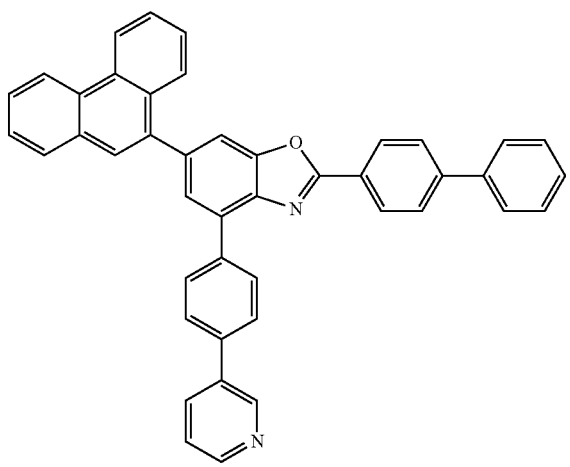

-continued
[Chemical Formula 308]
(2-91)
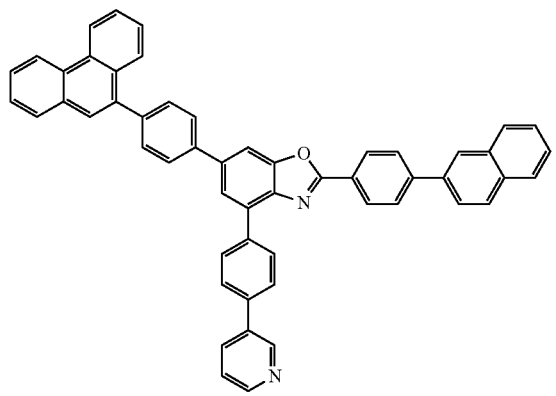
[Chemical Formula 309]
(2-92)
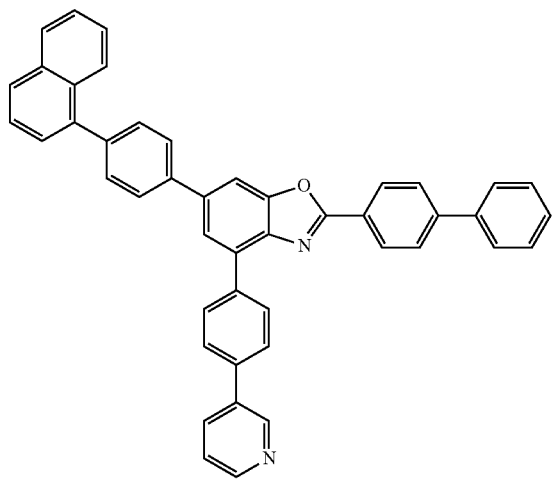
[Chemical Formula 310]
(2-93)
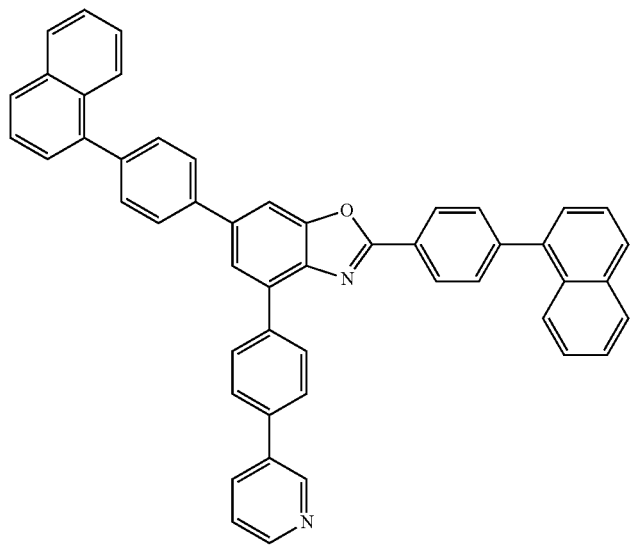
[Chemical Formula 311]
(2-94)
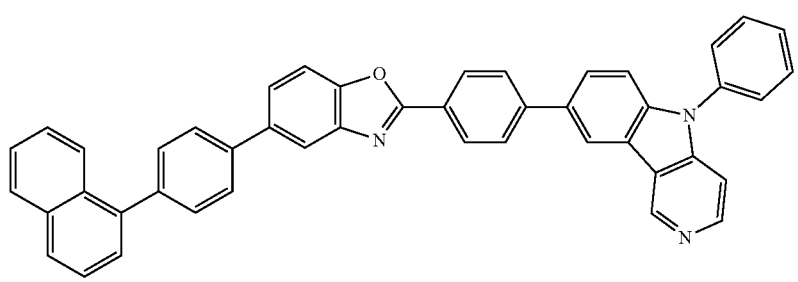

[Chemical Formula 312]
(2-95)
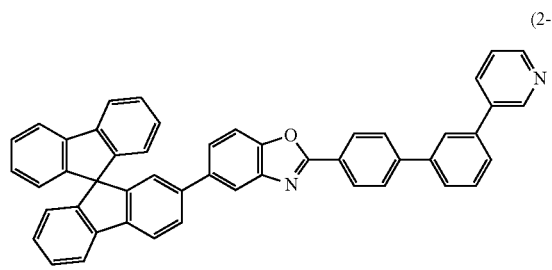
[Chemical Formula 313]
(2-96)
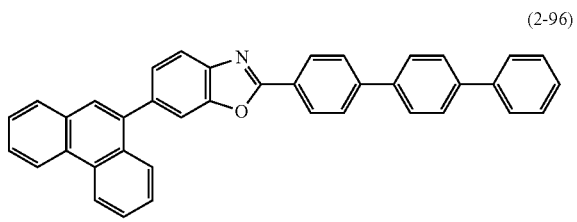
[Chemical Formula 314]
(2-97)
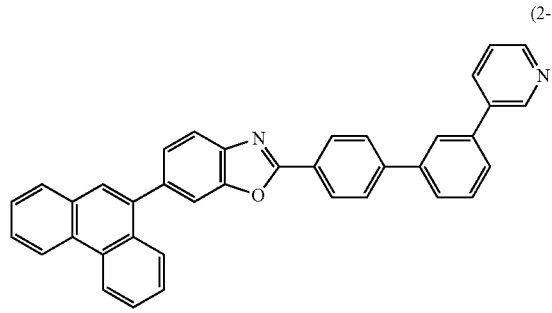
[Chemical Formula 315]
(2-98)
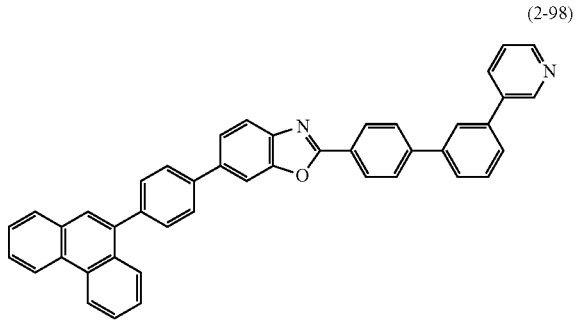
[Chemical Formula 316]
(2-99)
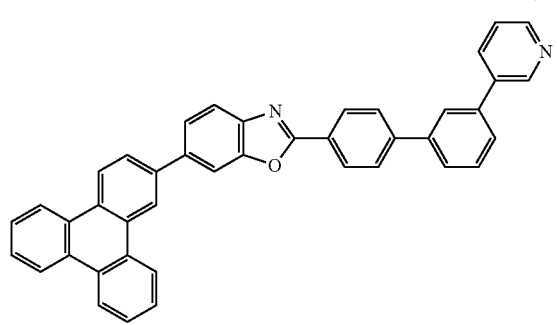
[Chemical Formula 317]
(2-100)
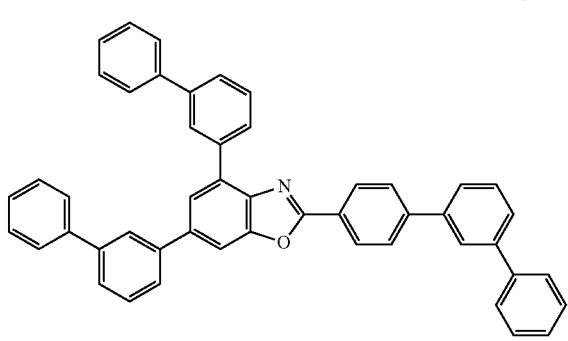
[Chemical Formula 318]
(2-101)
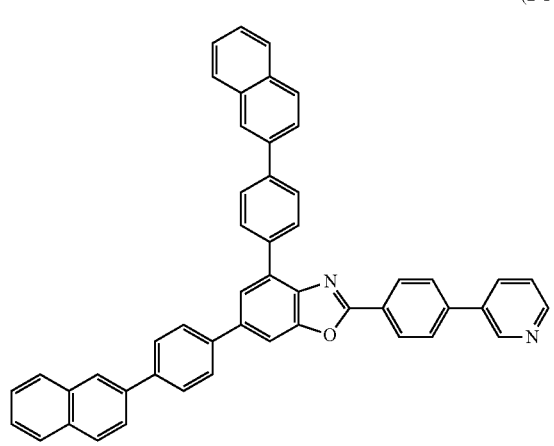
[Chemical Formula 319]
(2-102)
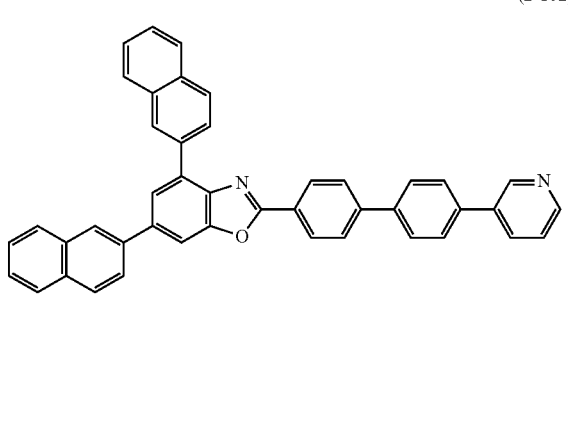

-continued
[Chemical Formula 320]
(2-103)
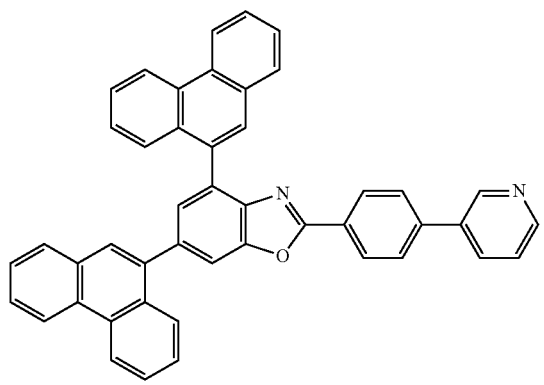
[Chemical Formula 321]
(2-104)
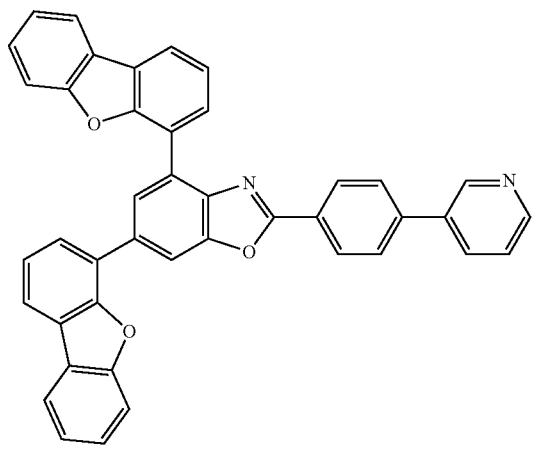
[Chemical Formula 322]
(2-105)
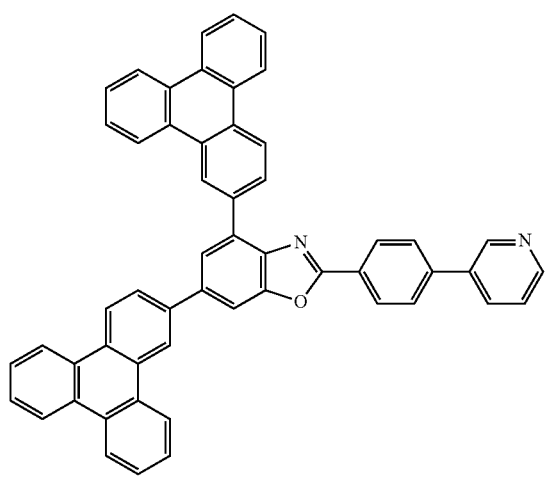
[Chemical Formula 323]
(2-106)
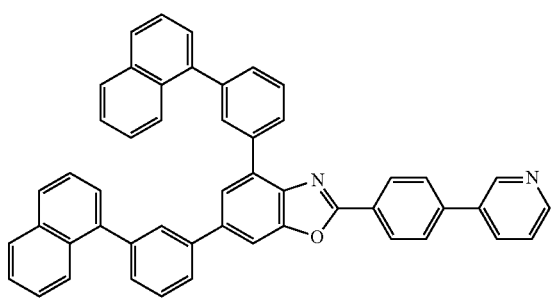
[Chemical Formula 324]
(2-107)
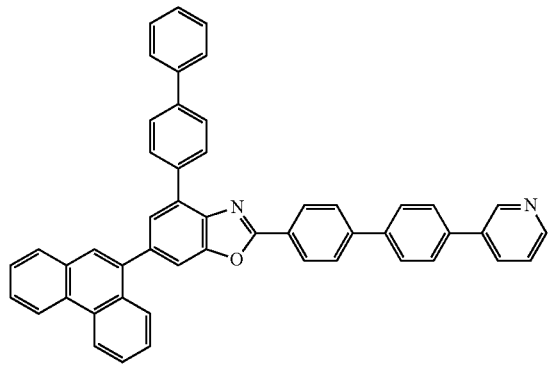
[Chemical Formula 325]
(2-108)
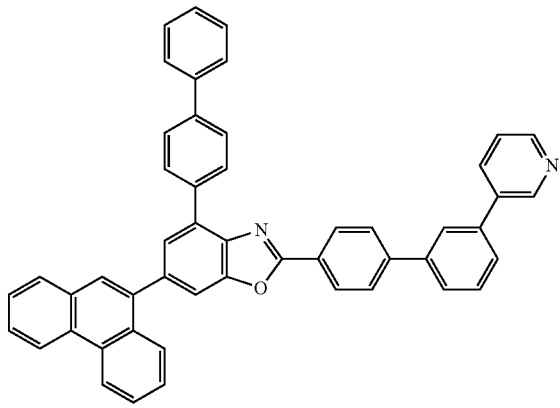

-continued
[Chemical Formula 326]
(2-109)
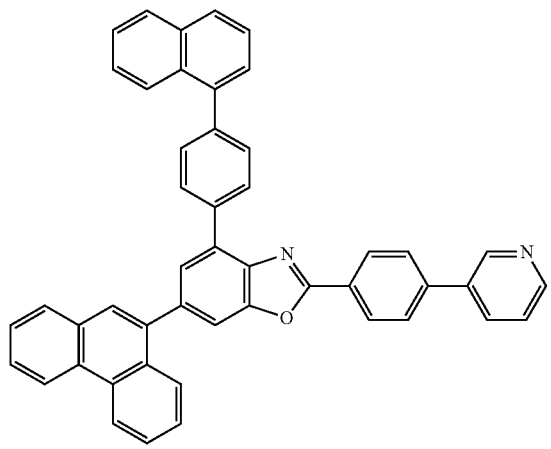
[Chemical Formula 327]
(2-110)
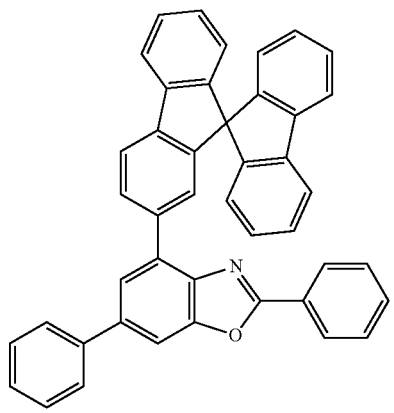
[Chemical Formula 328]
(2-111)
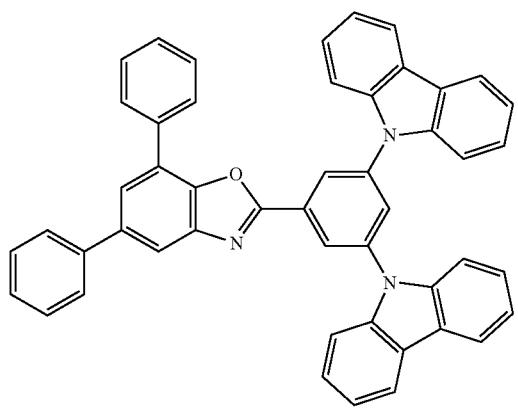
[Chemical Formula 329]
(2-112)
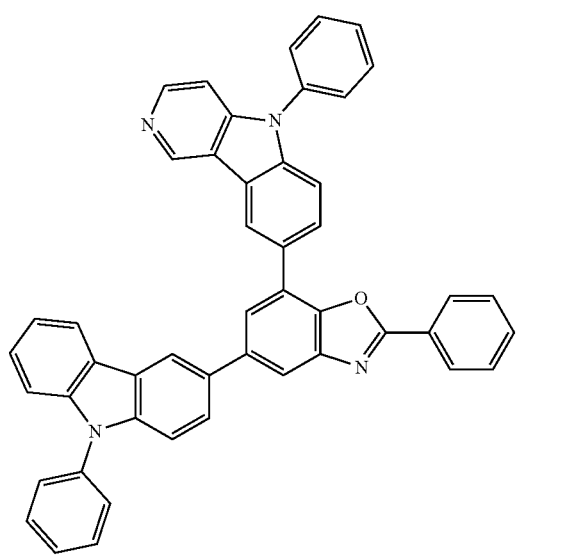
[Chemical Formula 330]
(2-113)
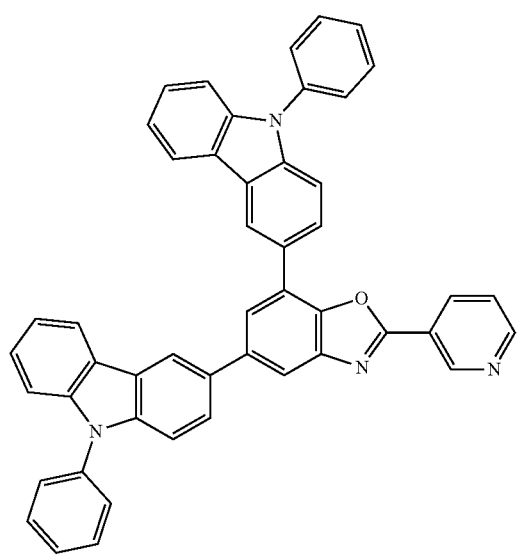
[Chemical Formula 331]
(2-114)

-continued
[Chemical Formula 332]
(2-115)
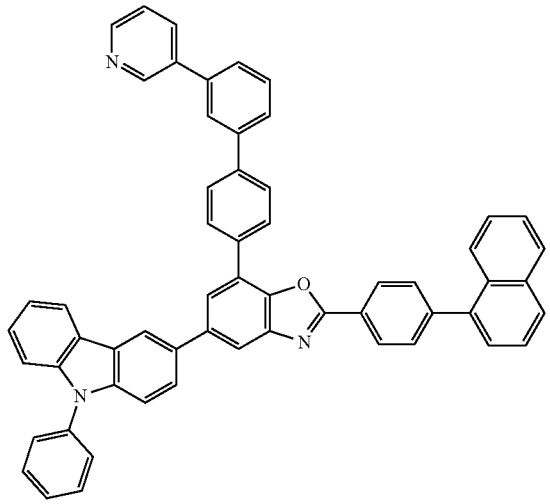
[Chemical Formula 333]
(2-116)
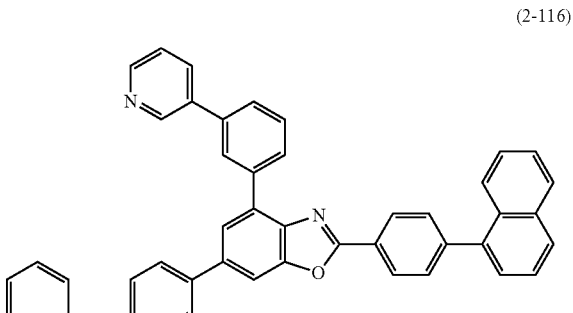
[Chemical Formula 334]
(2-117)
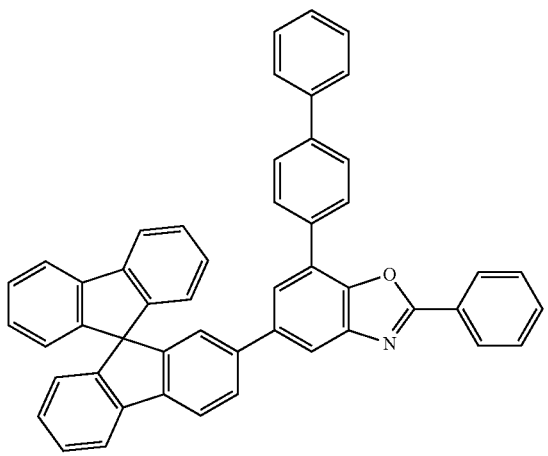
[Chemical Formula 335]
(2-118)
[Chemical Formula 336]
(2-119)
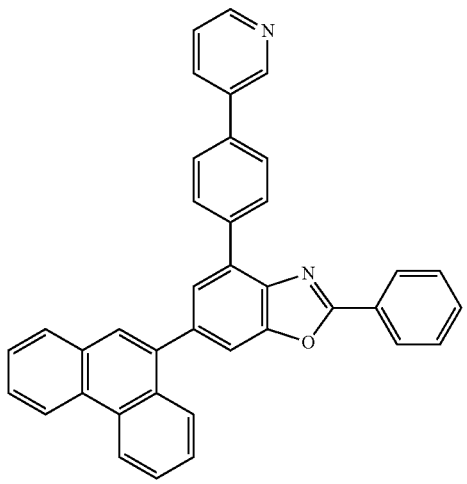
[Chemical Formula 337]
(2-120)
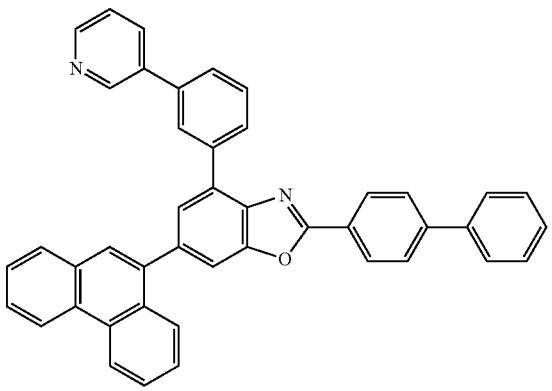

-continued
[Chemical Formula 338]
(2-121)
[Chemical Formula 339]
(2-122)
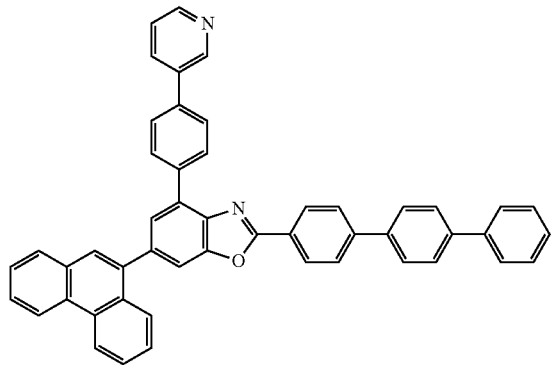
[Chemical Formula 340]
(2-123)
[Chemical Formula 341]
(2-124)
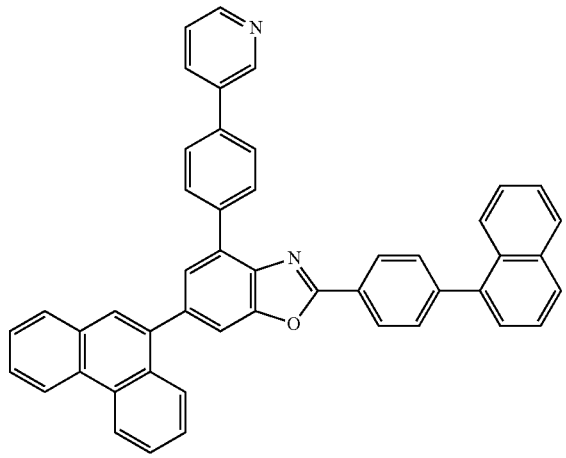
[Chemical Formula 342]
(2-125)
[Chemical Formula 343]
(2-126)
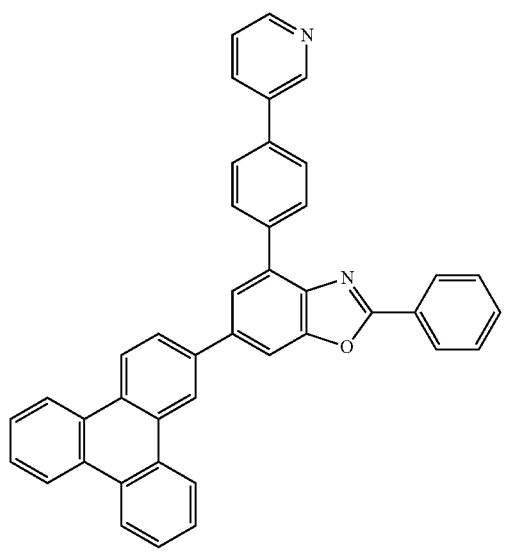
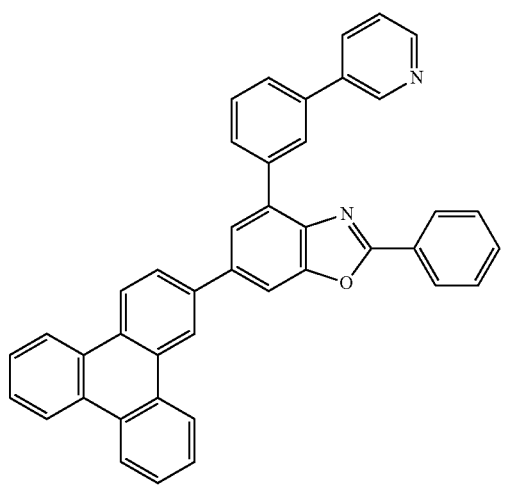

[Chemical Formula 344]
(2-127)
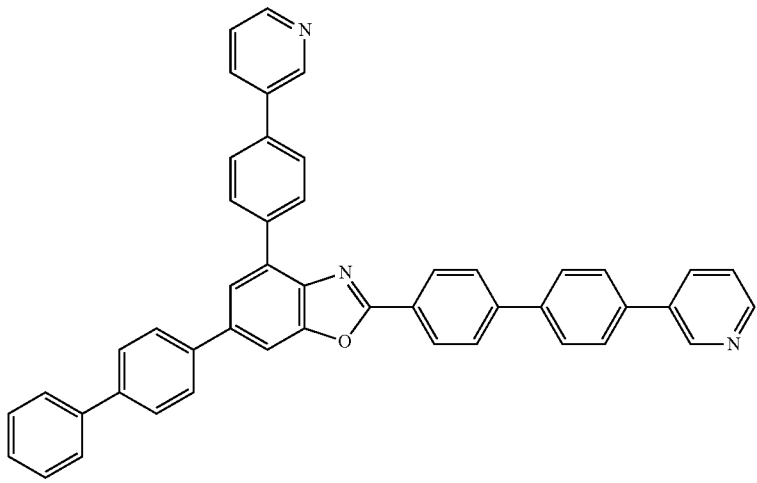
[Chemical Formula 345]
(2-128)
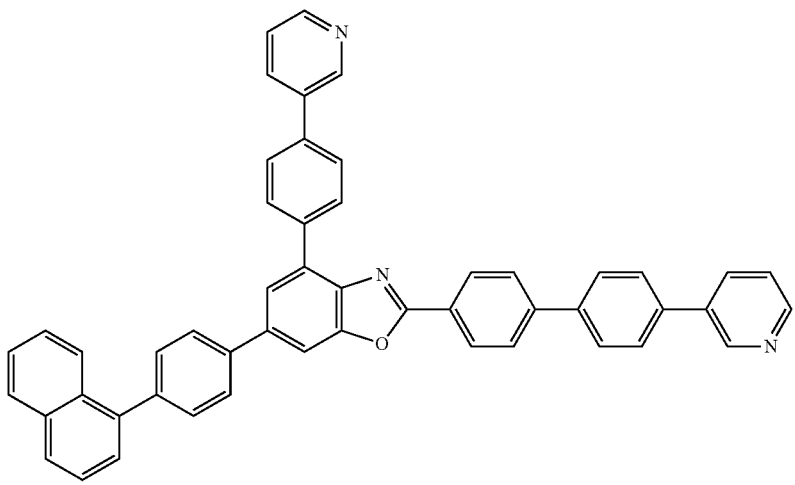
[Chemical Formula 346]
(2-129)
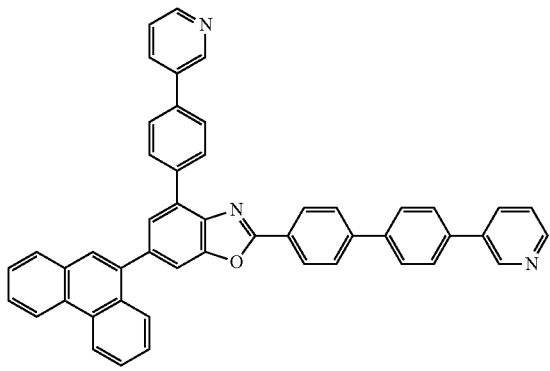
[Chemical Formula 347]
(2-130)
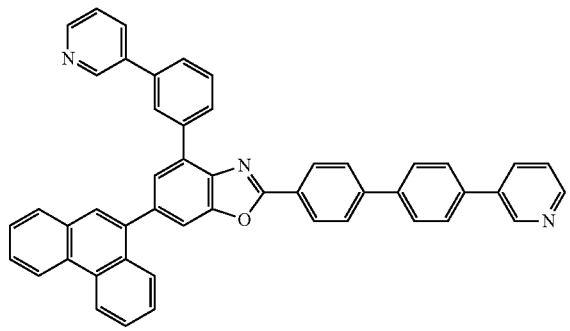

-continued
[Chemical Formula 348]
(2-131)
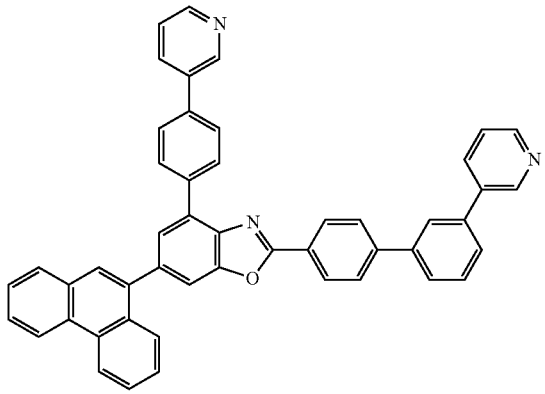
[Chemical Formula 349]
(2-132)
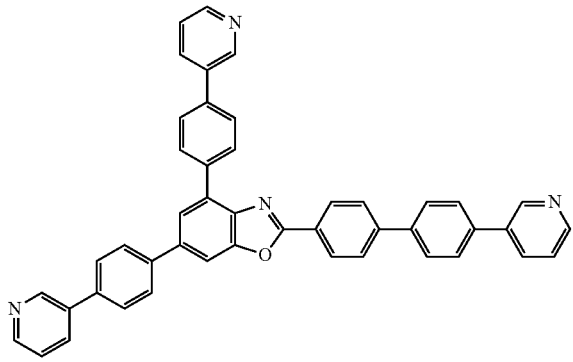
[Chemical Formula 350]
(2-133)
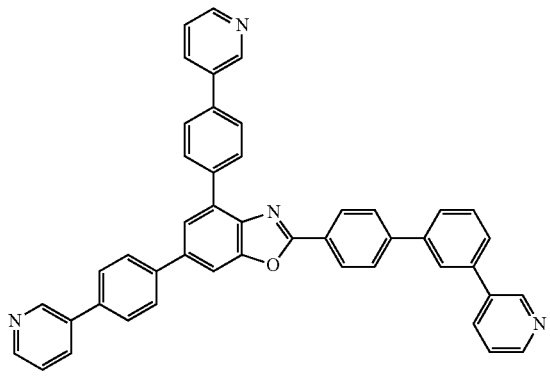
[Chemical Formula 351]
(2-134)
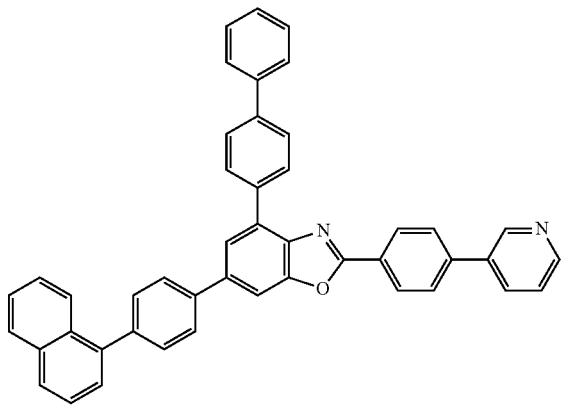
[Chemical Formula 352]
(2-135)
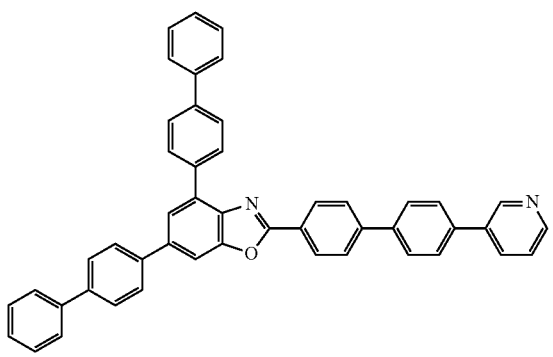
[Chemical Formula 353]
(2-136)
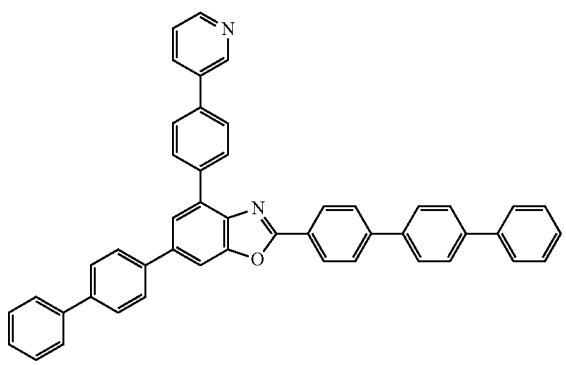

[Chemical Formula 354]

(2-137)

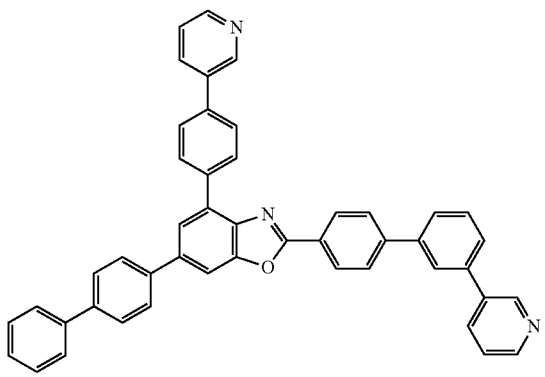

[Chemical Formula 355]

(2-138)

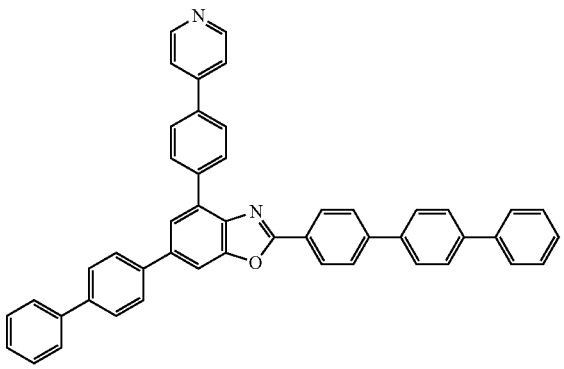

[Chemical Formula 356]

(2-139)

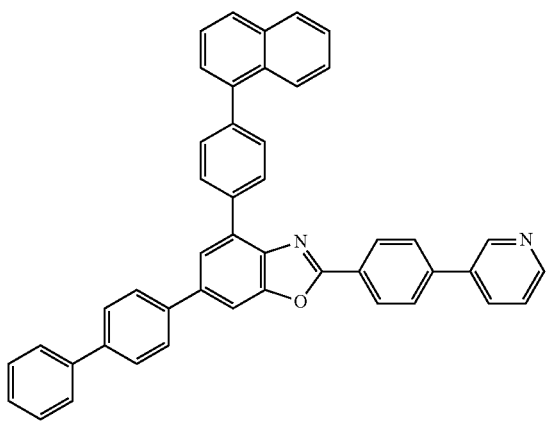

[Chemical Formula 357]

(2-140)

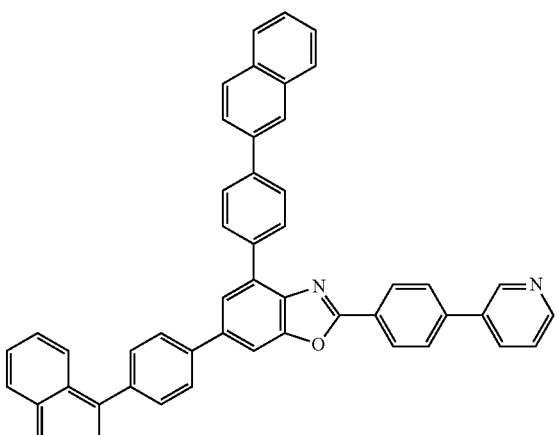

The following presents specific examples (X represents a sulfur atom) of preferred compounds among the compounds having a benzazole ring structure of the general formula (2) preferably used in the organic EL device of the present invention. The present invention, however, is not restricted to these compounds.

[Chemical Formula 358]

(3-1)

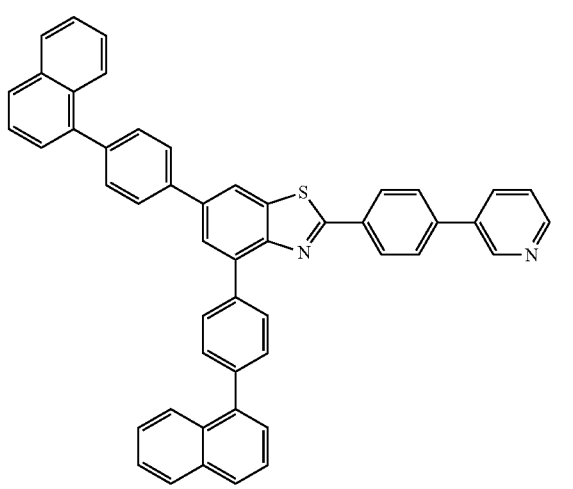

[Chemical Formula 359]
(3-2)
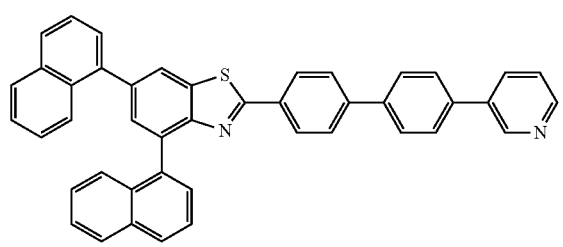
[Chemical Formula 360]
(3-3)
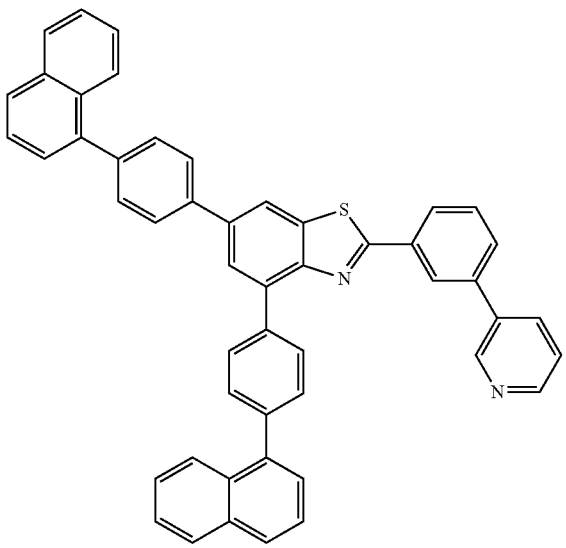
[Chemical Formula 361]
(3-4)
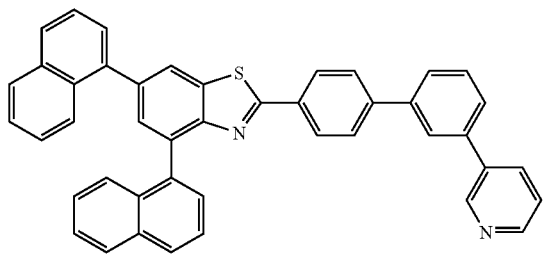
[Chemical Formula 362]
(3-5)
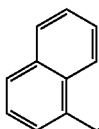
[Chemical Formula 363]
(3-6)
[Chemical Formula 364]
(3-7)

[Chemical Formula 365]
(3-8)
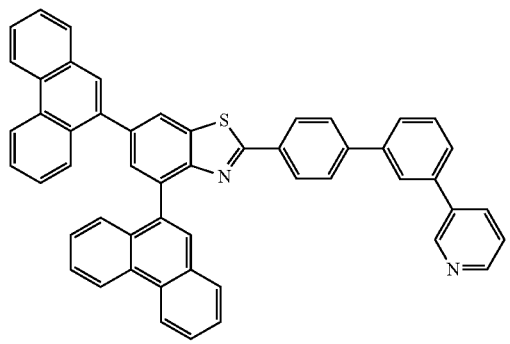
[Chemical Formula 366]
(3-9)
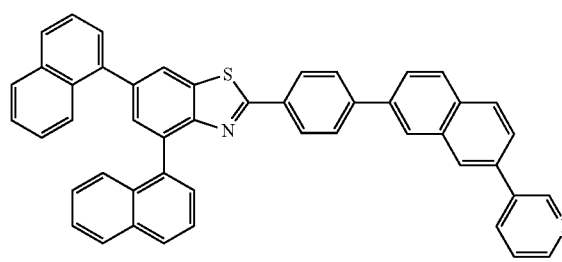
[Chemical Formula 367]
(3-10)
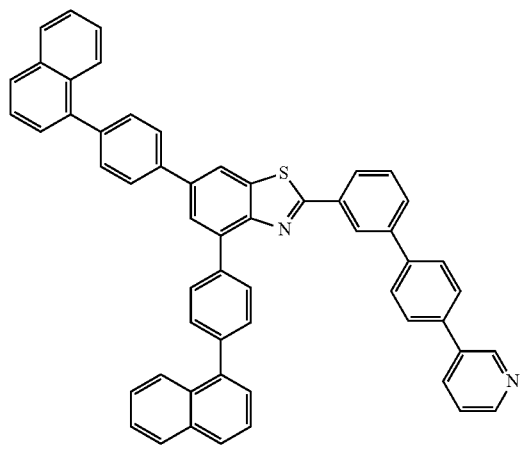
[Chemical Formula 368]
(3-11)
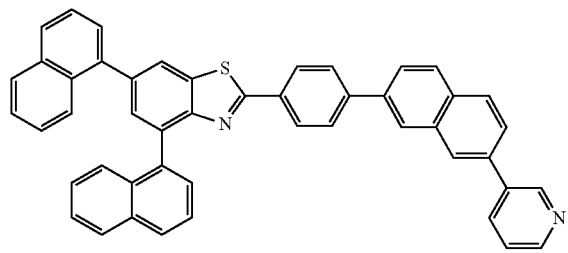
[Chemical Formula 369]
(3-12)
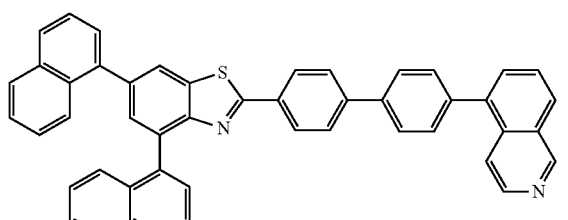
[Chemical Formula 370]
(3-13)
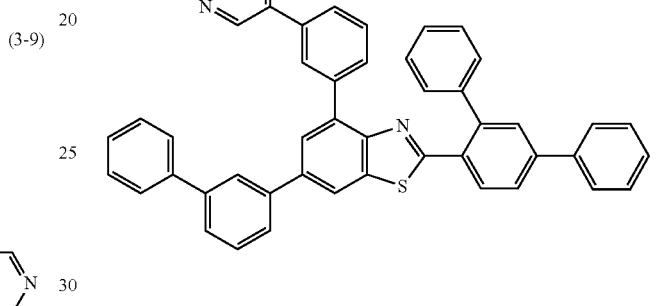
[Chemical Formula 371]
(3-14)
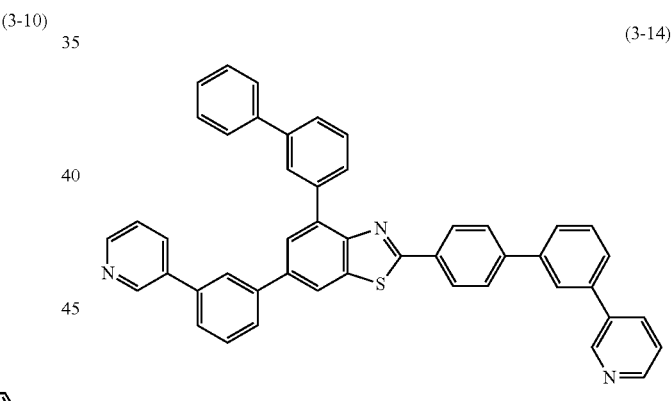
[Chemical Formula 372]
(3-15)
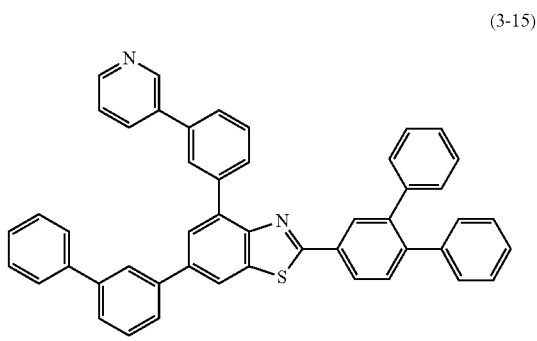

[Chemical Formula 373]
(3-16)
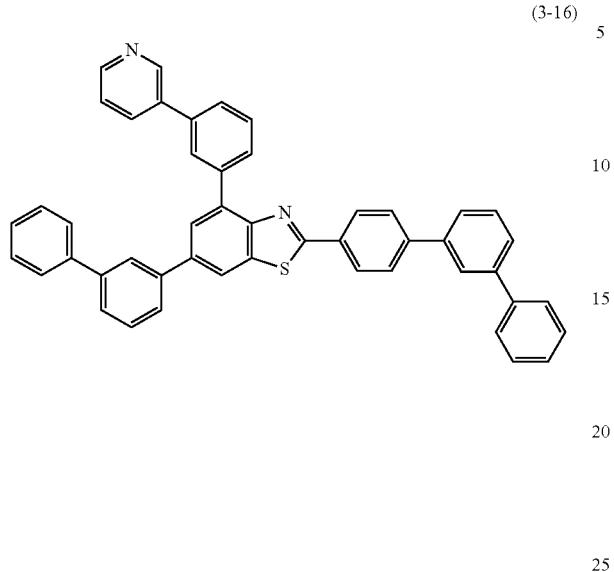
[Chemical Formula 374]
(3-17)
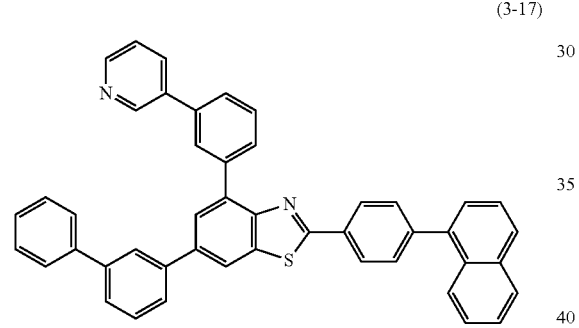
[Chemical Formula 375]
(3-18)
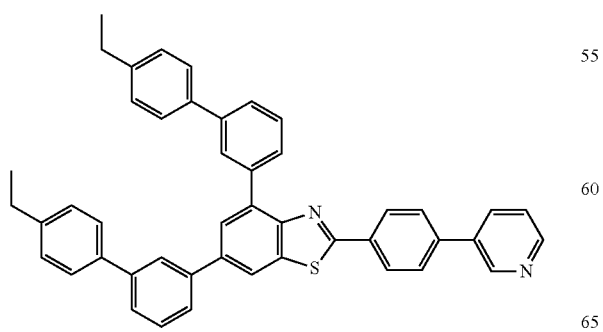
[Chemical Formula 376]
(3-19)
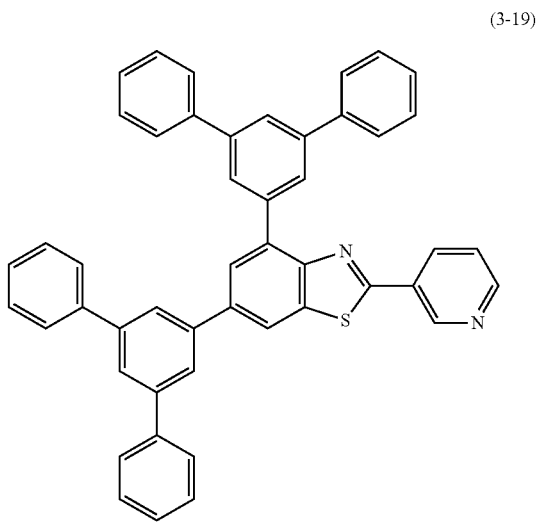
[Chemical Formula 377]
(3-20)
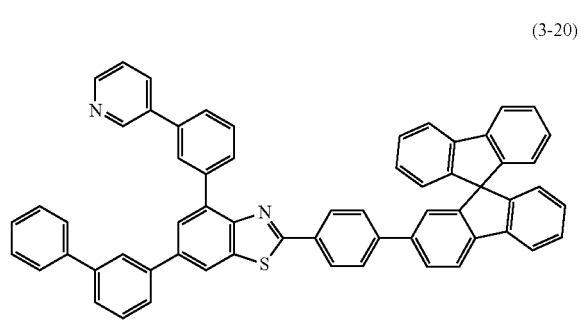
[Chemical Formula 378]
(3-21)
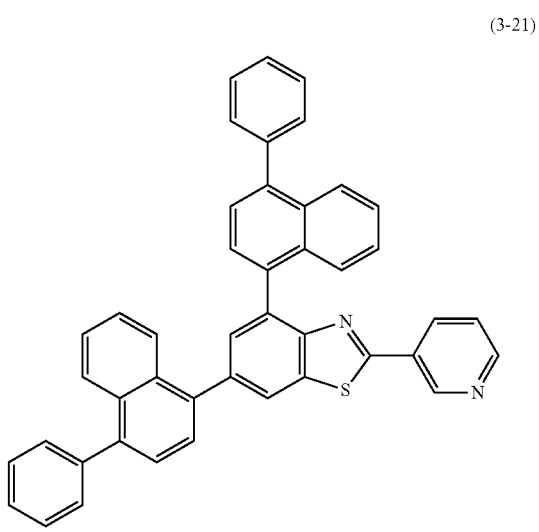

-continued
[Chemical Formula 379]
(3-22)
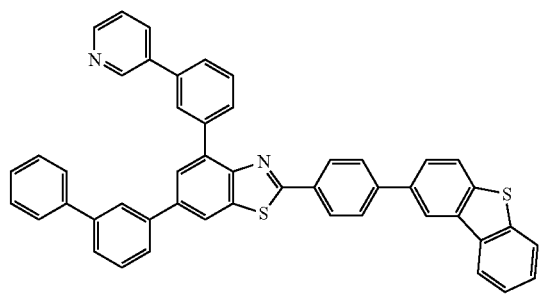
[Chemical Formula 380]
(3-23)
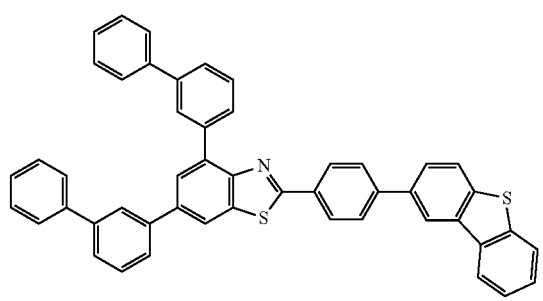
[Chemical Formula 381]
(3-24)
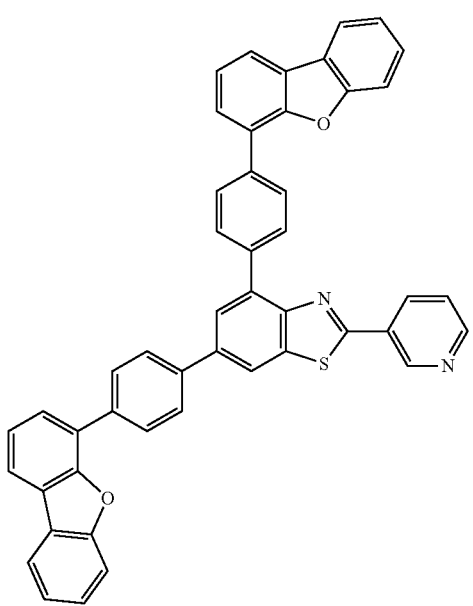
-continued
[Chemical Formula 382]
(3-25)
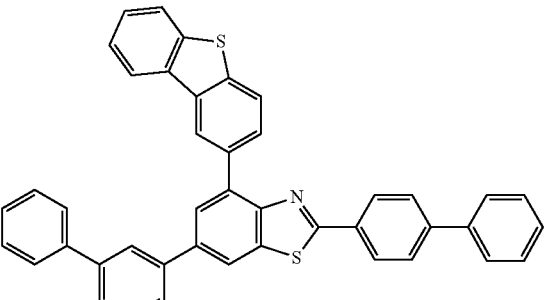
[Chemical Formula 383]
(3-26)
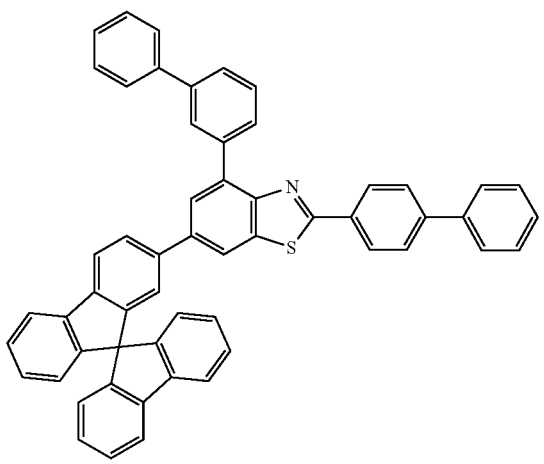
[Chemical Formula 384]
(3-27)
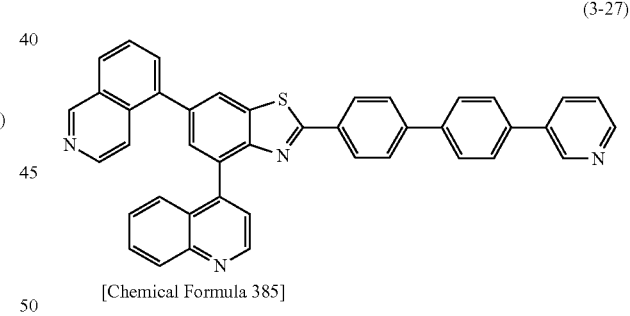
[Chemical Formula 385]
(3-28)
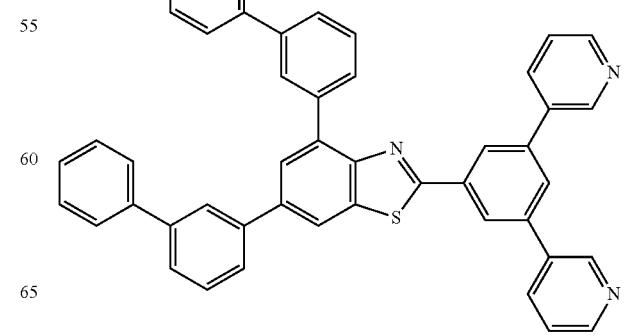

[Chemical Formula 386]
(3-29)
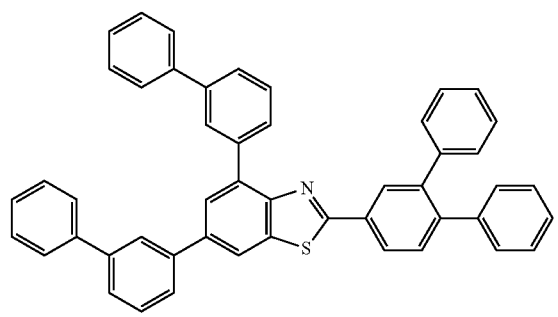
[Chemical Formula 387]
(3-30)
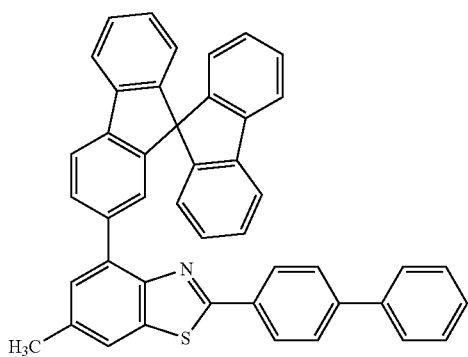
[Chemical Formula 388]
(3-31)
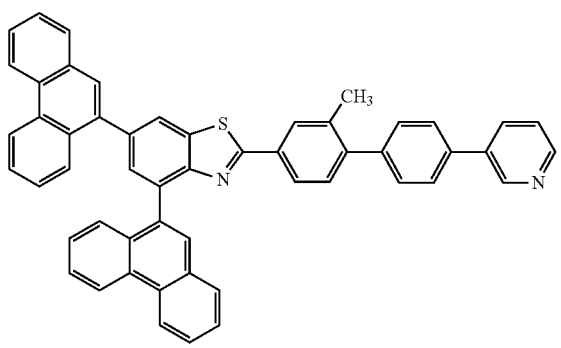
[Chemical Formula 389]
(3-32)
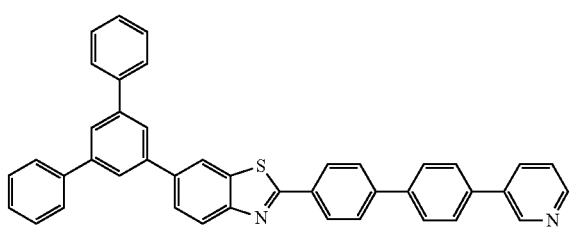
[Chemical Formula 390]
(3-33)
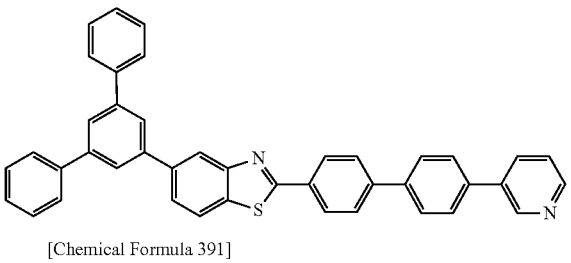
[Chemical Formula 391]
(3-34)
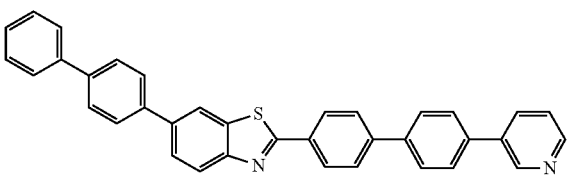
[Chemical Formula 392]
(3-35)
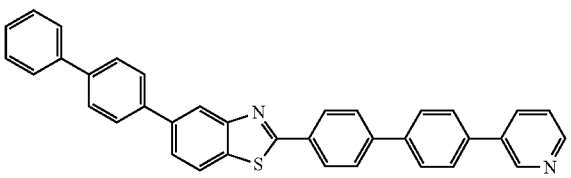
[Chemical Formula 393]
(3-36)
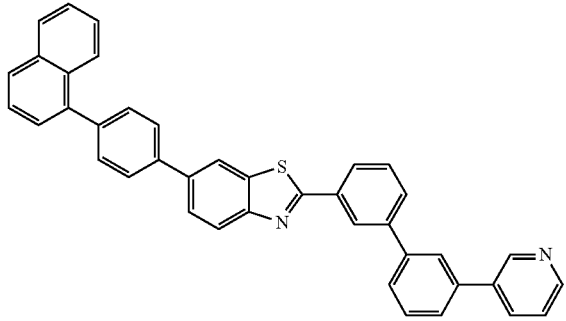
[Chemical Formula 394]
(3-37)
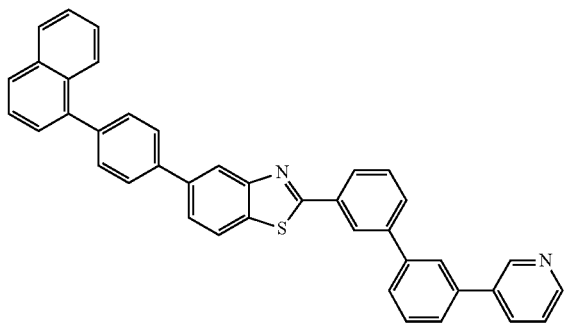

[Chemical Formula 395]
(3-38)
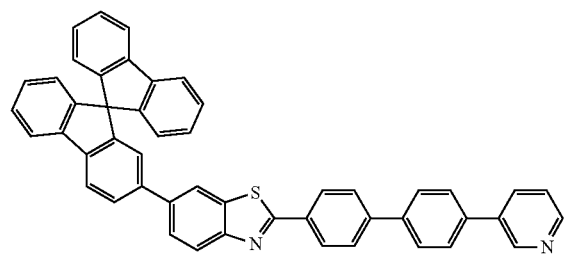
[Chemical Formula 396]
(3-39)
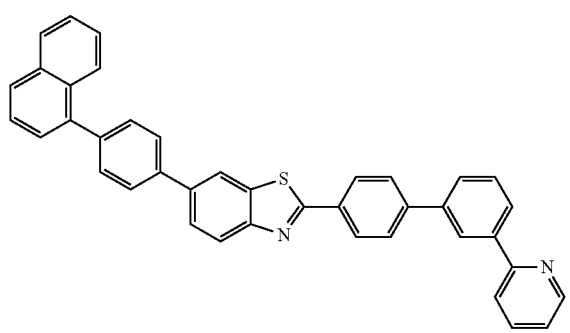
[Chemical Formula 397]
(3-40)
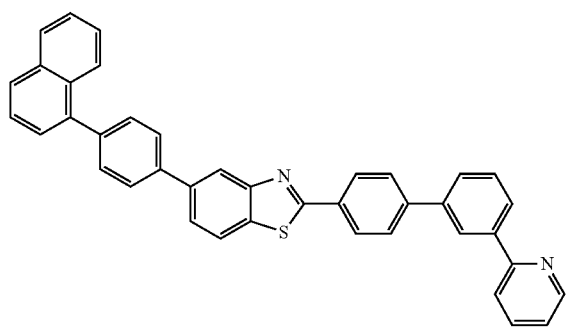
[Chemical Formula 398]
(3-41)
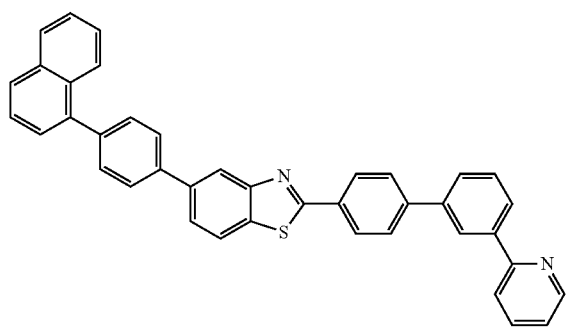
[Chemical Formula 399]
(3-42)
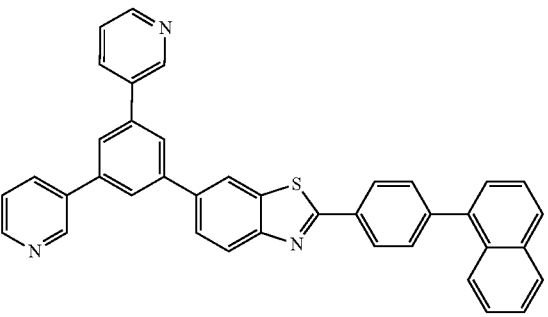
[Chemical Formula 400]
(3-43)
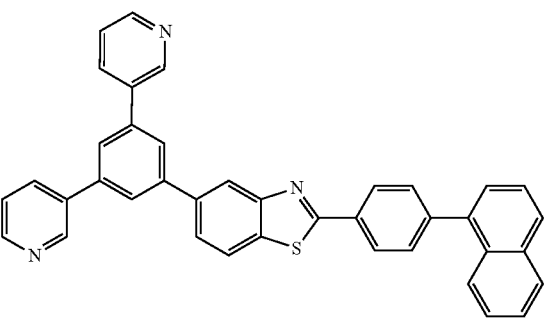
[Chemical Formula 401]
(3-44)
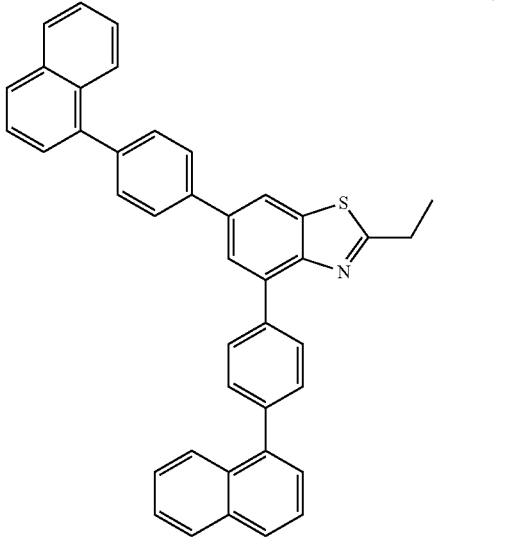
[Chemical Formula 402]
(3-45)
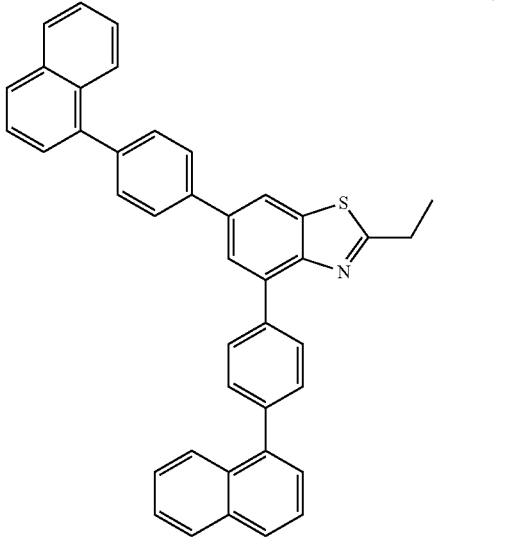

[Chemical Formula 403]
(3-46)
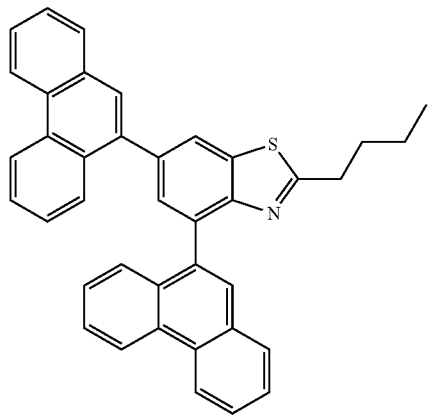
[Chemical Formula 404]
(3-47)
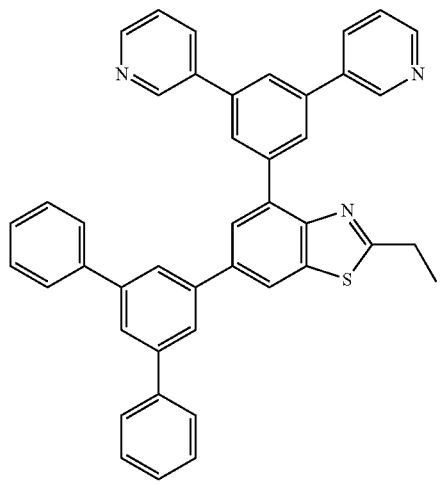
[Chemical Formula 405]
(3-48)
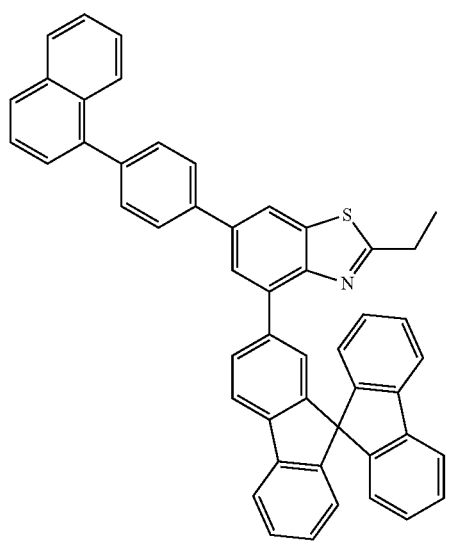
[Chemical Formula 406]
(3-49)
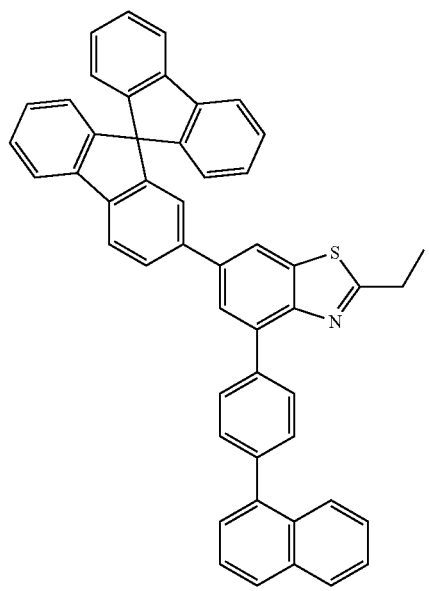
[Chemical Formula 407]
(3-50)
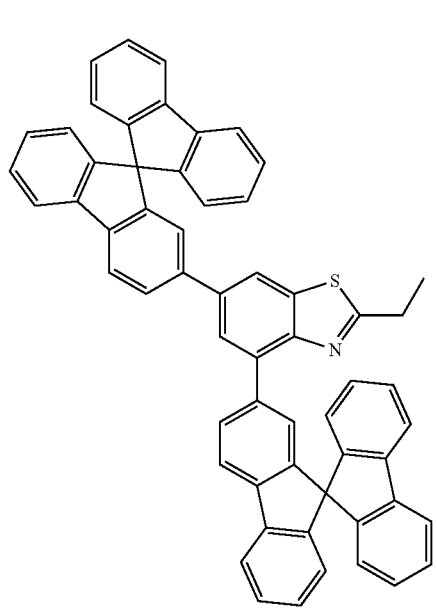

[Chemical Formula 408]
(3-51)
[Chemical Formula 410]
(3-53)
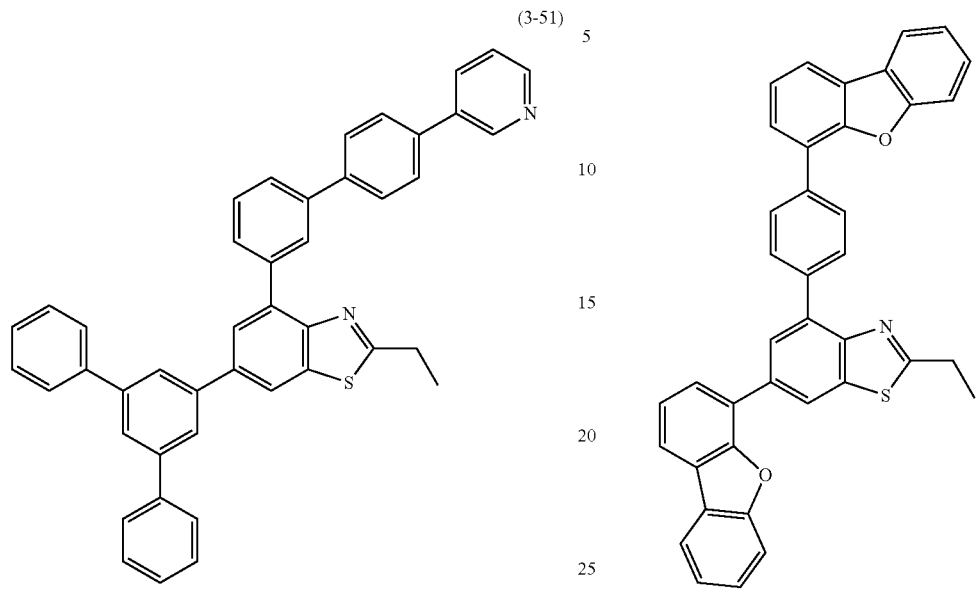
[Chemical Formula 409]
(3-52)
[Chemical Formula 411]
(3-54)

[Chemical Formula 412]
(3-55)
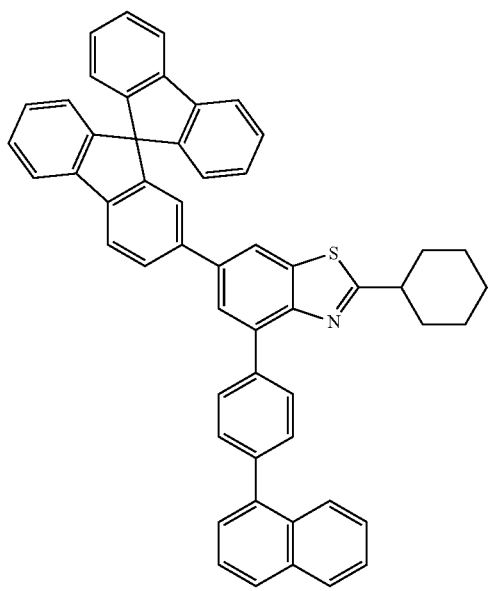
[Chemical Formula 413]
(3-56)
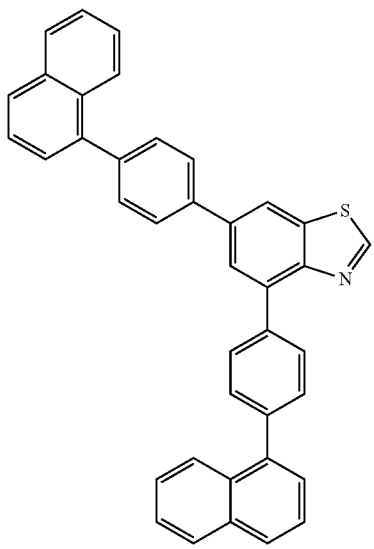
[Chemical Formula 414]
(3-57)
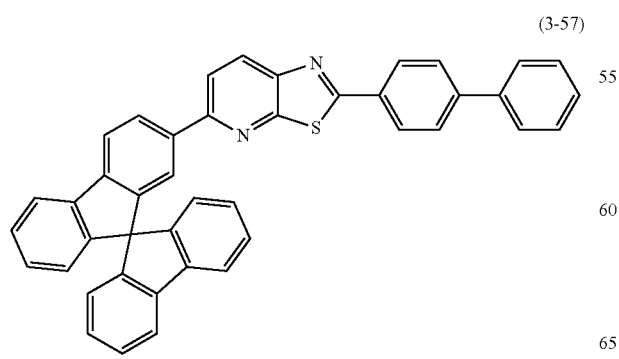
[Chemical Formula 415]
(3-58)
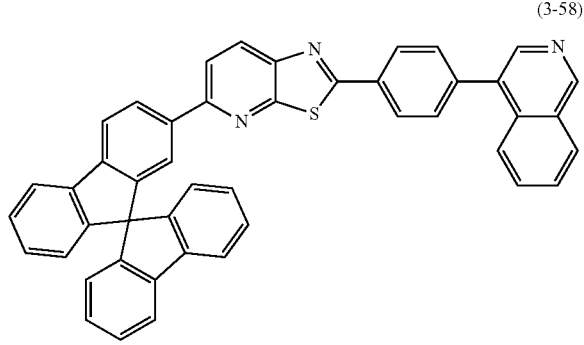
[Chemical Formula 416]
(3-59)
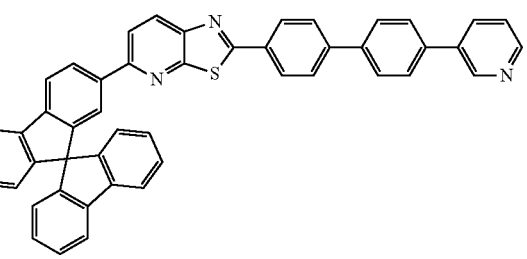
[Chemical Formula 417]
(3-60)
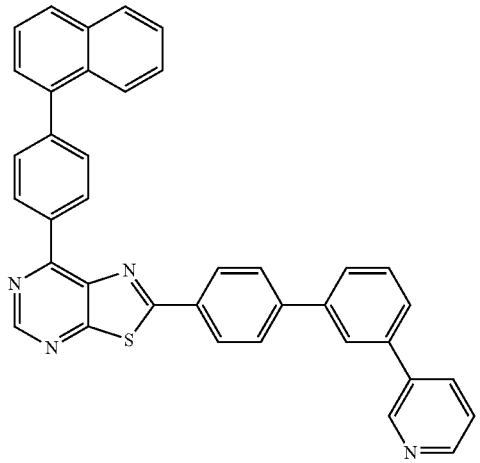

[Chemical Formula 418]

(3-61)

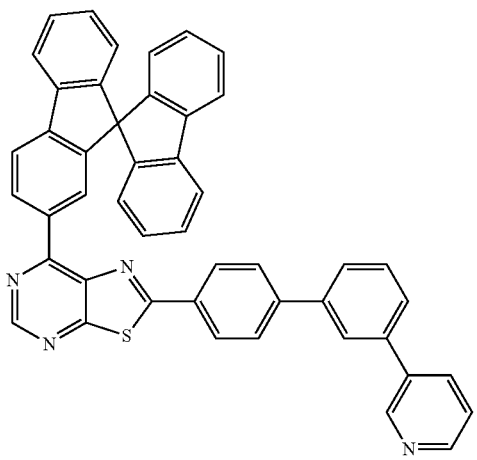

[Chemical Formula 419]

(3-62)

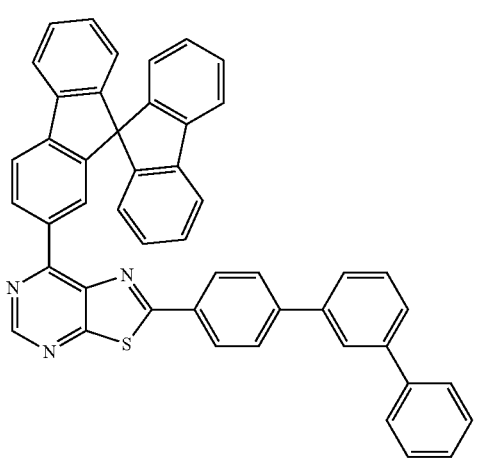

[Chemical Formula 420]

(3-63)

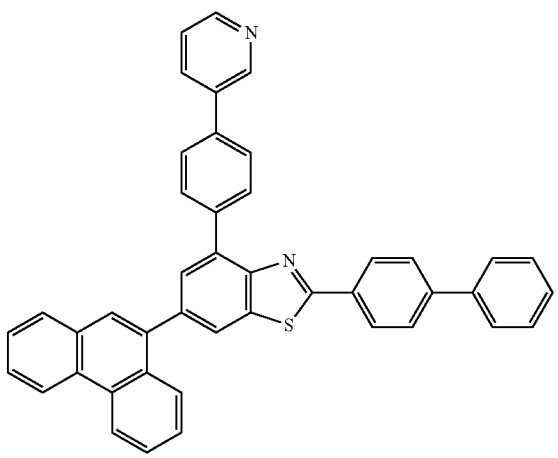

Among the arylamine compounds having a structure in which two triarylamine structures are joined within a molecule via a single bond or a divalent group that does not contain a hetero atom preferably used in the organic EL device of the present invention, an arylamine compound having a structure in which two triarylamine structures are joined within a molecule via a single bond or a divalent group that does not contain a hetero atom represented by the general formula (4) is more preferably used. The following presents specific examples of preferred compounds among the arylamine compounds having a structure in which two triarylamine structures are joined within a molecule via a single bond or a divalent group that does not contain a hetero atom represented by the general formula (4) preferably used in the organic EL device of the present invention. The present invention, however, is not restricted to these compounds.

[Chemical Formula 421]

(4-1)

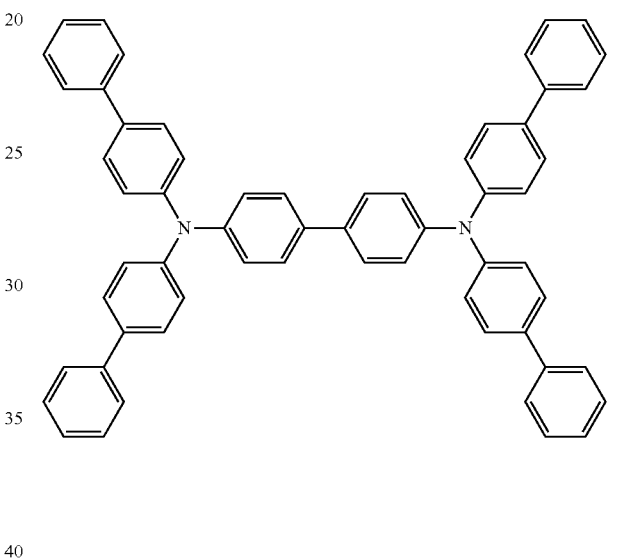

[Chemical Formula 422]

(4-2)

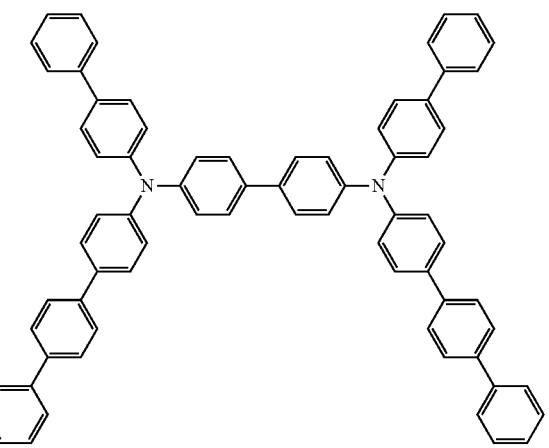

[Chemical Formula 423]
(4-3)
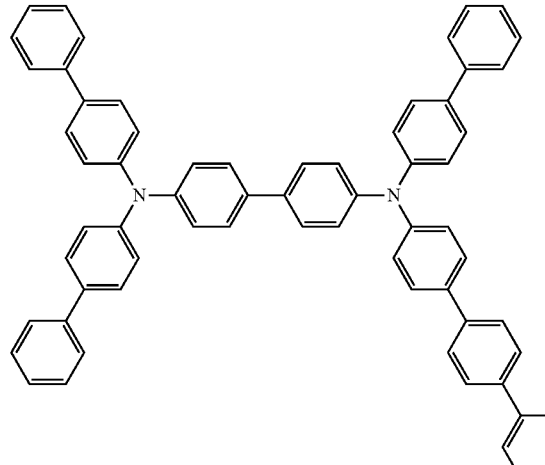
[Chemical Formula 424]
(4-4)
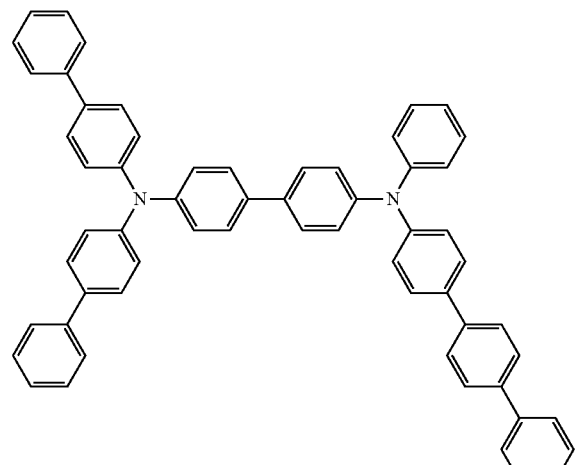
[Chemical Formula 425]
(4-5)
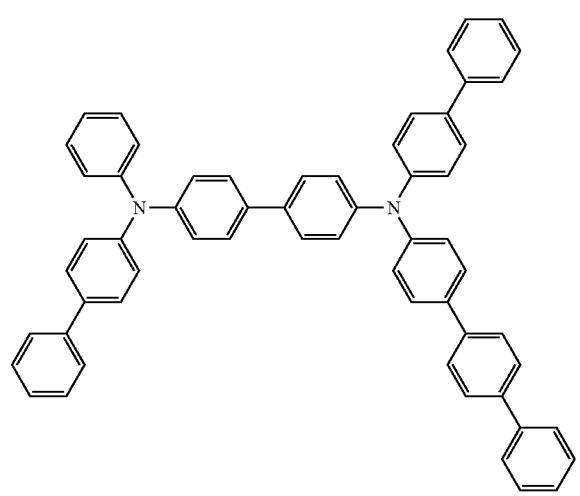
[Chemical Formula 426]
(4-6)
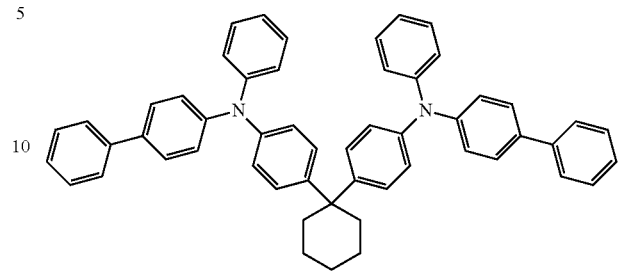
[Chemical Formula 427]
(4-7)
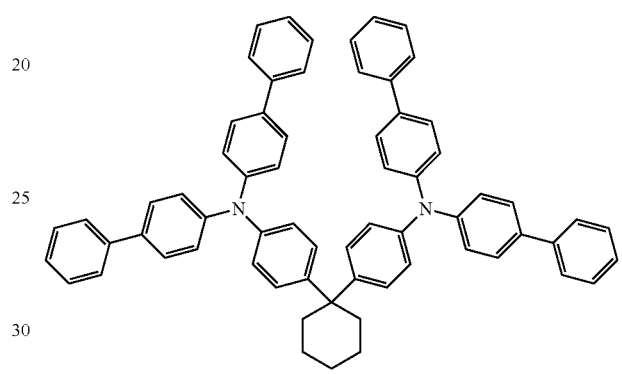
[Chemical Formula 428]
(4-8)
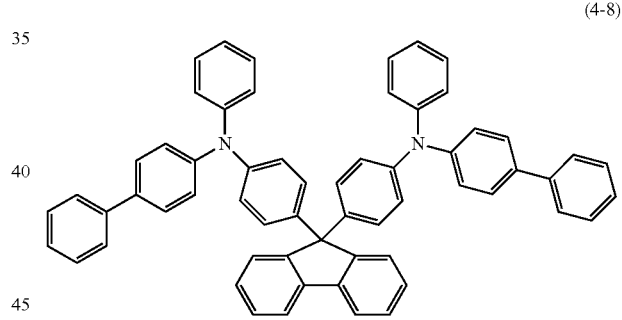
[Chemical Formula 429]
(4-9)
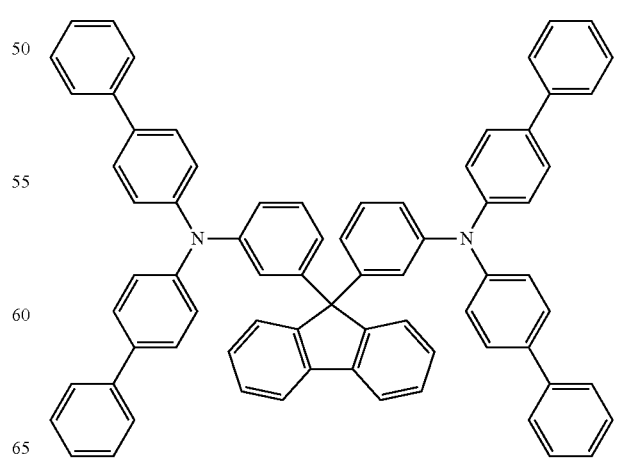

[Chemical Formula 430]
(4-10)
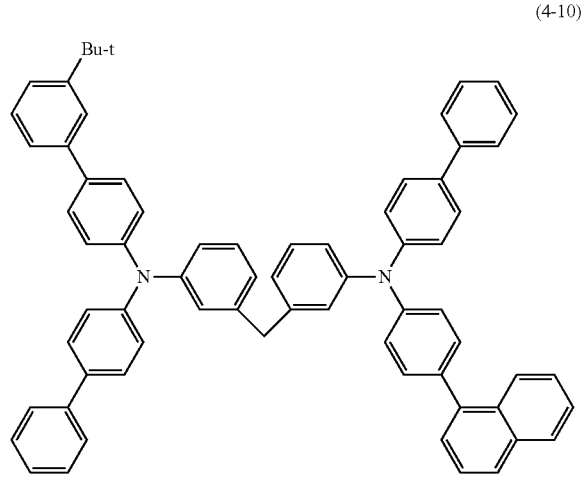
[Chemical Formula 431]
(4-11)
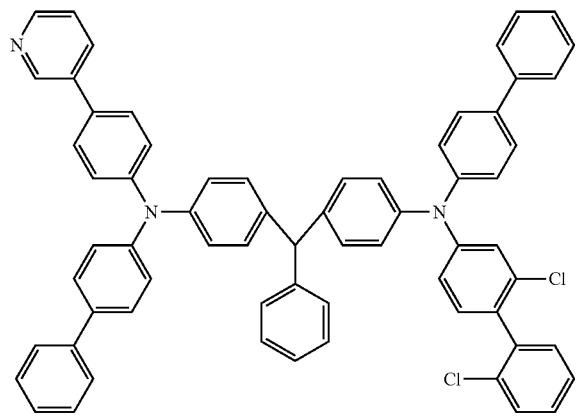
[Chemical Formula 432]
(4-12)
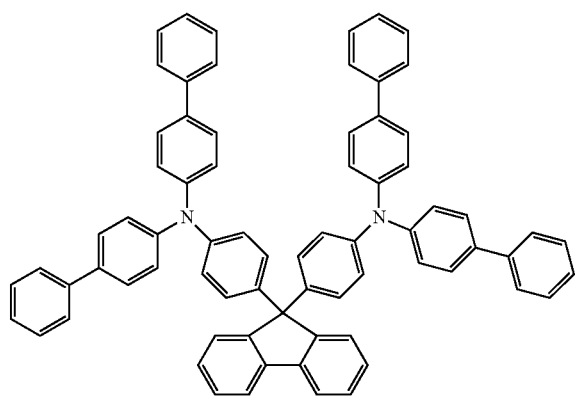
[Chemical Formula 433]
(4-13)
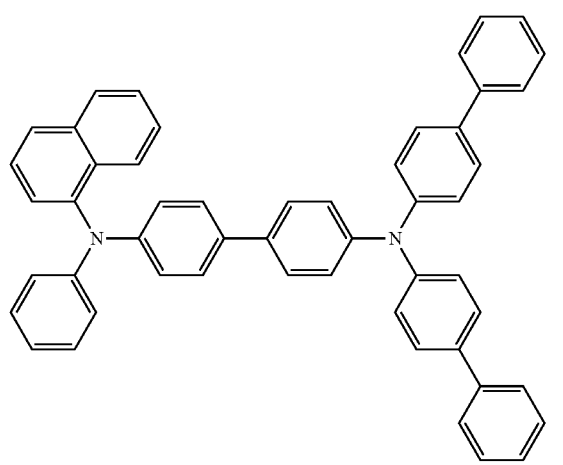
[Chemical Formula 434]
(4-14)
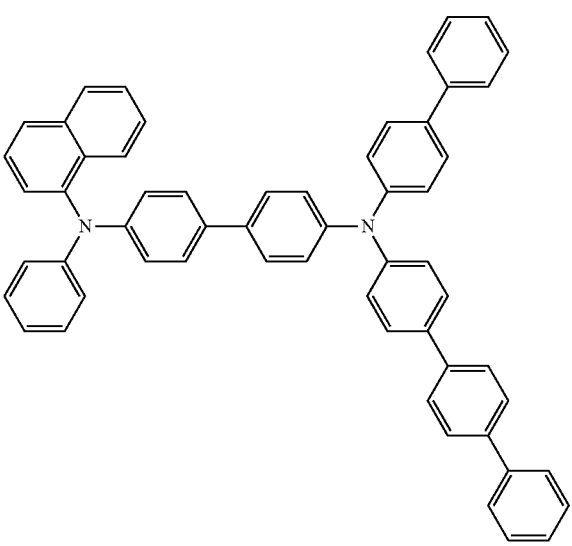
[Chemical Formula 435]
(4-15)
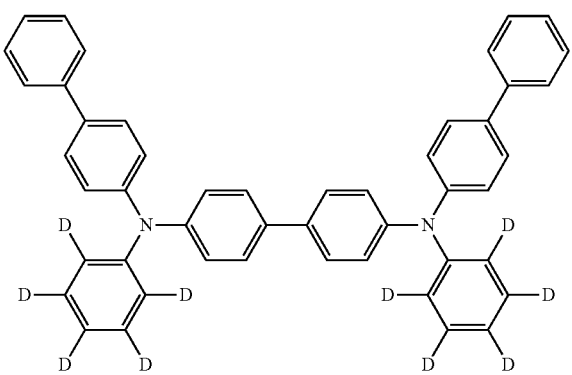

[Chemical Formula 436]
(4-16)
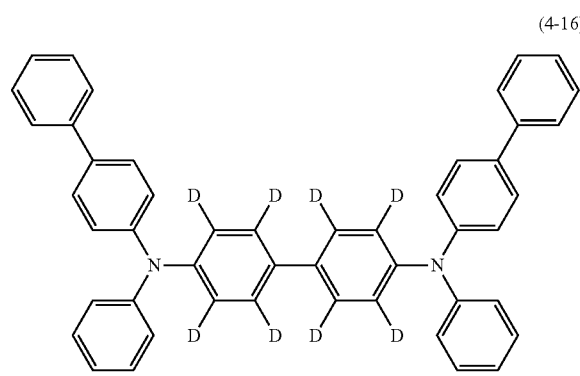
[Chemical Formula 437]
(4-17)
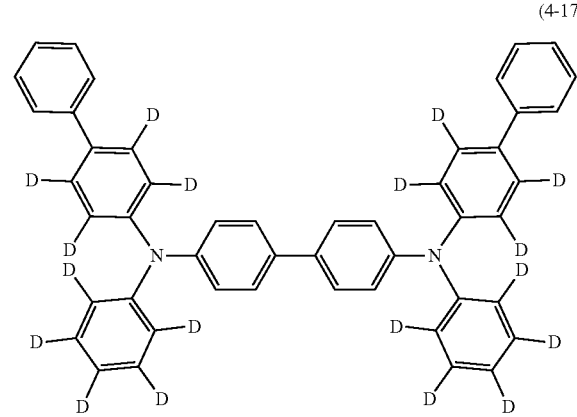
[Chemical Formula 438]
(4-18)
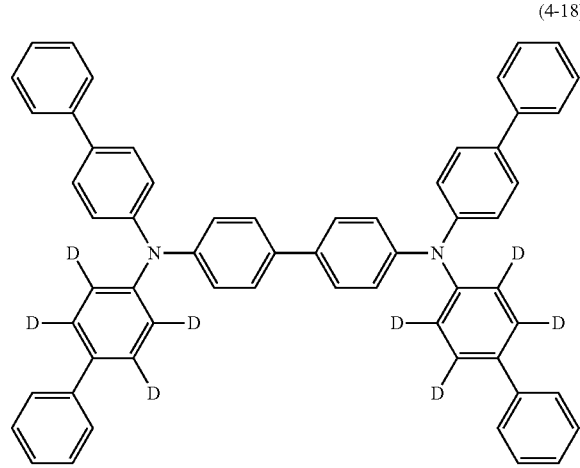
[Chemical Formula 439]
(4-19)
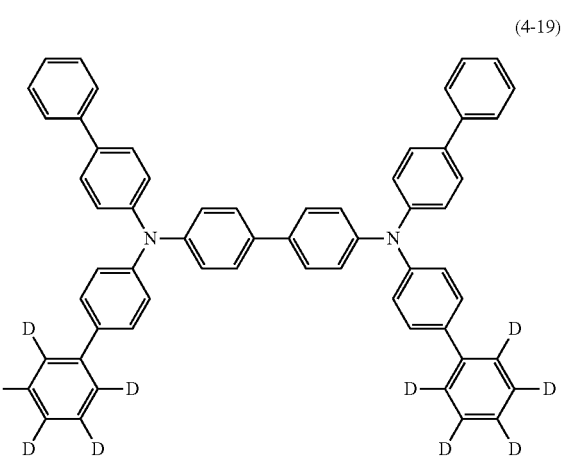
[Chemical Formula 440]
(4-20)
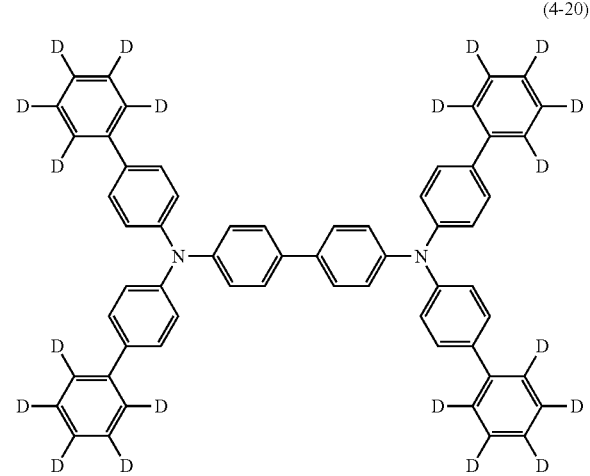
[Chemical Formula 441]
(4-21)
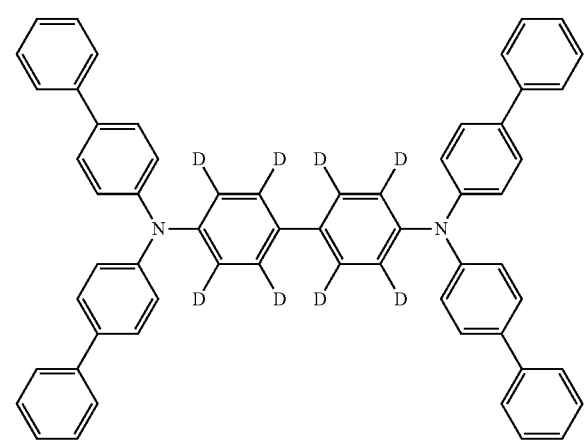

[Chemical Formula 442]

(4-22)

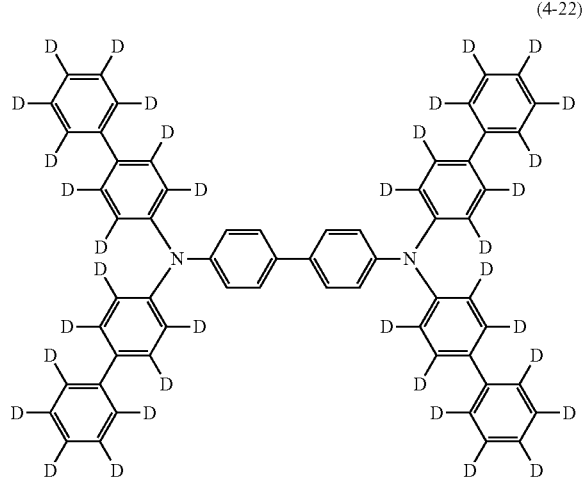

[Chemical Formula 443]

(4-23)

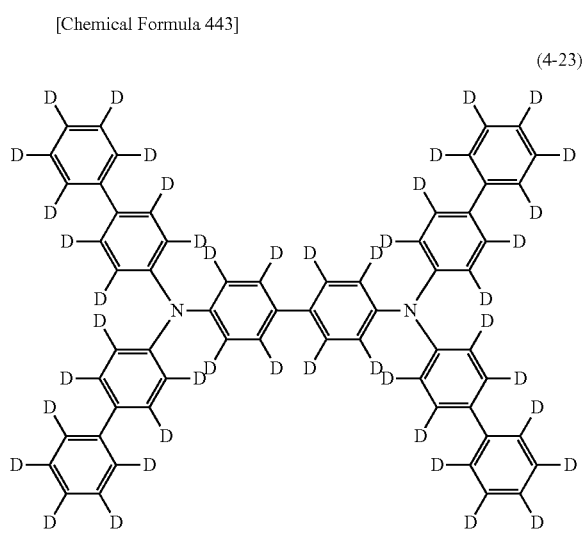

The following presents specific examples of preferred compounds among the arylamine compounds having a structure in which two triarylamine structures are joined within a molecule via a single bond or a divalent group that does not contain a hetero atom preferably used in the organic EL device of the present invention, in addition to the arylamine compounds having a structure in which two triarylamine structures are joined within a molecule via a single bond or a divalent group that does not contain a hetero atom of the general formula (4). The present invention, however, is not restricted to these compounds.

[Chemical Formula 444]

(4'-1)

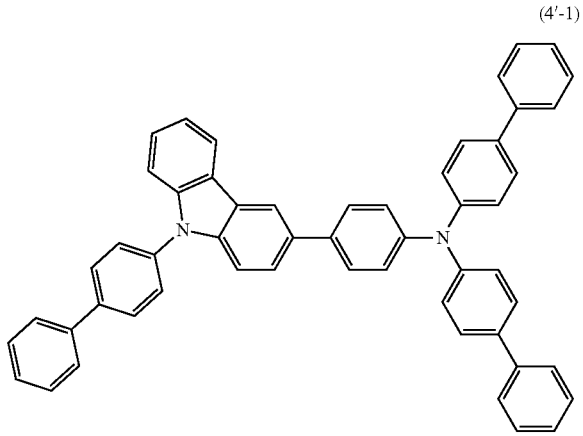

[Chemical Formula 445]

(4'-2)

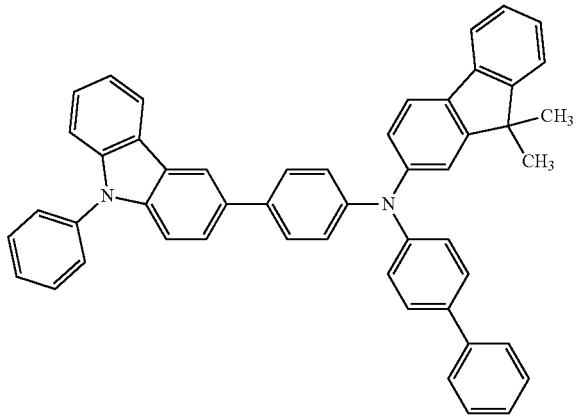

Among the arylamine compounds having a structure in which three to six triarylamine structures are joined within a molecule via a single bond or a divalent group that does not contain a hetero atom preferably used in the organic EL device of the present invention, an arylamine compound having a structure in which four triarylamine structures are joined within a molecule via a single bond or a divalent group that does not contain a hetero atom represented by the general formula (5), is more preferably used. The following presents specific examples of preferred compounds among the arylamine compounds having a structure in which four triarylamine structures are joined within a molecule via a single bond or a divalent group that does not contain a hetero atom of the general formula (5) preferably used in the organic EL device of the present invention. The present invention, however, is not restricted to these compounds.

[Chemical Formula 446]
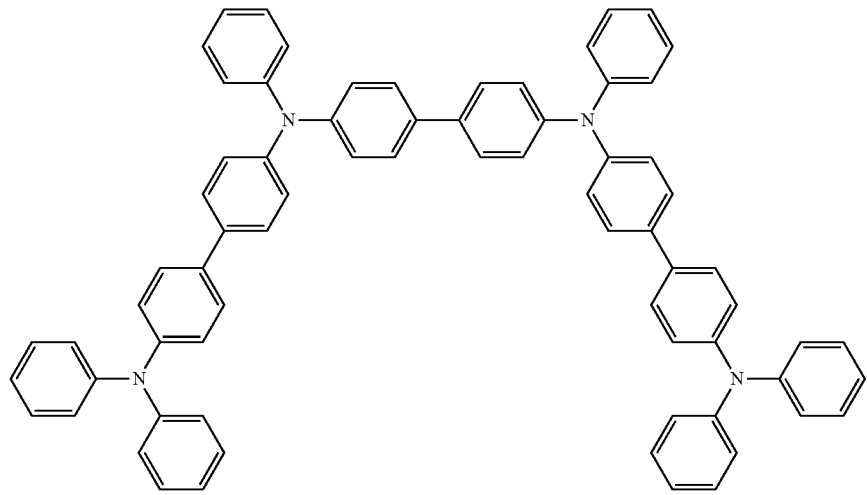
(5-1)
[Chemical Formula 447]
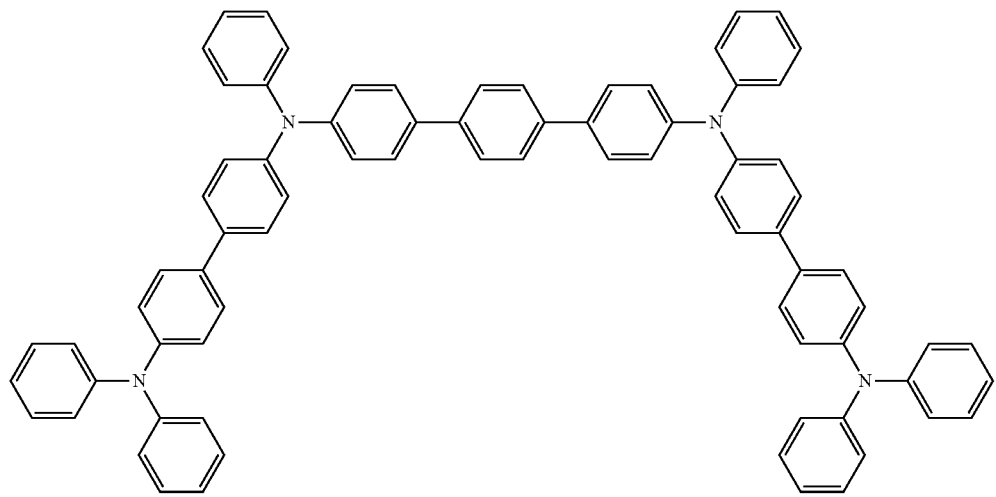
(5-2)

[Chemical Formula 448]
(5-3)
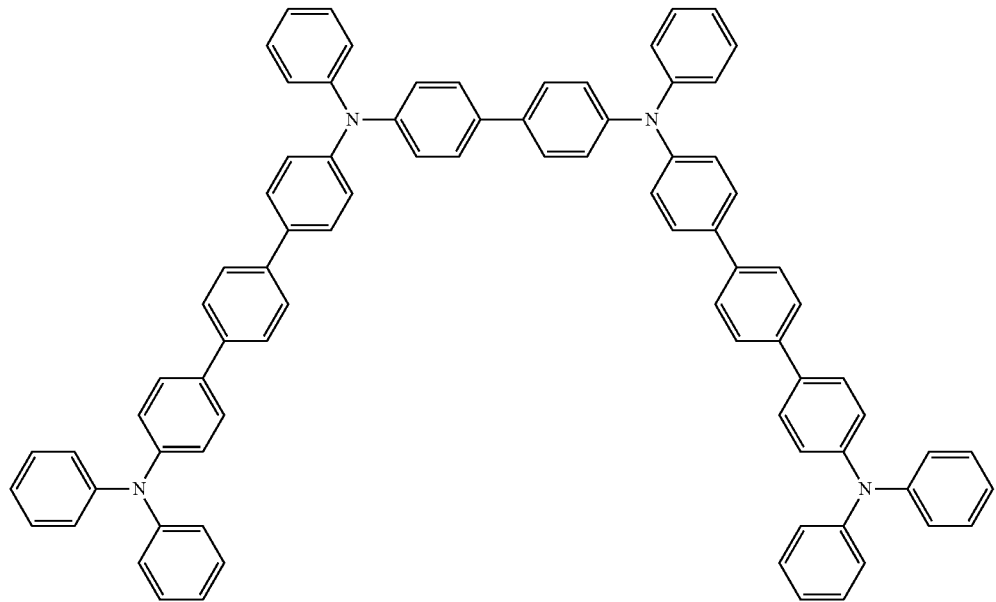
[Chemical Formula 449]
(5-4)
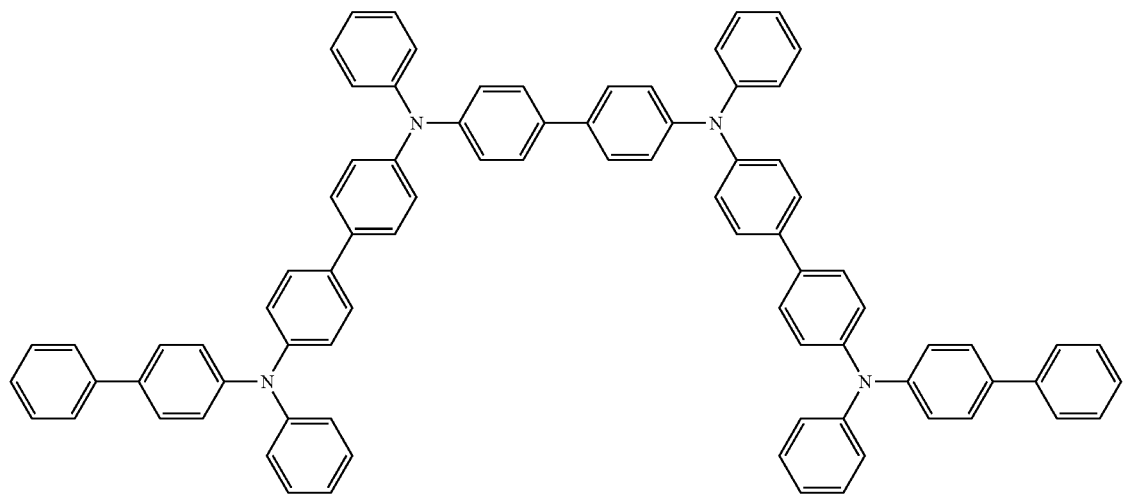

[Chemical Formula 450]
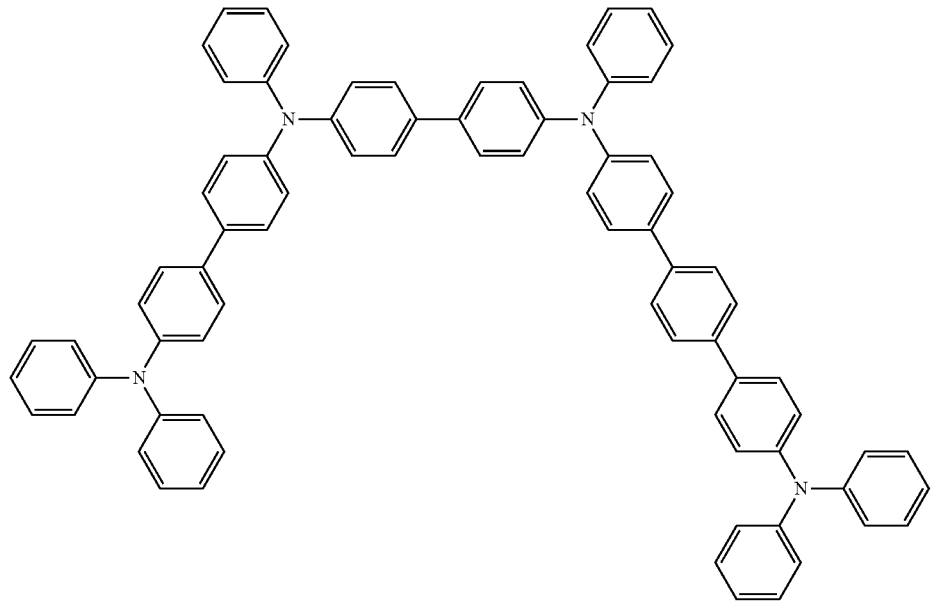
(5-5)
[Chemical Formula 451]
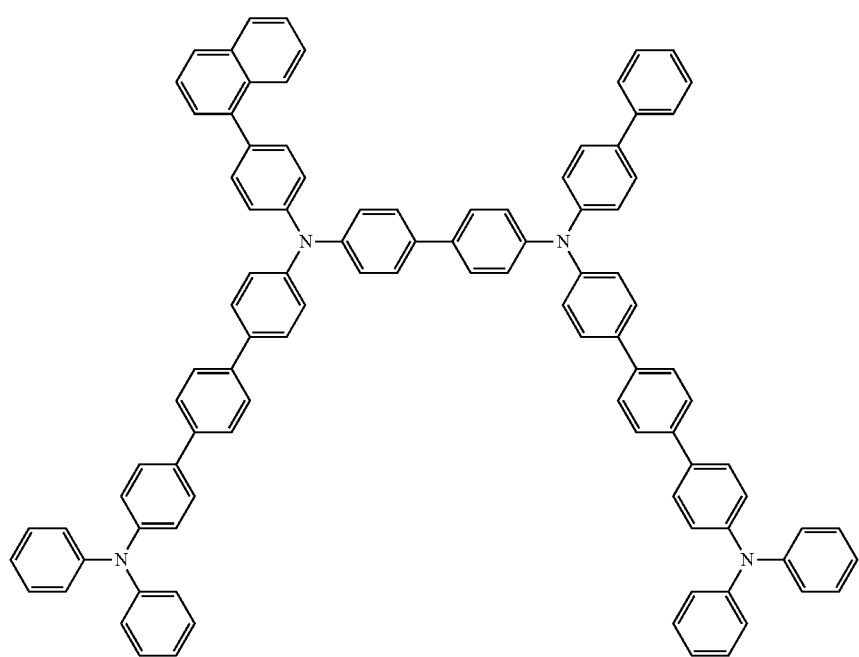
(5-6)

[Chemical Formula 452]
(5-7)
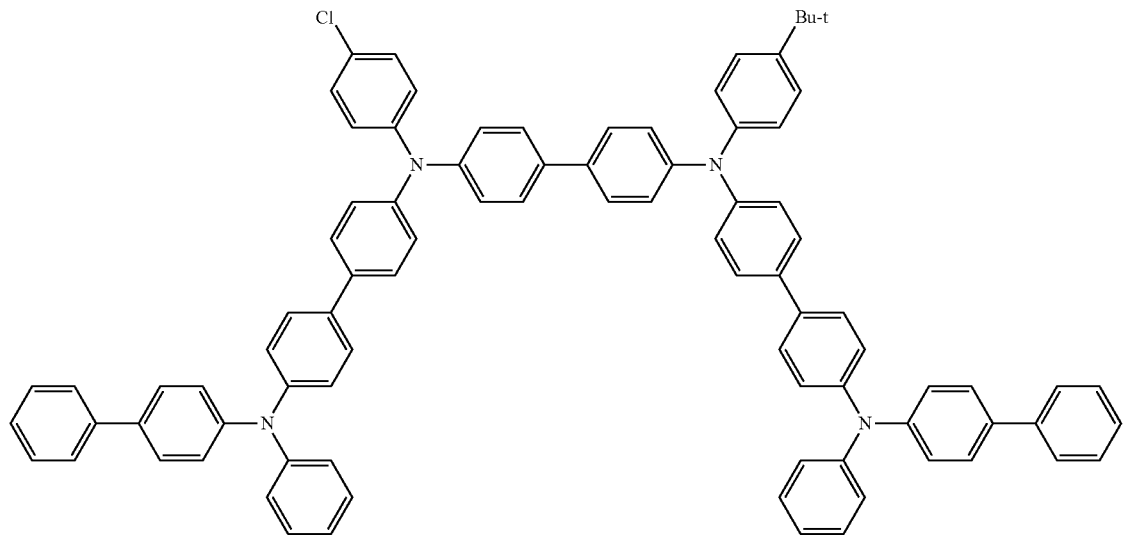
[Chemical Formula 453]
(5-8)
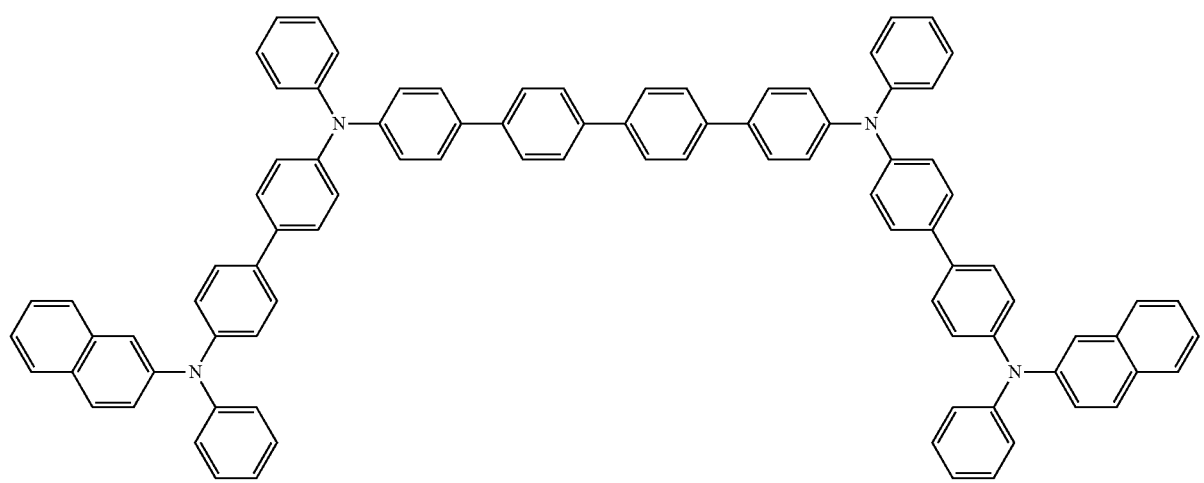
[Chemical Formula 454]
(5-9)
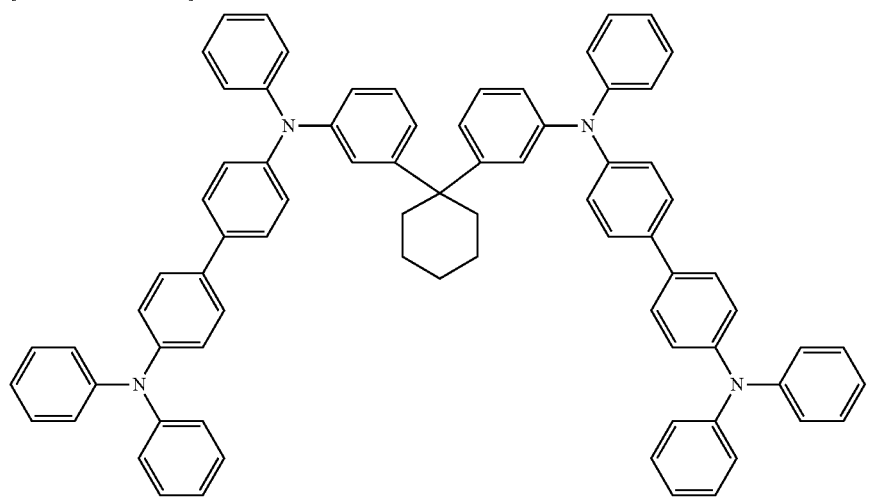

[Chemical Formula 455]
(5-10)
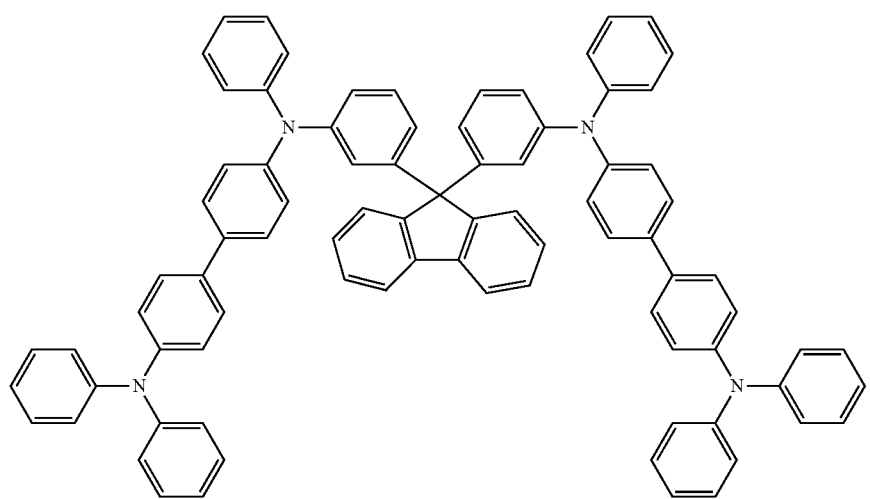
[Chemical Formula 456]
(5-11)
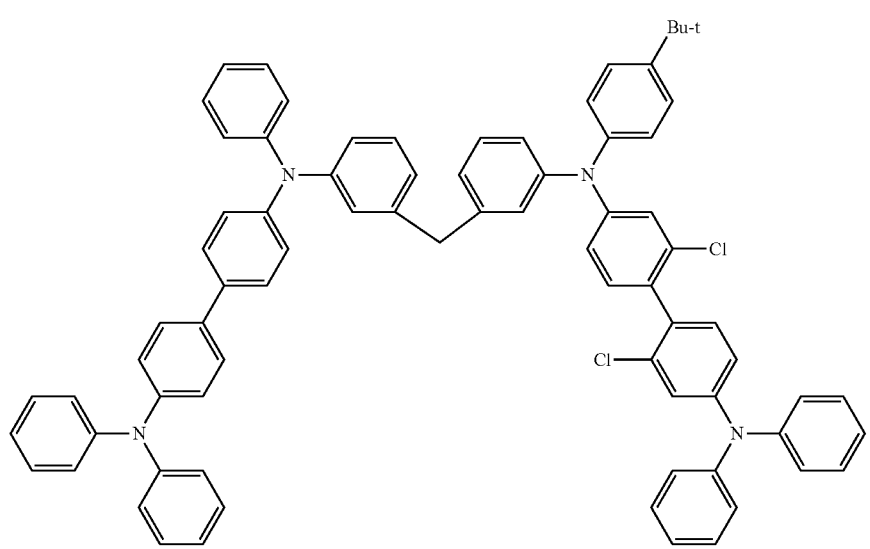

[Chemical Formula 457]
(5-12)
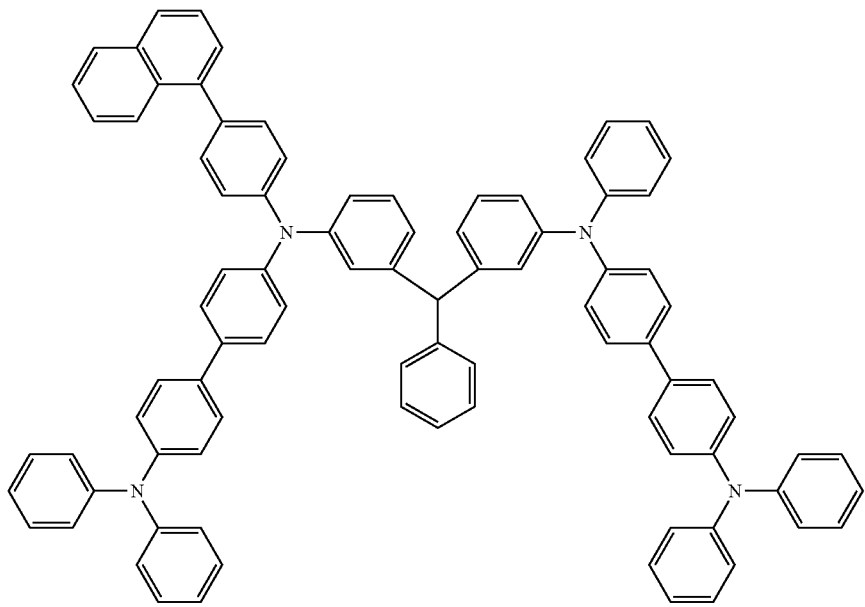
[Chemical Formula 458]
(5-13)
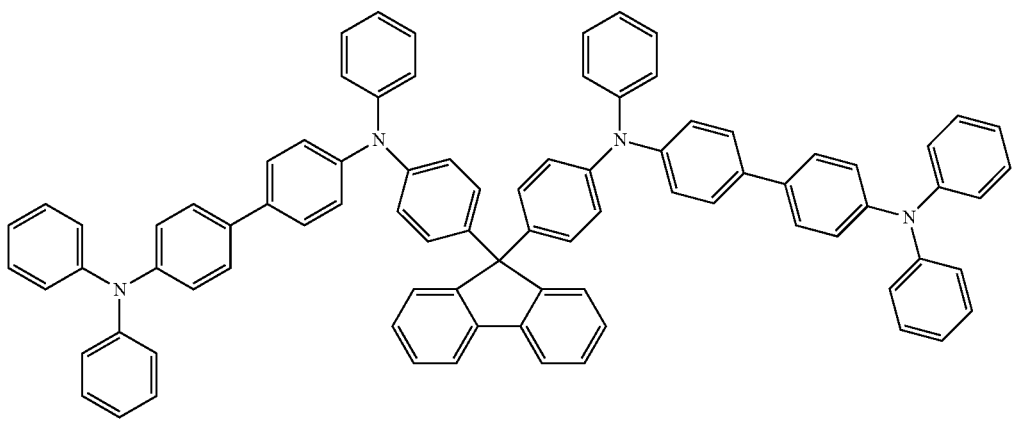
[Chemical Formula 459]
(5-14)
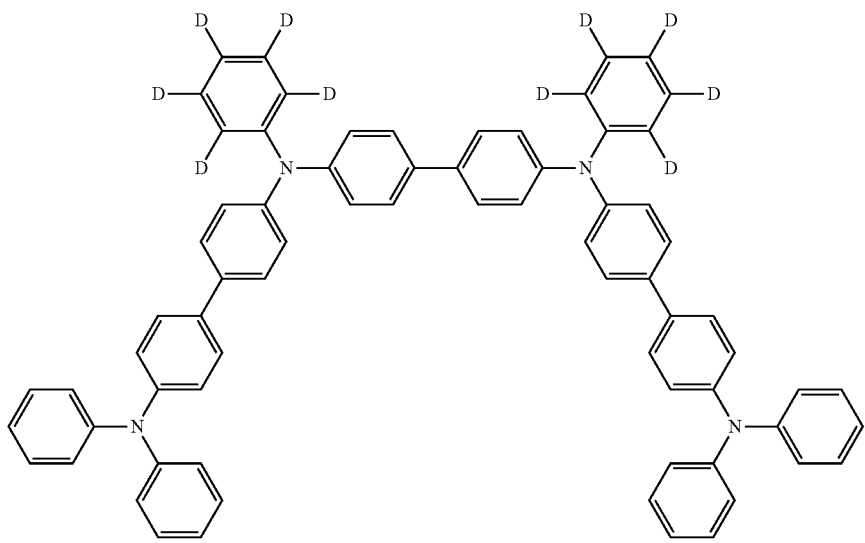

[Chemical Formula 460]
(5-15)
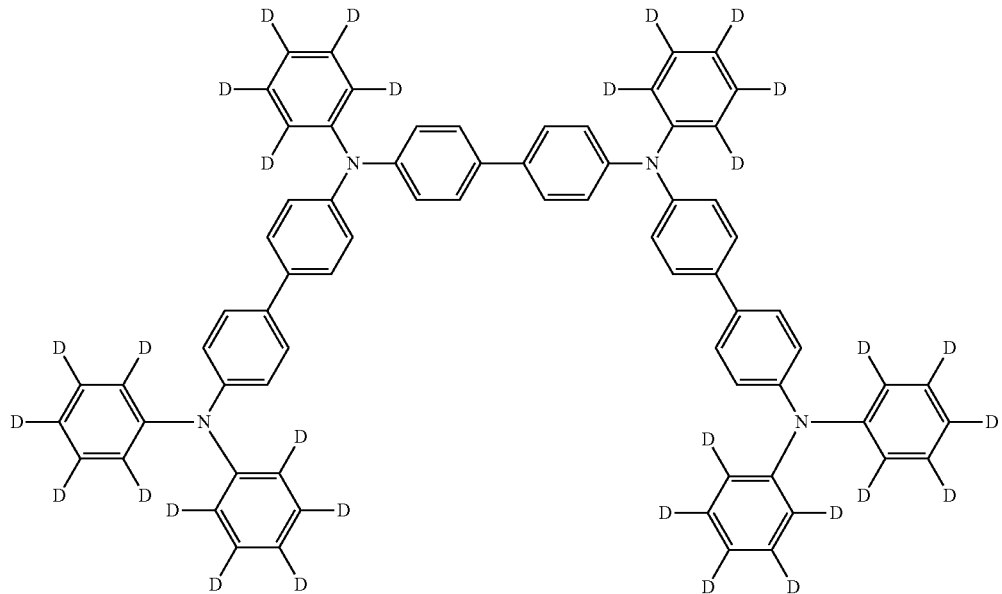
[Chemical Formula 461]
(5-16)
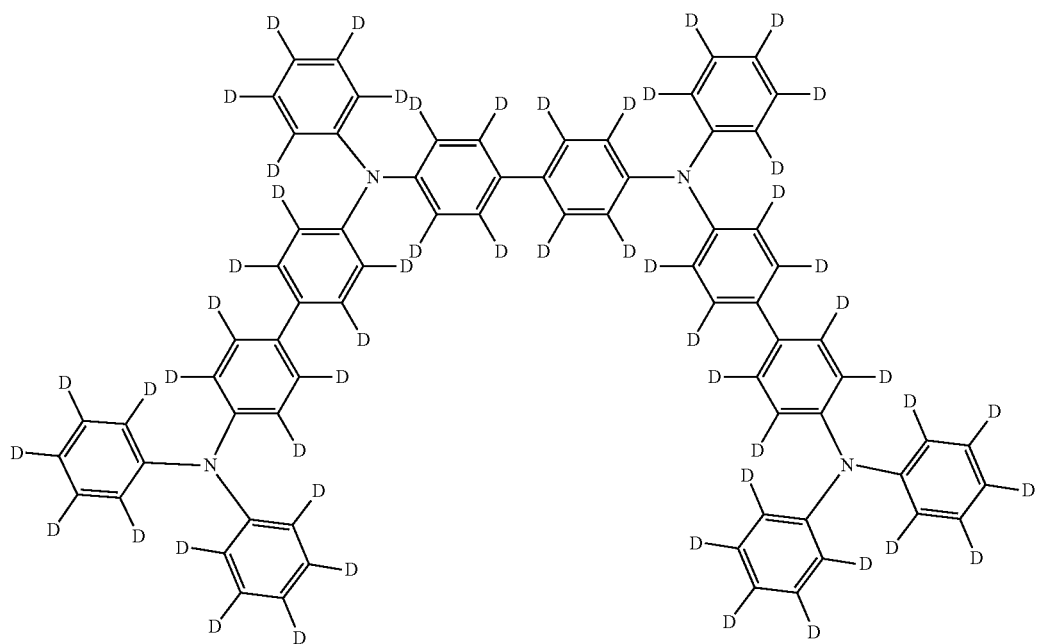

[Chemical Formula 462]

(5-17)

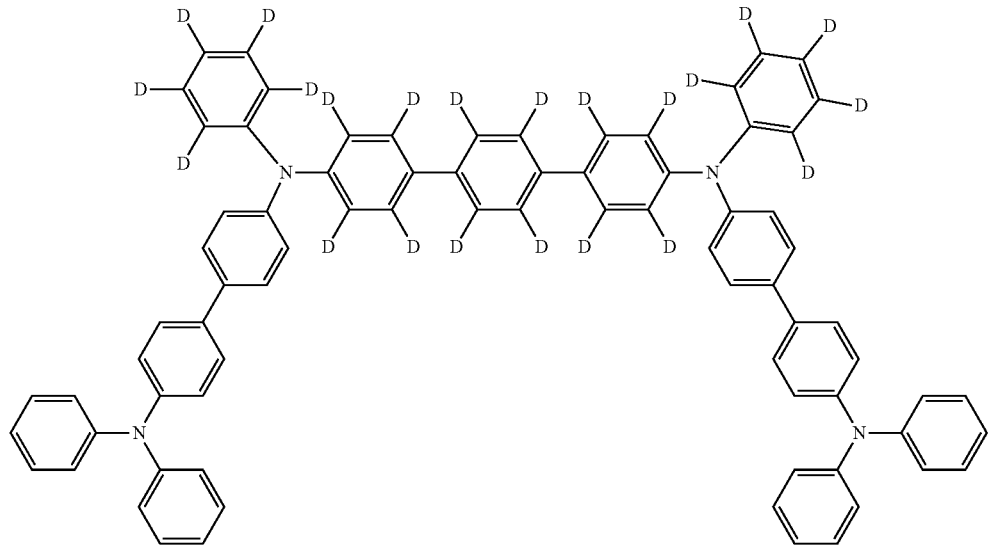

The following presents specific examples of preferred compounds among the arylamine compounds having a structure in which three to six triarylamine structures are joined within a molecule via a single bond or a divalent group that does not contain a hetero atom preferably used in the organic EL device of the present invention, in addition to the arylamine compounds having a structure in which four triarylamine structures are joined within a molecule via a single bond or a divalent group that does not contain a hetero atom of the general formula (5). The present invention, however, is not restricted to these compounds.

[Chemical Formula 463]

(5'-1)

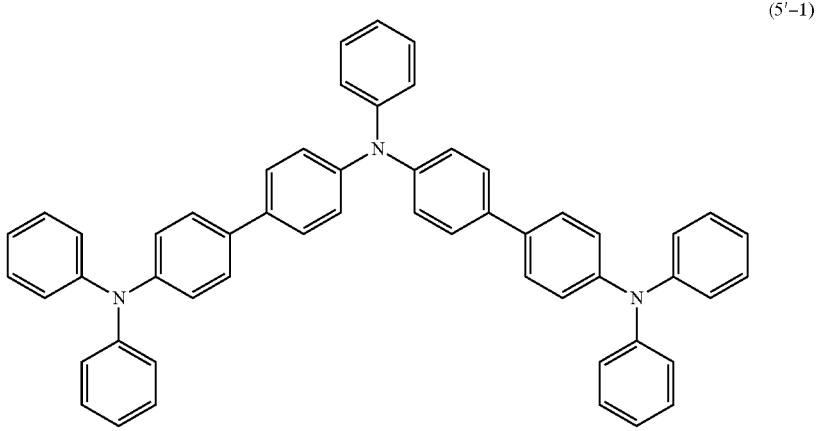

[Chemical Formula 464]

(5'-2)

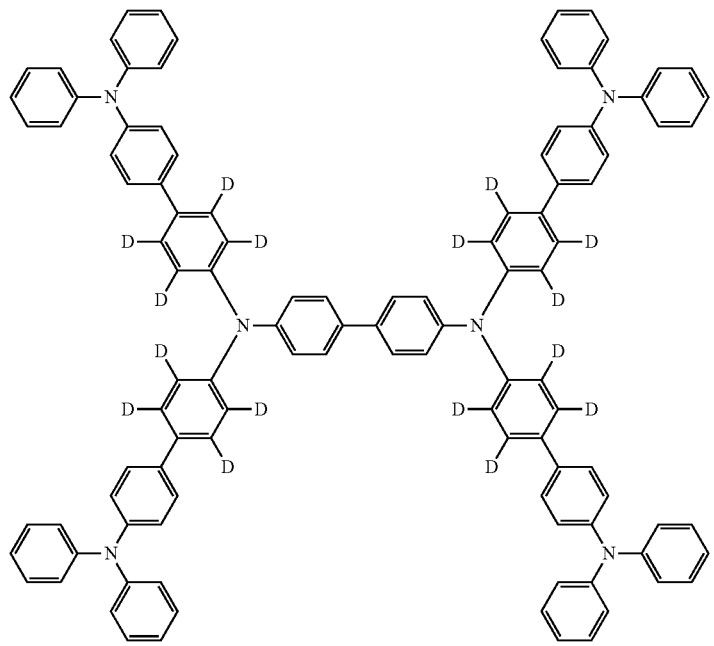

The arylamine compounds having a structure in which three to six triarylamine structures are joined within a molecule via a single bond or a divalent group that does not contain a hetero atom or the arylamine compounds having a structure in which two triarylamine structures are joined within a molecule via a single bond or a divalent group that does not contain a hetero atom can be synthesized by a known method (refer to PTLs 6 to 8, for example).

Compounds of the general formulas (1) to (5) were purified by methods such as column chromatography, adsorption using, for example, a silica gel, activated carbon, or activated clay, and recrystallization or crystallization using a solvent, and finally purified by a sublimation purification method and the like. The compounds were identified by an NMR analysis. A glass transition point (Tg), and a work function were measured as material property values. The glass transition point (Tg) can be used as an index of stability in a thin-film state, and the work function can be used as an index of hole transportability performance.

The melting point and the glass transition point (Tg) were measured by a high-sensitive differential scanning calorimeter (DSC3100 SA produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a hole transport layer, a light emitting layer, an electron transport layer, an electron injection layer, and a cathode successively formed on a substrate, optionally with an electron blocking layer between the hole transport layer and the light emitting layer, and a hole blocking layer between the light emitting layer and the electron transport layer. Some of the organic layers in the multilayer structure may be omitted, or may serve more than one function. For example, a single organic layer may serve as the hole injection layer and the hole transport layer, or as the electron injection layer and the electron transport layer, and so on. Further, any of the layers may be configured to laminate two or more organic layers having the same function, and the hole transport layer may have a two-layer laminated structure, the light emitting layer may have a two-layer laminated structure, the electron transport layer may have a two-layer laminated structure, and so on.

Electrode materials with high work functions such as ITO and gold are used as the anode of the organic EL device of the present invention. The hole injection layer of the organic EL device of the present invention may be made of, for example, material such as starburst-type triphenylamine derivatives and various triphenylamine tetramers; porphyrin compounds as represented by copper phthalocyanine; accepting heterocyclic compounds such as hexacyano azatriphenylene; and coating-type polymer materials, in addition to the arylamine compounds of the general formula (1). These materials may be formed into a thin film by a vapor deposition method or other known methods such as a spin coating method and an inkjet method.

The arylamine compounds of the general formula (1) are used as the hole transport layer of the organic EL device of the present invention. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by a vapor deposition method or other known methods such as a spin coating method and an inkjet method.

The material used for the hole injection layer or the hole transport layer may be obtained by p-doping materials such as trisbromophenylamine hexachloroantimony, and radialene derivatives (refer to WO2014/009310, for example) into a material commonly used for these layers, or may be, for example, polymer compounds each having, as a part of the compound structure, a structure of a benzidine derivative such as TPD.

In the case where the hole transport layer of the organic EL device of the present invention have a laminate structure of two or more layers, examples of material used for the hole transport layer of second and succeeding layers can be arylamine compounds having a structure in which two triphenylamine structures are joined within a molecule via a single bond or a divalent group that does not contain a heteroatom such as benzidine derivatives such as N,N'-diphenyl-N,N'-di(m-tolyl)benzidine (TPD), N,N'-diphenyl-N,N'-di(a-naphthyl)benzidine (NPD), and N,N,N',N'-tetra-biphenylylbenzidine; and 1,1-bis[4-(di-4-tolylamino)phenyl]cyclohexane (TAPC), arylamine compounds having a structure in which four triphenylamine structures are joined within a molecule via a single bond or a divalent group that does not contain a heteroatom, and various triphenylamine trimers, in addition to the arylamine compounds of the general formula (1). These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylene-dioxythiophene) (PEDOT)/poly(styrene sulfonate) (PSS). These materials may be formed into a thin-film by a vapor deposition method or other known methods such as a spin coating method and an inkjet method.

Examples of material used for the electron blocking layer of the organic EL device of the present invention can be compounds having an electron blocking effect, including, for example, arylamine compounds having a structure in which four triphenylamine structures are joined within a molecule via a single bond or a divalent group that does not contain a heteroatom, arylamine compounds having a structure in which two triphenylamine structures are joined within a molecule via a single bond or a divalent group that does not contain a heteroatom, carbazole derivatives such as 4,4',4''-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-yl-phenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the arylamine compounds of the general formula (1). These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the light emitting layer of the organic EL device of the present invention can be various metal complexes, anthracene derivatives, bis(styryl)benzene derivatives, pyrene derivatives, oxazole derivatives, and polyparaphenylene vinylene derivatives, in addition to quinolinol derivative metal complexes such as $Alq_3$. Further, the light emitting layer may be made of a host material and a dopant material. Examples of the host material can be preferably anthracene derivatives. Other examples of the host material can be heterocyclic compounds having indole ring as a part of a condensed ring, heterocyclic compounds having carbazole ring as a part of a condensed ring, carbazole derivatives, thiazole derivatives, benzimidazole derivatives, and polydialkyl fluorene derivatives, in addition to the above light-emitting materials. Examples of the dopant material can be preferably pyrene derivatives, amine derivatives having fluorene ring as a part of a condensed ring. Other examples of the dopant material can be quinacridone, coumarin, rubrene, perylene, derivatives thereof, benzopyran derivatives, indenophenanthrene derivatives, rhodamine derivatives, and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be a phosphorescent material. Phosphorescent materials as metal complexes of metals such as iridium and platinum may be used. Examples of the phosphorescent materials include green phosphorescent materials such as $Ir(ppy)_3$, blue phosphorescent materials such as FIrpic and FIr6, and red phosphorescent materials such as $Btp_2Ir(acac)$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2) and 2,2',2''-(1,3,5-phenylene)-tris(1-phenyl-1H-benzimidazole) (TPBI) may be used as the electron transporting host material. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, examples of the light-emitting material may be delayed fluorescent-emitting material such as a CDCB derivative of PIC-TRZ, CC2TA, PXZ-TRZ, 4CzIPN or the like (refer to NPL 3, for example).

These materials may be formed into a thin-film by using a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to phenanthroline derivatives such as bathocuproin (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Material used for the electron transport layer of the organic EL device of the present invention can be the compounds of the general formula (2) having a benzazole ring structure, far preferably, the compounds of the general formula (3) having a benzazole ring structure. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by a vapor deposition method or other known methods such as a spin coating method and an inkjet method.

In the case where the electron transport layer of the organic EL device of the present invention have a laminate structure of two or more layers, examples of material used for the electron transport layer of second and succeeding layers can be the compounds of the general formula (2) having a benzazole ring structure, far preferably, the compounds of the general formula (3) having a benzazole ring structure. Other examples of material can be metal complexes of quinolinol derivatives such as $Alq_3$ and BAlq, various metal complexes, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of bis(biphenyl-4-yl)-(1,1':2,1''-terphenyl-4-yl)amine Compound 1-1

Bis(biphenyl-4-yl)-(6-bromobiphenyl-3-yl)amine (11.8 g), toluene (94 mL), phenylboronic acid (2.7 g), and an aqueous solution obtained by previously dissolving potassium carbonate (5.9 g) in water (36 mL) were added into a nitrogen-substituted reaction vessel and aerated with nitrogen gas under ultrasonic irradiation for 30 minutes. Tetrakistriphenylphosphine palladium (0.74 g) was added thereto, and the resulting mixture was heated and stirred at 72° C. for 18 hours. After the mixture was cooled to a room temperature, an organic layer was collected by liquid separation. The organic layer was washed with water, and washed with a saturated salt solution sequentially, and then dried over anhydrous magnesium sulfate and concentrated to obtain a crude product. Subsequently, the crude product was purified using column chromatography, whereby a white powder of bis(biphenyl-4-yl)-(1,1':2,1''-terphenyl-4-yl)amine (Compound 1-1, 8.4 g, yield: 72%) was obtained.

[Chemical Formula 465]

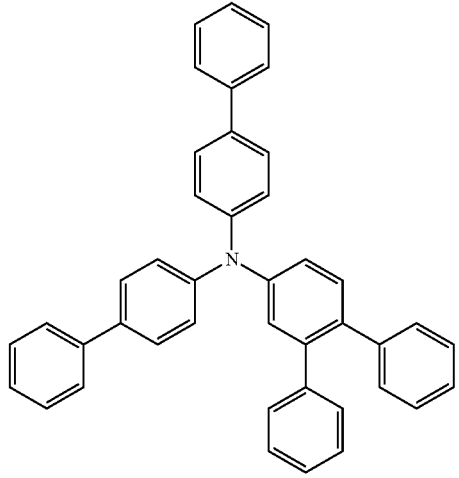

(1-1)

The structure of the obtained white powder was identified by NMR.

$^1$H-NMR (CDCl$_3$) detected 31 hydrogen signals, as follows.

δ (ppm)=7.56-7.68 (7H), 7.45-7.52 (4H), 7.14-7.41 (20H).

Example 2

Synthesis of bis(biphenyl-4-yl)-{6-(naphthyl-1-yl)biphenyl-3-yl}amine Compound 1-2

The reaction was carried out under the same conditions as those of Example 1, except that phenylboronic acid was replaced with 1-naphthylboronic acid, whereby a white powder of bis(biphenyl-4-yl)-{6-(naphthyl-1-yl)biphenyl-3-yl}amine (Compound 1-2, 9.2 g, yield: 61%) was obtained.

[Chemical Formula 466]

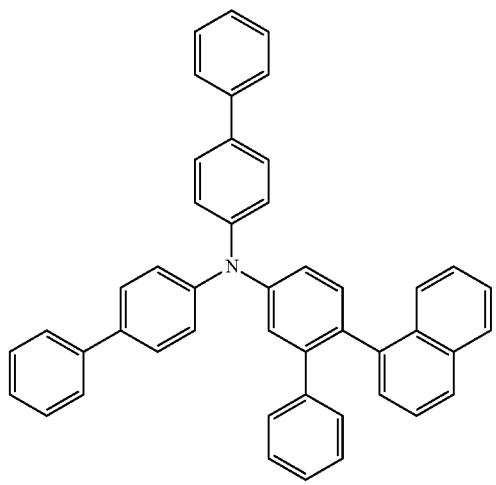

(1-2)

The structure of the obtained white powder was identified by NMR.

¹H-NMR (CDCl₃) detected 33 hydrogen signals, as follows.

δ (ppm)=7.84-7.87 (3H), 7.67-7.83(6H), 7.26-7.64 (18H), 7.02-7.04 (6H).

Example 3

Synthesis of bis(biphenyl-4-yl)-{6-(9,9-dimethyl-fluoren-2-yl)biphenyl-3-yl}amine Compound 1-3

The reaction was carried out under the same conditions as those of Example 1, except that phenylboronic acid was replaced with (9,9-dimethylfluoren-2-yl)boronic acid, whereby a white powder of bis(biphenyl-4-yl)-{6-(9,9-dimethylfluoren-2-yl)biphenyl-3-yl}amine (Compound 1-3, 9.0 g, yield: 57%) was obtained.

[Chemical Formula 467]

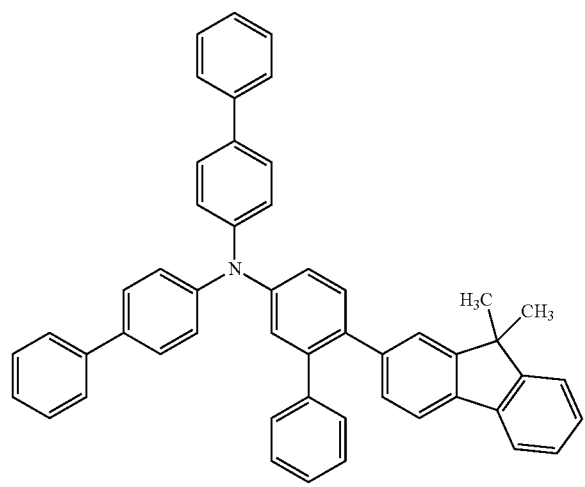

(1-3)

The structure of the obtained white powder was identified by NMR.

¹H-NMR (CDCl₃) detected 39 hydrogen signals, as follows.

δ (ppm)=7.56-7.64 (10H), 7.26-7.50 (18H), 7.02-7.16 (5H), 1.26 (6H).

Example 4

Synthesis of bis(biphenyl-4-yl)-(1,1':2',1":4",1'''-quaterphenyl-5'-yl)amine Compound 1-4

The reaction was carried out under the same conditions as those of Example 1, except that phenylboronic acid was replaced with 4-biphenylboronic acid, whereby a white powder of bis(biphenyl-4-yl)-(1,1':2',1":4",1'''-quaterphenyl-5'-yl)amine (Compound 1-4, 8.6 g, yield: 64%) was obtained.

[Chemical Formula 468]

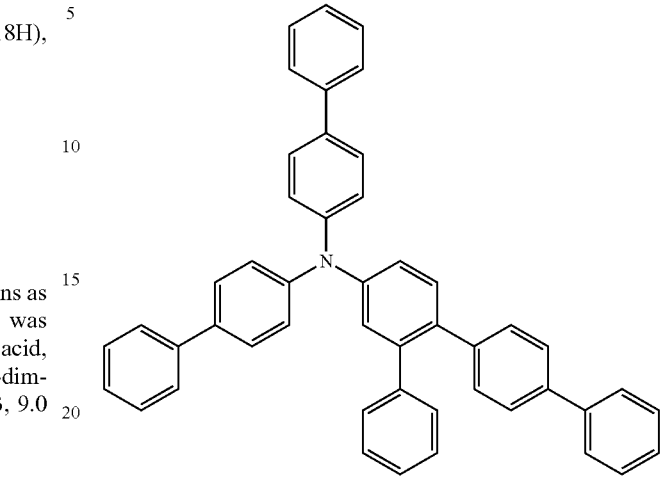

(1-4)

The structure of the obtained white powder was identified by NMR.

¹H-NMR (CDCl₃) detected 35 hydrogen signals, as follows.

δ (ppm)=7.66-7.53 (8H), 7.51-7.15 (27H).

Example 5

Synthesis of bis(6-phenylbiphenyl-3-yl)-(biphenyl-4-yl)amine Compound 1-94

The reaction was carried out under the same conditions as those of Example 1, except that bis(biphenyl-4-yl)-(6-bromobiphenyl-3-yl)amine was replaced with bis(6-bromobiphenyl-3-yl)-(biphenyl-4-yl)amine, whereby a white powder of bis(6-phenylbiphenyl-3-yl)-(biphenyl-4-yl)amine (Compound 1-94, 10.2 g, yield: 73%) was obtained.

[Chemical Formula 469]

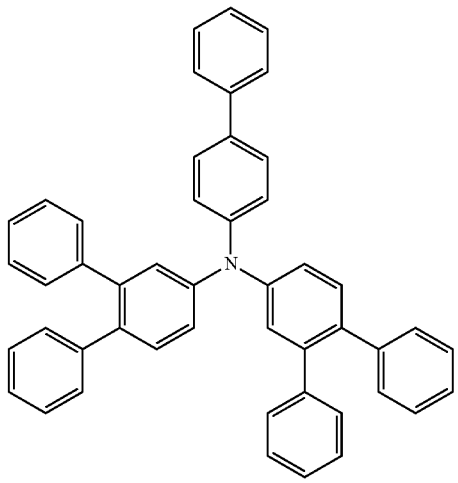

(1-94)

The structure of the obtained white powder was identified by NMR.

$^1$H-NMR (CDCl$_3$) detected 35 hydrogen signals, as follows.

δ (ppm)=7.57-7.66 (4H), 7.10-7.49 (31H).

Example 6

Synthesis of tris(6-phenylbiphenyl-3-yl)amine Compound 1-129

The reaction was carried out under the same conditions as those of Example 1, except that bis(biphenyl-4-yl)-(6-bromobiphenyl-3-yl)amine was replaced with tris(6-bromobiphenyl-3-yl)amine, whereby a white powder of tris(6-phenylbiphenyl-3-yl)amine (Compound 1-129, 11.1 g, yield: 75%) was obtained.

[Chemical Formula 470]

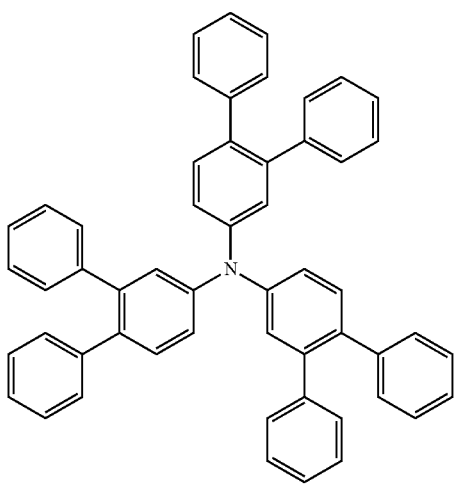

(1-129)

The structure of the obtained white powder was identified by NMR.

$^1$H-NMR (CDCl$_3$) detected 39 hydrogen signals, as follows.

δ (ppm)=7.35-7.42 (6H), 7.15-7.35 (33H).

Example 7

Synthesis of (biphenyl-4-yl)-{4-(naphthalene-2-yl)phenyl}-(6-phenyl-1,1':4',1''-terphenyl-3-yl)amine Compound 1-143

The reaction was carried out under the same conditions as those of Example 1, except that bis(biphenyl-4-yl)-(6-bromobiphenyl-3-yl)amine was replaced with (biphenyl-4-yl)-{4-(naphthalen-2-yl)phenyl}-(6-bromo-1,1': 4',1''-terphenyl-3-yl)amine, whereby a white powder of (biphenyl-4-yl)-{4-(naphthalen-2-yl)phenyl}-(6-phenyl-1,1': 4',1''-terphenyl-3-yl)amine (Compound 1-143, 5.8 g, yield: 56%) was obtained.

[Chemical Formula 471]

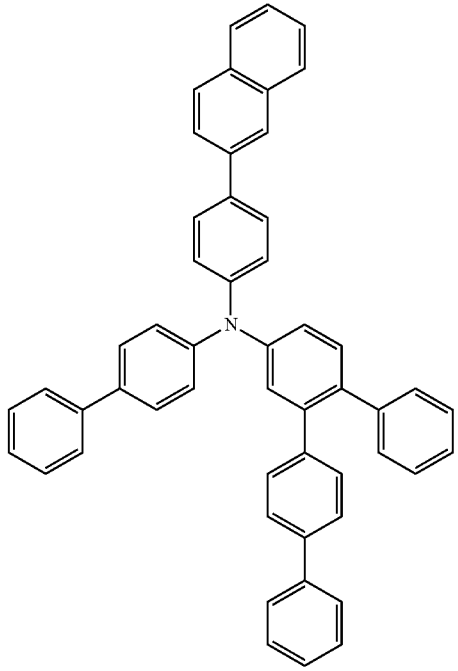

(1-143)

The structure of the obtained white powder was identified by NMR.

$^1$H-NMR (CDCl$_3$) detected 37 hydrogen signals, as follows.

δ (ppm)=8.08 (1H), 7.81-7.96 (3H), 7.79-7.81 (1H), 7.21-7.73 (32H).

Example 8

Synthesis of (biphenyl-4-yl)-{4-(naphthalen-2-yl)phenyl}-(1,1':2',1'':2''',1''': 4''', 1''''-quinquephenyl-4''-yl)amine Compound 1-146

The reaction was carried out under the same conditions as those of Example 1, except that bis(biphenyl-4-yl)-(6-bromobiphenyl-3-yl)amine was replaced with (biphenyl-4-yl)-{4-(naphthalen-2-yl)phenyl}-(6-bromo-1,1':4',1''-terphenyl-3-yl)amine, and phenylboronic acid was replaced with 2-biphenylboronic acid, whereby a white powder of (biphenyl-4-yl)-{4-(naphthalen-2-yl)phenyl}-(1,1':2',1'':2''',1''':4''', 1''''-quinquephenyl-4''-yl)amine (Compound 1-146, 8.5 g, yield: 49%) was obtained.

[Chemical Formula 472]

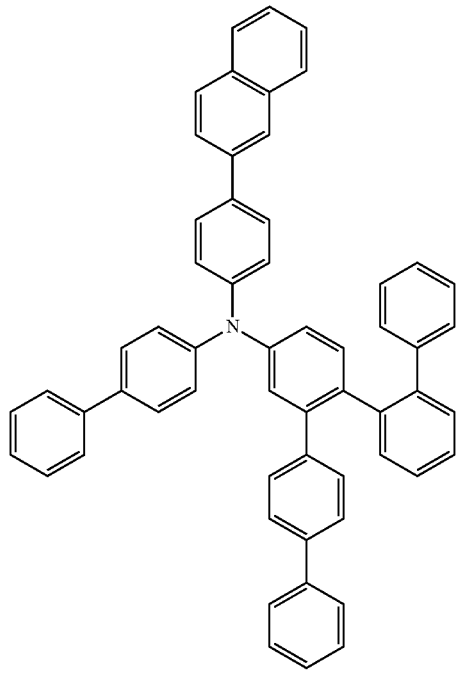

(1-146)

The structure of the obtained white powder was identified by NMR.

¹H-NMR (CDCl₃) detected 41 hydrogen signals, as follows.

δ (ppm)=8.1 (1H), 7.86-7.98 (4H), 7.10-7.72 (32H), 6.65-6.76 (4H).

Example 9

Synthesis of bis{4-(naphthalen-1-yl)phenyl}-(1,1':2', 1":4",1'''-quaterphenyl-5'-yl)amine Compound 1-148

The reaction was carried out under the same conditions as those of Example 1, except that bis(biphenyl-4-yl)-(6-bromobiphenyl-3-yl)amine was replaced with bis{4-(naphthalen-1-yl)phenyl}-(6-bromobiphenyl-3-yl)amine, and phenylboronic acid was replaced with 4-biphenylboronic acid, whereby a white powder of bis{4-(naphthalen-1-yl)phenyl}-(1,1':2',1":4",1'''-quaterphenyl-5'-yl)amine (Compound 1-148, 10.6 g, yield: 79%) was obtained.

[Chemical Formula 473]

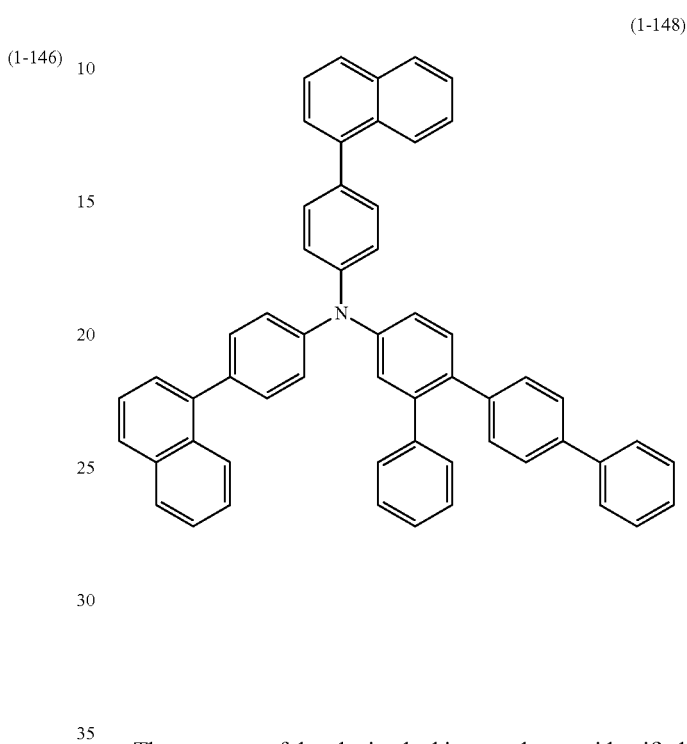

(1-148)

The structure of the obtained white powder was identified by NMR.

¹H-NMR (CDCl₃) detected 39 hydrogen signals, as follows.

δ (ppm)=8.08-8.14 (2H), 7.88-7.96 (4H), 7.24-7.64 (33H).

Example 10

Synthesis of bis{4-(naphthalen-1-yl)phenyl}-(1,1':2', 1":2",1''':4''',1''''-quinquephenyl-4"-yl)amine Compound 1-153

The reaction was carried out under the same conditions as those of Example 1, except that bis(biphenyl-4-yl)-(6-bromobiphenyl-3-yl)amine was replaced with bis{4-(naphthalen-1-yl)phenyl}-(6-bromo-1,1':4',1"-terphenyl-3-yl)amine, and phenylboronic acid was replaced with 2-biphenylboronic acid, whereby a white powder of bis{4-(naphthalen-1-yl)phenyl}-(1,1':2',1":2",1''':4''',1''''-quinquephenyl-4"-yl)amine (Compound 1-153, 7.5 g, yield: 55%) was obtained.

[Chemical Formula 474]

(1-153)

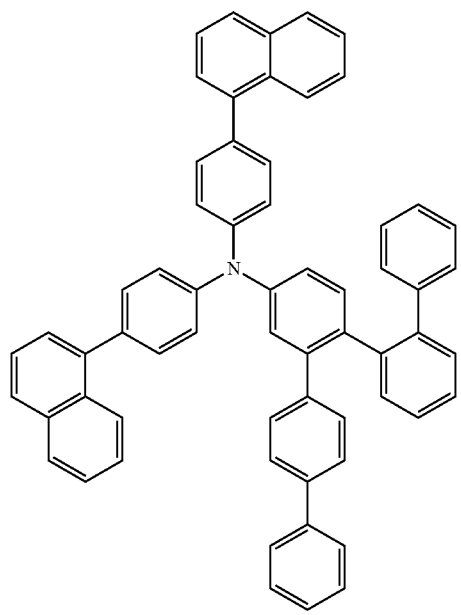

The structure of the obtained white powder was identified by NMR.

¹H-NMR (CDCl$_3$) detected 43 hydrogen signals, as follows.

δ (ppm)=8.09-8.12 (2H), 7.88-7.97 (4H), 7.10-7.60 (33H), 6.67-6.75 (4H).

Example 11

Synthesis of bis{4-(naphthalen-2-yl)phenyl}-(1,1':2', 1":4",1'''-quaterphenyl-5'-yl)amine Compound 1-155

The reaction was carried out under the same conditions as those of Example 1, except that bis(biphenyl-4-yl)-(6-bromobiphenyl-3-yl)amine was replaced with bis{4-(naphthalen-2-yl)phenyl}-(6-bromobiphenyl-3-yl)amine, and phenylboronic acid was replaced with 4-biphenylboronic acid, whereby a white powder of bis{4-(naphthalen-2-yl)phenyl}-(1,1':2',1":4",1'''-quaterphenyl-5'-yl)amine (Compound 1-155, 6.6 g, yield: 80%) was obtained.

[Chemical Formula 475]

(1-155)

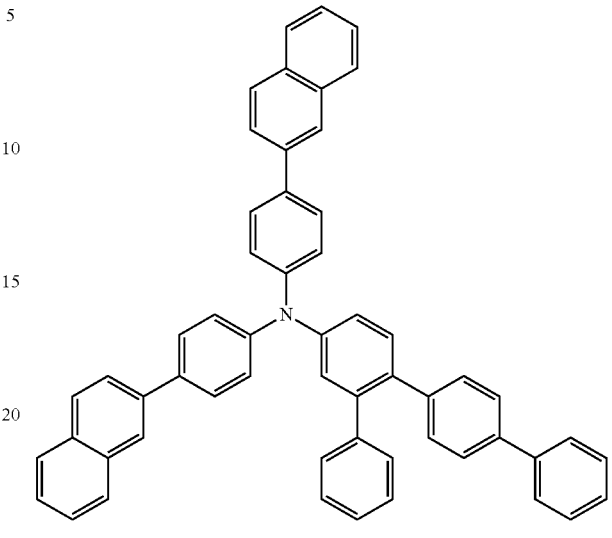

The structure of the obtained white powder was identified by NMR.

¹H-NMR (CDCl$_3$) detected 39 hydrogen signals, as follows.

δ (ppm)=8.12 (2H), 7.91-7.98 (6H), 7.64-7.84 (8H), 7.28-7.59 (23H).

Example 12

Synthesis of bis{4-(naphthalen-2-yl)phenyl}-{4-(naphthalen-1-yl)-1,1':2',1"-terphenyl-4'-yl}amine Compound 1-158

The reaction was carried out under the same conditions as those of Example 11, except that 4-biphenylboronic acid was replaced with 4-(naphthalen-1-yl)phenylboronic acid, whereby a white powder of bis{4-(naphthalen-2-yl)phenyl}-{4-(naphthalen-1-yl)-1,1':2',1"-terphenyl-4'-yl}amine (Compound 1-158, 6.5 g, yield: 73%) was obtained.

[Chemical Formula 476]

(1-158)

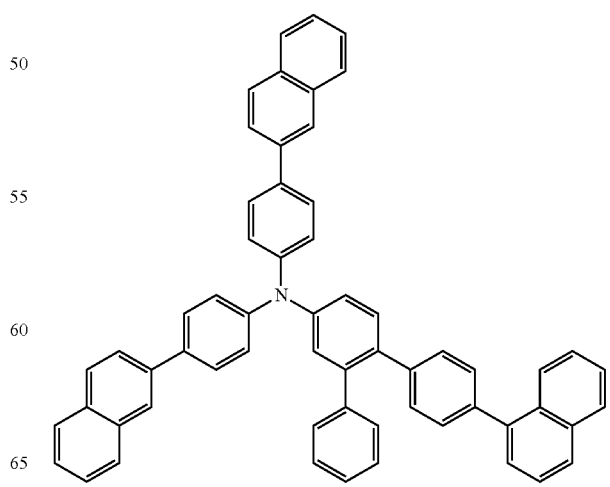

The structure of the obtained white powder was identified by NMR.

¹H-NMR (CDCl₃) detected 41 hydrogen signals, as follows.

δ (ppm)=8.11 (2H), 7.68-7.98 (18H), 7.23-7.59 (21H).

Example 13

Synthesis of bis{4-(naphthalen-2-yl)phenyl}-{4-(naphthalen-2-yl)-1,1':2',1''-terphenyl-4'-yl}amine Compound 1-159

The reaction was carried out under the same conditions as those of Example 11, except that 4-biphenylboronic acid was replaced with 4-(naphthalen-2-yl)phenylboronic acid, whereby a white powder of bis{4-(naphthalen-2-yl)phenyl}-{4-(naphthalen-2-yl)-1,1':2',1''-terphenyl-4'-yl}amine (Compound 1-159, 7.4 g, yield: 83%) was obtained.

[Chemical Formula 477]

(1-159)

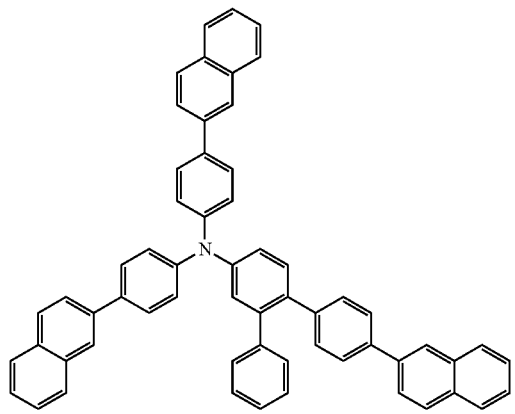

The structure of the obtained white powder was identified by NMR.

¹H-NMR (CDCl₃) detected 41 hydrogen signals, as follows.

δ (ppm)=8.10-8.12 (3H), 7.89-7.98 (9H), 7.65-7.84 (9H), 7.32-7.58 (20H).

Example 14

Synthesis of (biphenyl-4-yl)-(1,1':2',1'':4'',1'''-quaterphenyl-5'-yl)-(9,9-dimethylfluoren-2-yl)amine Compound 1-56

The reaction was carried out under the same conditions as those of Example 1, except that bis(biphenyl-4-yl)-(6-bromobiphenyl-3-yl)amine was replaced with (6-bromobiphenyl-3-yl)-(biphenyl-4-yl)-(9,9-dimethylfluoren-2-yl)amine, and phenylboronic acid was replaced with 4-biphenylboronic acid, whereby a white powder of (biphenyl-4-yl)-(1,1':2',1'':4'',1'''-quaterphenyl-5'-yl)-(9,9-dimethylfluoren-2-yl)amine (Compound 1-56, 17.8 g, yield: 89%) was obtained.

[Chemical Formula 478]

(1-56)

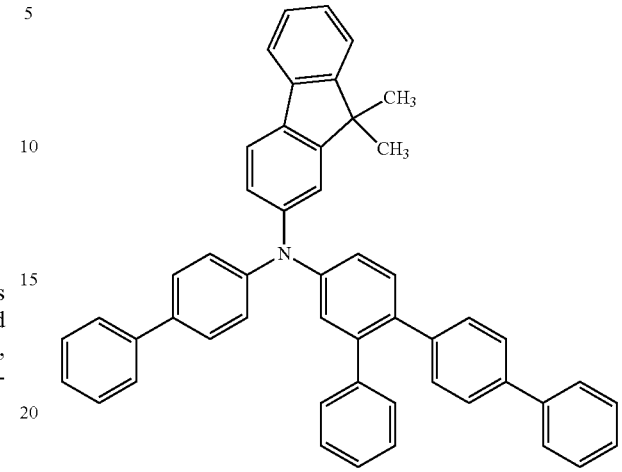

The structure of the obtained white powder was identified by NMR.

¹H-NMR (CDCl₃) detected 39 hydrogen signals, as follows.

δ (ppm)=7.57-7.70 (7H), 7.18-7.52 (26H), 1.52 (6H).

Example 15

Synthesis of (biphenyl-4-yl)-{4-(naphthalen-1-yl)-(1,1':2',1''-terphenyl)-4'-yl}-(9,9-dimethylfluoren-2-yl)amine Compound 1-163

The reaction was carried out under the same conditions as those of Example 14, except that 4-biphenylboronic acid was replaced with 4-(naphthalen-1-yl)phenylboronic acid, whereby a white powder of (biphenyl-4-yl)-{4-(naphthalen-1-yl)-(1,1':2',1''-terphenyl)-4'-yl}-(9,9-dimethylfluoren-2-yl)amine (Compound 1-163, 17.8 g, yield: 89%) was obtained.

[Chemical Formula 479]

(1-163)

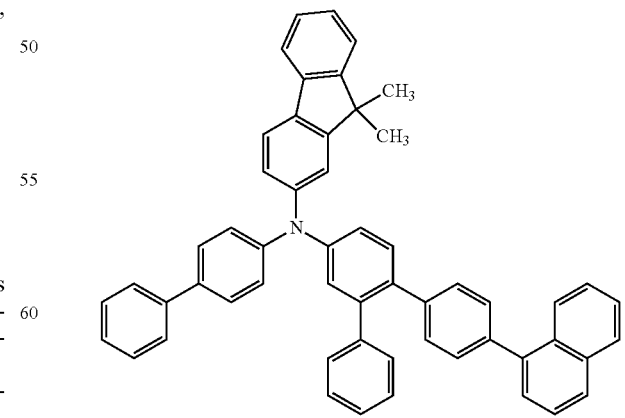

The structure of the obtained white powder was identified by NMR.

$^1$H-NMR (CDCl$_3$) detected 41 hydrogen signals, as follows. δ (ppm)=7.85-7.96 (3H), 7.18-7.74 (32H), 1.53 (6H).

Example 16

Synthesis of (biphenyl-4-yl)-(1,1':2',1''-terphenyl-4'-yl)-(9,9-diphenylfluoren-2-yl)amine Compound 1-165

The reaction was carried out under the same conditions as those of Example 1, except that bis(biphenyl-4-yl)-(6-bromobiphenyl-3-yl)amine was replaced with (6-bromobiphenyl-3-yl)-(biphenyl-4-yl)-(9,9-diphenylfluoren-2-yl)amine, whereby a white powder of (biphenyl-4-yl)-(1,1':2',1''-terphenyl-4'-yl)-(9,9-diphenylfluoren-2-yl)amine (Compound 1-165, 11.0 g, yield: 61%) was obtained.

[Chemical Formula 480]

(1-165)

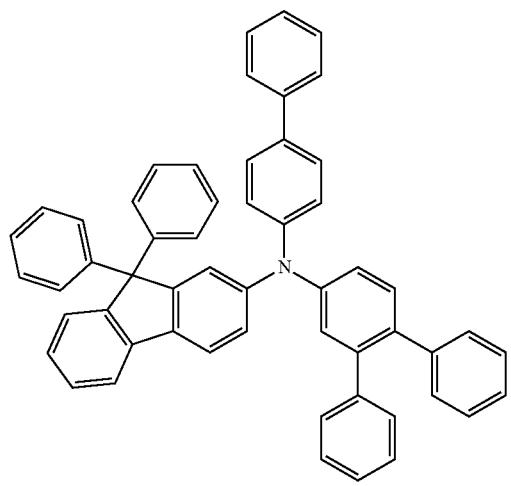

The structure of the obtained white powder was identified by NMR.

$^1$H-NMR (CDCl$_3$) detected 39 hydrogen signals, as follows.

δ (ppm)=7.60-7.74 (4H), 7.14-7.52 (33H), 7.00-7.03 (2H).

Example 17

Synthesis of (biphenyl-4-yl)-(1,1':2',1'':4'',1'''-quaterphenyl-5'-yl)-(9,9-diphenylfluoren-2-yl)amine Compound 1-166

The reaction was carried out under the same conditions as those of Example 16, except that phenylboronic acid was replaced with 4-biphenylboronic acid, whereby a white powder of (biphenyl-4-yl)-(1,1':2',1'':4'',1'''-quaterphenyl-5'-yl)-(9,9-diphenylfluoren-2-yl)amine (Compound 1-166, 6.5 g, yield: 71%) was obtained.

[Chemical Formula 481]

(1-166)

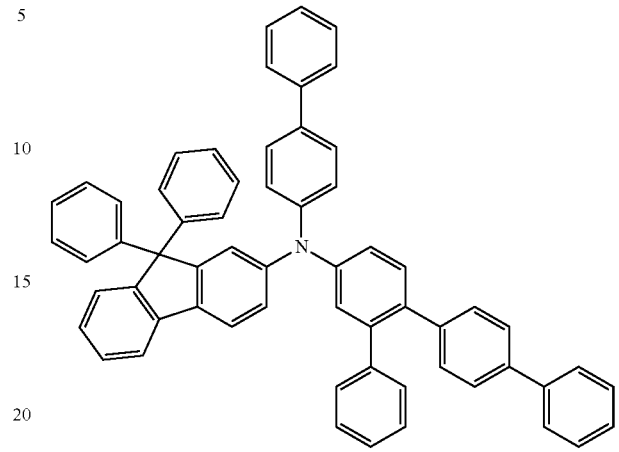

The structure of the obtained white powder was identified by NMR.

$^1$H-NMR (CDCl$_3$) detected 43 hydrogen signals, as follows.

δ (ppm)=7.61-7.77 (6H), 7.20-7.51 (34H), 7.06-7.11 (3H).

Example 18

Synthesis of (biphenyl-4-yl)-(1,1':2',1'':3'',1'''-quaterphenyl-5'-yl)-(9,9-diphenylfluoren-2-yl)amine Compound 1-167

The reaction was carried out under the same conditions as those of Example 16, except that phenylboronic acid was replaced with 3-biphenylboronic acid, whereby a white powder of (biphenyl-4-yl)-(1,1':2',1'':3'',1'''-quaterphenyl-5'-yl)-(9,9-diphenylfluoren-2-yl)amine (Compound 1-167, 8.0 g, yield: 87%) was obtained.

[Chemical Formula 482]

(1-167)

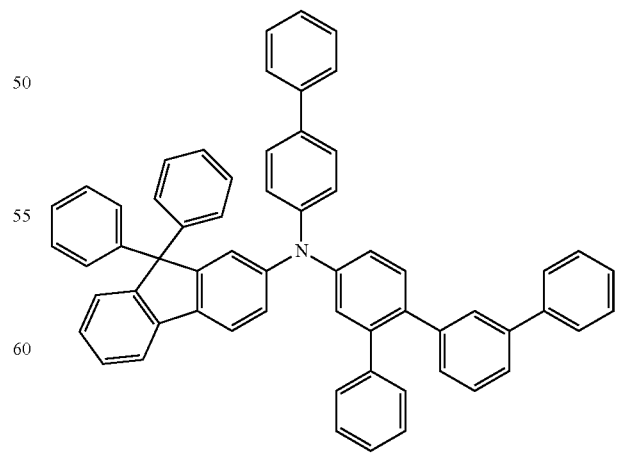

The structure of the obtained white powder was identified by NMR.

$^1$H-NMR (CDCl$_3$) detected 43 hydrogen signals, as follows.

δ (ppm)=7.70-7.76 (2H), 7.63-7.65 (2H), 7.18-7.54 (36H), 7.08-7.12 (3H).

Example 19

Synthesis of (biphenyl-4-yl)-(1,1':2',1":2",1'''-quaterphenyl-5'-yl)-(9,9-diphenylfluoren-2-yl)amine Compound 1-168

The reaction was carried out under the same conditions as those of Example 16, except that phenylboronic acid was replaced with 2-biphenylboronic acid, whereby a white powder of (biphenyl-4-yl)-(1,1':2',1":2",1'''-quaterphenyl-5'-yl)-(9,9-diphenylfluoren-2-yl)amine (Compound 1-168, 5.2 g, yield: 57%) was obtained.

[Chemical Formula 483]

(1-168)

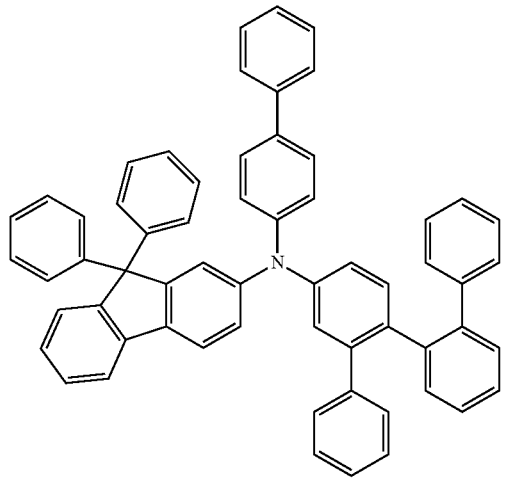

The structure of the obtained white powder was identified by NMR.

$^1$H-NMR (CDCl$_3$) detected 43 hydrogen signals, as follows.

δ (ppm)=7.60-7.74 (4H), 6.95-7.49 (35H), 6.68-6.71 (2H), 6.54-6.57 (2H).

Example 20

Synthesis of phenyl-(1,1':2',1":4",1'''-quaterphenyl-5'-yl)-(9,9-diphenylfluoren-2-yl)amine Compound 1-169

The reaction was carried out under the same conditions as those of Example 1, except that bis(biphenyl-4-yl)-(6-bromobiphenyl-3-yl)amine was replaced with (6-bromobiphenyl-3-yl)-phenyl-(9,9-diphenylfluoren-2-yl)amine, and phenylboronic acid was replaced with 4-biphenylboronic acid, whereby a white powder of phenyl-(1,1':2',1":4",1'''-quaterphenyl-5' yl-(9,9-diphenylfluoren-2-yl)amine (Compound 1-169, 4.2 g, yield: 37%) was obtained.

[Chemical Formula 484]

(1-169)

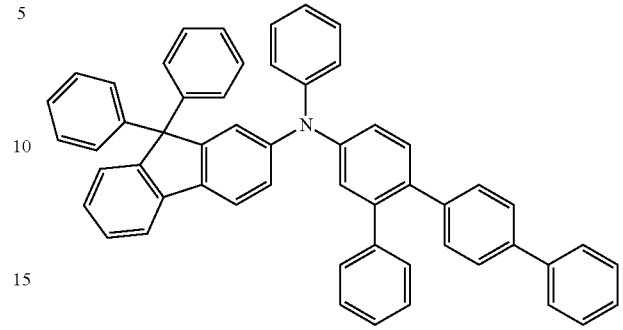

The structure of the obtained white powder was identified by NMR.

$^1$H-NMR (CDCl$_3$) detected 39 hydrogen signals, as follows.

δ (ppm)=7.55-7.79 (4H), 7.06-7.52 (35H).

Example 21

Synthesis of (biphenyl-4-yl)-(1,1':2',1"-terphenyl-4'-yl)-(9,9'-spirobi[fluoren]-2-yl)amine Compound 1-172

The reaction was carried out under the same conditions as those of Example 1, except that bis(biphenyl-4-yl)-(6-bromobiphenyl-3-yl)amine was replaced with (biphenyl-4-yl)-(6-bromobiphenyl-3-yl)-(9,9'-spirobi[fluoren]-2-yl)amine, whereby a white powder of (biphenyl-4-yl)-(1,1':2',1"-terphenyl-4'-yl)-(9,9'-spirobi[fluoren]-2-yl)amine (Compound 1-172, 6.0 g, yield: 52%) was obtained.

[Chemical Formula 485]

(1-172)

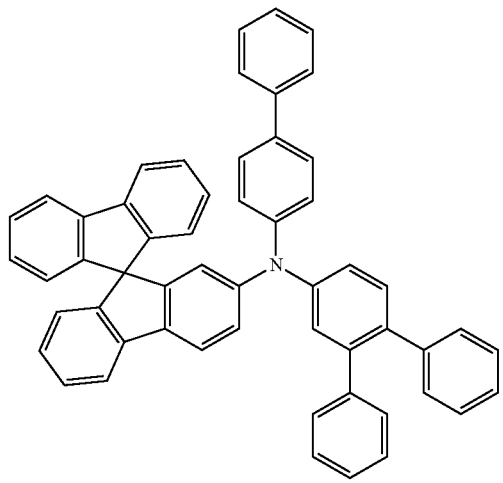

The structure of the obtained white powder was identified by NMR.

$^1$H-NMR (CDCl$_3$) detected 37 hydrogen signals, as follows.

δ (ppm)=7.81-7.88 (4H), 7.59-7.62 (2H), 7.34-7.50 (8H), 7.03-7.28 (15H), 6.73-6.92 (8H).

Example 22

Synthesis of (biphenyl-4-yl)-(1,1':2',1":2",1'''-quaterphenyl-5'-yl)-(9,9'-spirobi[fluoren]-2-yl)amine Compound 1-175

The reaction was carried out under the same conditions as those of Example 21, except that phenylboronic acid was replaced with 2-biphenylboronic acid, whereby a white powder of (biphenyl-4-yl)-(1,1':2',1":2",1'''-quaterphenyl-5'-yl)-(9,9'-spirobi[fluoren]-2-yl)amine (Compound 1-175, 6.1 g, yield: 42%) was obtained.

[Chemical Formula 486]

(1-175)

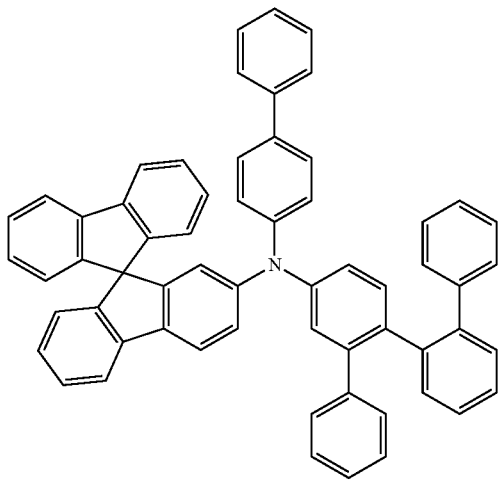

The structure of the obtained white powder was identified by NMR.
¹H-NMR (CDCl₃) detected 41 hydrogen signals, as follows.
δ (ppm)=7.75-7.86 (4H), 7.34-7.58 (14H), 6.85-7.20 (17H), 6.70-6.72 (2H), 6.59-6.62 (2H), 6.40-6.42 (2H).

Example 23

Synthesis of {4-(naphthalen-2-yl)phenyl}-(1,1':2',1":4",1'''-quaterphenyl-5'-yl)-(9,9'-spirobi[fluoren]-2-yl)amine Compound 1-184

The reaction was carried out under the same conditions as those of Example 1, except that bis(biphenyl-4-yl)-(6-bromobiphenyl-3-yl)amine was replaced with {4-(naphthalen-2-yl)phenyl}-(6-bromobiphenyl-3-yl)-(9,9'-spirobi[fluoren]-2-yl)amine, and phenylboronic acid was replaced with 4-biphenylboronic acid, whereby a white powder of {4-(naphthalen-2-yl)phenyl}-(1,1':2',1":4",1'''-quaterphenyl-5'-yl)-(9,9'-spirobi[fluoren]-2-yl)amine (Compound 1-184, 12.8 g, yield: 80%) was obtained.

[Chemical Formula 487]

(1-184)

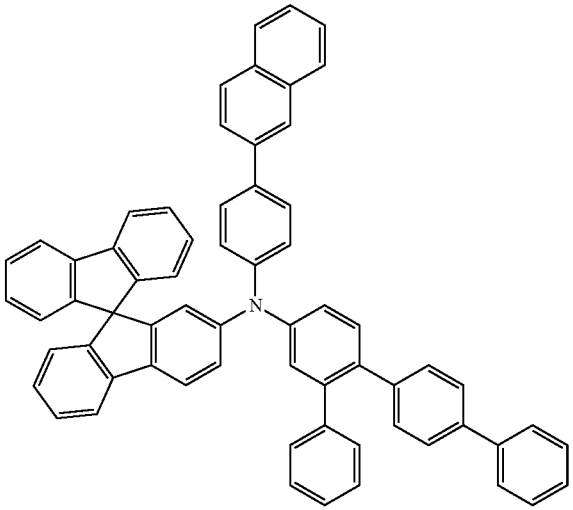

The structure of the obtained white powder was identified by NMR.
¹H-NMR (CDCl₃) detected 43 hydrogen signals, as follows.
δ (ppm)=8.00 (1H), 7.74-7.93 (8H), 7.33-7.56 (10H), 6.85-7.19 (18H), 6.58-6.72 (5H), 6.39-6.42 (1H).

Example 24

Synthesis of {4-(naphthalen-2-yl)phenyl}-(1,1':2',1":2",1'''-quaterphenyl-5'-yl)-(9,9'-spirobi[fluoren]-2-yl)amine Compound 1-186

The reaction was carried out under the same conditions as those of Example 23, except that 4-biphenylboronic acid was replaced with 2-biphenylboronic acid, whereby a white powder of {4-(naphthalen-2-yl)phenyl}-(1,1':2',1":2",1'''-quaterphenyl-5'-yl)-(9,9'-spirobi[fluoren]-2-yl)amine (Compound 1-186, 14.5 g, yield: 91%) was obtained.

[Chemical Formula 488]

(1-186)

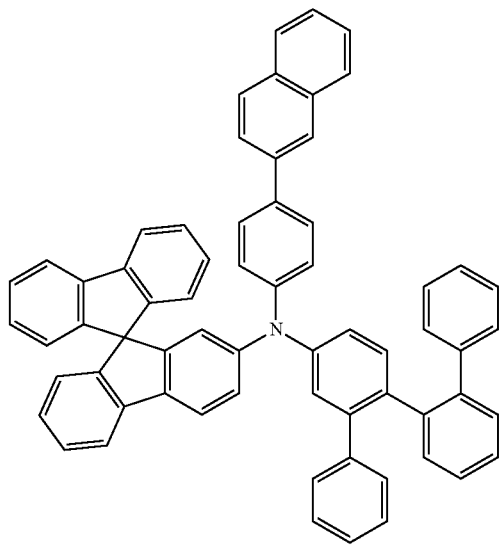

The structure of the obtained white powder was identified by NMR.

¹H-NMR (CDCl₃) detected 43 hydrogen signals, as follows.

δ (ppm)=8.03 (1H), 7.76-7.94 (8H), 7.07-7.62 (28H), 6.84-6.96 (5H), 6.72-6.74 (1H).

Example 25

Synthesis of (biphenyl-4-yl)-{(1,1':2',1''-terphenyl-4'-yl}-(phenanthren-9-yl)amine Compound 1-187

The reaction was carried out under the same conditions as those of Example 1, except that bis(biphenyl-4-yl)-(6-bromobiphenyl-3-yl)amine was replaced with (6-bromobiphenyl-3-yl)-(biphenyl-4-yl)-(phenanthren-9-yl)amine, whereby a white powder of (biphenyl-4-yl)-{(1,1':2',1''-terphenyl-4'-yl}-(phenanthren-9-yl)amine (Compound 1-187, 3.5 g, yield: 22%) was obtained.

[Chemical Formula 489]

(1-187)

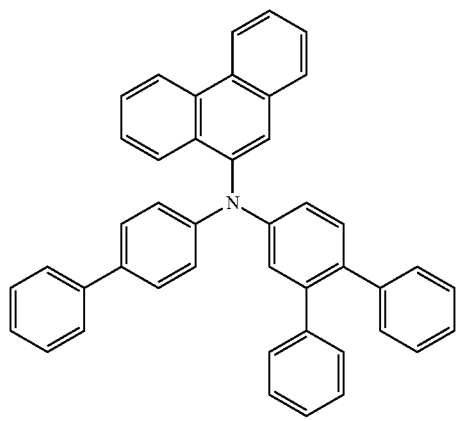

The structure of the obtained white powder was identified by NMR.

¹H-NMR (CDCl₃) detected 31 hydrogen signals, as follows.

δ (ppm)=8.70-8.81 (2H), 8.17 (1H), 7.83 (1H), 7.78 (1H), 7.72-7.74 (26H).

Example 26

Synthesis of (biphenyl-4-yl)-{(1,1':2',1'':4'',1'''-quaterphenyl-5'-yl}-(phenanthren-9-yl)amine Compound 1-188

The reaction was carried out under the same conditions as those of Example 25, except that phenylboronic acid was replaced with 4-biphenylboronic acid, whereby a white powder of (biphenyl-4-yl)-{(1,1':2',1'':4'',1'''-quaterphenyl-5'-yl}-(phenanthren-9-yl)amine (Compound 1-188, 13.0 g, yield: 77%) was obtained.

[Chemical Formula 490]

(1-188)

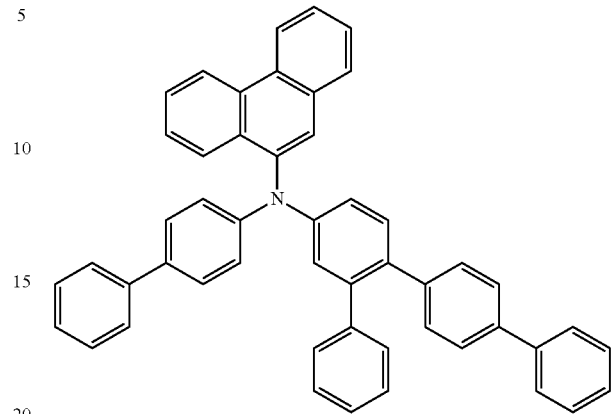

The structure of the obtained white powder was identified by NMR.

¹H-NMR (CDCl₃) detected 35 hydrogen signals, as follows.

δ (ppm)=8.73-8.82 (2H), 8.17 (1H), 7.85 (1H), 7.78 (1H), 7.09-7.75 (30H).

Example 27

Synthesis of (biphenyl-4-yl)-{(1,1':2',1'':3'',1'''-quaterphenyl-5'-yl}-(phenanthren-9-yl)amine Compound 1-189

The reaction was carried out under the same conditions as those of Example 25, except that phenylboronic acid was replaced with 3-biphenylboronic acid, whereby a white powder of (biphenyl-4-yl)-{(1,1':2',1'':3'',1'''-quaterphenyl-5'-yl}-(phenanthren-9-yl)amine (Compound 1-189, 5.0 g, yield: 40%) was obtained.

[Chemical Formula 491]

(1-189)

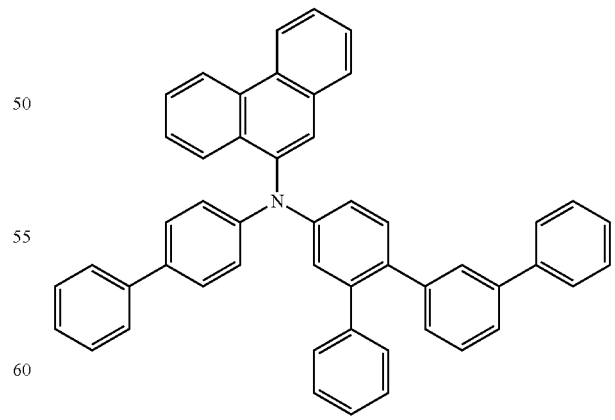

The structure of the obtained white powder was identified by NMR.

¹H-NMR (CDCl₃) detected 35 hydrogen signals, as follows.

δ (ppm)=8.76-8.83 (2H), 8.21-8.24 (1H), 7.12-7.87 (32H).

Example 28

Synthesis of (biphenyl-4-yl)-{(1,1':2',1":2",1'''-quaterphenyl-5'-yl}-(phenanthren-9-yl)amine Compound 1-190

The reaction was carried out under the same conditions as those of Example 25, except that phenylboronic acid was replaced with 2-biphenylboronic acid, whereby a white powder of (biphenyl-4-yl)-{(1,1':2',1":2",1'''-quaterphenyl-5'-yl}-(phenanthren-9-yl)amine (Compound 1-190, 13.0 g, yield: 77%) was obtained.

[Chemical Formula 492]

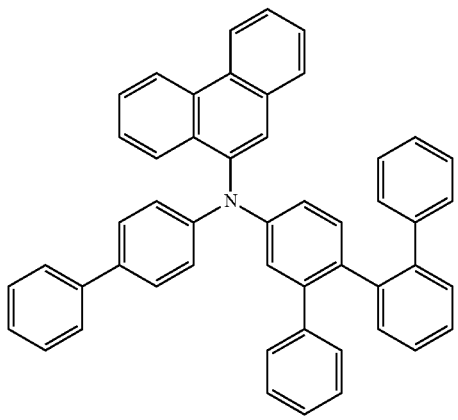

(1-190)

The structure of the obtained white powder was identified by NMR.

$^1$H-NMR (CDCl$_3$) detected 35 hydrogen signals, as follows.

δ (ppm)=8.75-8.83 (2H), 8.17-8.19 (1H), 6.93-7.73 (28H), 6.69-6.72 (2H), 6.54-6.56 (2H).

Example 29

The glass transition points of the arylamine compounds of the general formula (1) were measured using a high-sensitive differential scanning calorimeter (DSC3100SA produced by Bruker AXS).

|  | Glass transition point |
|---|---|
| Compound of Example 1 | 101° C. |
| Compound of Example 2 | 103° C. |
| Compound of Example 3 | 115° C. |
| Compound of Example 4 | 104° C. |
| Compound of Example 5 | 101° C. |
| Compound of Example 6 | 112° C. |
| Compound of Example 7 | 112° C. |
| Compound of Example 8 | 115° C. |
| Compound of Example 9 | 117° C. |
| Compound of Example 10 | 123° C. |
| Compound of Example 11 | 114° C. |
| Compound of Example 12 | 116° C. |
| Compound of Example 13 | 119° C. |
| Compound of Example 14 | 116° C. |
| Compound of Example 15 | 119° C. |
| Compound of Example 16 | 125° C. |
| Compound of Example 17 | 137° C. |
| Compound of Example 18 | 124° C. |
| Compound of Example 19 | 126° C. |
| Compound of Example 20 | 125° C. |
| Compound of Example 21 | 128° C. |
| Compound of Example 22 | 134° C. |
| Compound of Example 23 | 137° C. |
| Compound of Example 24 | 148° C. |
| Compound of Example 25 | 115° C. |
| Compound of Example 26 | 129° C. |
| Compound of Example 27 | 116° C. |
| Compound of Example 28 | 117° C. |

The arylamine compounds of the general formula (1) have glass transition points of 100° C. or higher, demonstrating that the compounds have a stable thin-film state.

Example 30

A 100 nm-thick vapor-deposited film was fabricated on an ITO substrate using the arylamine compounds of the general formula (1), and a work function was measured using an ionization potential measuring device (PYS-202 produced by Sumitomo Heavy Industries, Ltd.).

|  | Work function |
|---|---|
| Compound of Example 1 | 5.68 eV |
| Compound of Example 2 | 5.72 eV |
| Compound of Example 3 | 5.66 eV |
| Compound of Example 4 | 5.67 eV |
| Compound of Example 5 | 5.72 eV |
| Compound of Example 6 | 5.75 eV |
| Compound of Example 7 | 5.70 eV |
| Compound of Example 8 | 5.70 eV |
| Compound of Example 9 | 5.72 eV |
| Compound of Example 10 | 5.79 eV |
| Compound of Example 11 | 5.67 eV |
| Compound of Example 12 | 5.68 eV |
| Compound of Example 13 | 5.69 eV |
| Compound of Example 14 | 5.62 eV |
| Compound of Example 15 | 5.63 eV |
| Compound of Example 16 | 5.66 eV |
| Compound of Example 17 | 5.67 eV |
| Compound of Example 18 | 5.68 eV |
| Compound of Example 19 | 5.64 eV |
| Compound of Example 20 | 5.75 eV |
| Compound of Example 21 | 5.64 eV |
| Compound of Example 22 | 5.65 eV |
| Compound of Example 23 | 5.63 eV |
| Compound of Example 24 | 5.63 eV |
| Compound of Example 25 | 5.76 eV |
| Compound of Example 26 | 5.74 eV |
| Compound of Example 27 | 5.75 eV |
| Compound of Example 28 | 5.76 eV |

As the results show, the arylamine compounds of the general formula (1) have desirable energy levels compared to the work function 5.4 eV of common hole transport materials such as NPD and TPD, and thus possess desirable hole transportability.

Example 31

Synthesis of 4,6-bis(4-naphthalene-1-yl-phenyl)-2-(+4-pyridine-3-yl-phenyl)-benzoxazole Compound 2-1

2-(4-chlorophenyl)-4,6-bis(4-naphthalene-1-yl-phenyl)-benzoxazole (4.5 g), 3-pyridylboronic acid (1.0 g), bis (dibenzylideneacetone)palladium(0) (0.32 g), tricyclohexylphosphine (0.4 g), and tripotassium phosphate (4.7 g) were added into reaction vessel. The mixture was refluxed for overnight while stirring. After cooling, an organic layer was collected by liquid separation, and ethyl acetate were added to the aqueous layer for extraction. The collected organic layer was concentrated, and then the resulting crude product was purified by column chromatography (support: silica gel, eluent: dichloromethane/ethyl acetate), whereby a white powder of 4,6-bis(4-naphthalene-1-yl-phenyl)-2-(4-pyridine-3-yl-phenyl)-benzoxazole (Compound 2-1; 1.8 g; yield: 38%) was obtained.

[Chemical Formula 493]

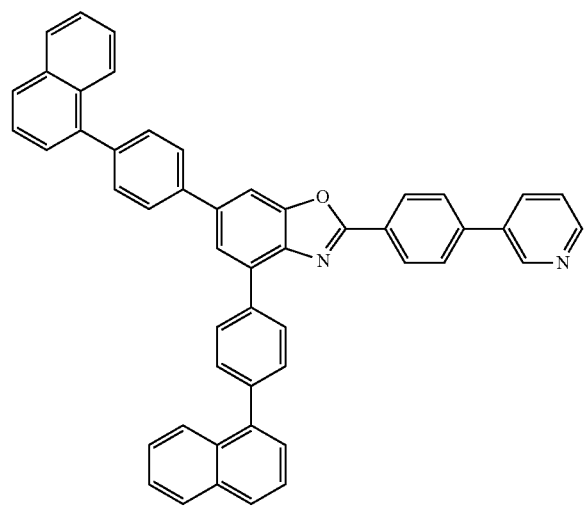

(2-1)

The structure of the obtained white powder was identified by NMR.

$^1$H-NMR (CDCl$_3$) detected 32 hydrogen signals, as follows.

δ (ppm)=8.98 (1H), 8.68 (1H), 8.52 (2H), 8.34 (2H), 8.12 (1H), 8.07-7.89 (10H), 7.82 (2H), 7.76 (2H), 7.69 (2H), 7.64 (9H).

Example 32

Synthesis of 2-{4'-(pyridine-3-yl)-biphenyl-4-yl}-4,6-di(naphthalene-1-yl)-benzoxazole Compound 2-2

The reaction was carried out under the same conditions as those of Example 31, except that 2-(4-chlorophenyl)-4,6-bis(4-naphthalene-1-yl-phenyl)-benzoxazole was replaced with 2-(4-chlorophenyl)-4,6-di(naphthalene-1-yl)-benzoxazole, and 3-pyridylboronic acid was replaced with 4-(pyridine-3-yl)-phenylboronic acid, whereby a white powder of 2-{4'-(pyridine-3-yl)-biphenyl-4-yl}-4,6-di(naphthalene-1-yl)-benzoxazole (Compound 2-2; 2.1 g; yield: 34%) was obtained.

[Chemical Formula 494]

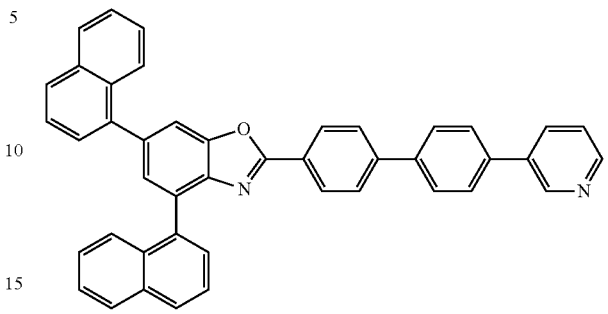

(2-2)

The structure of the obtained white powder was identified by NMR.

$^1$H-NMR (CDCl$_3$) detected 28 hydrogen signals, as follows.

δ (ppm)=8.94 (1H), 8.64 (1H), 8.35 (2H), 8.13 (1H), 8.05-7.91 (6H), 7.85 (1H), 7.82-7.76 (5H), 7.72 (2H), 7.68 (2H), 7.64-7.38 (7H).

Example 33

Synthesis of 4,6-bis(4-naphthalene-1-yl-phenyl)-2-(3-pyridine-3-yl-phenyl)-benzoxazole Compound 2-3

The reaction was carried out under the same conditions as those of Example 31, except that 2-(4-chlorophenyl)-4,6-bis(4-naphthalene-1-yl-phenyl)-benzoxazole was replaced with 2-(3-chlorophenyl)-4,6-bis(4-naphthalene-1-yl-phenyl)-benzoxazole, and bis(dibenzylideneacetone)palladium(0) was replaced with tris(dibenzylideneacetone)palladium(0), whereby a white powder of 4,6-bis(4-naphthalene-1-yl-phenyl)-2-(3-pyridine-3-yl-phenyl)-benzoxazole (Compound 2-3; 3.6 g; yield: 48%) was obtained.

[Chemical Formula 495]

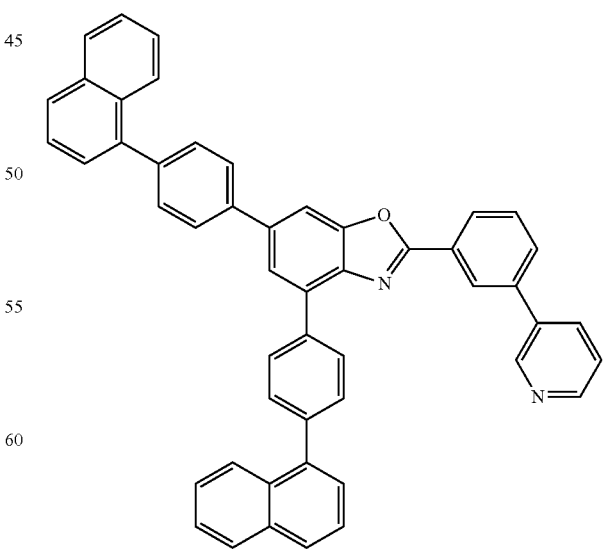

(2-3)

The structure of the obtained white powder was identified by NMR.

$^1$H-NMR (CDCl$_3$) detected 32 hydrogen signals, as follows.

δ (ppm)=9.01 (1H), 8.69 (1H), 8.60 (1H), 8.43 (1H), 8.32 (2H), 8.11 (1H), 8.07-8.01 (3H), 7.98-7.88 (7H), 7.83-7.67 (6H), 7.62-7.42 (9H).

Example 34

Synthesis of 2-{3'-(pyridine-3-yl)-biphenyl-4-yl}-4,6-di(4-naphthalene-1-yl)-benzoxazole Compound 2-4

The reaction was carried out under the same conditions as those of Example 31, except that 2-(4-chlorophenyl)-4,6-bis(4-naphthalene-1-yl-phenyl)-benzoxazole was replaced with 2-(4-chlorophenyl)-4,6-di(naphthalene-1-yl)-benzoxazole, and 3-pyridylboronic acid was replaced with 3-(pyridine-3-yl)-phenylboronic acid, and bis(dibenzylideneacetone)palladium(0) was replaced with tris(dibenzylideneacetone)palladium(0), whereby a white powder of 2-{3'-(pyridine-3-yl)-biphenyl-4-yl}-4,6-di(naphthalene-1-yl)-benzoxazole (Compound 2-4; 4.4 g; yield: 71%) was obtained.

[Chemical Formula 496]

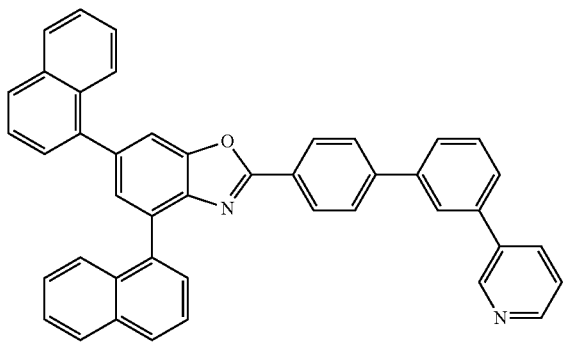

(2-4)

The structure of the obtained white powder was identified by NMR.

$^1$H-NMR (CDCl$_3$) detected 28 hydrogen signals, as follows.

δ (ppm)=8.94 (1H), 8.65 (1H), 8.36 (2H), 8.21 (1H), 8.05-7.92 (6H), 7.85 (2H), 7.83-7.76 (3H), 7.75-7.74 (12H).

Example 35

Synthesis of 2-(3-pyridine-4-yl-phenyl)-4,6-bis(4-naphthalene-1-yl)-phenyl-benzoxazole Compound 2-5

The reaction was carried out under the same conditions as those of Example 31, except that 2-(4-chlorophenyl)-4,6-bis(4-naphthalene-1-yl-phenyl)-benzoxazole was replaced with 2-(3-chlorophenyl)-4,6-bis(4-naphthalene-1-yl-phenyl)-benzoxazole, and 3-pyridylboronic acid was replaced with 4-pyridylboronic acid, and bis(dibenzylideneacetone)palladium(0) was replaced with tris(dibenzylideneacetone)palladium(0), whereby a white powder of 2-(3-pyridine-4-yl-phenyl)-4,6-bis(4-naphthalene-1-yl-phenyl)-benzoxazole (Compound 2-5; 3.0 g; yield: 40%) was obtained.

[Chemical Formula 497]

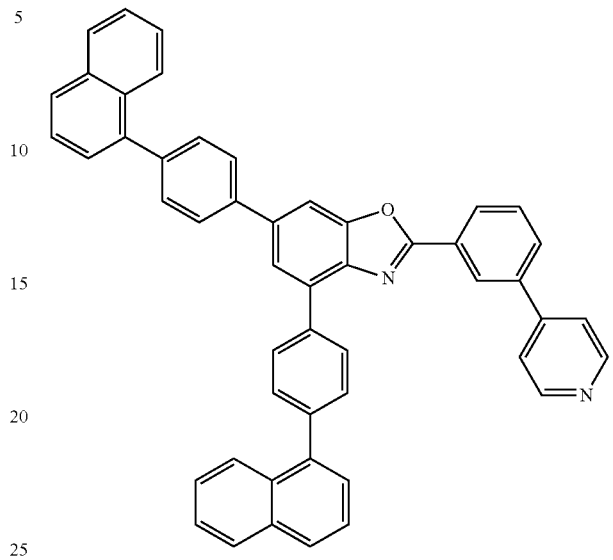

(2-5)

The structure of the obtained white powder was identified by NMR.

$^1$H-NMR (CDCl$_3$) detected 32 hydrogen signals, as follows.

δ (ppm)=8.76 (2H), 8.66 (1H), 8.47 (1H), 8.32 (2H), 8.11 (1H), 8.07-8.02 (2H), 7.99-7.89 (7H), 7.85 (1H), 7.78-7.48 (15H).

Example 36

Synthesis of 2-{4'-(pyridine-3-yl)-biphenyl-4-yl}-4,6-di(phenanthrene-9-yl)-benzoxazole Compound 2-6

The reaction was carried out under the same conditions as those of Example 31, except that 2-(4-chlorophenyl)-4,6-bis(naphthalene-1-yl-phenyl)-benzoxazole was replaced with 2-(4-chlorophenyl)-4,6-di(phenanthrene-9-yl)-benzoxazole, and 3-pyridylboronic acid was replaced with 4-(pyridine-3-yl)phenylboronic acid, and bis(dibenzylideneacetone)palladium(0) was replaced with tris(dibenzylideneacetone)palladium(0), whereby a white powder of 2-{4'-(pyridine-3-yl)-biphenyl-4-yl}-4,6-di(phenanthrene-9-yl)-benzoxazole (Compound 2-6; 2.1 g; yield: 17%) was obtained.

[Chemical Formula 498]

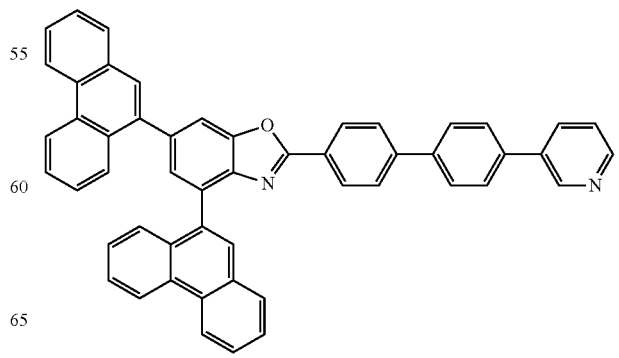

(2-6)

The structure of the obtained white powder was identified by NMR.

¹H-NMR (CDCl₃) detected 32 hydrogen signals, as follows.

δ (ppm)=8.93 (1H), 8.87-8.63 (4H), 8.62 (1H), 8.33 (2H), 8.18 (1H), 8.08-7.88 (7H), 7.80-7.55 (15H), 7.40 (1H).

Example 37

Synthesis of 2-{3'-(pyridine-3-yl)-biphenyl-3-yl}-4,6-bis(4-naphthalene-1-yl-phenyl)-benzoxazole Compound 2-7

The reaction was carried out under the same conditions as those of Example 31, except that 2-(4-chlorophenyl)-4,6-bis(4-naphthalene-1-yl-phenyl)-benzoxazole was replaced with 2-(3-chlorophenyl)-4,6-bis(4-naphthalene-1-yl-phenyl)-benzoxazole, and 3-pyridylboronic acid was replaced with 3-(pyridine-3-yl)-phenylboronic acid, and bis(dibenzylideneacetone)palladium(0) was replaced with tris(dibenzylideneacetone)palladium(0), whereby a white powder of 2-{3'-(pyridine-3-yl)-biphenyl-3-yl}-4,6-bis(4-naphthalene-1-yl-phenyl)-benzoxazole (Compound 2-7; 2.0 g; yield: 27%) was obtained.

[Chemical Formula 499]

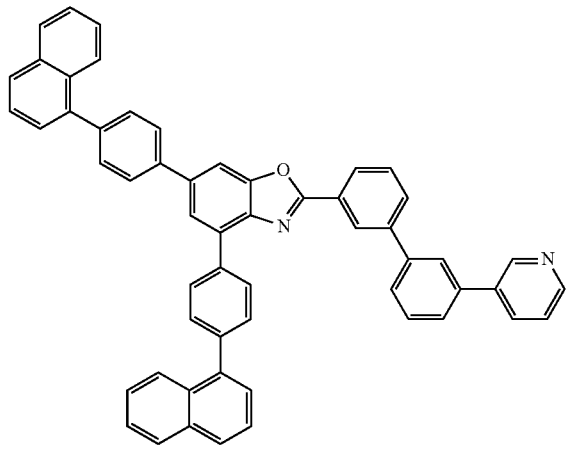

(2-7)

The structure of the obtained white powder was identified by NMR.

¹H-NMR (CDCl₃) detected 36 hydrogen signals, as follows.

δ (ppm)=8.98 (1H), 8.68-8.61 (2H), 8.42 (1H), 8.32 (2H), 8.15-7.40 (30H).

Example 38

Synthesis of 2-{3'-(pyridine-3-yl)-biphenyl-4-yl}-4,6-di(phenanthrene-9-yl)-benzoxazole Compound 2-8

The reaction was carried out under the same conditions as those of Example 31, except that 2-(4-chlorophenyl)-4,6-bis(4-naphthalene-1-yl-phenyl)-benzoxazole was replaced with 2-(4-chlorophenyl)-4,6-di(phenanthrene-9-yl)-benzoxazole, and 3-pyridylboronic acid was replaced with 3-(pyridine-3-yl)-phenylboronic acid, and bis(dibenzylideneacetone)palladium(0) was replaced with tris(dibenzylideneacetone)palladium(0), whereby a white powder of 2-{3'-(pyridine-3-yl)-biphenyl-4-yl}-4,6-di(phenanthrene-9-yl)-benzoxazole (Compound 2-8; 4.0 g; yield: 33%) was obtained.

[Chemical Formula 500]

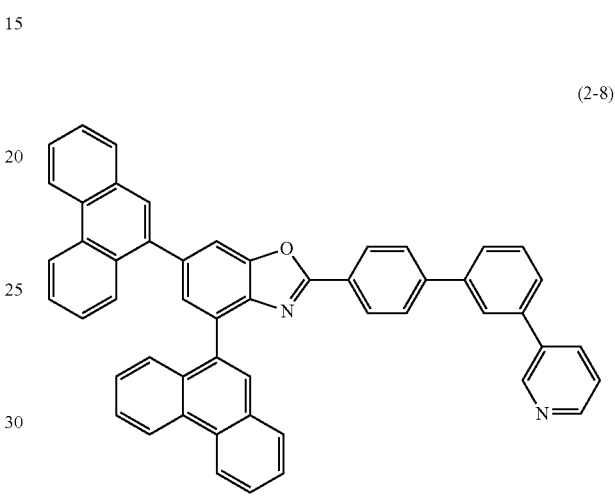

(2-8)

The structure of the obtained white powder was identified by NMR.

¹H-NMR (CDCl₃) detected 32 hydrogen signals, as follows.

δ (ppm)=8.93 (1H), 8.87-8.73 (4H), 8.65 (1H), 8.36 (2H), 8.18 (1H), 8.08-7.83 (8H), 7.79-7.54 (14H), 7.42 (1H).

Example 39

Synthesis of 2-(biphenyl-4-yl)-6-(phenanthrene-9-yl)-4-{4-(pyridine-3-yl)-phenyl}-benzoxazole Compound 2-90

The reaction was carried out under the same conditions as those of Example 31, except that 2-(4-chlorophenyl)-4,6-bis(4-naphthalene-1-yl-phenyl)-benzoxazole was replaced with 2-(4-chlorophenyl)-6-(phenanthrene-9-yl)-4-{4-(pyridine-3-yl)-phenyl}-benzoxazole, and 3-pyridylboronic acid was replaced with phenylboronic acid, and bis(dibenzylideneacetone)palladium(0) was replaced with tris(dibenzylideneacetone)palladium(0), whereby a white powder of 2-(biphenyl-4-yl)-6-(phenanthrene-9-yl)-4-{4-(pyridine-3-yl)-phenyl}-benzoxazole (Compound 2-90; 4.3 g; yield: 67%) was obtained.

[Chemical Formula 501]

(2-90)

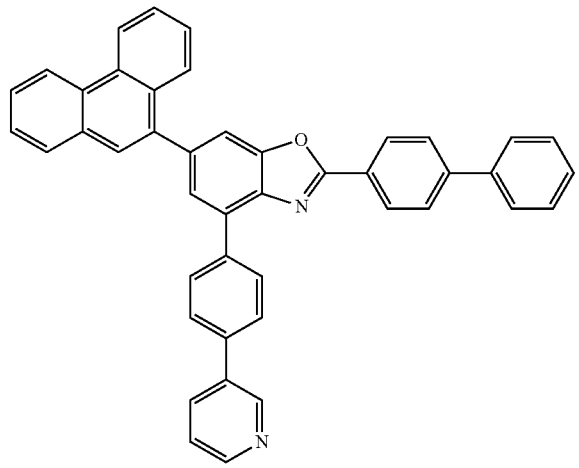

The structure of the obtained white powder was identified by NMR.
¹H-NMR (CDCl₃) detected 28 hydrogen signals, as follows.
δ (ppm)=8.98 (1H), 8.86 (1H), 8.80 (1H), 8.64 (1H), 8.46 (2H), 8.32 (2H), 8.07 (1H), 7.98 (2H), 7.88-7.57 (13H), 7.52 (2H), 7.44 (2H).

Example 40

Synthesis of 2-{3,5-di([9H]-carbazol-9-yl)-phenyl}-4,6-diphenyl-benzoxazole Compound 2-111

The reaction was carried out under the same conditions as those of Example 31, except that 2-(4-chlorophenyl)-4,6-bis(4-naphthalene-1-yl-phenyl)-benzoxazole was replaced with 2-(3,5-dichlorophenyl)-4,6-diphenyl-benzoxazole, and 3-pyridylboronic acid was replaced with carbazol, whereby a white powder of 2-{3,5-A27,AMDM di([9H]-carbazol-9-yl)-phenyl}-4,6-diphenyl-benzoxazole (Compound 2-111; 4.8 g; yield: 30%) was obtained.

[Chemical Formula 502]

(2-111)

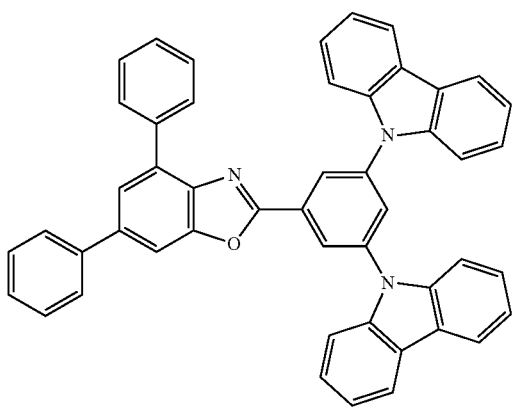

The structure of the obtained white powder was identified by NMR.

¹H-NMR (CDCl₃) detected 31 hydrogen signals, as follows.
δ (ppm)=8.67 (2H), 8.21 (4H), 8.10 (2H), 8.01 (1H), 7.85 (1H), 7.79 (1H), 7.73 (2H), 7.63 (4H), 7.57-7.46 (8H), 7.46-7.33 (6H).

Example 41

Synthesis of 4,6-di(biphenyl-4-yl)-2-{4'-(pyridine-3-yl)-biphenyl-4-yl}-benzoxazole Compound 2-135

The reaction was carried out under the same conditions as those of Example 31, except that 2-(4-chlorophenyl)-4,6-bis(4-naphthalene-1-yl-phenyl)-benzoxazole was replaced with 4,6-di(biphenyl-4-yl)-2-(4-chlorophenyl)-benzoxazole, and 3-pyridylboronic acid was replaced with 4-(pyridine-3-yl)phenylboronic acid, whereby a pale yellow powder of 4,6-di(biphenyl-4-yl)-2-{4'-(pyridine-3-yl)-biphenyl-4-yl}-benzoxazole (Compound 2-135; 13.3 g; yield: 78%) was obtained.

[Chemical Formula 503]

(2-135)

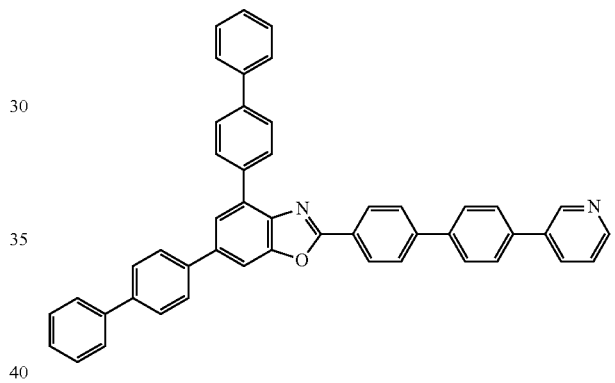

The structure of the obtained pale yellow powder was identified by NMR.
¹H-NMR (CDCl₃) detected 32 hydrogen signals, as follows.
δ (ppm)=8.93 (1H), 8.63 (1H), 8.43 (2H), 8.23 (2H), 7.94 (1H), 7.89 (1H), 7.83-7.79 (9H), 7.76-7.67 (8H), 7.52-7.46 (4H), 7.42-7.36 (3H).

Example 42

Synthesis of 6-(biphenyl-4-yl)-4-(3-pyridine-3-yl)-phenyl)-2-([1,1';4',1"]terphenyl-4-yl)-benzoxazole Compound 2-138

The reaction was carried out under the same conditions as those of Example 31, except that 2-(4-chlorophenyl)-4,6-bis(4-naphthalene-1-yl-phenyl)-benzoxazole was replaced with 2-(4-chlorophenyl)-6-(biphenyl-4-yl)-4-(3-pyridine-3-yl-phenyl)-benzoxazole, and 3-pyridylboronic acid was replaced with 4-biphenylboronic acid, and bis(dibenzylideneacetone)palladium(0) was replaced with tris(dibenzylideneacetone)palladium(0), whereby a pale yellow powder of 6-(biphenyl-4-yl)-4-(3-pyridine-3-yl-phenyl)-2-([1,1';4',1"]terphenyl-4-yl)-benzoxazole (Compound 2-138; 7.5 g; yield: 75%) was obtained.

[Chemical Formula 504]

(2-138)

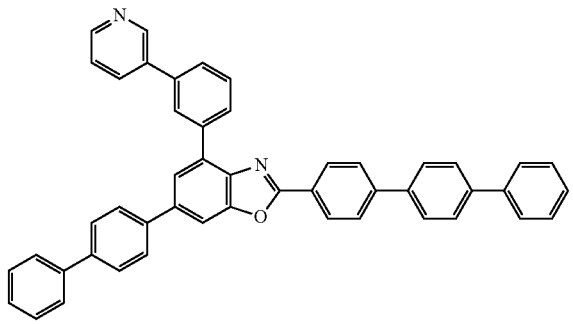

The structure of the obtained pale yellow powder was identified by NMR.

$^1$H-NMR (CDCl$_3$) detected 32 hydrogen signals, as follows.

δ (ppm)=9.03 (1H), 8.65 (1H), 8.42-8.37 (3H), 8.16 (1H), 8.03 (1H), 7.88 (2H), 7.85-7.78 (5H), 7.75 (4H), 7.72 (1H), 7.70-7.66 (6H), 7.52-7.44 (4H), 7.41-7.36 (3H).

Example 43

The melting points and the glass transition points of the compounds of the general formula (2) having a benzazole ring structure were measured using a high-sensitive differential scanning calorimeter (DSC3100SA produced by Bruker AXS).

|  | Melting point | Glass transition point |
| --- | --- | --- |
| Compound of Example 31 | No melting point observed | 123° C. |
| Compound of Example 32 | 277° C. | 119° C. |
| Compound of Example 33 | No melting point observed | 117° C. |
| Compound of Example 34 | 254° C. | 109° C. |
| Compound of Example 35 | No melting point observed | 124° C. |
| Compound of Example 36 | 279° C. | 164° C. |
| Compound of Example 37 | No melting point observed | 117° C. |
| Compound of Example 38 | No melting point observed | 148° C. |
| Compound of Example 39 | No melting point observed | 132° C. |
| Compound of Example 40 | 273° C. | 144° C. |
| Compound of Example 41 | 236° C. | 120° C. |
| Compound of Example 42 | 277° C. | No glass transition point observed |

The benzazole compounds of the compounds of the general formula (2) having a benzazole ring structure have glass transition points of 100° C. or higher, demonstrating that the compounds have a stable thin-film state.

Example 44

A 100 nm-thick vapor-deposited film was fabricated on an ITO substrate using the compounds of the general formula (2) having a benzazole ring structure, and a work function was measured using an ionization potential measuring device (PYS-202 produced by Sumitomo Heavy Industries, Ltd.).

|  | Work function |
| --- | --- |
| Compound of Example 31 | 6.34 eV |
| Compound of Example 32 | 6.40 eV |
| Compound of Example 33 | 6.40 eV |
| Compound of Example 34 | 6.43 eV |
| Compound of Example 35 | 6.41 eV |
| Compound of Example 36 | 6.38 eV |
| Compound of Example 37 | 6.37 eV |
| Compound of Example 38 | 6.40 eV |
| Compound of Example 39 | 6.43 eV |
| Compound of Example 40 | 6.28 eV |
| Compound of Example 41 | 6.35 eV |
| Compound of Example 42 | 6.29 eV |

As the results show, the compound having a benzazole ring structure of the general formula (2) has a larger value as compared with the work function 5.4 eV possessed by general hole transport materials such as NPD and TPD, and thus has a large hole blocking ability.

Example 45

The organic EL device, as shown in FIG. 1, was fabricated by vapor-depositing a hole injection layer 3, a first hole transport layer 4, a second hole transport layer 5, a light emitting layer 6, an electron transport layer 7, an electron injection layer 8, and a cathode (aluminum electrode) 9 in this order on a glass substrate 1 on which an ITO electrode was formed as a transparent anode 2 beforehand.

Specifically, the glass substrate 1 having ITO having a film thickness of 150 nm formed thereon was subjected to ultrasonic washing in isopropyl alcohol for 20 minutes and then dried for 10 minutes on a hot plate heated to 200° C. Thereafter, after performing a UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, an electron acceptor (Acceptor-1) of the structural formula below and Compound (4-1) of the structural formula below were formed in a film thickness of 10 nm by dual vapor deposition at a vapor deposition rate that satisfies a vapor deposition rate ratio of Acceptor-1/Compound (4-1)=3/97. As the first hole transport layer 4 on the hole injection layer 3, Compound (4-1) of the structural formula below was formed in a film thickness of 50 nm. As the second hole transport layer 5 on the first hole transport layer 4, Compound (1-4) of Example 4 was formed in a film thickness of 5 nm. As the light emitting layer 6 on the second hole transport layer 5, Compound (EMD-1) of the structural formula below and Compound (EMH-1) of the structural formula below were formed in a film thickness of 20 nm by dual vapor deposition at a vapor deposition rate that satisfies a vapor deposition rate ratio of EMD-1/EMH-1=5/95. As the electron transport layer 7 on the light emitting layer 6, Compound (2-1) of Example 31 and Compound (ETM-1) of the structural formula below were formed in a film thickness of 30 nm by dual vapor deposition at a vapor deposition rate that satisfies a vapor deposition rate ratio of Compound (2-1)/ETM-1=50/50. As the electron injection layer 8 on the electron transport layer 7, lithium fluoride was formed in a film thickness of 1 nm. Finally, aluminum was vapor-deposited in a thickness of 100 nm to form the cathode 9. The characteristics of the organic EL device were measured in the atmosphere at ordinary temperature. Table 1 summarizes the results of measurement of emission characteristics when applying a DC voltage to the fabricated organic EL device.
[Chemical Formula 505]
(Acceptor-1)
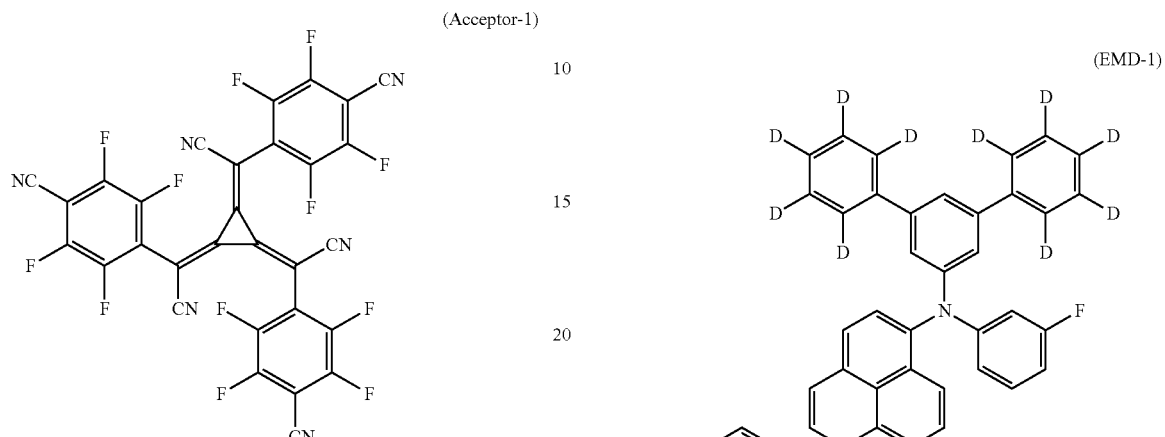
[Chemical Formula 506]
(4-1)
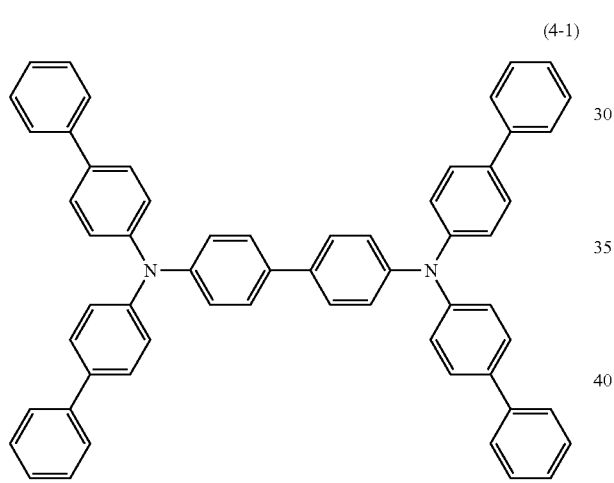
[Chemical Formula 507]
(1-4)
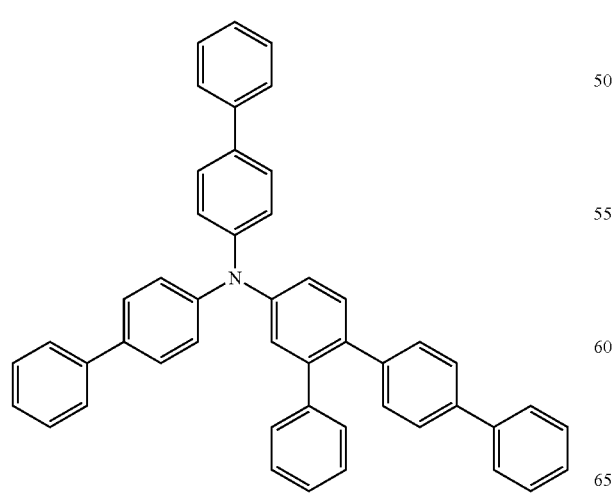
[Chemical Formula 508]
(EMD-1)
[Chemical Formula 509]
(EMH-1)
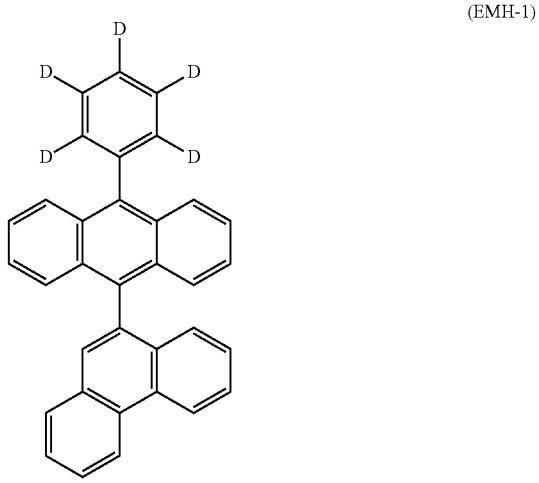

-continued

[Chemical Formula 510]

(2-1)

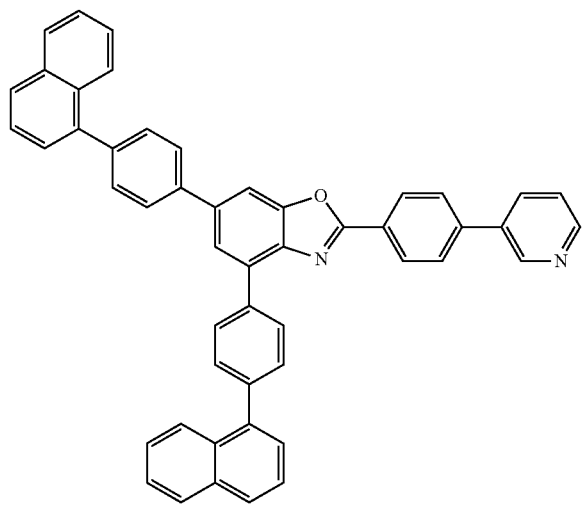

[Chemical Formula 511]

(ETM-1)

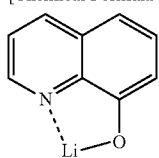

Example 46

An organic EL device was fabricated under the same conditions used in Example 45, except that the second hole transport layer 5 was formed by forming the compound (1-158) of Example 12, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 512]

(1-158)

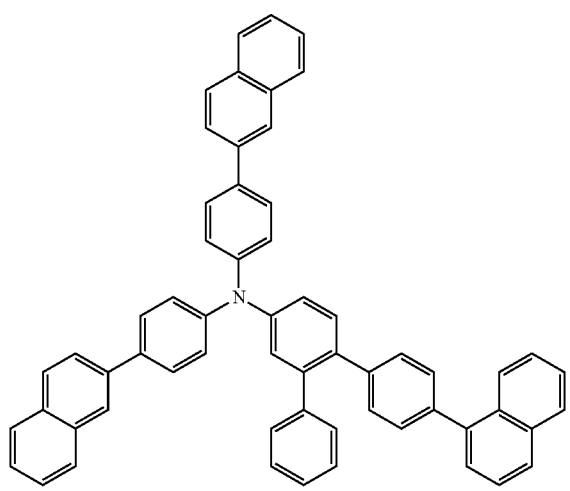

Example 47

An organic EL device was fabricated under the same conditions used in Example 45, except that the second hole transport layer 5 was formed by forming the compound (1-165) of Example 16, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 513]

(1-165)

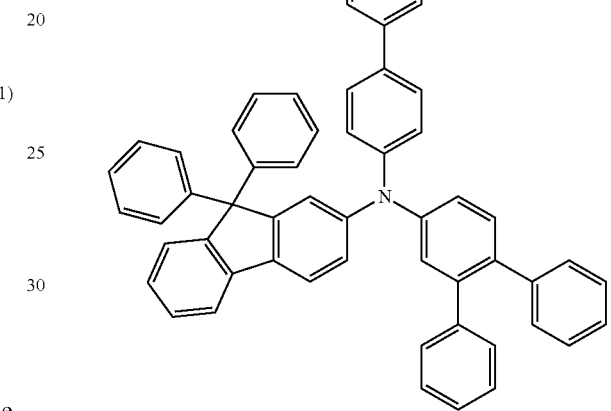

Example 48

An organic EL device was fabricated under the same conditions used in Example 45, except that the electron transport layer 7 was formed by forming the compound (2-2) of Example 32, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 514]

(2-2)

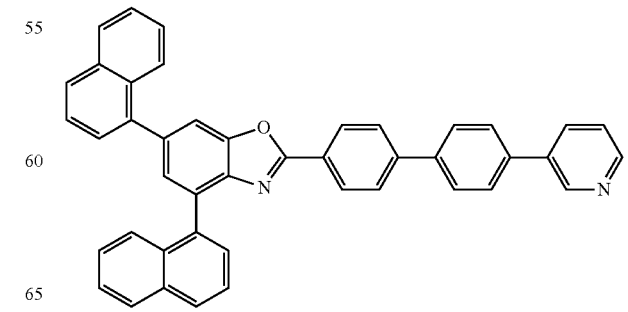

Example 49

An organic EL device was fabricated under the same conditions used in Example 48, except that the second hole transport layer 5 was formed by forming the compound (1-158) of Example 12, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 50

An organic EL device was fabricated under the same conditions used in Example 48, except that the second hole transport layer 5 was formed by forming the compound (1-165) of Example 16, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 51

An organic EL device was fabricated under the same conditions used in Example 45, except that the electron transport layer 7 was formed by forming the compound (2-90) of Example 39, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 515]

(2-90)

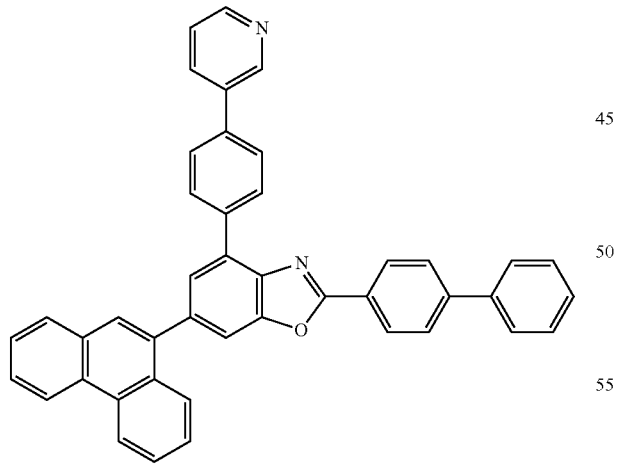

Example 52

An organic EL device was fabricated under the same conditions used in Example 51, except that the second hole transport layer 5 was formed by forming the compound (1-158) of Example 12, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 53

An organic EL device was fabricated under the same conditions used in Example 51, except that the second hole transport layer 5 was formed by forming the compound (1-165) of Example 16, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 54

An organic EL device was fabricated under the same conditions used in Example 45, except that the electron transport layer 7 was formed by forming the compound (2-111) of Example 40, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 516]

(2-111)

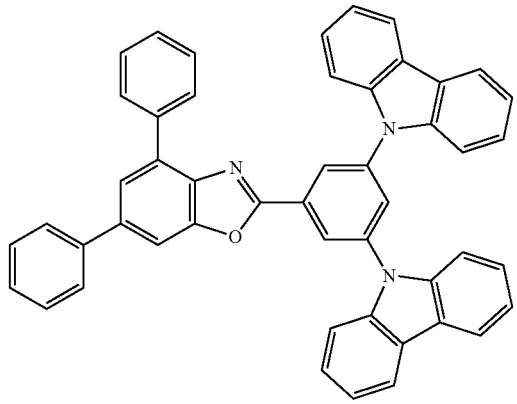

Example 55

An organic EL device was fabricated under the same conditions used in Example 54, except that the second hole transport layer 5 was formed by forming the compound (1-158) of Example 12, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 56

An organic EL device was fabricated under the same conditions used in Example 54, except that the second hole transport layer 5 was formed by forming the compound (1-165) of Example 16, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 57

An organic EL device was fabricated under the same conditions used in Example 45, except that the electron transport layer 7 was formed by forming the compound (2-135) of Example 41, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 517]

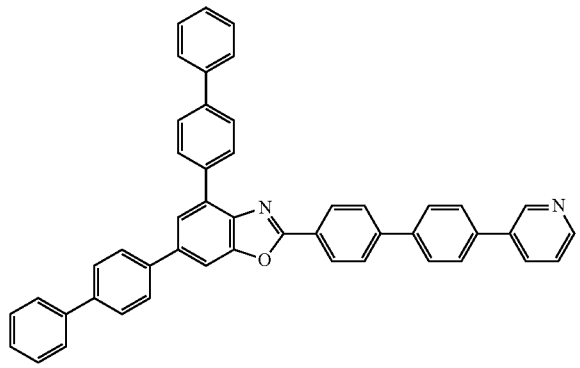

(2-135)

Example 58

An organic EL device was fabricated under the same conditions used in Example 57, except that the second hole transport layer 5 was formed by forming the compound (1-158) of Example 12, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 59

An organic EL device was fabricated under the same conditions used in Example 57, except that the second hole transport layer 5 was formed by forming the compound (1-165) of Example 16, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 60

An organic EL device was fabricated under the same conditions used in Example 45, except that the electron transport layer 7 was formed by forming the compound (2-138) of Example 42, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 518]

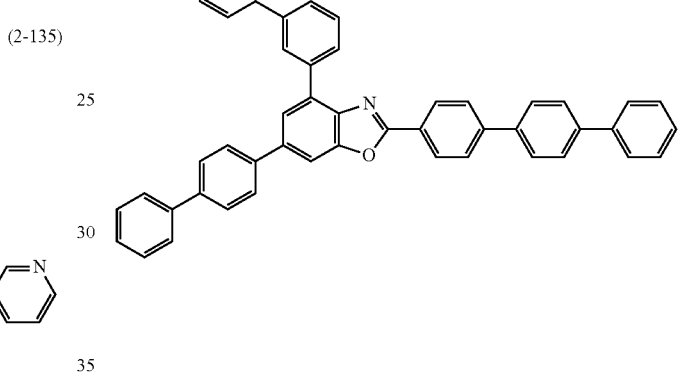

(2-138)

Example 61

An organic EL device was fabricated under the same conditions used in Example 60, except that the second hole transport layer 5 was formed by forming the compound (1-158) of Example 12, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Example 62

An organic EL device was fabricated under the same conditions used in Example 60, except that the second hole transport layer 5 was formed by forming the compound (1-165) of Example 16, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 1

For comparison, an organic EL device was fabricated under the same conditions used in Example 45, except that the second hole transport layer 5 was formed by forming the compound (4-1) of the above structural formula, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 2

For comparison, an organic EL device was fabricated under the same conditions used in Example 48, except that the second hole transport layer 5 was formed by forming the compound (4-1) of the above structural formula, instead of using the compound (1-4) of Example 4. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 3

For comparison, an organic EL device was fabricated under the same conditions used in Example 45, except that the electron transport layer 7 was formed by forming the compound (ETM-2) of the structural formula below, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

[Chemical Formula 519]

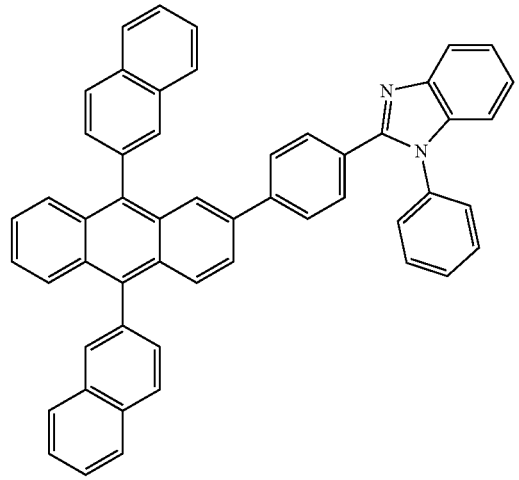

(ETM-2)

Comparative Example 4

For comparison, an organic EL device was fabricated under the same conditions used in Example 45, except that the second hole transport layer 5 was formed by forming the compound (4-1) of the above structural formula, instead of using the compound (1-4) of Example 4, and except that the electron transport layer 7 was formed by forming the compound (ETM-2) of the above structural formula, instead of using the compound (2-1) of Example 31. The characteristics of the organic EL device thus fabricated were measured in the atmosphere at an ordinary temperature. Table 1 summarizes the results of emission characteristics measurements performed by applying a DC voltage to the fabricated organic EL device.

Table 1 summarizes the results of measurement of a device lifetime using the organic EL devices fabricated in Examples 45 to 62 and Comparative Examples 1 to 4. The device lifetime was measured as a time elapsed until the emission luminance of 2,000 cd/m$^2$ (initial luminance) at the start of emission was attenuated to 1,900 cd/m$^2$ (corresponding to 95% when taking the initial luminance as 100%: Attenuation to 95%) when carrying out constant current driving.

TABLE 1

| | First hole transport layer | Second hole transport layer | Light emitting layer | Electron transport layer | Voltage [V] (@10 mA/cm$^2$) | Luminance [cd/m$^2$] (@10 mA/cm$^2$) | Luminous efficiency [cd/A] (@10 mA/cm$^2$) | Power efficiency [lm/W] (@10 mA/cm$^2$) | Lifetime of device, attenuation to 95% |
|---|---|---|---|---|---|---|---|---|---|
| Example 45 | Compound 4-1 | Compound 1-4 | EMD-1/ EMH-1 | Compound 2-1/ ETM-1 | 3.51 | 994 | 9.94 | 8.91 | 186 hours |
| Example 46 | Compound 4-1 | Compound 1-158 | EMD-1/ EMH-1 | Compound 2-1/ ETM-1 | 3.51 | 997 | 9.97 | 8.94 | 155 hours |
| Example 47 | Compound 4-1 | Compound 1-165 | EMD-1/ EMH-1 | Compound 2-1/ ETM-1 | 3.52 | 983 | 9.83 | 8.78 | 152 hours |
| Example 48 | Compound 4-1 | Compound 1-4 | EMD-1/ EMH-1 | Compound 2-2/ ETM-1 | 3.67 | 989 | 9.89 | 8.48 | 172 hours |
| Example 49 | Compound 4-1 | Compound 1-158 | EMD-1/ EMH-1 | Compound 2-2/ ETM-1 | 3.67 | 992 | 9.92 | 8.51 | 144 hours |

TABLE 1-continued

| | First hole transport layer | Second hole transport layer | Light emitting layer | Electron transport layer | Voltage [V] (@10 mA/cm$^2$) | Luminance [cd/m$^2$] (@10 mA/cm$^2$) | Luminous efficiency [cd/A] (@10 mA/cm$^2$) | Power efficiency [lm/W] (@10 mA/cm$^2$) | Lifetime of device, attenuation to 95% |
|---|---|---|---|---|---|---|---|---|---|
| Example 50 | Compound 4-1 | Compound 1-165 | EMD-1/ EMH-1 | Compound 2-2/ ETM-1 | 3.62 | 976 | 9.76 | 8.47 | 143 hours |
| Example 51 | Compound 4-1 | Compound 1-4 | EMD-1/ EMH-1 | Compound 2-90/ ETM-1 | 3.46 | 984 | 9.84 | 8.95 | 168 hours |
| Example 52 | Compound 4-1 | Compound 1-158 | EMD-1/ EMH-1 | Compound 2-90/ ETM-1 | 3.46 | 1026 | 10.26 | 9.32 | 187 hours |
| Example 53 | Compound 4-1 | Compound 1-165 | EMD-1/ EMH-1 | Compound 2-90/ ETM-1 | 3.48 | 1009 | 10.09 | 9.12 | 166 hours |
| Example 54 | Compound 4-1 | Compound 1-4 | EMD-1/ EMH-1 | Compound 2-111/ ETM-1 | 3.70 | 980 | 9.80 | 8.33 | 141 hours |
| Example 55 | Compound 4-1 | Compound 1-158 | EMD-1/ EMH-1 | Compound 2-111/ ETM-1 | 3.65 | 1023 | 10.23 | 8.80 | 165 hours |
| Example 56 | Compound 4-1 | Compound 1-165 | EMD-1/ EMH-1 | Compound 2-111/ ETM-1 | 3.66 | 1001 | 10.01 | 8.59 | 152 hours |
| Example 57 | Compound 4-1 | Compound 1-4 | EMD-1/ EMH-1 | Compound 2-135/ ETM-1 | 3.47 | 971 | 9.71 | 8.79 | 194 hours |
| Example 58 | Compound 4-1 | Compound 1-158 | EMD-1/ EMH-1 | Compound 2-135/ ETM-1 | 3.47 | 974 | 9.74 | 8.82 | 211 hours |
| Example 59 | Compound 4-1 | Compound 1-165 | EMD-1/ EMH-1 | Compound 2-135/ ETM-1 | 3.48 | 964 | 9.64 | 8.71 | 202 hours |
| Example 60 | Compound 4-1 | Compound 1-4 | EMD-1/ EMH-1 | Compound 2-138/ ETM-1 | 3.61 | 999 | 9.99 | 8.70 | 156 hours |
| Example 61 | Compound 4-1 | Compound 1-158 | EMD-1/ EMH-1 | Compound 2-138/ ETM-1 | 3.61 | 1013 | 10.13 | 8.82 | 171 hours |
| Example 62 | Compound 4-1 | Compound 1-165 | EMD-1/ EMH-1 | Compound 2-138/ ETM-1 | 3.57 | 1008 | 10.08 | 8.88 | 168 hours |
| Comparative Example 1 | Compound 4-1 | Compound 4-1 | EMD-1/ EMH-1 | Compound 2-1/ ETM-1 | 3.67 | 840 | 8.40 | 7.21 | 126 hours |
| Comparative Example 2 | Compound 4-1 | Compound 4-1 | EMD-1/ EMH-1 | Compound 2-2/ ETM-1 | 3.69 | 811 | 8.11 | 6.92 | 107 hours |
| Comparative Example 3 | Compound 4-1 | Compound 1-4 | EMD-1/ EMH-1 | ETM-2/ ETM-1 | 3.75 | 843 | 8.43 | 7.06 | 105 hours |
| Comparative Example 4 | Compound 4-1 | Compound 4-1 | EMD-1/ EMH-1 | ETM-2/ ETM-1 | 3.80 | 720 | 7.20 | 5.95 | 52 hours |

As shown in Table 1, the luminous efficiency upon passing a current with a current density of 10 mA/cm$^2$ was 9.64 to 10.26 cd/A for the organic EL devices in Examples 45 to 62, which was higher than 7.20 to 8.43 cd/A for the organic EL devices in Comparative Examples 1 to 4. Further, the power efficiency was 8.33 to 9.32 lm/W for the organic EL devices in Examples 45 to 62, which was higher than 5.95 to 7.21 lm/W for the organic EL devices in Comparative Examples 1 to 4. Table 1 also shows that the device lifetime (attenuation to 95%) was 141 to 211 hours for the organic EL devices in Examples 45 to 62, showing achievement of a far longer lifetime than 52 to 126 hours for the organic EL devices in Comparative Examples 1 to 4.

It was found that the organic EL device of the present invention can achieve an organic EL device having high luminous efficiency and a long lifetime compared to the conventional organic EL devices by combining a specific arylamine compound and a compound having a specific benzazole ring structure so that carrier balance inside the organic EL device is improved, and further by combining the compounds so that the carrier balance matches the characteristics of the light-emitting material.

INDUSTRIAL APPLICABILITY

In the organic EL device of the present invention in which a specific arylamine compound and a compound having a specific benzazole ring structure are combined, luminous efficiency can be improved, and also durability of the organic EL device can be improved to attain potential applications for, for example, home electric appliances and illuminations.

REFERENCE SIGNS LIST

1 Glass substrate
2 Transparent anode
3 Hole injection layer

4 First hole transport layer
5 Second hole transport layer
6 Light emitting layer
7 Electron transport layer
8 Electron injection layer
9 Cathode

The invention claimed is:

1. An organic electroluminescent device comprising at least an anode, a hole transport layer, a light emitting layer, an electron transport layer and a cathode in this order, wherein the hole transport layer comprises an arylamine compound of the following general formula (1), and the electron transport layer comprises a compound of the following general formula (2) having a benzazole ring structure:

[Chemical Formula 1]

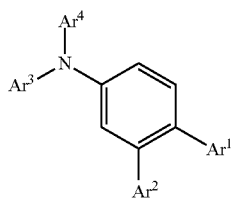

(1)

wherein $Ar^1$ to $Ar^4$ may be the same or different, and represent a substituted or unsubstituted aromatic hydrocarbon group, a substituted or unsubstituted aromatic heterocyclic group, or a substituted or unsubstituted condensed polycyclic aromatic group,

[Chemical Formula 2]

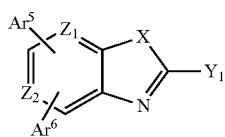

(2)

wherein, $Ar^5$ to $Ar^6$ may be the same or different, and represent a hydrogen atom, a deuterium atom, a substituted or unsubstituted aromatic hydrocarbon group, a substituted or unsubstituted aromatic heterocyclic group, or a substituted or unsubstituted condensed polycyclic aromatic group, $Y_1$ represents a substituted or unsubstituted aromatic hydrocarbon group, a substituted or unsubstituted aromatic heterocyclic group, a substituted or unsubstituted condensed polycyclic aromatic group, or alkyl, X represents an oxygen atom or a sulfur atom, $Z_1$ and $Z_2$ may be the same or different, and represent a carbon atom or a nitrogen atom, and wherein the hole transport layer has a two-layer structure of a first hole transport layer and a second hole transport layer, and the second hole transport layer comprises the arylamine compound.

2. The organic electroluminescent device according to claim 1, wherein the electron transport layer comprises a compound of the following general formula (3) having a benzazole ring structure:

[Chemical Formula 3]

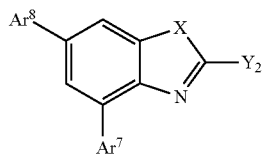

(3)

wherein, $Ar^7$ to $Ar^8$ may be the same or different, and represent a hydrogen atom, a deuterium atom, a substituted or unsubstituted aromatic hydrocarbon group, a substituted or unsubstituted aromatic heterocyclic group, or a substituted or unsubstituted condensed polycyclic aromatic group, $Y_2$ represents a substituted or unsubstituted aromatic hydrocarbon group, a substituted or unsubstituted aromatic heterocyclic group, a substituted or unsubstituted condensed polycyclic aromatic group, or alkyl, X represents an oxygen atom or a sulfur atom.

3. The organic electroluminescent device according to claim 1, wherein the first hole transport layer comprises a triphenylamine derivative different from the arylamine compound included in the second hole transport layer, and the triphenylamine derivative is a compound having a molecular structure containing two triphenylamine skeletons bonded to each other via a single bond or a divalent hydrocarbon group, and having 2 to 6 triphenylamine skeletons as a whole molecule.

4. The organic electroluminescent device according to claim 3, wherein the triphenylamine derivative included in the first hole transport layer is represented by the following general formula (4):

[Chemical Formula 4]

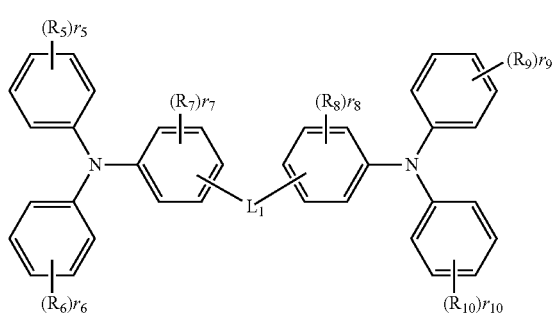

(4)

wherein, $R_5$ to $R_{10}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and $r_5$ to $r_{10}$ may be the same or different, $r_5$, $r_6$, $r_9$ and $r_{10}$ representing 0 to 5, and $r_7$ and $r_8$ representing 0 to 4, and when $r_5$, $r_6$, $r_9$ and $r_{10}$ are 2 to 5, or when $r_7$ and $r_8$ are 2 to 4, $R_5$ to $R_{10}$, a plurality of which bind to the same benzene ring, may be the same or different and may bind to each other via a single bond, substituted or unsubstituted methylene, an oxygen atom, or a sulfur atom to form a ring, and $L_1$ represents a divalent group of the following structural formulas (C) to (G), or a single bond.

[Chemical Formula 5]

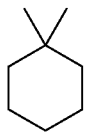
(C)

[Chemical Formula 6]

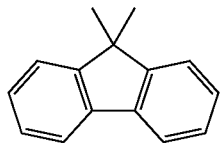
(D)

[Chemical Formula 7]

(E)

—CH$_2$—

[Chemical Formula 8]

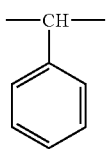
(F)

[Chemical Formula 9]

(G)

5. The organic electroluminescent device according to claim 3, wherein the triphenylamine derivative included in the first hole transport layer is represented by the following general formula (5):

[Chemical Formula 10]

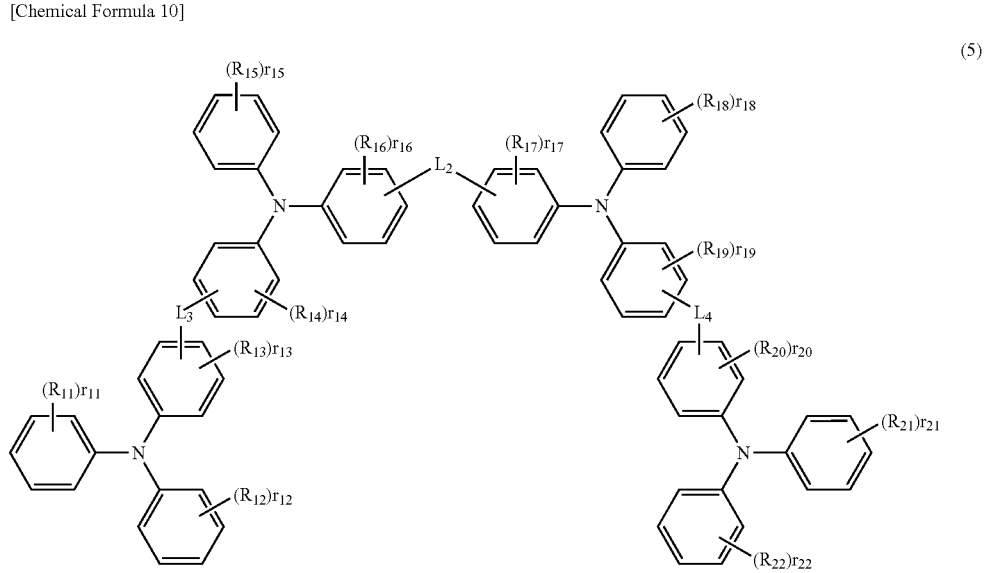
(5)

wherein, $R_{11}$ to $R_{22}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, and $r_{11}$ to $r_{22}$ may be the same or different, $r_{11}$, $r_{12}$, $r_{15}$, $r_{18}$, $r_{21}$ and $r_{22}$ representing 0 to 5, and $r_{13}$, $r_{14}$, $r_{16}$, $r_{17}$, $r_{19}$ and $r_{20}$ representing 0 to 4, and when $r_{11}$, $r_{12}$, $r_{15}$, $r_{18}$, $r_{21}$ and $r_{22}$ are 2 to 5, or when $r_{13}$, $r_{14}$, $r_{16}$, $r_{17}$, $r_{19}$ and $r_{20}$ are 2 to 4, $R_{11}$ to $R_{22}$, a plurality of which bind to the same benzene ring, may be the same or different and may bind to each other via a single bond, substituted or unsubstituted methylene, an oxygen atom, or a sulfur atom to form a ring, and $L_2$, $L_3$ and $L_4$ may be the same or different, and represent a divalent group of the following structural formulas (B) to (G), or a single bond,

[Chemical Formula 11]

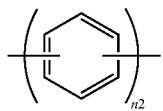
(B)

wherein, n2 represents 1 to 3

[Chemical Formula 12]

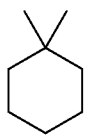
(C)

[Chemical Formula 13]

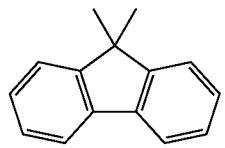
(D)

[Chemical Formula 14]

—CH$_2$—
(E)

[Chemical Formula 15]

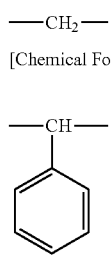
(F)

[Chemical Formula 16]

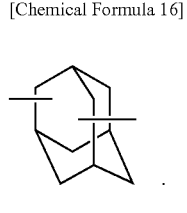
(G)

* * * * *